(12) United States Patent
Horikoshi et al.

(10) Patent No.: US 9,301,525 B2
(45) Date of Patent: Apr. 5, 2016

(54) PEST CONTROL COMPOSITION INCLUDING NOVEL IMINOPYRIDINE DERIVATIVE

(71) Applicant: MEIJI SEIKA PHARMA CO., LTD., Chuo-ku, Tokyo (JP)

(72) Inventors: Ryo Horikoshi, Yokohama (JP); Yasumichi Onozaki, Yokohama (JP); Satoshi Nakamura, Yokohama (JP); Masahiro Nomura, Yokohama (JP); Makoto Matsumura, Yokohama (JP); Masaaki Mitomi, Yokohama (JP)

(73) Assignee: MEUI SEIKA PHARMA CO., LTD., Tokyo (JP)

( * ) Notice: Subject to any disclaimer, the term of this patent is extended or adjusted under 35 U.S.C. 154(b) by 0 days.

(21) Appl. No.: 14/320,808

(22) Filed: Jul. 1, 2014

(65) Prior Publication Data

US 2014/0315839 A1 Oct. 23, 2014

Related U.S. Application Data

(63) Continuation of application No. PCT/JP2013/056051, filed on Feb. 27, 2013.

(30) Foreign Application Priority Data

Feb. 29, 2012 (JP) ................................ 2012-044514

(51) Int. Cl.
*C07D 401/00* (2006.01)
*A01N 43/40* (2006.01)
(Continued)

(52) U.S. Cl.
CPC ................. *A01N 43/40* (2013.01); *A01N 43/08* (2013.01); *A01N 43/22* (2013.01); *A01N 43/50* (2013.01);
(Continued)

(58) Field of Classification Search
CPC .. C07D 401/06; C07D 255/02; C07D 253/02; C07D 213/89; C07D 213/76; C07D 213/75
See application file for complete search history.

(56) References Cited

U.S. PATENT DOCUMENTS 4,803,277 A 2/1989 Shiokawa et al.
5,250,498 A * 10/1993 Andree et al. ................. 504/105
(Continued)

FOREIGN PATENT DOCUMENTS

DE 3639877 A1 * 5/1988 ............. C07D 41/06
EP 0 259 738 A2 3/1988
(Continued)

OTHER PUBLICATIONS

English machine translation of DE3639877, (May 1988) downloaded from http://translationportal.epo.org.*
(Continued)

*Primary Examiner* — Eric Olson
(74) *Attorney, Agent, or Firm* — Sughrue Mion, PLLC

(57) ABSTRACT

Provided is a pest control composition containing an iminopyridine derivative represented by the following Formula (I) and at least one of other pest control agents:

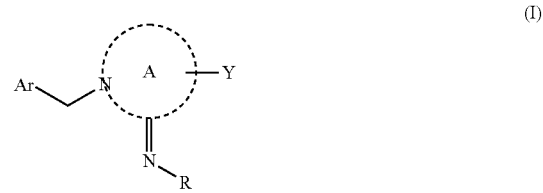

[in the formula (I), Ar represents a 5- to 6-membered heterocycle which may be substituted, A represents a heterocycle having a 5- to 10-membered unsaturated bond including one or more nitrogen atoms, and has an imino group substituted with an R group at a position adjacent to the nitrogen atom present on the cycle, Y represents hydrogen, halogen and the like, and R represents any one of groups represented by the following Formulae (a) to (e), (y) or (z)].

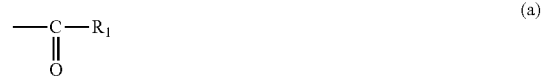
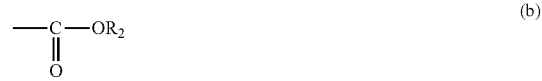
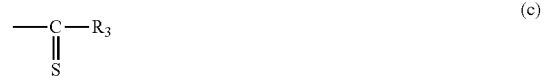
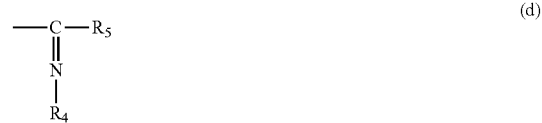
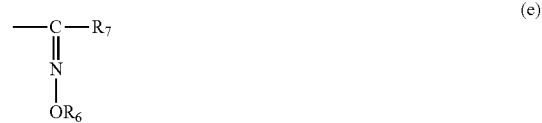
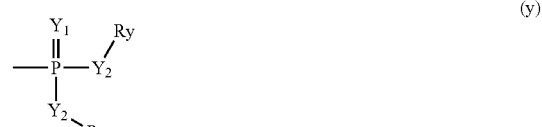
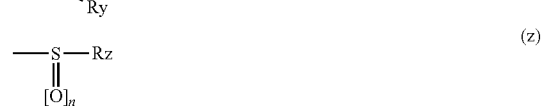

9 Claims, No Drawings

(51) Int. Cl.
- *A01N 43/54* (2006.01)
- *A01N 43/78* (2006.01)
- *C07D 401/06* (2006.01)
- *C07D 213/75* (2006.01)
- *C07D 213/76* (2006.01)
- *C07D 417/06* (2006.01)
- *A01N 43/08* (2006.01)
- *A01N 43/22* (2006.01)
- *A01N 43/50* (2006.01)
- *A01N 43/56* (2006.01)
- *A01N 43/707* (2006.01)
- *A01N 43/88* (2006.01)
- *A01N 43/90* (2006.01)

(52) U.S. Cl.
CPC ............... *A01N 43/54* (2013.01); *A01N 43/56* (2013.01); *A01N 43/707* (2013.01); *A01N 43/78* (2013.01); *A01N 43/88* (2013.01); *A01N 43/90* (2013.01); *C07D 213/75* (2013.01); *C07D 213/76* (2013.01); *C07D 401/00* (2013.01); *C07D 401/06* (2013.01); *C07D 417/06* (2013.01)

(56) References Cited

U.S. PATENT DOCUMENTS

| | | | |
|---|---|---|---|
| 2011/0172433 A1 | 7/2011 | Kagabu et al. | |
| 2012/0055076 A1* | 3/2012 | Smith et al. | 43/131 |
| 2013/0165482 A1* | 6/2013 | Kagabu et al. | 514/332 |

FOREIGN PATENT DOCUMENTS

| | | |
|---|---|---|
| EP | 0 268 915 A2 | 6/1988 |
| EP | 0 432 600 A2 | 6/1991 |
| EP | 0 639 569 A1 | 2/1995 |
| EP | 2 305 658 A1 | 4/2011 |
| JP | 5-78323 A | 3/1993 |
| WO | 2012/029672 A1 | 3/2012 |

OTHER PUBLICATIONS

Fenoll et al., "Dissipation rates of insecticides and fungicides in peppers grown in greenhouse and under cold storage conditions" Food Chemistry (2009) vol. 113, 727-732.*

Ziogas, "Alternative Respiration: a Biochemical Mechanism of Resistance to Azoxystrobin (ICIA 5504) in Septoria tritici" Pesticide Science (1997) vol. 50 pp. 28-34.*

Hanning, "Feeding cessation effects of chlorantraniliprole, a new anthranilic diamide insecticide, in comparison with several insecticides in distinct chemical classes and mode-of-action groups" Pest Management Science (2009) vol. 65 pp. 969-974.*

Corbel et al., "Dinotefuran: A Potential Neonicotinoid Insecticide Against Resistant Mosquitoes" Journal of Medical Entomology (2004) vol. 41 No. 4 pp. 712-717.*

Fritz Krohnke et al., "Syhtnesen von Imidazo-pyridinen, II", Chemische Berichte, Apr. 2, 1955, pp. 1103-1108, vol. 88.

International Search Report for PCT/JP2013/056051 dated Jun. 13, 2013.

* cited by examiner

PEST CONTROL COMPOSITION INCLUDING NOVEL IMINOPYRIDINE DERIVATIVE

BACKGROUND OF THE INVENTION

1. Field of the Invention

The present invention relates to a pest control composition containing a novel iminopyridine derivative and at least one of other pest control agents.

2. Related Background Art

Although numerous pest control agents have been discovered so far, the development of novel drugs which has high safety is still required in view of the problem of reduction in drug sensitivity, the issue of long-term efficacy, safety to workers or safety in terms of environmental impacts. Further, in agriculture, in order to achieve a reduction in labor for the pest control work, it is general to mix a plurality of components of a chemical for pest control and treat seeds or farm products during the growing seedling period with the chemical, and under these circumstances, it is required to use a long-term residual efficacy type chemical having penetrating and migrating property. In addition, it is also possible to solve problems such as scattering of a chemical to the surrounding environment outside agricultural land or exposure to a person who performs pest control by seed treatment or treatment during the growing seedling period.

European Patent Application Laid-Open No. 432600 (PTL1) discloses a plurality of compounds having the same ring structure as that of a compound represented by Formula (I), but the compounds are used as herbicides and there is no description about pest control.

Japanese Patent Application Laid-Open (JP-A) No. 5-78323 (PTL2) discloses the structural formula of N-[1-((6-chloropyridin-3-yl)methyl)pyridin-2(1H)-ylidene]-2,2,2-trifluoroacetamide (Compound No. 3 in Table 1 of JP-A No. 5-78323), but fails to disclose a preparation method thereof and the compound is not included in a list of the group of compounds that are recognized to have pest control activity (Tables 2 and 3 of JP-A No. 5-78323).

European Patent Application Laid-Open No. 268915 (PTL3) discloses the structural formula of N-[1-((6-chloropyridin-3-yl)methyl)pyridin-2(1H)-ylidene]-2,2,2-trifluoroacetamide (Example No. 12 in Table 7 of European Patent Application Laid-Open No. 268915), but fails to disclose a preparation method thereof and the Example does not include the compound as an example of the compounds having pest control activity.

Chemische Berichte (1955), 88, 1103-8 (NPL1) discloses a plurality of compounds having a ring structure similar to that of a compound represented by Formula (I) to be described below, but the compounds are disclosed only as synthetic intermediates.

European Patent Application Laid-Open No. 259738 (PTL4) discloses a plurality of compounds having a ring structure similar to that of a compound represented by Formula (I), but fails to disclose or suggest a compound having a trifluoroacetic acid imino structure.

Furthermore, these documents do not describe pest control activity when the novel iminopyridine derivative of the present invention is mixed with another pest control agent.

SUMMARY OF THE INVENTION

The present invention is contrived to provide a novel pest control agent to solve problems which chemicals in the related art have, such as reduction in drug sensitivity, long-term efficacy, safety during the use thereof and the like in the field of pest control.

In order to solve the problems, the present inventors have intensively studied, and as a result, have found that a novel iminopyridine derivative represented by Formula (I) has excellent pest control effects against pests and discovered a composition showing excellent pest control effects by containing these novel iminopyridine derivatives and at least one of other pest control agents, compared to when a single agent is used, and a use method thereof. The present invention is based on the finding.

Therefore, an object of the present invention is to provide a pest control composition prepared by containing at least one of a novel iminopyridine derivative represented by the following Formula (I) or acid addition salts thereof and at least one of other pest control agents, which is used in a low dose and shows excellent pest control effects against a wide range of pests.

(1) There is provided a pest control composition containing at least one of a novel iminopyridine derivative represented by the following Formula (I) or acid addition salts thereof as an active ingredient and at least one of other pest control agents:

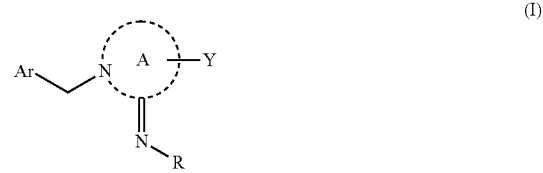

[in the formula (I), Ar represents a phenyl group which may be substituted, a 5- to 6-membered heterocycle which may be substituted, or a 4- to 10-membered heterocycloalkyl group, A represents a heterocycle having a 5- to 10-membered unsaturated bond including one or more nitrogen atoms, and has an imino group substituted with an R group at a position adjacent to the nitrogen atom present on the cycle, Y represents a hydrogen atom, a halogen atom, a hydroxyl group, a C1 to C6 alkyl group which may be substituted with a halogen atom, a C1 to C6 alkyloxy group which may be substituted with a halogen atom, a cyano group, or a nitro group, and R represents any one of groups represented by the following Formulae (a) to (e), (y) or (z),

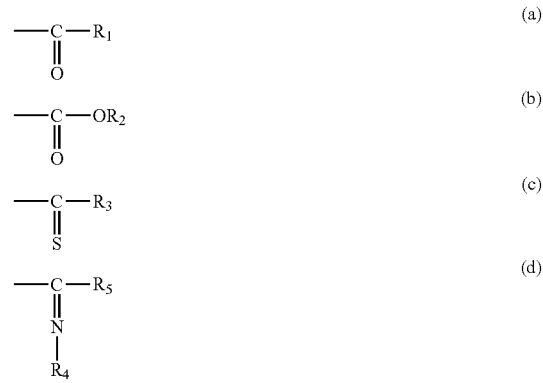

-continued

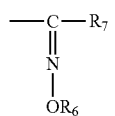 (e)

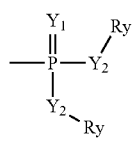 (y)

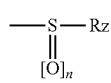 (z)

[here, R1 represents a hydrogen atom, a substituted C1 to C6 alkyl group, a C2 to C6 alkenyl group which may be substituted with a halogen atom, a C2 to C6 alkynyl group which may be substituted with a halogen atom, or a pentafluorophenyl group, R2 represents a C1 to C6 alkyl group substituted with a halogen atom, an unsubstituted C3 to C6 branched or cyclic alkyl group, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted 5- to 10-membered heterocycle, or a substituted or unsubstituted benzyl group, R3 represents a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, or a (C1 to C4) alkylthio (C2 to C5) alkynyl group, R4 represents a hydrogen atom, a formyl group, a C1 to C6 alkyl group which may be substituted, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, a (C1 to C4) alkylthio (C2 to C5) alkynyl group, or a group represented by any of the following Formulae (f) to (n)

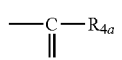 (f)

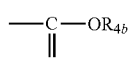 (g)

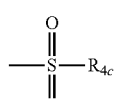 (h)

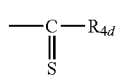 (i)

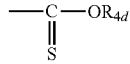 (j)

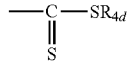 (k)

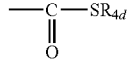 (l)

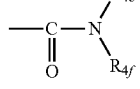 (m)

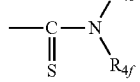 (n)

here, R4a, R4b and R4c represent a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle group, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, or a (C1 to C4) alkylthio (C2 to C5) alkynyl group, R4d represents a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, or a substituted or unsubstituted 5- to 10-membered heterocycle, and R4e and R4f each independently represent a hydrogen atom, a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, or a substituted or unsubstituted 5- to 10-membered heterocycle, R5 represents a C1 to C6 alkyl group which may be substituted with a halogen atom, a C1 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, or a (C1 to C4) alkylthio (C2 to C5) alkynyl group, R6 represents a hydrogen atom, a formyl group, a O,O'-C1 to C4 alkyl phosphoryl group, a C1 to C18 alkyl group which may be substituted, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, a (C1 to C4) alkylthio (C2 to C5) alkynyl group, or a group represented by any of the following Formulae (o) to (x)

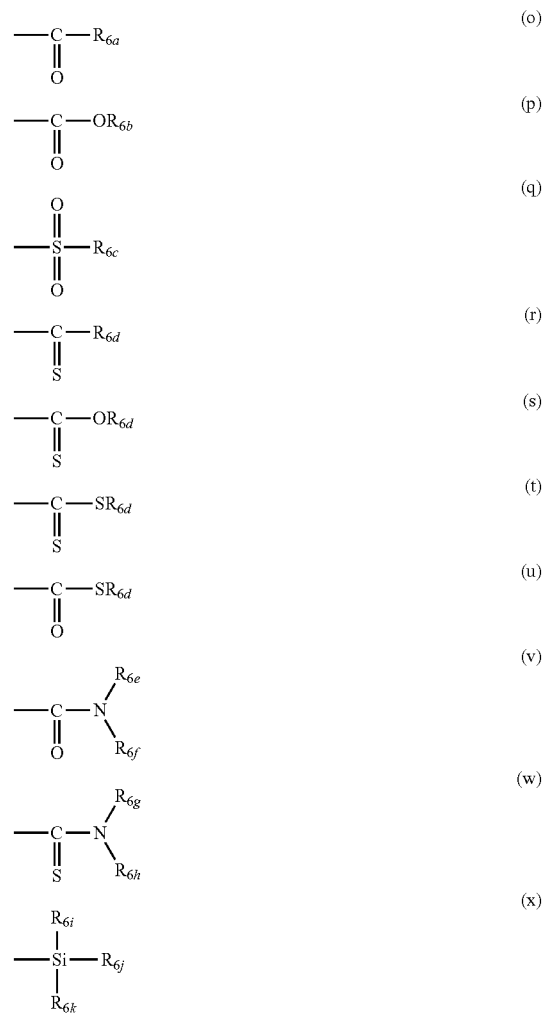

here, R6a, R6b and R6c represent a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle group, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, and a (C1 to C4) alkylthio (C2 to C5) alkynyl group, R6d represents a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, or a substituted or unsubstituted 5- to 10-membered heterocycle, R6e and R6f each independently represent a hydrogen atom, a C1 to C6 alkyl group which may be substituted with a halogen atom, a C2 to C6 alkenyl group which may be substituted with a halogen atom, a C2 to C6 alkynyl group which may be substituted with a halogen atom, a (C1 to C4) alkoxy (C1 to C5) alkyl group, a (C1 to C4) alkylthio (C1 to C5) alkyl group, a substituted or unsubstituted (C6 to C10) aryl group, a substituted or unsubstituted (C6 to C10) aryl (C1 to C6) alkyl group, or a substituted or unsubstituted 5- to 10-membered heterocycle, R6g and R6h each independently represent a hydrogen atom, a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, or a substituted or unsubstituted 5- to 10-membered heterocycle, and R6i, R6j and R6k each independently represent a hydrogen atom, a C1 to C6 alkyl group which may be substituted with a halogen atom, a C2 to C6 alkenyl group which may be substituted with a halogen atom, a C2 to C6 alkynyl group which may be substituted with a halogen atom, or a substituted or unsubstituted (C6 to C10) aryl group), and R7 represents a C1 to C6 alkyl group which may be substituted with a halogen atom, a C1 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, or a (C1 to C4) alkylthio (C2 to C5) alkynyl group, $Y_1$ and $Y_2$ represent an oxygen atom or a sulfur atom, and may be the same or different, and Ry represents a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, or a substituted or unsubstituted 5- to 10-membered heterocycle (C2 to C6) alkynyl group, Rz represents a C1 to C6 alkyl group which may be substituted with a halogen atom, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, or a (C1 to C4) alkylthio (C2 to C5) alkynyl group, and n represents 1 or 2], (2) There is provided the pest control composition according to (1), containing at least one of an amine derivative represented by the following Formula (Ia) or acid addition salts thereof as an active ingredient and at least one of other pest control agents:

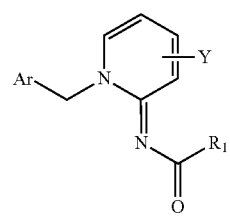

(Ia)

[here, Ar represents a pyridyl group which may be substituted with a halogen atom, a hydroxyl group, a C1 to C6 alkyl group which may be substituted with a halogen atom, a C1 to C6 alkyloxy group which may be substituted with a halogen atom, a cyano group, or a nitro group, or a pyrimidyl group which may be substituted with a halogen atom, a C1 to C4 alkyl group which may be substituted with a halogen atom, an alkyloxy group which may be substituted with a halogen atom, a hydroxyl group, a cyano group, or a nitro group, Y represents a hydrogen atom, a halogen atom, a hydroxyl group, a C1 to C6 alkyl group which may be substituted with a halogen atom, a C1 to C6 alkyloxy group which may be substituted with a halogen atom, a cyano group, or a nitro group, and $R_1$ represents a C1 to C6 alkyl group which is substituted with a halogen atom].

(3) There is provided the pest control composition according to (1), wherein Ar is a 6-chloro-3-pyridyl group, a 6-chloro-5-fluoro-3-pyridyl group, a 6-fluoro-3-pyridyl group, a 6-bromo-3-pyridyl group, or a 2-chloro-5-pyrimidyl group.

(4) There is provided the pest control composition according to (1) or (3), wherein in Formula (I), A is the following Formula (A-1):

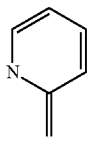

(A-1)

and Y is a hydrogen atom, a halogen atom, or a cyano group.

(5) There is provided the pest control composition according to (1), (3) to (4), wherein R in Formula (I) is a group with Formula (c).

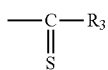

(c)

(6) There is provided the pest control composition according to (1), (3) to (4), wherein R in Formula (I) is a group with Formula (a).

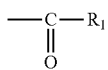

(a)

(7) There is provided the pest control composition according to (1), (3) to (4), wherein R in Formula (I) is a group with Formula (d)

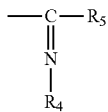

(d)

and $R_4$ is a C1 to C18 alkyl group which may be substituted, a C2 to C6 alkenyl group which may be substituted with a halogen atom, a C2 to C6 alkynyl group which may be substituted with a halogen atom, a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group, a substituted or unsubstituted (C6 to C10) aryl (C2 to C6) alkynyl group, a substituted or unsubstituted phenoxy (C1 to C6) alkyl group, a substituted or unsubstituted phenoxy (C2 to C6) alkenyl group, a substituted or unsubstituted phenoxy (C2 to C6) alkynyl group, a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group, a substituted or unsubstituted 5- to 10-membered heterocycle (C2 to C6) alkynyl group, a (C1 to C4) alkoxy (C1 to C5) alkyl group, a (C1 to C4) alkoxy (C2 to C5) alkenyl group, a (C1 to C4) alkoxy (C2 to C5) alkynyl group, a (C1 to C4) alkylthio (C1 to C5) alkyl group, a (C1 to C4) alkylthio (C2 to C5) alkenyl group, or a (C1 to C4) alkylthio (C2 to C5) alkynyl group, and $R_5$ is a C1 to C6 alkyl group which may be substituted with a halogen atom, a C2 to C6 alkenyl group which may be substituted with a halogen atom, a C2 to C6 alkynyl group which may be substituted with a halogen atom, and $R_5$ is a C1 to C6 alkyl group which may be substituted with a halogen atom, a C2 to C6 alkenyl group which may be substituted with a halogen atom, or a C2 to C6 alkynyl group which may be substituted with a halogen atom.

(8) There is provided the pest control composition according to (1), wherein the iminopyridine derivative is N-[1-((6-chloropyridin-3-yl)methyl)pyridin-2(1H)-ylidene]-2,2,2-trifluoroacetamide, N-[1-((6-chloropyridin-3-yl)methyl)pyridin-2(1H)-ylidene]-2,2,2-trifluoroethanethioamide, or N-[1-((6-chloropyridin-3-yl)methyl)pyridin-2(1H)-ylidene]-2,2,2-trifluoro-N'-isopropylacetimidamide.

(9) There is provided a method for protecting useful plants or animals from pests, including: treating pests, useful plants, seeds of useful plants, soil, cultivation carriers or animals as a target with an effective amount of the pest control composition.

(10) There is provided a combination (combined product) including the iminopyridine derivative represented by Formula (I) and at least one of other pest control agents.

(11) There is provided a use of the pest control composition for protecting useful plants or animals from pests.

It is possible to effectively perform pest control against cabbage moths, *Spodoptera litura*, aphids, planthoppers, leafhoppers, thrips and other numerous pests by using novel iminopyridine derivative of the present invention.

BRIEF DESCRIPTION OF THE DRAWINGS

A novel iminopyridine derivative represented by Formula (I) may be prepared by the following method.

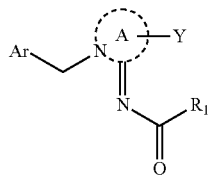

(I-1)

(I-1) may be obtained by reacting a compound represented by the following Formula (II-1) with a compound represented by ArCH2X [the definition of Ar, A, Y and R1 has the same meaning as the definition described above, and X represents a halogen atom or OTs, OMs and the like] in the presence or absence of a base.

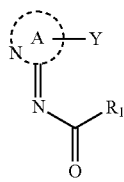

(II-1)

When the reaction is performed in the presence of a base, it is possible to use, for example, an alkali metal hydride such as sodium hydride, a carbonate such as potassium carbonate or sodium carbonate, an alkali metal hydroxide such as potassium hydroxide, and sodium hydroxide, tertiary amines such as triethylamine and 1,8-diazabicyclo[4.3.0]non-5-ene, and unsubstituted or substituent-containing pyridines, such as pyridine and 4-dimethylaminopyridine, as the base.

The reaction may be performed without a solvent or using a solvent which does not affect the reaction, and when a solvent is used, it is possible to use solvents such as, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, alcohols such as methanol, ethanol, propanol and isopropyl alcohol, ketones such as acetone and methyl ethyl ketone, aliphatic hydrocarbons such as hexane, heptane and octane, and halogen hydrocarbons such as dichloromethane, chloroform, chlorobenzene and dichlorobenzene, either alone or in combination of two or more thereof, but N,N-dimethylformamide and the like are preferably used.

The reaction may be performed usually at 0° C. to 200° C., and it is preferred that reagents are added at 20° C. to 40° C. and the reaction is performed at 60° C. to 80° C.

The compound represented by Formula (II-1) may be obtained by reacting a compound represented by R1-C(=O)X, R1-C(=O)OC(=O)R1, R1C(=O)OR' [X represents a halogen atom or OTs, OMs and the like, R' represents a C1 to C6 alkyl group, and the definition of R1, A and Y has the same meaning as the definition described above] and the like with a compound represented by the following Formula (III) in the presence or absence of a base.

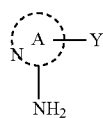

(III)

When the reaction is performed in the presence of a base, it is possible to use, for example, an alkali metal hydride such as sodium hydride, a carbonate such as potassium carbonate or sodium carbonate, an alkali metal hydroxide such as potassium hydroxide and sodium hydroxide, tertiary amines such as triethylamine and 1,8-diazabicyclo[4.3.0]non-5-ene, and unsubstituted or substituent-containing pyridines, such as pyridine and 4-dimethylaminopyridine as the base.

The reaction may be performed without a solvent or using a solvent which does not affect the reaction. When a solvent is used, it is possible to use solvents such as, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, alcohols such as methanol, ethanol and propanol, ketones such as acetone and methyl ethyl ketone, aliphatic hydrocarbons such as hexane, heptane and octane, halogen hydrocarbons such as dichloromethane, chloroform, chlorobenzene and dichlorobenzene, and water, either alone or in combination of two or more thereof, but toluene, N,N-dimethylformamide, acetonitrile, ethers, dichloromethane, chloroform and the like are preferably used.

The reaction may be performed usually at −80° C. to 100° C., and is performed preferably in a range from 20° C. to 50° C. The compound represented by Formula (II-1) may be obtained by reacting the compound represented by Formula (III) with a carboxylic acid represented by R1-COOH [the definition of R1 has the same meaning as the definition described above] using a dehydration condensation agent in the presence or absence of a base, or may be obtained by performing the reaction using phosphorus pentaoxide, sulfuric acid, polyphosphoric acid, thionyl chloride, phosphorus oxychloride and oxalyl dichloride in the absence of a base.

It is possible to use a carbodiimide-based compound such as dicyclohexylcarbodiimide and 1-ethyl-3-(3-[dimethylaminopropyl])carbodiimide hydrochloride as the dehydration condensation agent.

When the reaction is performed in the presence of a base, it is possible to use, for example, a carbonate such as potassium carbonate or sodium carbonate, tertiary amines such as triethylamine and 1,8-diazabicyclo[4.3.0]non-5-ene, and unsubstituted or substituent-containing pyridines, such as pyridine and 4-dimethylaminopyridine, as the base.

The reaction is preferably performed by using a solvent, and it is possible to use solvents such as, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, ketones such as acetone and methyl ethyl ketone, aliphatic hydrocarbons such as hexane, heptane and octane, and halogen hydrocarbons such as dichloromethane, chloroform, chlorobenzene and dichlorobenzene, either alone or in combination of two or more thereof, but dichloromethane, chloroform and the like are preferably used.

The reaction may be performed usually at −80° C. to 100° C., and is performed preferably in a range from 20° C. to 50° C. The compound represented by Formula (I-1) may be obtained by reacting a compound represented by R1-C(=O)X, R1-C(=O)OC(=O)R1, R1C(=O)OR' [X represents a halogen atom or OTs, OMs and the like, R' represents a C1 to C6 alkyl group, and the definition of Ar, A, Y and R1 has the same meaning as the definition described above] and the like with a compound represented by the following Formula (IV) in the presence or absence of a base.

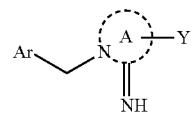

(IV)

When the reaction is performed in the presence of a base, it is possible to use, for example, an alkali metal hydride such as sodium hydride, a carbonate such as potassium carbonate or sodium carbonate, an alkali metal hydroxide such as potassium hydroxide and sodium hydroxide, tertiary amines such as triethylamine and 1,8-diazabicyclo[4.3.0]non-5-ene, and unsubstituted or substituent-containing pyridines, such as pyridine and 4-dimethylaminopyridine as the base.

The reaction may be performed without a solvent or using a solvent which does not affect the reaction. When a solvent is used, it is possible to use solvents such as, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, alcohols such as methanol, ethanol and propanol, ketones such as acetone and methyl ethyl ketone, aliphatic hydrocarbons such as hexane, heptane and octane, halogen hydrocarbons such as dichloromethane, chloroform, chlorobenzene and dichlorobenzene, and water, either alone or in combination of two or more thereof, but toluene, N,N-dimethylformamide, acetonitrile, ethers, dichloromethane, chloroform and the like are preferably used.

The reaction may be performed usually at −80° C. to 100° C., and is performed preferably in a range from 20° C. to 50° C. The compound represented by Formula (I-1) may be obtained by reacting the above-described compound represented by Formula (IV) with a carboxylic acid represented by R1-COOH [the definition of R1 has the same meaning as the definition described above] using a dehydration condensation agent in the presence or absence of a base, or may be obtained by performing the reaction using phosphorus pentaoxide, sulfuric acid, polyphosphoric acid, thionyl chloride, phosphorus oxychloride and oxalyl dichloride in the absence of a base.

It is possible to use a carbodiimide-based compound such as dicyclohexylcarbodiimide and 1-ethyl-3-(3-dimethylaminopropyl)carbodiimide hydrochloride as the dehydration condensation agent.

When the reaction is performed in the presence of a base, it is possible to use, for example, a carbonate such as potassium carbonate or sodium carbonate, tertiary amines such as triethylamine and 1,8-diazabicyclo[4.3.0]non-5-ene, and unsubstituted or substituent-containing pyridines, such as pyridine and 4-dimethylaminopyridine, as the base.

The reaction is preferably performed by using a solvent, and it is possible to use solvents such as, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, ketones such as acetone and methyl ethyl ketone, aliphatic hydrocarbons such as hexane, heptane and octane, and halogen hydrocarbons such as dichloromethane, chloroform, chlorobenzene and dichlorobenzene, either alone or in combination of two or more thereof, but dichloromethane, chloroform and the like are preferably used.

The reaction may be performed usually at −80° C. to 100° C., and is performed preferably in a range from 20° C. to 50° C. The compound represented by Formula (IV) may be obtained by reacting the above-described compound represented by Formula (III) with a compound represented by ArCH2X [the definition of Ar and X has the same meaning as the definition described above] in the presence or absence of a base.

When the reaction is performed in the presence of a base, it is possible to use, for example, an alkali metal hydride such as sodium hydride, a carbonate such as potassium carbonate or sodium carbonate, an alkali metal hydroxide such as potassium hydroxide and sodium hydroxide, tertiary amines such as triethylamine and 1,8-diazabicyclo[4.3.0]non-5-ene, and unsubstituted or substituent-containing pyridines, such as pyridine and 4-dimethylaminopyridine, as the base.

The reaction may be performed without a solvent or using a solvent which does not affect the reaction. When a solvent is used, it is possible to use solvents such as, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, alcohols such as methanol, ethanol and propanol, ketones such as acetone and methyl ethyl ketone, aliphatic hydrocarbons such as hexane, heptane and octane, halogen hydrocarbons such as dichloromethane, chloroform, chlorobenzene and dichlorobenzene, and water, either alone or in combination of two or more thereof, but N,N-dimethylformamide, acetonitrile, ethers, dichloromethane, chloroform and the like are preferably used.

The reaction may be performed usually at −80° C. to 100° C., and is performed preferably in a range from 20° C. to 80° C.

When Formula (I-1) is synthesized via Formula (II-1) from the compound represented by Formula (III), or when Formula (I-1) is synthesized via Formula (IV) from the compound represented by Formula (III), the reaction may be continuously performed without taking out Formula (II-1) or Formula (IV), or the reactions from Formula (III) to Formula (I-1) may be simultaneously performed in the same vessel.

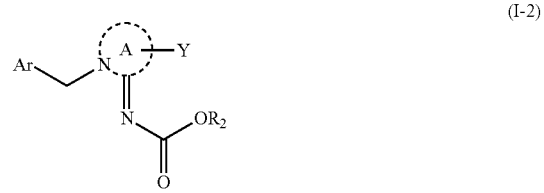

(I-2)

The compound represented by Formula (I-2) may be obtained by reacting a compound represented by the following Formula (I-2a) with a compound represented by ArCH2X [the definition of Ar, A, Y and R2 has the same meaning as the definition described above, and X represents a halogen atom or OTs, OMs and the like] in the presence or absence of a base.

(I-2a)

When the reaction is performed in the presence of a base, it is possible to use, for example, an alkali metal hydride such as sodium hydride, a carbonate such as potassium carbonate or sodium carbonate, an alkali metal hydroxide such as potassium hydroxide and sodium hydroxide, tertiary amines such as triethylamine and 1,8-diazabicyclo[4.3.0]non-5-ene, and unsubstituted or substituent-containing pyridines, such as pyridine and 4-dimethylaminopyridine, as the base.

The reaction may be performed without a solvent or using a solvent which does not affect the reaction, and when a solvent is used, it is possible to use solvents such as, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, alcohols such as methanol, ethanol, propanol and isopropyl alcohol, ketones such as acetone and methyl ethyl ketone, aliphatic hydrocarbons such as hexane, heptane and octane, and halogen hydrocarbons such as dichloromethane, chloroform, chlorobenzene and dichlorobenzene, either alone or in combination of two or more thereof, but N,N-dimethylformamide and the like are preferably used.

The reaction may be performed usually at 0° C. to 200° C., and it is preferred that reagents are added at 20° C. to 40° C. and the reaction is performed at 60° C. to 80° C.

The compound represented by Formula (I-2a) may be obtained by reacting the above-described compound represented by Formula (III) with a compound represented by R2OC(=O)X (the definition of R2 and X has the same meaning as the definition described above] or represented by the following Formula (I-2b) in the presence or absence of a base.

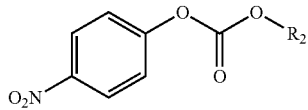

(I-2b)

When the reaction is performed in the presence of a base, it is possible to use, for example, an alkali metal hydride such as sodium hydride, a carbonate such as potassium carbonate or sodium carbonate, an alkali metal hydroxide such as potassium hydroxide and sodium hydroxide, tertiary amines such as triethylamine and 1,8-diazabicyclo[4.3.0]non-5-ene, and unsubstituted or substituent-containing pyridines, such as pyridine and 4-dimethylaminopyridine as the base.

The reaction may be performed without a solvent or using a solvent which does not affect the reaction, and when a solvent is used, it is possible to use solvents such as, for example, amides such as N,N-dimethylformamide and N,N-dimethylacetamide, nitriles such as acetonitrile, sulfoxides such as dimethyl sulfoxide, ethers such as diethyl ether, and tetrahydrofuran, esters such as ethyl acetate and butyl acetate, aromatic hydrocarbons such as benzene, xylene and toluene, alcohols such as methanol, ethanol, propanol and isopropyl alcohol, ketones such as acetone and methyl ethyl ketone, aliphatic hydrocarbons such as hexane, heptane and octane, and halogen hydrocarbons such as dichloromethane, chloroform, chlorobenzene and dichlorobenzene, either alone or in combination of two or more thereof, but acetonitrile, dichloromethane or the like is preferably used.

The reaction may be performed usually at 0° C. to 200° C., and is performed preferably at 20° C. to 80° C.

The compound represented by Formula (I-2) may be obtained by reacting the above-described compound represented by Formula (IV) with a compound represented by R2OC(=O)X (the definition of R2 and X has the same meaning as the definition described above] or represented by the above-described Formula (I-2b) in the presence or absence of a base. When the reaction is performed in the presence of a base, it is possible to use, for example, an alkali metal hydride such as sodium hydride, a carbonate such as potassium carbonate or sodium carbonate, an alkali metal hydroxide such as potassium hydroxide and sodium hydroxide, tertiary amines such as triethylamine and 1,8-diazabicyclo[4.3.0]non-5-ene, and unsubstituted or substituent-containing pyridines, such as pyridine and 4-dimethylaminopyridine as the base.

The reaction may be performed without a solvent or using a solvent which does not affect the reaction, and when a solvent is used, it is possible to use solvents such as, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, alcohols such as methanol, ethanol, propanol and isopropyl alcohol, ketones such as acetone and methyl ethyl ketone, aliphatic hydrocarbons such as hexane, heptane and octane, and halogen hydrocarbons such as dichloromethane, chloroform, chlorobenzene and dichlorobenzene, either alone or in combination of two or more thereof, but acetonitrile, dichloromethane or the like is preferably used.

The reaction may be performed usually at 0° C. to 200° C., and is performed preferably at 20° C. to 80° C.

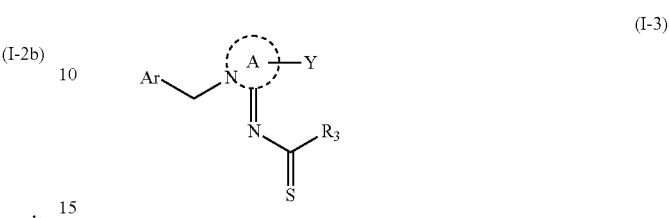

(I-3)

The compound represented by Formula (I-3) may be synthesized by acting a sulfurizing reagent on a compound (the definition of Ar, A, Y and R3 has the same meaning as the definition described above) represented by the following Formula (II-3a), which may be synthesized in the same manner as described in Formula (I-1), in the presence or absence of a base.

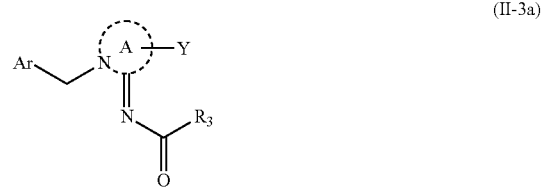

(II-3a)

When the reaction is performed in the presence of a base, it is possible to use, for example, an alkali metal hydride such as sodium hydride, a carbonate such as potassium carbonate or sodium carbonate, an alkali metal hydroxide such as potassium hydroxide and sodium hydroxide, tertiary amines such as triethylamine and 1,8-diazabicyclo[4.3.0]non-5-ene, and unsubstituted or substituent-containing pyridines, such as pyridine and 4-dimethylaminopyridine as the base, but potassium carbonate, sodium carbonate or the like is preferably used.

As the sulfurizing reagent, phosphorus pentasulfide, Lawesson's reagent, hydrogen sulfide and the like may be used.

The reaction may be performed without a solvent or using a solvent which does not affect the reaction, and when a solvent is used, it is possible to use solvents such as, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, alcohols such as methanol, ethanol and propanol, ketones such as acetone and methyl ethyl ketone, aliphatic hydrocarbons such as hexane, heptane and octane, and halogen hydrocarbons such as dichloromethane, chloroform, chlorobenzene and dichlorobenzene, either alone or in combination of two or more thereof, but toluene, tetrahydrofuran or the like is preferably used.

The reaction may be performed usually at −80° C. to 100° C., and is performed preferably in a range from 20° C. to 80° C. The compound represented by Formula (I-3) may be obtained by reacting a compound represented by the following Formula (II-3b) with a compound represented by ArCH2X [the definition of Ar, A, Y and R3 has the same meaning as the definition described above, and X represents a halogen atom or OTs, OMs and the like] in the presence or absence of a base.

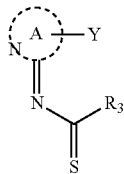

(II-3b)

When the reaction is performed in the presence of a base, it is possible to use, for example, an alkali metal hydride such as sodium hydride, a carbonate such as potassium carbonate or sodium carbonate, an alkali metal hydroxide such as potassium hydroxide and sodium hydroxide, tertiary amines such as triethylamine and 1,8-diazabicyclo[4.3.0]non-5-ene, and unsubstituted or substituent-containing pyridines, such as pyridine and 4-dimethylaminopyridine as the base.

The reaction may be performed without a solvent or using a solvent which does not affect the reaction, and when a solvent is used, it is possible to use solvents such as, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, alcohols such as methanol, ethanol, propanol and isopropyl alcohol, ketones such as acetone and methyl ethyl ketone, aliphatic hydrocarbons such as hexane, heptane and octane, and halogen hydrocarbons such as dichloromethane, chloroform, chlorobenzene and dichlorobenzene, either alone or in combination of two or more thereof, but N,N-dimethylformamide and the like are preferably used.

The reaction may be performed usually at 0° C. to 200° C., and it is preferred that reagents are added at 20° C. to 40° C. and the reaction is performed at 60° C. to 80° C.

The compound represented by Formula (II-3b) may be synthesized by acting a sulfurizing reagent on a compound (the definition of A, Y and R3 has the same meaning as the definition described above) represented by Formula (II-3c), which may be synthesized in the same manner as described in Formula (II-1), in the presence or absence of a base.

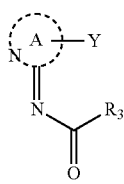

(II-3c)

When the reaction is performed in the presence of a base, it is possible to use, for example, an alkali metal hydride such as sodium hydride, a carbonate such as potassium carbonate or sodium carbonate, an alkali metal hydroxide such as potassium hydroxide and sodium hydroxide, tertiary amines such as triethylamine and 1,8-diazabicyclo[4.3.0]non-5-ene, and unsubstituted or substituent-containing pyridines, such as pyridine and 4-dimethylaminopyridine as the base, but potassium carbonate, sodium carbonate or the like is preferably used.

As the sulfurizing reagent, phosphorus pentasulfide, Lawesson's reagent, hydrogen sulfide and the like may be used. The reaction may be performed without a solvent or using a solvent which does not affect the reaction, and when a solvent is used, it is possible to use solvents such as, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, alcohols such as methanol, ethanol and propanol, ketones such as acetone and methyl ethyl ketone, aliphatic hydrocarbons such as hexane, heptane and octane, and halogen hydrocarbons such as dichloromethane, chloroform, chlorobenzene and dichlorobenzene, either alone or in combination of two or more thereof, but toluene, tetrahydrofuran and the like are preferably used.

The reaction may be performed usually at −80° C. to 100° C., and is performed preferably in a range from 20° C. to 80° C.

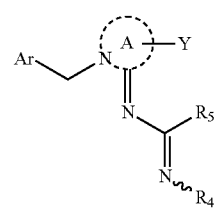

(I-4)

The compound represented by Formula (I-4) may be obtained by reacting a compound represented by the following Formula (II-4a), which may be synthesized in the same manner as described in Formula (I-3) with a compound represented by R4-NH2 (the definition of Ar, A, Y, R4 and R5 has the same meaning as the definition described above).

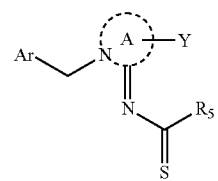

(II-4a)

The reaction may be performed without a solvent or using a solvent which does not affect the reaction, and when a solvent is used, it is possible to use solvents such as, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, alcohols such as methanol, ethanol and propanol, ketones such as acetone and methyl ethyl ketone, aliphatic hydrocarbons such as hexane, heptane and octane, and halogen hydrocarbons such as dichloromethane, chloroform, chlorobenzene and dichlorobenzene, either alone or in combination of two or more thereof, but alcohols such as methanol and ethanol are preferably used.

The reaction, if performed in the presence of silver carbonate, copper carbonate and the like, progresses quickly, but may proceed without the compound.

The reaction may be performed usually at −80° C. to 100° C., and is performed preferably in a range from 20° C. to 80° C.

The compound represented by Formula (I-4) may be obtained by reacting a compound represented by the following Formula (I-4b) or a salt thereof with R4-X, R4-O—R4 and R4-OR' (the definition of R4, R', Ar, A, Y and R5 has the same meaning as the definition described above, and X represents a halogen atom) in the presence or absence of a base.

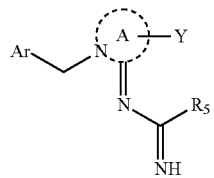

(I-4b)

When the reaction is performed in the presence of a base, it is possible to use, for example, an alkali metal hydride such as sodium hydride, a carbonate such as potassium carbonate or sodium carbonate, an alkali metal hydroxide such as potassium hydroxide and sodium hydroxide, tertiary amines such as triethylamine and 1,8-diazabicyclo[4.3.0]non-5-ene, and unsubstituted or substituent-containing pyridines, such as pyridine and 4-dimethylaminopyridine as the base.

The reaction may be performed without a solvent or using a solvent which does not affect the reaction. When a solvent is used, it is possible to use solvents such as, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, alcohols such as methanol, ethanol and propanol, ketones such as acetone and methyl ethyl ketone, aliphatic hydrocarbons such as hexane, heptane and octane, halogen hydrocarbons such as dichloromethane, chloroform, chlorobenzene and dichlorobenzene, and water either alone or in combination of two or more thereof, but toluene, dimethylformamide, acetonitrile, ethers, dichloromethane, chloroform and the like are preferably used.

The reaction may be performed usually at −80° C. to 100° C., and is performed preferably in a range from 20° C. to 50° C. The compound represented by Formula (I-4b) may be obtained by reacting a compound represented by Formula (II-4a) with ammonia or an alcohol solution thereof, ammonium chloride and the like.

The reaction may be performed without a solvent or using a solvent which does not affect the reaction. When a solvent is used, it is possible to use solvents such as, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, alcohols such as methanol, ethanol and propanol, ketones such as acetone and methyl ethyl ketone, aliphatic hydrocarbons such as hexane, heptane and octane, halogen hydrocarbons such as dichloromethane, chloroform, chlorobenzene and dichlorobenzene, and water, either alone or in combination of two or more thereof, but alcohols such as methanol and ethanol are preferably used.

The reaction may be performed usually at −80° C. to 100° C., and is performed preferably in a range from 20° C. to 50° C.

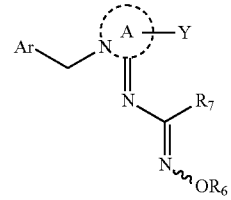

(I-5)

The compound represented by Formula (I-5) may be obtained by reacting a compound represented by the following Formula (II-5b) with R6-X (the definition of AR, A, Y, R6 and R7 has the same meaning as the definition described above, and X represents a halogen atom), R6-O—R6 or R6-OR' (the definition of R' has the same meaning as the definition described above) in the presence or absence of a base.

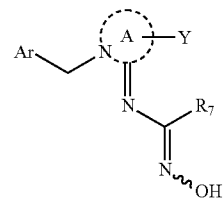

(II-5b)

When the reaction is performed in the presence of a base, it is possible to use, for example, an alkali metal hydride such as sodium hydride, a carbonate such as potassium carbonate or sodium carbonate, an alkali metal hydroxide such as potassium hydroxide and sodium hydroxide, tertiary amines such as triethylamine and 1,8-diazabicyclo[4.3.0]non-5-ene, and unsubstituted or substituent-containing pyridines, such as pyridine and 4-dimethylaminopyridine as the base.

The reaction may be performed without a solvent or using a solvent which does not affect the reaction. When a solvent is used, it is possible to use solvents such as, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, alcohols such as methanol, ethanol and propanol, ketones such as acetone and methyl ethyl ketone, aliphatic hydrocarbons such as hexane, heptane and octane, halogen hydrocarbons such as dichloromethane, chloroform, chlorobenzene and dichlorobenzene, and water, either alone or in combination of two or more thereof, but toluene, N,N-dimethylformamide, acetonitrile, ethers, dichloromethane and chloroform are preferably used.

The reaction may be performed usually at −80° C. to 100° C., and is performed preferably in a range from 20° C. to 50° C.

When R6 represents —C(=O)R6a (R6a has the same meaning as described above), the compound represented by Formula (I-5) may be obtained by reacting the compound represented by Formula (II-5b) with a carboxylic acid represented by R6a-C(=O)OH (the definition of R6a has the same meaning as the definition described above) using a dehydration condensation agent in the presence or absence of a base, or may be obtained by performing the reaction using phosphorus pentaoxide, sulfuric acid, polyphosphoric acid, thionyl chloride, phosphorus oxychloride and oxalyl dichloride in the absence of a base.

It is possible to use a carbodiimide-based compound such as dicyclohexylcarbodiimide, 1-ethyl-3-(3-dimethylaminopropyl)carbodiimide hydrochloride and the like as the dehydration condensation agent.

When the reaction is performed in the presence of a base, it is possible to use, for example, a carbonate such as potassium carbonate or sodium carbonate, tertiary amines such as triethylamine and 1,8-diazabicyclo[4.3.0]non-5-ene, and unsubstituted or substituent-containing pyridines, such as pyridine and 4-dimethylaminopyridine as the base.

The reaction is preferably performed by using a solvent, and it is possible to use, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, ketones such as acetone and methyl ethyl ketone, aliphatic hydrocarbons such as hexane, heptane and octane, and halogen hydrocarbons such as dichloromethane, chloroform, chlorobenzene and dichlorobenzene, either alone or in combination of two or more thereof, but dichloromethane, chloroform and the like are preferably used.

The reaction may be performed usually at −80° C. to 100° C., and is performed preferably in a range from 20° C. to 50° C.

When R6 represents CONR6eR6f (the definition of R6e and R6f has the same meaning as the definition described above, and R6e or R6f represents a hydrogen atom) or CSNR6gR6h (the definition of R6g and R6h has the same meaning as the definition described above, and R6g or R6h represents a hydrogen atom), the compound of Formula (I-5) may be obtained by reacting the Formula (II-5b) with a compound represented by R"N=C=O (R" represents a C1 to C6 alkyl group which may be substituted with a halogen atom, a C2 to C6 alkenyl group which may be substituted with a halogen atom, a C2 to C6 alkynyl group which may be substituted with a halogen atom, a (C1 to C4) alkoxy (C1 to C5) alkyl group, a (C1 to C4) alkylthio (C1 to C5) alkyl group, a substituted or unsubstituted (C6 to C10) aryl group, and a substituted or unsubstituted 5- to 10-membered heterocycle) in the presence or absence of a base. When the reaction is performed in the presence of a base, it is possible to use, for example, an alkali metal hydride such as sodium hydride, a carbonate such as potassium carbonate or sodium carbonate, an alkali metal hydroxide such as potassium hydroxide and sodium hydroxide, tertiary amines such as triethylamine and 1,8-diazabicyclo[4.3.0]non-5-ene, and unsubstituted or substituent-containing pyridines, such as pyridine and 4-dimethylaminopyridine as the base. The reaction is preferably performed by using a solvent, and it is possible to use, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, ketones such as acetone and methyl ethyl ketone, aliphatic hydrocarbons such as hexane, heptane and octane, and halogen hydrocarbons such as dichloromethane, chloroform, chlorobenzene and dichlorobenzene, either alone or in combination of two or more thereof, but nitriles such as acetonitrile are preferably used.

The reaction may be performed usually at −80° C. to 100° C., and is performed preferably in a range from 20° C. to 80° C.

When R6 represents CONR6eR6f (the definition of R6e and R6f has the same meaning as the definition described above), the compound of Formula (I-5) may be obtained by reacting the above-described compound represented by Formula (II-5b) with a compound represented by the following Formula (II-5c) in the presence or absence of a base.

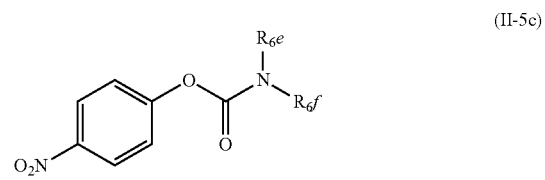

(II-5c)

When the reaction is performed in the presence of a base, it is possible to use, for example, an alkali metal hydride such as sodium hydride, a carbonate such as potassium carbonate or sodium carbonate, an alkali metal hydroxide such as potassium hydroxide and sodium hydroxide, tertiary amines such as triethylamine and 1,8-diazabicyclo[4.3.0]non-5-ene, and unsubstituted or substituent-containing pyridines, such as pyridine and 4-dimethylaminopyridine as the base.

The reaction is preferably performed by using a solvent, and it is possible to use, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, ketones such as acetone and methyl ethyl ketone, aliphatic hydrocarbons such as hexane, heptane and octane, and halogen hydrocarbons such as dichloromethane, chloroform, chlorobenzene and dichlorobenzene, either alone or in combination of two or more thereof, but nitriles such as acetonitrile are preferably used.

The reaction may be performed usually at −80° C. to 100° C., and is performed preferably in a range from 20° C. to 80° C.

The compound represented by Formula (II-5b) may be obtained by reacting the compound (the definition of Ar, A, Y and R7 has the same meaning as the definition described above) represented by Formula (II-5a), which may be synthesized in the same manner as described in Formula (I-3) with hydroxylamine or a salt thereof in the presence or absence of a base.

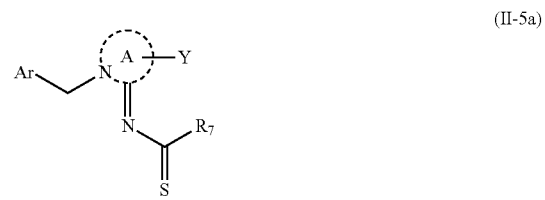

(II-5a)

When the reaction is performed in the presence of a base, it is possible to use, for example, an alkali metal hydride such as sodium hydride, a carbonate such as potassium carbonate or sodium carbonate, an alkali metal hydroxide such as potassium hydroxide and sodium hydroxide, tertiary amines such as triethylamine and 1,8-diazabicyclo[4.3.0]non-5-ene, and unsubstituted or substituent-containing pyridines, such as pyridine and 4-dimethylaminopyridine as the base.

The reaction may be performed without a solvent or using a solvent which does not affect the reaction. When a solvent is used, it is possible to use solvents such as, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, alcohols such as methanol, ethanol and propanol, ketones such as acetone and methyl ethyl ketone, aliphatic hydrocarbons such as hexane, heptane and octane, halogen hydrocarbons such as dichloromethane, chloroform, chlorobenzene and dichlorobenzene, and water, either alone or in combination of two or more thereof, but toluene, N,N-dimethylformamide, acetonitrile, ethers, dichloromethane, chloroform and the like are preferably used.

The reaction may be performed usually at −80° C. to 100° C., and is performed preferably in a range from 20° C. to 80° C.

The compound represented by Formula (I-5) may also be obtained by reacting the compound represented by Formula (II-5a) with a compound represented by R6-ONH2 or a salt thereof in the presence or absence of a base.

When the reaction is performed in the presence of a base, it is possible to use, for example, an alkali metal hydride such as sodium hydride, a carbonate such as potassium carbonate or sodium carbonate, an alkali metal hydroxide such as potassium hydroxide and sodium hydroxide, tertiary amines such as triethylamine and 1,8-diazabicyclo[4.3.0]non-5-ene, and unsubstituted or substituent-containing pyridines, such as pyridine and 4-dimethylaminopyridine as the base.

The reaction may be performed without a solvent or using a solvent which does not affect the reaction. When a solvent is used, it is possible to use solvents such as, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, alcohols such as methanol, ethanol and propanol, ketones such as acetone and methyl ethyl ketone, aliphatic hydrocarbons such as hexane, heptane and octane, halogen hydrocarbons such as dichloromethane, chloroform, chlorobenzene and dichlorobenzene, and water, either alone or in combination of two or more thereof, but alcohols such as methanol and ethanol are preferably used.

The reaction may be performed usually at −80° C. to 100° C., and is performed preferably in a range from 20° C. to 80° C.

The reaction, if performed in the presence of silver carbonate, copper carbonate and the like, progresses quickly, but may proceed without the compound.

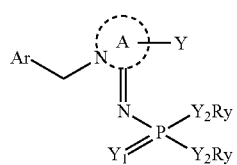
(I-6)

The compound represented by Formula (I-6) [the definition of Ar, A, Y, Y1, Y2, and Ry has the same meaning as the definition described above] may be obtained by reacting according to Phosphorus, sulfur, and silicon and the related elements (2006) 181, 2337-2344.

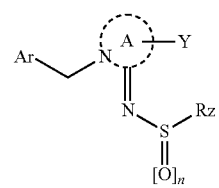
(I-7)

The compound represented by Formula (I-7) [the definition of Ar, A, Y, Ry and n has the same meaning as the definition described above] may be obtained by reacting a compound represented by the following Formula (II-7a) with a compound represented by ArCH2X [the definition of Ar has the same meaning as the definition described above, and X represents a halogen atom or OTs, OMs and the like] in the presence or absence of a base.

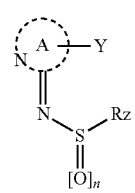
(II-7a)

When the reaction is performed in the presence of a base, it is possible to use, for example, an alkali metal hydride such as sodium hydride and the like, a carbonate such as potassium carbonate or sodium carbonate and the like, an alkali metal hydroxide such as potassium hydroxide, sodium hydroxide and the like, tertiary amines such as triethylamine, 1,8-diazabicyclo[4.3.0]non-5-ene and the like, and unsubstituted or substituent-containing pyridines, such as pyridine, 4-dimethylaminopyridine and the like, as the base.

The reaction may be performed without a solvent or using a solvent which does not affect the reaction, and when the solvent is used, it is possible to use solvents such as, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, alcohols such as methanol, ethanol, propanol and isopropyl alcohol, ketones such as acetone and methyl ethyl ketone, aliphatic hydrocarbons such as hexane, heptane and octane, and halogen hydrocarbons such as dichloromethane, chloroform, chlorobenzene and dichlorobenzene, either alone or in combination of two or more thereof, but N,N-dimethylformamide and the like are preferably used.

The reaction may be performed usually at from 0° C. to 200° C., and it is preferred that reagents are added at from 20° C. to 40° C. and the reaction is performed at from 60° C. to 80° C.

The compound represented by Formula (II-7a) may be obtained by reacting a compound represented by (II-7b) [X represents a halogen atom, and the definition of Rz and n has the same meaning as the definition described above] with a compound represented by in the following Formula (III) in the presence or absence of a base.

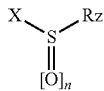
(II-7b)

When the reaction is performed in the presence of a base, it is possible to use, for example, an alkali metal hydride such as sodium hydride and the like, a carbonate such as potassium carbonate or sodium carbonate and the like, an alkali metal hydroxide such as potassium hydroxide, sodium hydroxide and the like, tertiary amines such as triethylamine, 1,8-diazabicyclo[4.3.0]non-5-ene and the like, and unsubstituted or substituent-containing pyridines, such as pyridine, 4-dimethylaminopyridine and the like, as the base.

The reaction may be performed without a solvent or using a solvent which does not affect the reaction, and when the solvent is used, it is possible to use solvents such as, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, alcohols such as methanol, ethanol, propanol and isopropyl alcohol, ketones such as acetone and methyl ethyl ketone, aliphatic hydrocarbons such as hexane, heptane and octane, and halogen hydrocarbons such as dichloromethane, chloroform, chlorobenzene and dichlorobenzene, either alone or in combination of two or more thereof, but N,N-dimethylformamide and the like are preferably used.

The reaction may be performed usually at from 0° C. to 200° C., and it is preferred that reagents are added at from 20° C. to 40° C. and the reaction is performed at from 60° C. to 80° C.

The compound represented by Formula (I-7) may be obtained by reacting a compound represented by (II-7b) [X represents a halogen atom, and the definition of Rz has the same meaning as the definition described above] with a compound represented by in the following Formula (IV) in the presence or absence of a base.

When the reaction is performed in the presence of a base, it is possible to use, for example, an alkali metal hydride such as sodium hydride and the like, a carbonate such as potassium carbonate or sodium carbonate and the like, an alkali metal hydroxide such as potassium hydroxide, sodium hydroxide and the like, tertiary amines such as triethylamine, 1,8-diazabicyclo[4.3.0]non-5-ene and the like, and unsubstituted or substituent-containing pyridines, such as pyridine, 4-dimethylaminopyridine and the like, as the base.

The reaction may be performed without a solvent or using a solvent which does not affect the reaction, and when the solvent is used, it is possible to use solvents such as, for example, amides such as N,N-dimethylformamide and N,N-dimethylacetamide, nitriles such as acetonitrile, sulfoxides such as dimethyl sulfoxide, ethers such as diethyl ether and tetrahydrofuran, esters such as ethyl acetate and butyl acetate, aromatic hydrocarbons such as benzene, xylene and toluene, alcohols such as methanol, ethanol, propanol and isopropyl alcohol, ketones such as acetone and methyl ethyl ketone, aliphatic hydrocarbons such as hexane, heptane and octane, and halogen hydrocarbons such as dichloromethane, chloroform, chlorobenzene and dichlorobenzene, either alone or in combination of two or more thereof, but N,N-dimethylformamide and the like are preferably used.

The reaction may be performed usually at from 0° C. to 200° C., and it is preferred that the reaction is performed at from 0° C. to 80° C.

Examples of a substituent that may be substituted of "a phenyl group which may be substituted" and "a 5- to 6-membered heterocycle which may be substituted", which are represented by Ar, include a halogen atom, a C1 to C4 alkyl group which may be substituted with a halogen atom, a C1 to C4 alkyloxy group which may be substituted with a halogen atom, a hydroxyl group, a cyano group, a nitro group and the like, preferably a halogen atom, a trifluoromethyl group and a cyano group, and particularly preferably a halogen atom.

Specific examples of the "a phenyl group which may be substituted" represented by Ar of a nitrogen-containing heterocyclic derivative compound having a 2-imino group represented by Formula (I) include a phenyl group and a 3-cyano phenyl group.

"A 5- to 6-membered heterocycle which may be substituted", represented by Ar of a nitrogen-containing heterocyclic derivative compound having a 2-imino group represented by Formula (I) represents an aromatic 5- to 6-membered heterocycle including one or two of a heteroatom such as an oxygen atom, a sulfur atom or a nitrogen atom, specific examples thereof include a pyridine ring, a pyrazine ring, a pyrimidine ring, a pyridazine ring, a thiazole ring, an oxazole ring and the like, and preferable aspects thereof include a 6-chloro-3-pyridyl group, a 6-chloro-5-fluoro-3-pyridyl group, a 6-bromo-3-pyridyl group, a 6-fluoro-3-pyridyl group, a 6-trifluoromethyl-3-pyridyl group, a 6-chloro-3-pyridazinyl group, a 5-chloro-2-pyrazinyl group, a 2-chloro-5-pyrimidinyl group, a 2-chloro-5-thiazolyl group, a 2-chloro-4-pyridyl group, and more preferably a 6-chloro-3-pyridyl group, a 6-fluoro-3-pyridyl group, a 6-chloro-5-fluoro-3-pyridyl group, a 6-bromo-3-pyridyl group and a 2-chloro-5-pyrimidinyl group.

Specific examples of "a 4- to 10-membered heterocycloalkyl group" represented by Ar of a nitrogen-containing hetero ring derivative having a 2-imino group represented by Formula (I) include a 2-tetrahydrofuranyl group, a 3-tetrahydrofuranyl group and the like and preferably a 3-tetrahydrofuranyl group. "A heterocycle having a 5- to 10-membered unsaturated bond including one or more nitrogen atoms", which A of a nitrogen-containing heterocyclic derivative having a 2-imino group represented by Formula (I) represents, means that

in Formula (I) represents any one ring represented by each of the following Formulae A-1 to A-40. In each formula, the end of a double bond is the substitution position of a nitrogen atom.

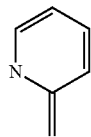
A-1

-continued
A-2 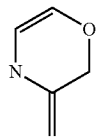
A-3 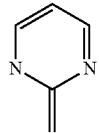
A-4 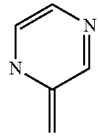
A-5 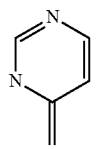
A-6 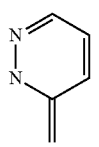
A-7 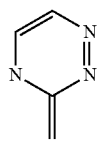
A-8 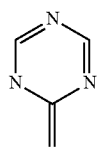
A-9 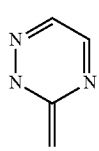
A-10 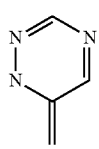
A-11 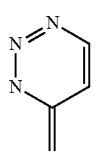
-continued
A-12 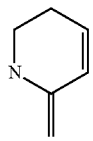
A-13 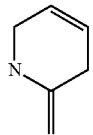
A-14 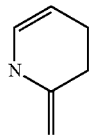
A-15 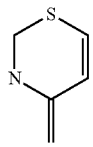
A-16 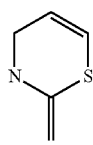
A-17 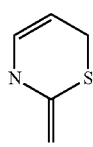
A-18 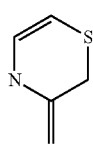
A-19 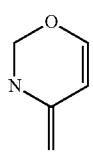
A-20 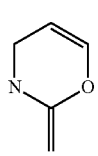
A-21 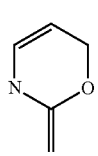

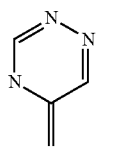 A-22
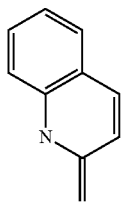 A-23
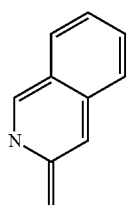 A-24
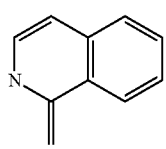 A-25
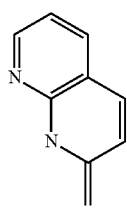 A-26
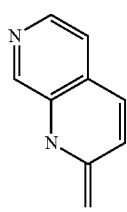 A-27
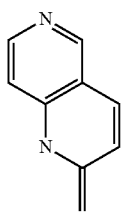 A-28
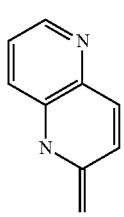 A-29
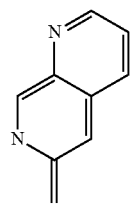 A-30
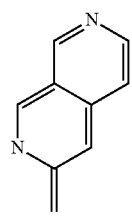 A-31
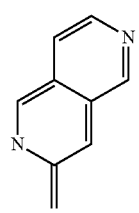 A-32
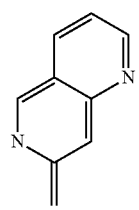 A-33
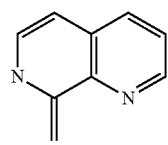 A-34
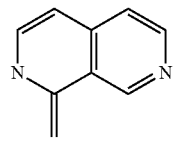 A-35
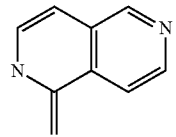 A-36
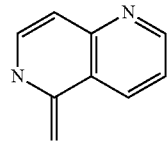 A-37
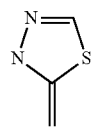 A-38

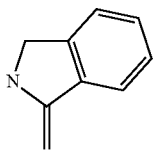

A-39

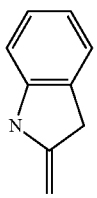

A-40

The ring is preferably the ring of Formulae A-1, A-13, A-14, A-15, A-16, A-23, A-25, A-38 and A-39 and more preferably the ring of Formula A-1.

"A C1 to C6 alkyl group which may be substituted with a halogen atom", which Y represents, is an alkyl group having 1 to 6 carbon atoms, which is chained, branched, cyclic or combination thereof, and the upper limit of the number of halogen atoms which may be substituted is the number of hydrogen atoms which the alkyl group has. When a branched or cyclic alkyl group is included, it is obvious that the number of carbons is 3 or more.

Specific examples of "a C1 to C6 alkyloxy group which may be substituted with a halogen atom" which Y represents include a methoxy group, an ethoxy group, a trifluoromethyloxy group and a difluoromethyloxy group.

A preferred aspect of Y is preferably a hydrogen atom or a halogen atom and more preferably a hydrogen atom.

A preferred aspect of R is a group represented by the Formula (a), (c) and (d) described above.

in Formula (I), "a substituted C1 to C6 alkyl group" which R1 represents is an alkyl group having 1 to 6 carbon atoms, which is chained, branched, cyclic or combination thereof, and the upper limit of the number of substituted substituents is the number of hydrogen atoms which the alkyl group has. Examples of the substituted substituent include a halogen atom, a hydroxyl group, a cyano group, a nitro group, a phenyl group (this phenyl group may be substituted with a C1 to C4 alkyl group which may be substituted with a halogen, a C1 to C4 alkyloxy group which may be substituted with a halogen, a hydroxyl group, or a halogen atom), a phenoxy group (this phenyl group may be substituted with a C1 to C4 alkyl group which may be substituted with a halogen, a C1 to C4 alkyloxy group which may be substituted with a halogen, a hydroxyl group, or a halogen atom), a benzyloxy group (the phenyl group in this benzyloxy group may be substituted with a C1 to C4 alkyl group which may be substituted with a halogen, a C1 to C4 alkyloxy group which may be substituted with a halogen, a hydroxyl group, or a halogen atom), and the like. Specific examples thereof include a 1,1,1-trifluoroethyl group, a trifluoromethyl group, a trichloromethyl group, a difluorochloromethyl group, a difluoromethyl group, a dichloromethyl group, a dibromomethyl group, a chloromethyl group, a difluoroethyl group, a dichloroethyl group, a 2,2,2-trifluoroethyl group, a pentafluoroethyl group, a difluorocyclopropyl group, a 2-cyanoethyl group, a 2-nitroethyl group and the like. A 1,1,1-trifluoroethyl group, a trifluoromethyl group, a difluorochloromethyl group, a difluoromethyl group and a pentafluoroethyl group are preferred, a trifluoromethyl group, a difluorochloromethyl group, a difluoromethyl group and a pentafluoroethyl group are more preferred, and a trifluoromethyl group are particularly preferred.

In Formula (I), "a C1 to C6 alkyl group which may be substituted with a halogen atom" which R3, R5, R7, Ry, and Rz represent is an alkyl group having 1 to 6 carbon atoms, which is chained, branched, cyclic or combination thereof, and the upper limit of the number of substituted halogen atoms is the number of hydrogen atoms which the alkyl group has. When a branched or cyclic alkyl group is included, it is obvious that the number of carbons is 3 or more. Specific examples thereof include a methyl group, an ethyl group, an n-propyl group, an isopropyl group, an n-butyl group, a t-butyl group, a cyclopropyl group, a cyclopentyl group, a cyclohexyl group, a trifluoromethyl group, a trichloromethyl group, a difluorochloromethyl group, a difluoromethyl group, a dichloromethyl group, a dibromomethyl group, a chloromethyl group, a difluoroethyl group, a dichloroethyl group, a 2,2,2-trifluoroethyl group, a pentafluoroethyl group, a difluorocyclopropyl group, a trifluoroisopropyl group, and a hexafluoroisopropyl group, and the like.

R3 is each preferably an ethyl group, an isopropyl group, a cyclopropyl group, a trifluoromethyl group, a difluorochloromethyl group, a difluoromethyl group and a pentafluoroethyl group, more preferably a trifluoromethyl group, a difluorochloromethyl group, a difluoromethyl group and a pentafluoroethyl group, and particularly preferably a trifluoromethyl group. R5 is preferably a trifluoromethyl group, a trichloromethyl group, a dichloromethyl group, a difluoromethyl group, a difluorochloromethyl group, a chloromethyl group and a pentafluoroethyl group, more preferably a trifluoromethyl group, a difluoromethyl group, a difluorochloromethyl group and a pentafluoroethyl group, and particularly preferably a trifluoromethyl group. R7 is preferably a trifluoromethyl group, a trichloromethyl group, a dichloromethyl group, a difluoromethyl group, a difluorochloromethyl group, a chloromethyl group and a pentafluoroethyl group, more preferably a trifluoromethyl group, a difluoromethyl group, a difluorochloromethyl group and a pentafluoroethyl group, and particularly preferably a trifluoromethyl group.

Ry is preferably a methyl group, ethyl group, propyl group or isopropyl group. Rz is preferably a methyl group or trifluoromethyl group.

"A C1 to C6 alkyl group which may be substituted with a halogen atom", which R2 represents, is an alkyl group having 1 to 6 carbon atoms, which is chained, branched, cyclic or combination thereof, and the upper limit of the number of substituted halogen atoms is the number of hydrogen atoms which the alkyl group has. When a branched or cyclic alkyl group is included, it is obvious that the number of carbons is 3 or more. Specific examples thereof include a trifluoromethyl group, a trichloromethyl group, a difluorochloromethyl group, a difluoromethyl group, a dichloromethyl group, a dibromomethyl group, a chloromethyl group, a difluoroethyl group, a dichloroethyl group, a 2,2,2-trifluoroethyl group, a pentafluoroethyl group, a difluorocyclopropyl group, a 1-(trifluoromethyl)ethyl group, a 1-trifluoromethyl-2,2,2-trifluoroethyl group, a pentafluoroethyl group, and a difluorocyclopropyl group, and the like, and preferred examples thereof include a 2,2,2-trifluoroethyl group, a 1-(trifluoromethyl)ethyl group and a 1-trifluoromethyl-2,2,2-trifluoroethyl group.

"A C1 to C6 alkyl group which may be substituted" which R4 and R6 represent is an alkyl group having 1 to 18 carbon atoms, which is chained, branched, cyclic or combination thereof, and the upper limit of the number of substituents which may be substituted is the number of hydrogen atoms which the alkyl group has. When a branched or cyclic alkyl group is included, it is obvious that the number of carbons is 3 or more. Examples of the substituent which may be substituted include a halogen atom, a hydroxyl group, a cyano group, a nitro group and the like. Specific examples thereof include a methyl group, an ethyl group, an n-propyl group, an isopropyl group, an n-butyl group, an s-butyl group, a t-butyl group, a 3-methyl-2-butyl group, a 3-pentyl group, a 4-heptyl group, a cyclopropyl group, a cyclobutyl group, a cyclopentyl group, a cyclohexyl group, an n-octyl group, an n-tridecyl group, an n-hexadecyl group, an n-octadecyl group, a trifluoromethyl group, a trichloromethyl group, a difluorochloromethyl group, a difluoromethyl group, a dichloromethyl group, a dibromomethyl group, a chloromethyl group, a difluoroethyl group, a dichloroethyl group, a 2,2,2-trifluoroethyl group, a pentafluoroethyl group, a difluorocyclopropyl group, a 2-hydroxyethyl group, a 2-hydroxy-n-propyl group, a 3-hydroxy-n-propyl group, a 2,3-dihydroxy-n-propyl group, a cyanomethyl group, a 2-cyanoethyl group, a 2-nitroethyl group and the like.

R4 is each preferably a methyl group, an ethyl group, a 2,2,2-trifluoroethyl group, a 2,2-difluoroethyl group, an n-propyl group, an isopropyl group, a cyclopropyl group, a t-butyl group, a cyclopentyl group, a cyclohexyl group and a 2-hydroxyethyl group, and more preferably a methyl group, an ethyl group and a cyclopropyl group. R6 is preferably a methyl group, an ethyl group, an isopropyl group a cyclopropyl group, a t-butyl group and a cyanomethyl group, and more preferably a methyl group, an ethyl group, a cyclopropyl group and a t-butyl group.

"A C1 to C6 alkyl group which may be substituted with a halogen atom", which R4a, R4b, R4c, R4d, R4e, R4f, R6a, R6b, R6c, R6d, R6e, R6f, R6g, R6h, R6i, R6j and R6k represent, is an alkyl group having 1 to 6 carbon atoms, which is chained, branched, cyclic or combination thereof, and the upper limit of the number of substituted halogen atoms is the number of hydrogen atoms which the alkyl group has. When a branched or cyclic alkyl group is included, it is obvious that the number of carbons is 3 or more. Specific examples thereof include a methyl group, an ethyl group, an n-propyl group, an isopropyl group, an n-butyl group, a t-butyl group, a cyclopropyl group, a cyclopentyl group, a cyclohexyl group, a trifluoromethyl group, a trichloromethyl group, a difluorochloromethyl group, a difluoromethyl group, a dichloromethyl group, a dibromomethyl group, a chloromethyl group, a difluoroethyl group, a 2-chloroethyl group, a dichloroethyl group, a 2,2,2-trifluoroethyl group, a pentafluoroethyl group, a difluorocyclopropyl group and the like. R6a is preferably a methyl group, an ethyl group, an isopropyl group and a cyclopropyl group. R6b is preferably a methyl group.

"A C2 to C6 alkenyl group which may be substituted with a halogen atom", which R1, R2, R3, R4, R4a, R4b, R4c, R4d, R4e, R4f, R5, R6, R6a, R6b, R6c, R6d, R6e, R6f, R6g, R6h, R6i, R6j, R6k, R7, Ry and Rz represent, is an alkenyl group having 2 to 6 carbon atoms, which is chained, branched, cyclic or combination thereof, and the upper limit of the number of substituted halogen atoms is the number of hydrogen atoms which the alkenyl group has. When a branched or cyclic alkenyl group is included, it is obvious that the number of carbons is 3 or more. Specific examples thereof include an ethenyl group, a 1-propenyl group, a 2-propenyl group, a 2-fluoro-1-propenyl group, a 2-methyl-1-propenyl group and the like, and preferred examples thereof include an ethenyl group.

"A C2 to C6 alkynyl group which may be substituted with a halogen atom", which R1, R2, R3, R4, R4a, R4b, R4c, R4d, R4e, R4f, R5, R6, R6a, R6b, R6c, R6d, R6e, R6f, R6g, R6h, R6i, R6j, R6k, R7, Ry and Rz represent, is an alkynyl group having 2 to 6 carbon atoms, which is chained, branched, cyclic or combination thereof, and the upper limit of the number of substituted halogen atoms is the number of hydrogen atoms which the alkynyl group has. When a branched or cyclic alkynyl group is included, it is obvious that the number of carbons is 3 or more. Specific examples thereof include a 1-propynyl group, a 2-propynyl group, a 1-butynyl group, a 2-butynyl group, a 1-pentynyl group, a 2-pentynyl group, a 3-pentynyl group and the like, and preferred examples thereof include a 1-propynyl group, a 2-propynyl group and a 2-butynyl group.

The (C6 to C10) aryl of "a substituted or unsubstituted (C6 to C10) aryl group, a substituted or unsubstituted (C6 to C10) aryl (C1 to C6) alkyl group, a substituted or unsubstituted (C6 to C10) aryl (C2 to C6) alkenyl group and a substituted or unsubstituted (C6 to C10) aryl (C2 to C6) alkynyl group", which R3, R4, R4a, R4b, R4c, R5, R6, R6a, R6b, R6c, R7, Ry and Rz represent, specifically represents a phenyl group and a naphthyl group, and the (C1 to C6) alkyl group, the (C2 to C6) alkenyl group and the (C2 to C6) alkynyl group may have a straight chain, branch or ring. Examples of the substituent which may be substituted with an aryl group include a halogen atom, a C1 to C4 alkyl group which may be substituted with halogen, a C1 to C4 alkyloxy group which may be substituted with halogen, a C3 to C6 cyclic alkyl group, a methylsulfonyl group, a methoxy group, a nitro group, a cyano group and the like. Specific examples thereof include a phenyl group, a benzyl group, a 2-phenylethyl group, a 2-phenylethenyl group, a 2-phenylethynyl group, a 4-methylphenyl group, a 2-cyanophenyl group, a 3-chlorophenyl group, a 4-methoxyphenyl group, a 3-cyanophenyl group, 1,1-diphenylmethyl group, a naphthylethyl group, a naphthylpropyl group and the like, and preferred examples thereof include a benzyl group and a 2-phenylethyl group, a naphthylethyl group, a naphthylpropyl group.

The (C1 to C6) alkyl group, (C2 to C6) alkenyl group and (C2 to C6) alkenyl group of "a substituted or unsubstituted phenoxy (C1 to C6) alkyl group, a substituted or unsubstituted phenoxy (C2 to C6) alkenyl group and a substituted or unsubstituted phenoxy (C2 to C6) alkynyl group", which R3, R4, R4a, R4b, R4c, R5, R6, R6a, R6b, R6c, R7, Ry and Rz represent, may have a straight chain, branch or ring. Examples of the substituent which may be substituted with a phenoxy group include a halogen atom, a C1 to C4 alkyl group which may be substituted with halogen, a C1 to C4 alkyloxy group which may be substituted with halogen, a C3 to C6 cyclic alkyl group, a methylsulfonyl group, a methoxy group, a nitro group, a cyano group and the like. Specific examples thereof include a phenoxy group, a phenoxymethyl group, a 2-phenoxyethyl group, a 2-phenoxyethenyl group, a 2-phenoxyethynyl group, a 4-chlorophenoxy group, a 2-methylphenoxy group and the like, and preferred examples thereof include a 2-phenoxyethyl group.

The 5- to 10-membered heterocycle of "a substituted or unsubstituted 5- to 10-membered heterocycle, a substituted or unsubstituted 5- to 10-membered heterocycle (C1 to C6) alkyl group, a substituted or unsubstituted 5- to 10-membered heterocycle (C2 to C6) alkenyl group and a substituted or unsubstituted 5- to 10-membered heterocycle (C2 to C6) alkynyl group", which R3, R4, R4a, R4b, R4c, R5, R6, R6a, R6b, R6c, R7, Ry and Rz represent, represents a ring including a hetero atom, such as an oxygen atom, a sulfur atom or a nitrogen atom as an atom constituting 1 to 4 rings, and examples thereof include a furanyl group, a thienyl group, a pyridyl group, a pyrrolidinyl group, a piperidinyl group, a piperazinyl group, a pyrimidinyl group, a morpholinyl group, a thiazolyl group, an imidazolyl group, a triazolyl group, a tetrahydrofuranyl group, a quinolinyl group and the like. Examples of the substituent which may be substituted with a heterocycle include a halogen atom, a C1 to C4 alkyl group which may be substituted with halogen, a C1 to C4 alkyloxy group which may be substituted with halogen, a C3 to C6 cyclic alkyl group, a methylsulfonyl group, a methoxy group, a nitro group, a cyano group and the like. The (C1 to C6) alkyl group, (C2 to C6) alkenyl group and (C2 to C6) alkenyl group may have a straight chain, branch or ring. Specific examples thereof include a 2-pyridyl group, a 3-pyridyl group, a 4-pyridyl group, a 2-pyridylmethyl group, a 3-pyridylmethyl group, a 4-pyridylmethyl group, a 2-(4-pyridyl)ethenyl group, a 2-(4-pyridyl)ethynyl group, a 2-furanylmethyl group, a 2-thienylmethyl group, a 2-tetrahydrofuranylmethyl group and the like, and preferred examples thereof include a 2-pyridylmethyl group, a 3-pyridylmethyl group, a 4-pyridylmethyl group, a 2-furanylmethyl group, a 2-thienylmethyl group and a 2-tetrahydrofuranylmethyl group.

The (C1 to C4) alkoxy of "a (C1 to C4) alkoxy (C1 to C5) alkyl group, a (C1 to C4) alkoxy (C2 to C5) alkenyl group and a (C1 to C4) alkoxy (C2 to C5) alkynyl group", which R3, R4, R4a, R4b, R4c, R5, R6, R6a, R6b, R6c, R6e, R6f, R7 and Rz represent, represents a (C1 to C4) alkyloxy, alkenyloxy and alkynyloxy having a straight chain, branch or ring. Specific examples thereof include a methoxymethyl group, a 2-methoxyethyl group, an ethoxymethyl group, a 2-ethoxyethyl group, a 3-methoxy-2-propenyl group, a 3-methoxy-2-propynyl group and the like. R4 is preferably a 2-methoxyethyl group.

The (C1 to C4) alkylthio of "a (C1 to C4) alkylthio (C1 to C5) alkyl group, a (C1 to C4) alkylthio (C2 to C5) alkenyl group and a (C1 to C4) alkylthio (C2 to C5) alkynyl group", which R3, R4, R4a, R4b, R4c, R5, R6, R6a, R6b, R6c, R6e, R6f, R7 and Rz represent, represents a (C1 to C4) alkylthio, alkenylthio and alkynylthio having a straight chain, branch or ring. Examples thereof include a methylthiomethyl group, a 2-methylthioethyl group, an ethylthiomethyl group, a 2-ethylthioethyl group, a 3-methylthio-2-propenyl group, a 3-methylthio-2-propynyl group and the like. R4 is preferably a 2-methylthioethyl group.

The (C6 to C10) aryl of "a substituted or unsubstituted (C6 to C10) aryl group", which R2, R4d, R4e, R4f, R6d, R6e, R6f, R6g, R6h, R6i, R6j and R6k represent, specifically represents a phenyl group and a naphthyl group, and the (C1 to C6) alkyl group, (C2 to C6) alkenyl group and (C2 to C6) alkenyl group may have a straight chain, branch or ring. Examples of the substituent which may be substituted with an aryl group include a halogen atom, a C1 to C4 alkyl group which may be substituted with halogen, a C1 to C4 alkyloxy group which may be substituted with halogen, a C3 to C6 cyclic alkyl group, a methylsulfonyl group, a methoxy group, a nitro group, a cyano group and the like. Specific examples thereof include a phenyl group, a 2-methylphenyl group, a 3-methoxyphenyl group, a 4-nitrophenyl group, a 4-cyanophenyl group and the like.

The 5- to 10-membered heterocycle of "a substituted or unsubstituted 5- to 10-membered heterocycle", which R2, R4d, R4e, R4f, R6d, R6e, R6f, R6g and R6h represent, represents a ring including a hetero atom, such as an oxygen atom, a sulfur atom or a nitrogen atom as an atom constituting 1 to 4 rings, and examples thereof include a furanyl group, a thienyl group, a pyridyl group, a pyrrolidinyl group, a piperidinyl group, a piperazinyl group, a pyrimidinyl group, a morpholinyl group, a thiazolyl group, an imidazolyl group, a triazolyl group, a tetrahydrofuranyl group, a quinolinyl group and the like. Examples of the substituent which may be substituted with a heterocycle include a halogen atom, a C1 to C4 alkyl group which may be substituted with halogen, a C1 to C4 alkyloxy group which may be substituted with halogen, a C3 to C6 cyclic alkyl group, a methylsulfonyl group, a methoxy group, a nitro group, a cyano group and the like. Specific examples thereof include a 2-pyridyl group, a 3-pyridyl group, a 4-pyridyl group, a 2-furanyl group, a 2-thienyl group, a 2-tetrahydrofuranyl group and the like.

As a preferred aspect of a compound represented by Formula (I),

R represents the following Formula (a),

Ar represents a 6-chloro-3-pyridyl group, a 2-chloro-5-thiazolyl group, a 6-chloro-5-fluoro-3-pyridyl group, a 6-fluoro-3-pyridyl group, a 6-bromo-3-pyridyl group, a 2-chloro-5-pyrimidinyl group, a 6-trifluoromethyl-3-pyridyl group and a 2-chloro-5-pyrimidinyl group, A represents a ring represented by A-1, A-13, A-14, A-15, A-16, A-23 and A-38, Y represents a hydrogen atom and a 3-cyano group, and R1 represents a trifluoromethyl group, a difluoromethyl group, a chlorodifluoromethyl group, a pentafluoroethyl group, a trifluoroethyl group, an ethenyl group and a 2-propynyl group.

As another preferred aspect of a compound represented by Formula (I),

R represents the following Formula (c),

Ar represents a 6-chloro-3-pyridyl group, a 2-chloro-5-thiazolyl group, a 6-chloro-5-fluoro-3-pyridyl group, a 6-fluoro-3-pyridyl group, a 6-bromo-3-pyridyl group, a 2-chloro-5-pyrimidyl group and a 6-trifluoromethyl-3-pyridyl group, A represents a ring represented by A-1, Y represents a hydrogen atom, and R3 represents a trifluoromethyl group, a difluoromethyl group, a chlorodifluoromethyl group and a pentafluoroethyl group.

As still another preferred aspect of a compound represented by Formula (I),

R represents the following Formula (d),

Ar represents a 6-chloro-3-pyridyl group, a 6-chloro-5-fluoro-3-pyridyl group, a 6-fluoro-3-pyridyl group, a 6-bromo-3-pyridyl group and a 2-chloro-5-pyrimidyl group, A represents a ring represented by A-1, Y represents a hydrogen atom, R4 represents a hydrogen atom, a methyl group, an ethyl group, an n-propyl group, an isopropyl group, a cyclopropyl group, a cyclobutyl group, a cyclohexyl group, and cyclopentyl group, and R5 represents a trifluoromethyl group, a difluoromethyl group, a chlorodifluoromethyl group and a pentafluoroethyl group.

As yet another preferred aspect of a compound represented by Formula (I),

R represents the following Formula (e) group

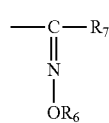

(e)

Ar represents a 6-chloro-3-pyridyl group, a 6-chloro-5-fluoro-3-pyridyl group, a 6-fluoro-3-pyridyl group, a 6-bromo-3-pyridyl group and a 2-chloro-5-pyrimidyl group, A represents a ring represented by A-1, Y represents a hydrogen atom, and R6 represents a hydrogen atom, a methyl group, an ethyl group, a 2-propenyl group, a methylcarbonyl group, an ethylcarbonyl group, a cyclopropylcarbonyl group, an ethenylcarbonyl group, a 2-propynylcarbonyl group, a benzoyl group, a 3-pyridylcarbonyl group, a methyloxycarbonyl group and a phenyloxycarbonyl group, and R7 represents a trifluoromethyl group, a difluoromethyl group, a chlorodifluoromethyl group and a pentafluoroethyl group.

Specific examples of the compound of Formula (I) include a compound represented by a combination of the following Table A and Table B.

TABLE 1

Table A

| Compound No. | Ar | A | Y | R |
|---|---|---|---|---|
| Table 1 1-5~1-710 | 6-Chloro-3-pyridyl | A-1 | H | represents a combination of substituents corresponding to each row of Nos. (1 and 6) below of Table B |
| Table 2 2-1~2-710 | 2-Chloro-5-thiazolyl | A-1 | H | represents a combination of substituents corresponding to each row of Table B |
| Table 3 3-2~3-710 | 6-Fluoro-3-pyridyl | A-1 | H | represents a combination of substituents corresponding to each row of Nos. (1 and 3) below of Table B |
| Table 4 4-2~4-710 | 6-Bromo-3-pyridyl | A-1 | H | represents a combination of substituents corresponding to each row of Nos. (1 and 3) below of Table B |
| Table 5 5-2~5-710 | 6-Chloro-5-fluoro-3-pyridyl | A-1 | H | represents a combination of substituents corresponding to each row of Nos. (1 and 3) below of Table B |

TABLE 1-continued

Table A

| Compound No. | Ar | A | Y | R |
|---|---|---|---|---|
| Table 6 6-2~6-710 | 2-Chloro-5-pyrimidinyl | A-1 | H | represents a combination of substituents corresponding to each row of Nos. (1 and 3) below of Table B |
| Table 7 7-1~7-710 | 5-Chloropyrazin-2-yl | A-1 | H | represents a combination of substituents corresponding to each row of Table B |
| Table 8 8-1~8-710 | 6-Chloropyridazin-3-yl | A-1 | H | represents a combination of substituents corresponding to each row of Table B |
| Table 9 9-1~9-710 | 2-Chloro-5-oxazolyl | A-1 | H | represents a combination of substituents corresponding to each row of Table B |
| Table 10 10-1~10-710 | 6-trifluoromethyl-3-pyridyl | A-1 | H | represents a combination of substituents corresponding to each row of Table B |
| Table 11 11-1~11-710 | 3-tetrahydrofuranyl | A-1 | H | represents a combination of substituents corresponding to each row of Table B |
| Table 12 12-1~12-710 | 2-Chloro-4-pyridyl | A-1 | H | represents a combination of substituents corresponding to each row of Table B |
| Table 13 13-1~13-710 | 3-Cyanophenyl | A-1 | H | represents a combination of substituents corresponding to each row of Table B |
| Table 14 14-1~14-710 | 6-Chloro-3-pyridyl | A-1 | 3-F | represents a combination of substituents corresponding to each row of Table B |
| Table 15 15-1~15-710 | 2-Chloro-5-thiazolyl | A-1 | 3-F | represents a combination of substituents corresponding to each row of Table B |
| Table 16 16-1~16-710 | 6-Fluoro-3-pyridyl | A-1 | 3-F | represents a combination of substituents corresponding to each row of Table B |
| Table 17 17-1~17-710 | 6-Bromo-3-pyridyl | A-1 | 3-F | represents a combination of substituents corresponding to each row of Table B |

TABLE 1-continued

Table A

| Compound No. | Ar | A | Y | R |
|---|---|---|---|---|
| Table 18-1~18-710 | 6-Chloro-5-fluoro-3-pyridyl | A-1 | 3-F | represents a combination of substituents corresponding to each row of Table B |
| Table 19-1~19-710 | 2-Chloro-5-pyrimidinyl | A-1 | 3-F | represents a combination of substituents corresponding to each row of Table B |
| Table 20-1~20-710 | 5-Chloropyrazin-2-yl | A-1 | 3-F | represents a combination of substituents corresponding to each row of Table B |
| Table 21-1~21-710 | 6-Chloropyridazin-3-yl | A-1 | 3-F | represents a combination of substituents corresponding to each row of Table B |
| Table 22-1~22-710 | 2-Chloro-5-oxazolyl | A-1 | 3-F | represents a combination of substituents corresponding to each row of Table B |
| Table 23-1~23-710 | 6-trifluoromethyl-3-pyridyl | A-1 | 3-F | represents a combination of substituents corresponding to each row of Table B |
| Table 24-1~24-710 | 3-tetrahydrofuranyl | A-1 | 3-F | represents a combination of substituents corresponding to each row of Table B |
| Table 25-1~25-710 | 6-Chloro-3-pyridyl | A-1 | 4-F | represents a combination of substituents corresponding to each row of Table B |
| Table 26-1~26-710 | 2-Chloro-5-thiazolyl | A-1 | 4-F | represents a combination of substituents corresponding to each row of Table B |
| Table 27-1~27-710 | 6-Fluoro-3-pyridyl | A-1 | 4-F | represents a combination of substituents corresponding to each row of Table B |
| Table 28-1~28-710 | 6-Bromo-3-pyridyl | A-1 | 4-F | represents a combination of substituents corresponding to each row of Table B |
| Table 29-1~29-710 | 6-Chloro-5-fluoro-3-pyridyl | A-1 | 4-F | represents a combination of substituents corresponding to each row of Table B |
| Table 30-1~30-710 | 2-Chloro-5-pyrimidinyl | A-1 | 4-F | represents a combination of substituents corresponding to each row of Table B |
| Table 31-1~31-710 | 5-Chloropyrazin-2-yl | A-1 | 4-F | represents a combination of substituents corresponding to each row of Table B |
| Table 32-1~32-710 | 6-Chloropyridazin-3-yl | A-1 | 4-F | represents a combination of substituents corresponding to each row of Table B |

TABLE 2

Table A

| Compound No. | Ar | A | Y | R |
|---|---|---|---|---|
| Table 33-1~33-710 | 2-Chloro-5-oxazolyl | A-1 | 4-F | represents a combination of substituents corresponding to each row of Table B |
| Table 34-1~34-710 | 6-trifluoromethyl-3-pyridyl | A-1 | 4-F | represents a combination of substituents corresponding to each row of Table B |
| Table 35-1~35-710 | 3-tetrahydrofuranyl | A-1 | 4-F | represents a combination of substituents corresponding to each row of Table B |
| Table 36-1~36-710 | 6-Chloro-3-pyridyl | A-1 | 5-F | represents a combination of substituents corresponding to each row of Table B |
| Table 37-1~37-710 | 2-Chloro-5-thiazolyl | A-1 | 5-F | represents a combination of substituents corresponding to each row of Table B |
| Table 38-1~38-710 | 6-Fluoro-3-pyridyl | A-1 | 5-F | represents a combination of substituents corresponding to each row of Table B |
| Table 39-1~39-710 | 6-Bromo-3-pyridyl | A-1 | 5-F | represents a combination of substituents corresponding to each row of Table B |

TABLE 2-continued

Table A

| Compound No. | | Ar | A | Y | R |
|---|---|---|---|---|---|
| Table 40 | 40-1~40-710 | 6-Chloro-5-fluoro-3-pyridyl | A-1 | 5-F | represents a combination of substituents corresponding to each row of Table B |
| Table 41 | 41-1~41-710 | 2-Chloro-5-pyrimidinyl | A-1 | 5-F | represents a combination of substituents corresponding to each row of Table B |
| Table 42 | 42-1~42-710 | 5-Chloropyrazin-2-yl | A-1 | 5-F | represents a combination of substituents corresponding to each row of Table B |
| Table 43 | 43-1~43-710 | 6-Chloropyridazin-3-yl | A-1 | 5-F | represents a combination of substituents corresponding to each row of Table B |
| Table 44 | 44-1~44-710 | 2-Chloro-5-oxazolyl | A-1 | 5-F | represents a combination of substituents corresponding to each row of Table B |
| Table 45 | 45-1~45-710 | 6-trifluoromethyl-3-pyridyl | A-1 | 5-F | represents a combination of substituents corresponding to each row of Table B |
| Table 46 | 46-1~46-710 | 3-tetrahydrofuranyl | A-1 | 5-F | represents a combination of substituents corresponding to each row of Table B |
| Table 47 | 47-1~47-710 | 6-Chloro-3-pyridyl | A-1 | 6-F | represents a combination of substituents corresponding to each row of Table B |
| Table 48 | 48-1~48-710 | 2-Chloro-5-thiazolyl | A-1 | 6-F | represents a combination of substituents corresponding to each row of Table B |
| Table 49 | 49-1~49-710 | 6-Fluoro-3-pyridyl | A-1 | 6-F | represents a combination of substituents corresponding to each row of Table B |
| Table 50 | 50-1~50-710 | 6-Bromo-3-pyridyl | A-1 | 6-F | represents a combination of substituents corresponding to each row of Table B |
| Table 51 | 51-1~51-710 | 6-Chloro-5-fluoro-3-pyridyl | A-1 | 6-F | represents a combination of substituents corresponding to each row of Table B |
| Table 52 | 52-1~52-710 | 2-Chloro-5-pyrimidinyl | A-1 | 6-F | represents a combination of substituents corresponding to each row of Table B |
| Table 53 | 53-1~53-710 | 5-Chloropyrazin-2-yl | A-1 | 6-F | represents a combination of substituents corresponding to each row of Table B |
| Table 54 | 54-1~54-710 | 6-Chloropyridazin-3-yl | A-1 | 6-F | represents a combination of substituents corresponding to each row of Table B |
| Table 55 | 55-1~55-710 | 2-Chloro-5-oxazolyl | A-1 | 6-F | represents a combination of substituents corresponding to each row of Table B |
| Table 56 | 56-1~56-710 | 6-trifluoromethyl-3-pyridyl | A-1 | 6-F | represents a combination of substituents corresponding to each row of Table B |
| Table 57 | 57-1~57-710 | 3-tetrahydrofuranyl | A-1 | 6-F | represents a combination of substituents corresponding to each row of Table B |
| Table 58 | 58-1~58-710 | 6-Chloro-3-pyridyl | A-1 | 3-Cl | represents a combination of substituents corresponding to each row of Table B |
| Table 59 | 59-1~59-710 | 2-Chloro-5-thiazolyl | A-1 | 3-Cl | represents a combination of substituents corresponding to each row of Table B |
| Table 60 | 60-1~60-710 | 6-Fluoro-3-pyridyl | A-1 | 3-Cl | represents a combination of substituents corresponding to each row of Table B |
| Table 61 | 61-1~61-710 | 6-Bromo-3-pyridyl | A-1 | 3-Cl | represents a combination of substituents corresponding to each row of Table B |
| Table 62 | 62-1~62-710 | 6-Chloro-5-fluoro-3-pyridyl | A-1 | 3-Cl | represents a combination of substituents corresponding to each row of Table B |
| Table 63 | 63-1~63-642 | 2-Chloro-5-pyrimidinyl | A-1 | 3-Cl | represents a combination of substituents corresponding to each row of Table B |

TABLE 2-continued

Table A

| Compound No. | Ar | A | Y | R |
|---|---|---|---|---|
| Table 64 | 64-1~64-710 | 5-Chloropyrazin-2-yl | A-1 | 3-Cl | represents a combination of substituents corresponding to each row of Table B |

TABLE 3

Table A

| Compound No. | Ar | A | Y | R |
|---|---|---|---|---|
| Table 65 | 65-1~65-710 | 6-Chloropyridazin-3-yl | A-1 | 3-Cl | represents a combination of substituents corresponding to each row of Table B |
| Table 66 | 66-1~66-710 | 2-Chloro-5-oxazolyl | A-1 | 3-Cl | represents a combination of substituents corresponding to each row of Table B |
| Table 67 | 67-1~67-710 | 6-trifluoromethyl-3-pyridyl | A-1 | 3-Cl | represents a combination of substituents corresponding to each row of Table B |
| Table 68 | 68-1~68-710 | 3-tetrahydrofuranyl | A-1 | 3-Cl | represents a combination of substituents corresponding to each row of Table B |
| Table 69 | 69-1~69-710 | 6-Chloro-3-pyridyl | A-1 | 4-Cl | represents a combination of substituents corresponding to each row of Table B |
| Table 70 | 70-1~70-710 | 2-Chloro-5-thiazolyl | A-1 | 4-Cl | represents a combination of substituents corresponding to each row of Table B |
| Table 71 | 71-1~71-710 | 6-Fluoro-3-pyridyl | A-1 | 4-Cl | represents a combination of substituents corresponding to each row of Table B |
| Table 72 | 72-1~72-710 | 6-Bromo-3-pyridyl | A-1 | 4-Cl | represents a combination of substituents corresponding to each row of Table B |
| Table 73 | 73-1~73-710 | 6-Chloro-5-fluoro-3-pyridyl | A-1 | 4-Cl | represents a combination of substituents corresponding to each row of Table B |

TABLE 3-continued

Table A

| Compound No. | Ar | A | Y | R |
|---|---|---|---|---|
| Table 74 | 74-1~74-710 | 2-Chloro-5-pyrimidinyl | A-1 | 4-Cl | represents a combination of substituents corresponding to each row of Table B |
| Table 75 | 75-1~75-710 | 5-Chloropyrazin-2-yl | A-1 | 4-Cl | represents a combination of substituents corresponding to each row of Table B |
| Table 76 | 76-1~76-710 | 6-Chloropyridazin-3-yl | A-1 | 4-Cl | represents a combination of substituents corresponding to each row of Table B |
| Table 77 | 77-1~77-710 | 2-Chloro-5-oxazolyl | A-1 | 4-Cl | represents a combination of substituents corresponding to each row of Table B |
| Table 78 | 78-1~78-710 | 6-trifluoromethyl-3-pyridyl | A-1 | 4-Cl | represents a combination of substituents corresponding to each row of Table B |
| Table 79 | 79-1~79-710 | 3-tetrahydrofuranyl | A-1 | 4-Cl | represents a combination of substituents corresponding to each row of Table B |
| Table 80 | 80-1~80-710 | 6-Chloro-3-pyridyl | A-1 | 5-Cl | represents a combination of substituents corresponding to each row of Table B |
| Table 81 | 81-1~81-710 | 2-Chloro-5-thiazolyl | A-1 | 5-Cl | represents a combination of substituents corresponding to each row of Table B |
| Table 82 | 82-1~82-710 | 6-Fluoro-3-pyridyl | A-1 | 5-Cl | represents a combination of substituents corresponding to each row of Table B |
| Table 83 | 83-1~83-710 | 6-Bromo-3-pyridyl | A-1 | 5-Cl | represents a combination of substituents corresponding to each row of Table B |
| Table 84 | 84-1~84-710 | 6-Chloro-5-fluoro-3-pyridyl | A-1 | 5-Cl | represents a combination of substituents corresponding to each row of Table B |
| Table 85 | 85-1~85-710 | 2-Chloro-5-pyrimidinyl | A-1 | 5-Cl | represents a combination of substituents corresponding to each row of Table B |

TABLE 3-continued

Table A

| Compound No. | Ar | A | Y | R |
|---|---|---|---|---|
| Table 86 | 86-1~86-710 | 5-Chloropyrazin-2-yl | A-1 | 5-Cl | represents a combination of substituents corresponding to each row of Table B |
| Table 87 | 87-1~87-710 | 6-Chloropyridazin-3-yl | A-1 | 5-Cl | represents a combination of substituents corresponding to each row of Table B |
| Table 88 | 88-1~88-710 | 2-Chloro-5-oxazolyl | A-1 | 5-Cl | represents a combination of substituents corresponding to each row of Table B |
| Table 89 | 89-1~89-710 | 6-trifluoromethyl-3-pyridyl | A-1 | 5-Cl | represents a combination of substituents corresponding to each row of Table B |
| Table 90 | 90-1~90-710 | 3-tetrahydrofuranyl | A-1 | 5-Cl | represents a combination of substituents corresponding to each row of Table B |
| Table 91 | 91-1~91-710 | 6-Chloro-3-pyridyl | A-1 | 6-Cl | represents a combination of substituents corresponding to each row of Table B |
| Table 92 | 92-1~92-710 | 2-Chloro-5-thiazolyl | A-1 | 6-Cl | represents a combination of substituents corresponding to each row of Table B |
| Table 93 | 93-1~93-710 | 6-Fluoro-3-pyridyl | A-1 | 6-Cl | represents a combination of substituents corresponding to each row of Table B |
| Table 94 | 94-1~94-710 | 6-Bromo-3-pyridyl | A-1 | 6-Cl | represents a combination of substituents corresponding to each row of Table B |
| Table 95 | 95-1~95-710 | 6-Chloro-5-fluoro-3-pyridyl | A-1 | 6-Cl | represents a combination of substituents corresponding to each row of Table B |
| Table 96 | 96-1~96-710 | 2-Chloro-5-pyrimidinyl | A-1 | 6-Cl | represents a combination of substituents corresponding to each row of Table B |

TABLE 4

Table A

| Compound No. | Ar | A | Y | R |
|---|---|---|---|---|
| Table 97 | 97-1~97-710 | 5-Chloropyrazin-2-yl | A-1 | 6-Cl | represents a combination of substituents corresponding to each row of Table B |
| Table 98 | 98-1~98-710 | 6-Chloropyridazin-3-yl | A-1 | 6-Cl | represents a combination of substituents corresponding to each row of Table B |
| Table 99 | 99-1~99-710 | 2-Chloro-5-oxazolyl | A-1 | 6-Cl | represents a combination of substituents corresponding to each row of Table B |
| Table 100 | 100-1~100-710 | 6-trifluoromethyl-3-pyridyl | A-1 | 6-Cl | represents a combination of substituents corresponding to each row of Table B |
| Table 101 | 101-1~101-710 | 3-tetrahydrofuranyl | A-1 | 6-Cl | represents a combination of substituents corresponding to each row of Table B |
| Table 102 | 102-1~102-710 | 6-Chloro-3-pyridyl | A-1 | 3-CN | represents a combination of substituents corresponding to each row of Table B |
| Table 103 | 103-1~103-710 | 2-Chloro-5-thiazolyl | A-1 | 3-CN | represents a combination of substituents corresponding to each row of Table B |
| Table 104 | 104-1~104-710 | 6-Fluoro-3-pyridyl | A-1 | 3-CN | represents a combination of substituents corresponding to each row of Table B |
| Table 105 | 105-1~105-710 | 6-Bromo-3-pyridyl | A-1 | 3-CN | represents a combination of substituents corresponding to each row of Table B |
| Table 106 | 106-1~106-710 | 6-Chloro-5-fluoro-3-pyridyl | A-1 | 3-CN | represents a combination of substituents corresponding to each row of Table B |
| Table 107 | 107-1~107-710 | 2-Chloro-5-pyrimidinyl | A-1 | 3-CN | represents a combination of substituents corresponding to each row of Table B |
| Table 108 | 108-1~108-710 | 5-Chloropyrazin-2-yl | A-1 | 3-CN | represents a combination of substituents corresponding to each row of Table B |

TABLE 4-continued

Table A

| Compound No. | | Ar | A | Y | R |
|---|---|---|---|---|---|
| Table 109 | 109-1~109-710 | 6-Chloropyridazin-3-yl | A-1 | 3-CN | represents a combination of substituents corresponding to each row of Table B |
| Table 110 | 110-1~110-710 | 2-Chloro-5-oxazolyl | A-1 | 3-CN | represents a combination of substituents corresponding to each row of Table B |
| Table 111 | 111-1~111-710 | 6-trifluoromethyl-3-pyridyl | A-1 | 3-CN | represents a combination of substituents corresponding to each row of Table B |
| Table 112 | 112-1~112-710 | 3-tetrahydrofuranyl | A-1 | 3-CN | represents a combination of substituents corresponding to each row of Table B |
| Table 113 | 113-1~113-710 | 6-Chloro-3-pyridyl | A-1 | 4-CN | represents a combination of substituents corresponding to each row of Table B |
| Table 114 | 114-1~114-710 | 2-Chloro-5-thiazolyl | A-1 | 4-CN | represents a combination of substituents corresponding to each row of Table B |
| Table 115 | 115-1~115-710 | 6-Fluoro-3-pyridyl | A-1 | 4-CN | represents a combination of substituents corresponding to each row of Table B |
| Table 116 | 116-1~116-710 | 6-Bromo-3-pyridyl | A-1 | 4-CN | represents a combination of substituents corresponding to each row of Table B |
| Table 117 | 117-1~117-710 | 6-Chloro-5-Fluoro-3-pyridyl | A-1 | 4-CN | represents a combination of substituents corresponding to each row of Table B |
| Table 118 | 118-1~118-710 | 2-Chloro-5-pyrimidinyl | A-1 | 4-CN | represents a combination of substituents corresponding to each row of Table B |
| Table 119 | 119-1~119-710 | 5-Chloropyrazin-2-yl | A-1 | 4-CN | represents a combination of substituents corresponding to each row of Table B |
| Table 120 | 120-1~120-710 | 6-Chloropyridazin-3-yl | A-1 | 4-CN | represents a combination of substituents corresponding to each row of Table B |
| Table 121 | 121-1~121-710 | 2-Chloro-5-oxazolyl | A-1 | 4-CN | represents a combination of substituents corresponding to each row of Table B |
| Table 122 | 122-1~122-710 | 6-trifluoromethyl-3-pyridyl | A-1 | 4-CN | represents a combination of substituents corresponding to each row of Table B |
| Table 123 | 123-1~123-710 | 3-tetrahydrofuranyl | A-1 | 4-CN | represents a combination of substituents corresponding to each row of Table B |
| Table 124 | 124-1~124-710 | 6-Chloro-3-pyridyl | A-1 | 5-CN | represents a combination of substituents corresponding to each row of Table B |
| Table 125 | 125-1~155-710 | 2-Chloro-5-thiazolyl | A-1 | 5-CN | represents a combination of substituents corresponding to each row of Table B |
| Table 126 | 126-1~126-710 | 6-Fluoro-3-pyridyl | A-1 | 5-CN | represents a combination of substituents corresponding to each row of Table B |
| Table 127 | 127-1~127-710 | 6-Bromo-3-pyridyl | A-1 | 5-CN | represents a combination of substituents corresponding to each row of Table B |
| Table 128 | 128-1~128-710 | 6-Chloro-5-fluoro-3-pyridyl | A-1 | 5-CN | represents a combination of substituents corresponding to each row of Table B |

TABLE 5

Table A

| Compound No. | | Ar | A | Y | R |
|---|---|---|---|---|---|
| Table 129 | 129-1~129-710 | 2-Chloro-5-pyrimidinyl | A-1 | 5-CN | represents a combination of substituents corresponding to each row of Table B |
| Table 130 | 130-1~130-710 | 5-Chloro-pyrazin-2-yl | A-1 | 5-CN | represents a combination of substituents corresponding to each row of Table B |

TABLE 5-continued

Table A

| Compound No. | | Ar | A | Y | R |
|---|---|---|---|---|---|
| Table 131 | 131-1~131-710 | 6-Chloro-pyridazin-3-yl | A-1 | 5-CN | represents a combination of substituents corresponding to each row of Table B |
| Table 132 | 132-1~132-710 | 2-Chloro-5-oxazolyl | A-1 | 5-CN | represents a combination of substituents corresponding to each row of Table B |
| Table 133 | 133-1~133-710 | 6-tri-fluoromethyl-3-pyridyl | A-1 | 5-CN | represents a combination of substituents corresponding to each row of Table B |
| Table 134 | 134-1~134-710 | 3-tetra-hydrofuranyl | A-1 | 5-CN | represents a combination of substituents corresponding to each row of Table B |
| Table 135 | 135-1~135-710 | 6-Chloro-3-pyridyl | A-1 | 6-CN | represents a combination of substituents corresponding to each row of Table B |
| Table 136 | 136-1~136-710 | 2-Chloro-5-thiazolyl | A-1 | 6-CN | represents a combination of substituents corresponding to each row of Table B |
| Table 137 | 137-1~137-710 | 6-Fluoro-3-pyridyl | A-1 | 6-CN | represents a combination of substituents corresponding to each row of Table B |
| Table 138 | 138-1~138-710 | 6-Bromo-3-pyridyl | A-1 | 6-CN | represents a combination of substituents corresponding to each row of Table B |
| Table 139 | 139-1~139-710 | 6-Chloro-5-fluoro-3-pyridyl | A-1 | 6-CN | represents a combination of substituents corresponding to each row of Table B |
| Table 140 | 140-1~140-710 | 2-Chloro-5-pyrimidinyl | A-1 | 6-CN | represents a combination of substituents corresponding to each row of Table B |
| Table 141 | 141-1~141-710 | 5-Chloro-pyrazin-2-yl | A-1 | 6-CN | represents a combination of substituents corresponding to each row of Table B |
| Table 142 | 142-1~142-710 | 6-Chloro-pyridazin-3-yl | A-1 | 6-CN | represents a combination of substituents corresponding to each row of Table B |
| Table 143 | 143-1~143-710 | 2-Chloro-5-oxazolyl | A-1 | 6-CN | represents a combination of substituents corresponding to each row of Table B |
| Table 144 | 144-1~144-710 | 6-tri-fluoromethyl-3-pyridyl | A-1 | 6-CN | represents a combination of substituents corresponding to each row of Table B |
| Table 145 | 145-1~145-710 | 3-tetra-hydrofuranyl | A-1 | 6-CN | represents a combination of substituents corresponding to each row of Table B |
| Table 146 | 146-1~146-710 | 6-Chloro-3-pyridyl | A-1 | 3-OH | represents a combination of substituents corresponding to each row of Table B |
| Table 147 | 147-1~147-710 | 2-Chloro-5-thiazolyl | A-1 | 3-OH | represents a combination of substituents corresponding to each row of Table B |
| Table 148 | 148-1~148-710 | 6-Fluoro-3-pyridyl | A-1 | 3-OH | represents a combination of substituents corresponding to each row of Table B |
| Table 149 | 149-1~149-710 | 6-Bromo-3-pyridyl | A-1 | 3-OH | represents a combination of substituents corresponding to each row of Table B |
| Table 150 | 150-1~150-710 | 6-Chloro-5-Fluoro-3-pyridyl | A-1 | 3-OH | represents a combination of substituents corresponding to each row of Table B |
| Table 151 | 151-1~151-710 | 2-Chloro-5-pyrimidinyl | A-1 | 3-OH | represents a combination of substituents corresponding to each row of Table B |
| Table 152 | 152-1~152-710 | 5-Chloro-pyrazin-2-yl | A-1 | 3-OH | represents a combination of substituents corresponding to each row of Table B |
| Table 153 | 153-1~153-710 | 6-Chloro-pyridazin-3-yl | A-1 | 3-OH | represents a combination of substituents corresponding to each row of Table B |
| Table 154 | 154-1~154-710 | 2-Chloro-5-oxazolyl | A-1 | 3-OH | represents a combination of substituents corresponding to each row of Table B |

TABLE 5-continued

Table A

| | Compound No. | Ar | A | Y | R |
|---|---|---|---|---|---|
| Table 155 | 155-1~155-710 | 6-tri-fluoromethyl-3-pyridyl | A-1 | 3-OH | represents a combination of substituents corresponding to each row of Table B |
| Table 156 | 156-1~156-710 | 3-tetra-hydrofuranyl | A-1 | 3-OH | represents a combination of substituents corresponding to each row of Table B |
| Table 157 | 157-1~157-710 | 6-Chloro-3-pyridyl | A-1 | 4-OH | represents a combination of substituents corresponding to each row of Table B |
| Table 158 | 158-1~158-710 | 2-Chloro-5-thiazolyl | A-1 | 4-OH | represents a combination of substituents corresponding to each row of Table B |
| Table 159 | 159-1~159-710 | 6-Fluoro-3-pyridyl | A-1 | 4-OH | represents a combination of substituents corresponding to each row of Table B |
| Table 160 | 160-1~160-710 | 6-Bromo-3-pyridyl | A-1 | 4-OH | represents a combination of substituents corresponding to each row of Table B |

TABLE 6

Table A

| | Compound No. | Ar | A | Y | R |
|---|---|---|---|---|---|
| Table 161 | 161-1~161-710 | 6-Chloro-5-fluoro-3-pyridyl | A-1 | 4-OH | represents a combination of substituents corresponding to each row of Table B |
| Table 162 | 162-1~162-710 | 2-Chloro-5-pyrimidinyl | A-1 | 4-OH | represents a combination of substituents corresponding to each row of Table B |
| Table 163 | 163-1~163-710 | 5-Chloro-pyrazin-2-yl | A-1 | 4-OH | represents a combination of substituents corresponding to each row of Table B |
| Table 164 | 164-1~164-710 | 6-Chloro-pyridazin-3-yl | A-1 | 4-OH | represents a combination of substituents corresponding to each row of Table B |

TABLE 6-continued

Table A

| | Compound No. | Ar | A | Y | R |
|---|---|---|---|---|---|
| Table 165 | 165-1~165-710 | 2-Chloro-5-oxazolyl | A-1 | 4-OH | represents a combination of substituents corresponding to each row of Table B |
| Table 166 | 166-1~166-710 | 6-tri-fluoromethyl-3-pyridyl | A-1 | 4-OH | represents a combination of substituents corresponding to each row of Table B |
| Table 167 | 167-1~167-710 | 3-tetra-hydrofuranyl | A-1 | 4-OH | represents a combination of substituents corresponding to each row of Table B |
| Table 168 | 168-1~168-710 | 6-Chloro-3-pyridyl | A-1 | 5-OH | represents a combination of substituents corresponding to each row of Table B |
| Table 169 | 169-1~169-710 | 2-Chloro-5-thiazolyl | A-1 | 5-OH | represents a combination of substituents corresponding to each row of Table B |
| Table 170 | 170-1~170-710 | 6-Fluoro-3-pyridyl | A-1 | 5-OH | represents a combination of substituents corresponding to each row of Table B |
| Table 171 | 171-1~171-710 | 6-Bromo-3-pyridyl | A-1 | 5-OH | represents a combination of substituents corresponding to each row of Table B |
| Table 172 | 172-1~172-710 | 6-Chloro-5-fluoro-3-pyridyl | A-1 | 5-OH | represents a combination of substituents corresponding to each row of Table B |
| Table 173 | 173-1~173-710 | 2-Chloro-5-pyrimidinyl | A-1 | 5-OH | represents a combination of substituents corresponding to each row of Table B |
| Table 174 | 174-1~174-710 | 5-Chloro-pyrazin-2-yl | A-1 | 5-OH | represents a combination of substituents corresponding to each row of Table B |
| Table 175 | 175-1~175-710 | 6-Chloro-pyridazin-3-yl | A-1 | 5-OH | represents a combination of substituents corresponding to each row of Table B |
| Table 176 | 176-1~176-710 | 2-Chloro-5-oxazolyl | A-1 | 5-OH | represents a combination of substituents corresponding to each row of Table B |
| Table 177 | 177-1~77-710 | 6-tri-fluoromethyl-3-pyridyl | A-1 | 5-OH | represents a combination of substituents |

TABLE 6-continued

Table A

| Compound No. | Ar | A | Y | R |
|---|---|---|---|---|
| Table 178 | 178-1~178-710 | 3-tetrahydrofuranyl | A-1 | 5-OH | represents a combination of substituents corresponding to each row of Table B |
| Table 179 | 179-1~179-710 | 6-Chloro-3-pyridyl | A-1 | 6-OH | represents a combination of substituents corresponding to each row of Table B |
| Table 180 | 180-1~180-710 | 2-Chloro-5-thiazolyl | A-1 | 6-OH | represents a combination of substituents corresponding to each row of Table B |
| Table 181 | 181-1~181-710 | 6-Fluoro-3-pyridyl | A-1 | 6-OH | represents a combination of substituents corresponding to each row of Table B |
| Table 182 | 182-1~182-710 | 6-Bromo-3-pyridyl | A-1 | 6-OH | represents a combination of substituents corresponding to each row of Table B |
| Table 183 | 183-1~183-710 | 6-Chloro-5-fluoro-3-pyridyl | A-1 | 6-OH | represents a combination of substituents corresponding to each row of Table B |
| Table 184 | 184-1~184-710 | 2-Chloro-5-pyrimidinyl | A-1 | 6-OH | represents a combination of substituents corresponding to each row of Table B |
| Table 185 | 185-1~185-710 | 5-Chloro-pyrazin-2-yl | A-1 | 6-OH | represents a combination of substituents corresponding to each row of Table B |
| Table 186 | 186-1~186-710 | 6-Chloro-pyridazin-3-yl | A-1 | 6-OH | represents a combination of substituents corresponding to each row of Table B |
| Table 187 | 187-1~187-710 | 2-Chloro-5-oxazolyl | A-1 | 6-OH | represents a combination of substituents corresponding to each row of Table B |
| Table 188 | 188-1~188-710 | 6-trifluoromethyl-3-pyridyl | A-1 | 6-OH | represents a combination of substituents corresponding to each row of Table B |
| Table 189 | 189-1~189-710 | 3-tetrahydrofuranyl | A-1 | 6-OH | represents a combination of substituents corresponding to each row of Table B |
| Table 190 | 190-1~190-710 | 6-Chloro-3-pyridyl | A-13 | H | represents a combination of substituents corresponding to each row of Table B |
| Table 191 | 191-1~191-710 | 2-Chloro-5-thiazolyl | A-13 | H | represents a combination of substituents corresponding to each row of Table B |
| Table 192 | 192-1~192-710 | 6-Fluoro-3-pyridyl | A-13 | H | represents a combination of substituents corresponding to each row of Table B |

TABLE 7

Table A

| Compound No. | Ar | A | Y | R |
|---|---|---|---|---|
| Table 193 | 193-1~193-710 | 6-Bromo-3-pyridyl | A-13 | H | represents a combination of substituents corresponding to each row of Table B |
| Table 194 | 194-1~194-710 | 6-Chloro-5-fluoro-3-pyridyl | A-13 | H | represents a combination of substituents corresponding to each row of Table B |
| Table 195 | 195-1~195-710 | 2-Chloro-5-pyrimidinyl | A-13 | H | represents a combination of substituents corresponding to each row of Table B |
| Table 196 | 196-1~196-710 | 5-Chloro-pyrazin-2-yl | A-13 | H | represents a combination of substituents corresponding to each row of Table B |
| Table 197 | 197-1~197-710 | 6-Chloro-pyridazin-3-yl | A-13 | H | represents a combination of substituents corresponding to each row of Table B |
| Table 198 | 198-1~198-710 | 2-Chloro-5-oxazolyl | A-13 | H | represents a combination of substituents corresponding to each row of Table B |
| Table 199 | 199-1~199-710 | 6-trifluoromethyl-3-pyridyl | A-13 | H | represents a combination of substituents corresponding to each row of Table B |
| Table 200 | 200-1~200-710 | 3-tetrahydrofuranyl | A-13 | H | represents a combination of substituents corresponding to |

TABLE 7-continued

Table A

| Compound No. | Ar | A | Y | R |
|---|---|---|---|---|
| Table 201 | 201-1~201-710 | 6-Chloro-3-pyridyl | A-14 | H | represents a combination of substituents corresponding to each row of Table B |
| Table 202 | 202-1~202-710 | 2-Chloro-5-thiazolyl | A-14 | H | represents a combination of substituents corresponding to each row of Table B |
| Table 203 | 203-1~203-710 | 6-Fluoro-3-pyridyl | A-14 | H | represents a combination of substituents corresponding to each row of Table B |
| Table 204 | 204-1~204-710 | 6-Bromo-3-pyridyl | A-14 | H | represents a combination of substituents corresponding to each row of Table B |
| Table 205 | 205-1~205-710 | 6-Chloro-5-fluoro-3-pyridyl | A-14 | H | represents a combination of substituents corresponding to each row of Table B |
| Table 206 | 206-1~206-710 | 2-Chloro-5-pyrimidinyl | A-14 | H | represents a combination of substituents corresponding to each row of Table B |
| Table 207 | 207-1~207-710 | 5-Chloro-pyrazin-2-yl | A-14 | H | represents a combination of substituents corresponding to each row of Table B |
| Table 208 | 208-1~208-710 | 6-Chloro-pyridazin-3-yl | A-14 | H | represents a combination of substituents corresponding to each row of Table B |
| Table 209 | 209-1~209-710 | 2-Chloro-5-oxazolyl | A-14 | H | represents a combination of substituents corresponding to each row of Table B |
| Table 210 | 210-1~210-710 | 6-trifluoromethyl-3-pyridyl | A-14 | H | represents a combination of substituents corresponding to each row of Table B |
| Table 211 | 211-1~211-710 | 3-tetrahydrofuranyl | A-14 | H | represents a combination of substituents corresponding to each row of Table B |
| Table 212 | 212-1~212-710 | 6-Chloro-3-pyridyl | A-15 | H | represents a combination of substituents corresponding to each row of Table B |
| Table 213 | 213-1~213-710 | 2-Chloro-5-thiazolyl | A-15 | H | represents a combination of substituents corresponding to each row of Table B |
| Table 214 | 214-1~214-710 | 6-Fluoro-3-pyridyl | A-15 | H | represents a combination of substituents corresponding to each row of Table B |
| Table 215 | 215-1~215-710 | 6-Bromo-3-pyridyl | A-15 | H | represents a combination of substituents corresponding to each row of Table B |
| Table 216 | 216-1~216-710 | 6-Chloro-5-fluoro-3-pyridyl | A-15 | H | represents a combination of substituents corresponding to each row of Table B |
| Table 217 | 217-1~217-710 | 2-Chloro-5-pyrimidinyl | A-15 | H | represents a combination of substituents corresponding to each row of Table B |
| Table 218 | 218-1~218-710 | 5-Chloro-pyrazin-2-yl | A-15 | H | represents a combination of substituents corresponding to each row of Table B |
| Table 219 | 219-1~219-710 | 6-Chloro-pyridazin-3-yl | A-15 | H | represents a combination of substituents corresponding to each row of Table B |
| Table 220 | 220-1~220-710 | 2-Chloro-5-oxazolyl | A-15 | H | represents a combination of substituents corresponding to each row of Table B |
| Table 221 | 221-1~221-710 | 6-trifluoromethyl-3-pyridyl | A-15 | H | represents a combination of substituents corresponding to each row of Table B |
| Table 222 | 222-1~222-710 | 3-tetrahydrofuranyl | A-15 | H | represents a combination of substituents corresponding to each row of Table B |
| Table 223 | 223-1~223-710 | 6-Chloro-3-pyridyl | A-16 | H | represents a combination of substituents corresponding to each row of Table B |
| Table 224 | 224-1~224-710 | 2-Chloro-5-thiazolyl | A-16 | H | represents a combination of substituents corresponding to each row of Table B |

TABLE 8

Table A

| Compound No. | Ar | A | Y | R |
|---|---|---|---|---|
| Table 225 | 225-1~225-710 | 6-Fluoro-3-pyridyl | A-16 | H | represents a combination of substituents corresponding to each row of Table B |
| Table 226 | 226-1~226-710 | 6-Bromo-3-pyridyl | A-16 | H | represents a combination of substituents corresponding to each row of Table B |
| Table 227 | 227-1~227-710 | 6-Chloro-5-fluoro-3-pyridyl | A-16 | H | represents a combination of substituents corresponding to each row of Table B |
| Table 228 | 228-1~228-710 | 2-Chloro-5-pyrimidinyl | A-16 | H | represents a combination of substituents corresponding to each row of Table B |
| Table 229 | 229-1~229-710 | 5-Chloro-pyrazin-2-yl | A-16 | H | represents a combination of substituents corresponding to each row of Table B |
| Table 230 | 230-1~230-710 | 6-Chloro-pyridazin-3-yl | A-16 | H | represents a combination of substituents corresponding to each row of Table B |
| Table 231 | 231-1~231-710 | 2-Chloro-5-oxazolyl | A-16 | H | represents a combination of substituents corresponding to each row of Table B |
| Table 232 | 232-1~232-710 | 6-trifluoromethyl-3-pyridyl | A-16 | H | represents a combination of substituents corresponding to each row of Table B |
| Table 233 | 233-1~233-710 | 3-tetrahydrofuranyl | A-16 | H | represents a combination of substituents corresponding to each row of Table B |
| Table 234 | 234-1~234-710 | 6-Chloro-3-pyridyl | A-2 | H | represents a combination of substituents corresponding to each row of Table B |
| Table 235 | 235-1~235-710 | 6-Chloro-3-pyridyl | A-3 | H | represents a combination of substituents corresponding to each row of Table B |
| Table 236 | 236-1~236-710 | 6-Chloro-3-pyridyl | A-4 | H | represents a combination of substituents corresponding to each row of Table B |
| Table 237 | 237-1~237-710 | 6-Chloro-3-pyridyl | A-5 | H | represents a combination of substituents corresponding to each row of Table B |
| Table 238 | 238-1~238-710 | 6-Chloro-3-pyridyl | A-6 | H | represents a combination of substituents corresponding to each row of Table B |
| Table 239 | 239-1~239-710 | 6-Chloro-3-pyridyl | A-7 | H | represents a combination of substituents corresponding to each row of Table B |
| Table 240 | 240-1~240-710 | 6-Chloro-3-pyridyl | A-8 | H | represents a combination of substituents corresponding to each row of Table B |
| Table 241 | 241-1~241-710 | 6-Chloro-3-pyridyl | A-9 | H | represents a combination of substituents corresponding to each row of Table B |
| Table 242 | 242-1~242-710 | 6-Chloro-3-pyridyl | A-10 | H | represents a combination of substituents corresponding to each row of Table B |
| Table 243 | 243-1~243-710 | 6-Chloro-3-pyridyl | A-11 | H | represents a combination of substituents corresponding to each row of Table B |
| Table 244 | 244-1~244-710 | 6-Chloro-3-pyridyl | A-12 | H | represents a combination of substituents corresponding to each row of Table B |
| Table 245 | 245-1~245-710 | 6-Chloro-3-pyridyl | A-17 | H | represents a combination of substituents corresponding to each row of Table B |
| Table 246 | 246-1~246-710 | 6-Chloro-3-pyridyl | A-18 | H | represents a combination of substituents corresponding to each row of Table B |
| Table 247 | 247-1~247-710 | 6-Chloro-3-pyridyl | A-19 | H | represents a combination of substituents corresponding to each row of Table B |
| Table 248 | 248-1~248-710 | 6-Chloro-3-pyridyl | A-20 | H | represents a combination of substituents corresponding to each row of Table B |
| Table 249 | 249-1~249-710 | 6-Chloro-3-pyridyl | A-21 | H | represents a combination of substituents corresponding to each row of Table B |

TABLE 8-continued

Table A

| Compound No. | Ar | A | Y | R |
|---|---|---|---|---|
| Table 250 | 250-1~250-710 | 6-Chloro-3-pyridyl | A-22 | H | represents a combination of substituents corresponding to each row of Table B |
| Table 251 | 251-1~251-710 | 6-Chloro-3-pyridyl | A-23 | H | represents a combination of substituents corresponding to each row of Table B |
| Table 252 | 252-1~252-710 | 6-Chloro-3-pyridyl | A-24 | H | represents a combination of substituents corresponding to each row of Table B |
| Table 253 | 253-1~253-710 | 6-Chloro-3-pyridyl | A-25 | H | represents a combination of substituents corresponding to each row of Table B |
| Table 254 | 254-1~254-710 | 6-Chloro-3-pyridyl | A-26 | H | represents a combination of substituents corresponding to each row of Table B |
| Table 255 | 255-1~255-710 | 6-Chloro-3-pyridyl | A-27 | H | represents a combination of substituents corresponding to each row of Table B |
| Table 256 | 256-1~256-710 | 6-Chloro-3-pyridyl | A-28 | H | represents a combination of substituents corresponding to each row of Table B |

TABLE 9

Table A

| Compound No. | Ar | A | Y | R |
|---|---|---|---|---|
| Table 257 | 257-1~257-710 | 6-Chloro-3-pyridyl | A-29 | H | represents a combination of substituents corresponding to each row of Table B |
| Table 258 | 258-1~258-710 | 6-Chloro-3-pyridyl | A-30 | H | represents a combination of substituents corresponding to each row of Table B |
| Table 259 | 259-1~259-710 | 6-Chloro-3-pyridyl | A-31 | H | represents a combination of substituents corresponding to each row of Table B |
| Table 260 | 260-1~260-710 | 6-Chloro-3-pyridyl | A-32 | H | represents a combination of substituents corresponding to each row of Table B |
| Table 261 | 261-1~261-710 | 6-Chloro-3-pyridyl | A-33 | H | represents a combination of substituents corresponding to each row of Table B |
| Table 262 | 262-1~262-710 | 6-Chloro-3-pyridyl | A-34 | H | represents a combination of substituents corresponding to each row of Table B |
| Table 263 | 263-1~263-710 | 6-Chloro-3-pyridyl | A-35 | H | represents a combination of substituents corresponding to each row of Table B |
| Table 264 | 264-1~264-710 | 6-Chloro-3-pyridyl | A-36 | H | represents a combination of substituents corresponding to each row of Table B |
| Table 265 | 265-1~265-710 | 6-Chloro-3-pyridyl | A-37 | H | represents a combination of substituents corresponding to each row of Table B |
| Table 266 | 266-1~266-710 | 6-Chloro-3-pyridyl | A-38 | H | represents a combination of substituents corresponding to each row of Table B |
| Table 267 | 267-1~267-710 | 6-Chloro-3-pyridyl | A-39 | H | represents a combination of substituents corresponding to each row of Table B |
| Table 268 | 268-1~268-710 | 6-Chloro-3-pyridyl | A-40 | H | represents a combination of substituents corresponding to each row of Table B |
| Table 269 | 269-1-269-710 | 6-Chloro-3-pyridyl | A-2 | H | represents a combination of substituents corresponding to each row of Table B |
| Table 270 | 270-1~270-710 | 6-Chloro-3-pyridyl | A-3 | H | represents a combination of substituents corresponding to each row of Table B |
| Table 271 | 271-1~271-710 | 6-Chloro-3-pyridyl | A-4 | H | represents a combination of substituents corresponding to each row of Table B |
| Table 272 | 272-1~272-710 | 6-Chloro-3-pyridyl | A-5 | H | represents a combination of substituents corresponding to each row of Table B |

TABLE 9-continued

Table A

| Compound No. | | Ar | A | Y | R |
|---|---|---|---|---|---|
| Table 273 | 273-1~273-710 | 6-Chloro-3-pyridyl | A-6 | H | represents a combination of substituents corresponding to each row of Table B |
| Table 274 | 274-1~274-710 | 6-Chloro-3-pyridyl | A-7 | H | represents a combination of substituents corresponding to each row of Table B |
| Table 275 | 275-1~275-710 | 6-Chloro-3-pyridyl | A-8 | H | represents a combination of substituents corresponding to each row of Table B |
| Table 276 | 276-1~276-710 | 6-Chloro-3-pyridyl | A-9 | H | represents a combination of substituents corresponding to each row of Table B |
| Table 277 | 277-1~277-710 | 6-Chloro-3-pyridyl | A-10 | H | represents a combination of substituents corresponding to each row of Table B |
| Table 278 | 278-1~278-710 | 6-Chloro-3-pyridyl | A-11 | H | represents a combination of substituents corresponding to each row of Table B |
| Table 279 | 279-1~279-710 | 6-Chloro-3-pyridyl | A-12 | H | represents a combination of substituents corresponding to each row of Table B |
| Table 280 | 280-1~280-710 | 6-Chloro-3-pyridyl | A-17 | H | represents a combination of substituents corresponding to each row of Table B |
| Table 281 | 281-1~281-710 | 6-Chloro-3-pyridyl | A-18 | H | represents a combination of substituents corresponding to each row of Table B |
| Table 282 | 282-1~282-710 | 6-Chloro-3-pyridyl | A-19 | H | represents a combination of substituents corresponding to each row of Table B |
| Table 283 | 283-1~283-710 | 6-Chloro-3-pyridyl | A-20 | H | represents a combination of substituents corresponding to each row of Table B |
| Table 284 | 284-1~284-710 | 6-Chloro-3-pyridyl | A-21 | H | represents a combination of substituents corresponding to each row of Table B |
| Table 285 | 285-1~285-710 | 6-Chloro-3-pyridyl | A-22 | H | represents a combination of substituents corresponding to each row of Table B |
| Table 286 | 286-1~286-710 | 6-Chloro-3-pyridyl | A-23 | H | represents a combination of substituents corresponding to each row of Table B |
| Table 287 | 287-1~287-710 | 6-Chloro-3-pyridyl | A-24 | H | represents a combination of substituents corresponding to each row of Table B |
| Table 288 | 288-1~288-710 | 6-Chloro-3-pyridyl | A-25 | H | represents a combination of substituents corresponding to each row of Table B |

TABLE A

| Compound No. | | Ar | A | Y | R |
|---|---|---|---|---|---|
| Table 289 | 289-1~289-710 | 6-Chloro-3-pyridyl | A-26 | H | represents a combination of substituents corresponding to each row of Table B |
| Table 290 | 290-1~290-710 | 6-Chloro-3-pyridyl | A-27 | H | represents a combination of substituents corresponding to each row of Table B |
| Table 291 | 291-1~291-710 | 6-Chloro-3-pyridyl | A-28 | H | represents a combination of substituents corresponding to each row of Table B |
| Table 292 | 292-1~292-710 | 6-Chloro-3-pyridyl | A-29 | H | represents a combination of substituents corresponding to each row of Table B |
| Table 293 | 293-1~293-710 | 6-Chloro-3-pyridyl | A-30 | H | represents a combination of substituents corresponding to each row of Table B |
| Table 294 | 294-1~294-710 | 6-Chloro-3-pyridyl | A-31 | H | represents a combination of substituents corresponding to each row of Table B |
| Table 295 | 295-1~295-710 | 6-Chloro-3-pyridyl | A-32 | H | represents a combination of substituents corresponding to each row of Table B |
| Table 296 | 296-1~296-710 | 6-Chloro-3-pyridyl | A-33 | H | represents a combination of substituents |

TABLE A-continued

| Compound No. | Ar | A | Y | R |
|---|---|---|---|---|
| Table 297 | 297-1~297-710 | 6-Chloro-3-pyridyl | A-34 | H | represents a combination of substituents corresponding to each row of Table B |
| Table 298 | 298-1~298-710 | 6-Chloro-3-pyridyl | A-35 | H | represents a combination of substituents corresponding to each row of Table B |
| Table 299 | 299-1~299-710 | 6-Chloro-3-pyridyl | A-36 | H | represents a combination of substituents corresponding to each row of Table B |
| Table 300 | 300-1~300-710 | 6-Chloro-3-pyridyl | A-37 | H | represents a combination of substituents corresponding to each row of Table B |
| Table 301 | 301-1~301-710 | 6-Chloro-3-pyridyl | A-38 | H | represents a combination of substituents corresponding to each row of Table B |
| Table 302 | 302-1~302-710 | 6-Chloro-3-pyridyl | A-39 | H | represents a combination of substituents corresponding to each row of Table B |
| Table 303 | 303-1~303-710 | 6-Chloro-3-pyridyl | A-40 | H | represents a combination of substituents corresponding to each row of Table B |
| Table 304 | 304-1~304-710 | 6-Chloro-3-pyridyl | A-2 | H | represents a combination of substituents corresponding to each row of Table B |
| Table 305 | 305-1~305-710 | 6-Chloro-3-pyridyl | A-3 | H | represents a combination of substituents corresponding to each row of Table B |
| Table 306 | 306-1~306-710 | 6-Chloro-3-pyridyl | A-4 | H | represents a combination of substituents corresponding to each row of Table B |
| Table 307 | 307-1~307-710 | 6-Chloro-3-pyridyl | A-5 | H | represents a combination of substituents corresponding to each row of Table B |
| Table 308 | 308-1~308-710 | 6-Chloro-3-pyridyl | A-6 | H | represents a combination of substituents corresponding to each row of Table B |
| Table 309 | 309-1~309-710 | 6-Chloro-3-pyridyl | A-7 | H | represents a combination of substituents corresponding to each row of Table B |
| Table 310 | 310-1~310-710 | 6-Chloro-3-pyridyl | A-8 | H | represents a combination of substituents corresponding to each row of Table B |
| Table 311 | 311-1~311-710 | 6-Chloro-3-pyridyl | A-9 | H | represents a combination of substituents corresponding to each row of Table B |
| Table 312 | 312-1~312-710 | 6-Chloro-3-pyridyl | A-10 | H | represents a combination of substituents corresponding to each row of Table B |
| Table 313 | 313-1~313-710 | 6-Chloro-3-pyridyl | A-11 | H | represents a combination of substituents corresponding to each row of Table B |
| Table 314 | 314-1~314-710 | 6-Chloro-3-pyridyl | A-12 | H | represents a combination of substituents corresponding to each row of Table B |
| Table 315 | 315-1~315-710 | 6-Chloro-3-pyridyl | A-17 | H | represents a combination of substituents corresponding to each row of Table B |
| Table 316 | 316-1~316-710 | 6-Chloro-3-pyridyl | A-18 | H | represents a combination of substituents corresponding to each row of Table B |
| Table 317 | 317-1~317-710 | 6-Chloro-3-pyridyl | A-19 | H | represents a combination of substituents corresponding to each row of Table B |
| Table 318 | 318-1~318-710 | 6-Chloro-3-pyridyl | A-20 | H | represents a combination of substituents corresponding to each row of Table B |
| Table 319 | 319-1~319-710 | 6-Chloro-3-pyridyl | A-21 | H | represents a combination of substituents corresponding to each row of Table B |
| Table 320 | 320-1~320-710 | 6-Chloro-3-pyridyl | A-22 | H | represents a combination of substituents corresponding to each row of Table B |

TABLE A

| Compound No | | Ar | A | Y | R |
|---|---|---|---|---|---|
| Table 321 | 321-1~321-710 | 6-Chloro-3-pyridyl | A-23 | H | represents a combination of substituents corresponding to each row of Table B |
| Table 322 | 322-1~322-710 | 6-Chloro-3-pyridyl | A-24 | H | represents a combination of substituents corresponding to each row of Table B |
| Table 323 | 323-1~323-710 | 6-Chloro-3-pyridyl | A-25 | H | represents a combination of substituents corresponding to each row of Table B |
| Table 324 | 324-1~324-710 | 6-Chloro-3-pyridyl | A-26 | H | represents a combination of substituents corresponding to each row of Table B |
| Table 325 | 325-1~325-710 | 6-Chloro-3-pyridyl | A-27 | H | represents a combination of substituents corresponding to each row of Table B |
| Table 326 | 326-1~326-710 | 6-Chloro-3-pyridyl | A-28 | H | represents a combination of substituents corresponding to each row of Table B |
| Table 327 | 327-1~327-710 | 6-Chloro-3-pyridyl | A-29 | H | represents a combination of substituents corresponding to each row of Table B |
| Table 328 | 328-1~328-710 | 6-Chloro-3-pyridyl | A-30 | H | represents a combination of substituents corresponding to each row of Table B |
| Table 329 | 329-1~329-710 | 6-Chloro-3-pyridyl | A-31 | H | represents a combination of substituents corresponding to each row of Table B |
| Table 330 | 330-1~330-710 | 6-Chloro-3-pyridyl | A-32 | H | represents a combination of substituents corresponding to each row of Table B |
| Table 331 | 331-1~331-710 | 6-Chloro-3-pyridyl | A-33 | H | represents a combination of substituents corresponding to each row of Table B |
| Table 332 | 332-1~332-710 | 6-Chloro-3-pyridyl | A-34 | H | represents a combination of substituents corresponding to each row of Table B |
| Table 333 | 333-1~333-710 | 6-Chloro-3-pyridyl | A-35 | H | represents a combination of substituents corresponding to each row of Table B |
| Table 334 | 334-1~334-710 | 6-Chloro-3-pyridyl | A-36 | H | represents a combination of substituents corresponding to each row of Table B |
| Table 335 | 335-1~335-710 | 6-Chloro-3-pyridyl | A-37 | H | represents a combination of substituents corresponding to each row of Table B |
| Table 336 | 336-1~336-710 | 6-Chloro-3-pyridyl | A-38 | H | represents a combination of substituents corresponding to each row of Table B |
| Table 337 | 337-1~337-710 | 6-Chloro-3-pyridyl | A-39 | H | represents a combination of substituents corresponding to each row of Table B |
| Table 338 | 338-1~338-710 | 6-Chloro-3-pyridyl | A-40 | H | represents a combination of substituents corresponding to each row of Table B |
| Table 339 | 339-1~339-710 | 2-Chloro-5-thiazolyl | A-2 | H | represents a combination of substituents corresponding to each row of Table B |
| Table 340 | 340-1~340-710 | 3-Trifluoromethylphenyl | A-3 | H | represents a combination of substituents corresponding to each row of Table B |
| Table 341 | 341-1~341-710 | 2-Methylphenyl | A-4 | H | represents a combination of substituents corresponding to each row of Table B |
| Table 342 | 342-1~342-710 | 3-Methylphenyl | A-5 | H | represents a combination of substituents corresponding to each row of Table B |
| Table 343 | 343-1~343-710 | 4-Methylphenyl | A-6 | H | represents a combination of substituents corresponding to each row of Table B |
| Table 344 | 344-1~344-710 | 4-Trifluoromethylphenyl | A-7 | H | represents a combination of substituents corresponding to each row of Table B |
| Table 345 | 345-1~345-710 | 2-Trifluoromethylphenyl | A-8 | H | represents a combination of substituents corresponding to each row of Table B |

TABLE A-continued

| Compound No | Ar | A | Y | R |
|---|---|---|---|---|
| Table 346 | 346-1~346-710 | 2-Methoxyphenyl | A-9 | H | represents a combination of substituents corresponding to each row of Table B |
| Table 347 | 347-1~347-710 | 3-Methoxyphenyl | A-10 | H | represents a combination of substituents corresponding to each row of Table B |
| Table 348 | 348-1~348-710 | 4-Methoxyphenyl | A-11 | H | represents a combination of substituents corresponding to each row of Table B |
| Table 349 | 349-1~349-710 | 2-Cyanophenyl | A-12 | H | represents a combination of substituents corresponding to each row of Table B |
| Table 350 | 350-1~350-710 | 3-Cyanophenyl | A-17 | H | represents a combination of substituents corresponding to each row of Table B |
| Table 351 | 351-1~351-710 | 4-Cyanophenyl | A-18 | H | represents a combination of substituents corresponding to each row of Table B |
| Table 352 | 352-1~352-710 | 2-Nitrophenyl | A-19 | H | represents a combination of substituents corresponding to each row of Table B |

TABLE A

| Compound No | Ar | A | Y | R |
|---|---|---|---|---|
| Table 353 | 353-1~353-710 | 3-Nitrophenyl | A-20 | H | represents a combination of substituents corresponding to each row of Table B |
| Table 354 | 354-1~354-710 | 4-Nitrophenyl | A-21 | H | represents a combination of substituents corresponding to each row of Table B |
| Table 355 | 355-1~355-710 | 3-Hydroxy-2-pyridyl | A-22 | H | represents a combination of substituents corresponding to each row of Table B |
| Table 356 | 356-1~356-710 | 4-hydroxy-2-pyridyl | A-23 | H | represents a combination of substituents corresponding to each row of Table B |

TABLE A-continued

| Compound No | Ar | A | Y | R |
|---|---|---|---|---|
| Table 357 | 357-1~357-710 | 5-hydroxy-2-pyridyl | A-24 | H | represents a combination of substituents corresponding to each row of Table B |
| Table 358 | 358-1~358-710 | 6-hydroxy-2-pyridyl | A-25 | H | represents a combination of substituents corresponding to each row of Table B |
| Table 359 | 359-1~359-710 | 2-Hydroxy-3-pyridyl | A-26 | H | represents a combination of substituents corresponding to each row of Table B |
| Table 360 | 360-1~360-710 | 5-Hydroxy-3-pyridyl | A-27 | H | represents a combination of substituents corresponding to each row of Table B |
| Table 361 | 361-1~361-710 | 6-Hydroxy-3-pyridyl | A-28 | H | represents a combination of substituents corresponding to each row of Table B |
| Table 362 | 362-1~362-710 | 4-Hydroxy-3-pyridyl | A-29 | H | represents a combination of substituents corresponding to each row of Table B |
| Table 363 | 363-1~363-710 | 2-Hydroxy-4-pyridyl | A-30 | H | represents a combination of substituents corresponding to each row of Table B |
| Table 364 | 364-1~364-710 | 3-Hydroxy-4-pyridyl | A-31 | H | represents a combination of substituents corresponding to each row of Table B |
| Table 365 | 365-1~365-710 | 3-Chloro-2-pyridyl | A-32 | H | represents a combination of substituents corresponding to each row of Table B |
| Table 366 | 366-1~366-710 | 4-Chloro-2-pyridyl | A-33 | H | represents a combination of substituents corresponding to each row of Table B |
| Table 367 | 367-1~367-710 | 5-Chloro-2-pyridyl | A-34 | H | represents a combination of substituents corresponding to each row of Table B |
| Table 368 | 368-1~368-710 | 6-Chloro-2-pyridyl | A-35 | H | represents a combination of substituents corresponding to each row of Table B |

TABLE A-continued

| Compound No | Ar | A | Y | R |
|---|---|---|---|---|
| Table 369 | 369-1~369-710 | 2-Chloro-3-pyridyl | A-36 | H | represents a combination of substituents corresponding to each row of Table B |
| Table 370 | 370-1~370-710 | 5-Chloro-3-pyridyl | A-37 | H | represents a combination of substituents corresponding to each row of Table B |
| Table 371 | 371-1~371-710 | 6-Chloro-3-pyridyl | A-38 | H | represents a combination of substituents corresponding to each row of Table B |
| Table 372 | 372-1~372-710 | 4-Chloro-3-pyridyl | A-39 | H | represents a combination of substituents corresponding to each row of Table B |
| Table 373 | 373-1~373-710 | 2-Chloro-4-pyridyl | A-40 | H | represents a combination of substituents corresponding to each row of Table B |
| Table 374 | 374-1~374-710 | 3-Chloro-4-pyridyl | A-2 | H | represents a combination of substituents corresponding to each row of Table B |
| Table 375 | 375-1~375-710 | 3-bromo-2-pyridyl | A-3 | H | represents a combination of substituents corresponding to each row of Table B |
| Table 376 | 376-1~376-710 | 4-bromo-2-pyridyl | A-4 | H | represents a combination of substituents corresponding to each row of Table B |
| Table 377 | 377-1~377-710 | 5-bromo-2-pyridyl | A-5 | H | represents a combination of substituents corresponding to each row of Table B |
| Table 378 | 378-1~378-710 | 6-bromo-2-pyridyl | A-6 | H | represents a combination of substituents corresponding to each row of Table B |
| Table 379 | 379-1~379-710 | 2-bromo-3-pyridyl | A-7 | H | represents a combination of substituents corresponding to each row of Table B |
| Table 380 | 380-1~380-710 | 5-bromo-3-pyridyl | A-8 | H | represents a combination of substituents corresponding to each row of Table B |
| Table 381 | 381-1~381-710 | 6-bromo-3-pyridyl | A-9 | H | represents a combination of substituents corresponding to each row of Table B |
| Table 382 | 382-1~382-710 | 4-bromo-3-pyridyl | A-10 | H | represents a combination of substituents corresponding to each row of Table B |
| Table 383 | 383-1~383-710 | 2-bromo-4-pyridyl | A-11 | H | represents a combination of substituents corresponding to each row of Table B |
| Table 384 | 384-1~384-710 | 3-bromo-4-pyridyl | A-12 | H | represents a combination of substituents corresponding to each row of Table B |

TABLE A

| Compound No | Ar | A | Y | R |
|---|---|---|---|---|
| Table 385 | 385-1~385-710 | 3-Fluoro-2-pyridyl | A-17 | H | represents a combination of substituents corresponding to each row of Table B |
| Table 386 | 386-1~386-710 | 4-Fluoro-2-pyridyl | A-18 | H | represents a combination of substituents corresponding to each row of Table B |
| Table 387 | 387-1~387-710 | 5-Fluoro-2-pyridyl | A-19 | H | represents a combination of substituents corresponding to each row of Table B |
| Table 388 | 388-1~388-710 | 6-Fluoro-2-pyridyl | A-20 | H | represents a combination of substituents corresponding to each row of Table B |
| Table 389 | 389-1~389-710 | 2-Fluoro-3-pyridyl | A-21 | H | represents a combination of substituents corresponding to each row of Table B |
| Table 390 | 390-1~390-710 | 5-Fluoro-3-pyridyl | A-22 | H | represents a combination of substituents corresponding to each row of Table B |
| Table 391 | 391-1~391-710 | 6-Fluoro-3-pyridyl | A-23 | H | represents a combination of substituents corresponding to each row of Table B |

TABLE A-continued

| Compound No | Ar | A | Y | R |
|---|---|---|---|---|
| Table 392 | 392-1~392-710 | 4-Fluoro-3-pyridyl | A-24 | H | represents a combination of substituents corresponding to each row of Table B |
| Table 393 | 393-1~393-710 | 2-Fluoro-4-pyridyl | A-25 | H | represents a combination of substituents corresponding to each row of Table B |
| Table 394 | 394-1~394-710 | 3-Fluoro-4-pyridyl | A-26 | H | represents a combination of substituents corresponding to each row of Table B |
| Table 395 | 395-1~395-710 | 6-Fluoro-3-pyridyl | A-27 | H | represents a combination of substituents corresponding to each row of Table B |
| Table 396 | 396-1~396-710 | 3-iodo-2-pyridyl | A-28 | H | represents a combination of substituents corresponding to each row of Table B |
| Table 397 | 397-1~397-710 | 4-iodo-2-pyridyl | A-29 | H | represents a combination of substituents corresponding to each row of Table B |
| Table 398 | 398-1~398-710 | 5-iodo-2-pyridyl | A- | H | represents a combination of substituents corresponding to each row of Table B |
| Table 399 | 399-1~399-710 | 6-iodo-2~pyridyl | A-31 | H | represents a combination of substituents corresponding to each row of Table B |
| Table 400 | 400-1~400-710 | 2-iodo-3-pyridyl | A-32 | H | represents a combination of substituents corresponding to each row of Table B |
| Table 401 | 401-1~401-710 | 5-iodo-3-pyridyl | A-33 | H | represents a combination of substituents corresponding to each row of Table B |
| Table 402 | 402-1~402-710 | 6-iodo-3-pyridyl | A-34 | H | represents a combination of substituents corresponding to each row of Table B |
| Table 403 | 403-1~403-710 | 4-iodo-3-pyridyl | A-35 | H | represents a combination of substituents corresponding to each row of Table B |
| Table 404 | 404-1~404-710 | 2-iodo-4-pyridyl | A-36 | H | represents a combination of substituents corresponding to each row of Table B |
| Table 405 | 405-1~405-710 | 3-iodo-4-pyridyl | A-37 | H | represents a combination of substituents corresponding to each row of Table B |
| Table 406 | 406-1~406-710 | 6-iodo-3-pyridyl | A-38 | H | represents a combination of substituents corresponding to each row of Table B |
| Table 407 | 407-1~407-710 | 6-iodo-3-pyridyl | A-39 | H | represents a combination of substituents corresponding to each row of Table B |
| Table 408 | 408-1~408-710 | 2-tetrahydrofuranyl | A-40 | H | represents a combination of substituents corresponding to each row of Table B |
| Table 409 | 409-1~409-710 | 3-tetrahydrofuranyl | A-2 | H | represents a combination of substituents corresponding to each row of Table B |
| Table 410 | 410-1~410-710 | 5-Chloro-2-thiazolyl | A-3 | H | represents a combination of substituents corresponding to each row of Table B |
| Table 411 | 411-1~411-710 | 6-Fluoro-3-pyridyl | A-4 | H | represents a combination of substituents corresponding to each row of Table B |
| Table 412 | 412-1~412-710 | 6-Bromo-3-pyridyl | A-5 | H | represents a combination of substituents corresponding to each row of Table B |
| Table 413 | 413-1~413-710 | 6-Chloro-5-Fluoro-3-pyridyl | A-6 | H | represents a combination of substituents corresponding to each row of Table B |
| Table 414 | 414-1~414-710 | 3,5-Dimethylphenyl | A-7 | H | represents a combination of substituents corresponding to each row of Table B |
| Table 415 | 415-1~415-710 | 2,3-Dimethylphenyl | A-8 | H | represents a combination of substituents corresponding to each row of Table B |

TABLE A-continued

| Compound No | | Ar | A | Y | R |
|---|---|---|---|---|---|
| Table 416 | 416-1~416-710 | 2,4-Dimethyophenyl | A-9 | H | represents a combination of substituents corresponding to each row of Table B |

TABLE 14

Table A

| Compound No. | | Ar | A | Y | R |
|---|---|---|---|---|---|
| Table 417 | 417-1~417-710 | Phenyl | A-10 | H | represents a combination of substituents corresponding to each row of Table B |
| Table 418 | 418-1~418-710 | cyclopentyl | A-11 | H | represents a combination of substituents corresponding to each row of Table B |
| Table 419 | 419-1~419-710 | cyclohexyl | A-12 | H | represents a combination of substituents corresponding to each row of Table B |
| Table 420 | 420-1~420-710 | 3-methyl-cyclohexyl | A-17 | H | represents a combination of substituents corresponding to each row of Table B |
| Table 421 | 421-1~421-710 | cyclobutyl | A-18 | H | represents a combination of substituents corresponding to each row of Table B |
| Table 422 | 422-1~422-710 | 2-oxetanyl | A-19 | H | represents a combination of substituents corresponding to each row of Table B |
| Table 423 | 423-1~423-710 | 3-oxetanyl | A-20 | H | represents a combination of substituents corresponding to each row of Table B |
| Table 424 | 424-1~424-710 | 2-thietanyl | A-21 | H | represents a combination of substituents corresponding to each row of Table B |
| Table 425 | 425-1~425-710 | 3-thietanyl | A-22 | H | represents a combination of substituents corresponding to each row of Table B |
| Table 426 | 426-1~426-710 | 2-azetidinyl | A-23 | H | represents a combination of substituents corresponding to each row of Table B |

TABLE 14-continued

Table A

| Compound No. | | Ar | A | Y | R |
|---|---|---|---|---|---|
| Table 427 | 427-1~427-710 | 3-azetidinyl | A-24 | H | represents a combination of substituents corresponding to each row of Table B |
| Table 428 | 428-1~428-710 | 6-iodo-3-pyridyl | A-25 | H | represents a combination of substituents corresponding to each row of Table B |
| Table 429 | 429-1~429-710 | 6-iodo-3-pyridyl | A-26 | H | represents a combination of substituents corresponding to each row of Table B |
| Table 430 | 430-1~430-710 | 2-tetrahydrofuranyl | A-27 | H | represents a combination of substituents corresponding to each row of Table B |
| Table 431 | 431-1~431-710 | 2-Chloro-3-pyridyl | A-28 | H | represents a combination of substituents corresponding to each row of Table B |
| Table 432 | 432-1~432-710 | 5-Chloro-3-pyridyl | A-29 | H | represents a combination of substituents corresponding to each row of Table B |
| Table 433 | 433-1~433-710 | 6-Chloro-3-pyridyl | A-30 | H | represents a combination of substituents corresponding to each row of Table B |
| Table 434 | 434-1~434-710 | 4-Chloro-3-pyridyl | A-31 | H | represents a combination of substituents corresponding to each row of Table B |
| Table 435 | 435-1~435-710 | 2-Chloro-4-pyridyl | A-32 | H | represents a combination of substituents corresponding to each row of Table B |
| Table 436 | 436-1~436-710 | 3-Chloro-4-pyridyl | A-33 | H | represents a combination of substituents corresponding to each row of Table B |
| Table 437 | 437-1~437-710 | 3-bromo-2-pyridyl | A-34 | H | represents a combination of substituents corresponding to each row of Table B |
| Table 438 | 438-1~438-710 | 4-bromo-2-pyridyl | A-35 | H | represents a combination of substituents corresponding to each row of Table B |

TABLE 14-continued

Table A

| Compound No. | Ar | A | Y | R |
|---|---|---|---|---|
| Table 439 | 439-1~439-710 | 2-Fluoro-4-pyridyl | A-36 | H | represents a combination of substituents corresponding to each row of Table B |
| Table 440 | 440-1~440-710 | 3-Fluoro-4-pyridyl | A-37 | H | represents a combination of substituents corresponding to each row of Table B |
| Table 441 | 441-1~441-710 | 6-Fluoro-3-pyridyl | A-38 | H | represents a combination of substituents corresponding to each row of Table B |
| Table 442 | 442-1~442-710 | 3-iodo-2-pyridyl | A-39 | H | represents a combination of substituents corresponding to each row of Table B |
| Table 443 | 443-1~443-710 | 6-Fluoro-3-pyridyl | A-40 | H | represents a combination of substituents corresponding to each row of Table B |
| Table 444 | 444-1~444-710 | 2-Chloro-5-thiazolyl | A-38 | H | represents a combination of substituents corresponding to each row of Table B |

TABLE 15

Table A

| Compound No. | Ar | A | Y | R |
|---|---|---|---|---|
| Table 445 | 445-1~445-710 | 6-Chloro-3-pyridyl | A-1 | 3-CH3 | represents a combination of substituents corresponding to each row of Table B |
| Table 446 | 446-1~446-710 | 2-Chloro-5-thiazolyl | A-1 | 3-CH3 | represents a combination of substituents corresponding to each row of Table B |
| Table 447 | 447-1~447-710 | 6-Fluoro-3-pyridyl | A-1 | 3-CH3 | represents a combination of substituents corresponding to each row of Table B |
| Table 448 | 448-1~448-710 | 6-Bromo-3-pyridyl | A-1 | 3-CH3 | represents a combination of substituents corresponding to each row of Table B |

TABLE 15-continued

Table A

| Compound No. | Ar | A | Y | R |
|---|---|---|---|---|
| Table 449 | 449-1~449-710 | 6-Chloro-5-fluoro-3-pyridyl | A-1 | 3-CH3 | represents a combination of substituents corresponding to each row of Table B |
| Table 450 | 450-1~450-710 | 2-Chloro-5-pyrimidinyl | A-1 | 3-CH3 | represents a combination of substituents corresponding to each row of Table B |
| Table 451 | 451-1~451-710 | 5-Chloropyrazin-2-yl | A-1 | 3-CH3 | represents a combination of substituents corresponding to each row of Table B |
| Table 452 | 452-1~452-710 | 6-Chloropyridazin-3-yl | A-1 | 3-CH3 | represents a combination of substituents corresponding to each row of Table B |
| Table 453 | 453-1~453-710 | 2-Chloro-5-oxazolyl | A-1 | 3-CH3 | represents a combination of substituents corresponding to each row of Table B |
| Table 454 | 454-1~454-710 | 6-trifluoromethyl-3-pyridyl | A-1 | 3-CH3 | represents a combination of substituents corresponding to each row of Table B |
| Table 455 | 455-1~455-710 | 3-tetrahydrofuranyl | A-1 | 3-CH3 | represents a combination of substituents corresponding to each row of Table B |
| Table 456 | 456-1~456-710 | 6-Chloro-3-pyridyl | A-1 | 4-CH3 | represents a combination of substituents corresponding to each row of Table B |
| Table 457 | 457-1~457-710 | 2-Chloro-5-thiazolyl | A-1 | 4-CH3 | represents a combination of substituents corresponding to each row of Table B |
| Table 458 | 458-1~458-710 | 6-Fluoro-3-pyridyl | A-1 | 4-CH3 | represents a combination of substituents corresponding to each row of Table B |
| Table 459 | 459-1~459-710 | 6-Bromo-3-pyridyl | A-1 | 4-CH3 | represents a combination of substituents corresponding to each row of Table B |
| Table 460 | 460-1~460-710 | 6-Chloro-5-Fluoro-3-pyridyl | A-1 | 4-CH3 | represents a combination of substituents corresponding to each row of Table B |
| Table 461 | 461-1~461-710 | 2-Chloro-5-pyrimidinyl | A-1 | 4-CH3 | represents a combination of substituents |

TABLE 15-continued

Table A

| Compound No. | | Ar | A | Y | R |
|---|---|---|---|---|---|
| Table 462 | 462-1~462-710 | 5-Chloropyrazin-2-yl | A-1 | 4-CH3 | represents a combination of substituents corresponding to each row of Table B |
| Table 463 | 463-1~463-710 | 6-Chloropyridazin-3-yl | A-1 | 4-CH3 | represents a combination of substituents corresponding to each row of Table B |
| Table 464 | 464-1~464-710 | 2-Chloro-5-oxazolyl | A-1 | 4-CH3 | represents a combination of substituents corresponding to each row of Table B |
| Table 465 | 465-1~465-710 | 6-trifluoromethyl-3-pyridyl | A-1 | 4-CH3 | represents a combination of substituents corresponding to each row of Table B |
| Table 466 | 466-1~466-710 | 3-tetrahydrofuranyl | A-1 | 4-CH3 | represents a combination of substituents corresponding to each row of Table B |
| Table 467 | 467-1~467-710 | 6-Chloro-3-pyridyl | A-1 | 5-CH3 | represents a combination of substituents corresponding to each row of Table B |
| Table 468 | 468-1~468-710 | 2-Chloro-5-thiazolyl | A-1 | 5-CH3 | represents a combination of substituents corresponding to each row of Table B |
| Table 469 | 469-1~469-710 | 6-Fluoro-3-pyridyl | A-1 | 5-CH3 | represents a combination of substituents corresponding to each row of Table B |
| Table 470 | 470-1~470-710 | 6-Bromo-3-pyridyl | A-1 | 5-CH3 | represents a combination of substituents corresponding to each row of Table B |
| Table 471 | 471-1~471-710 | 6-Chloro-5-fluoro-3-pyridyl | A-1 | 5-CH3 | represents a combination of substituents corresponding to each row of Table B |
| Table 472 | 472-1~472-710 | 2-Chloro-5-pyrimidinyl | A-1 | 5-CH3 | represents a combination of substituents corresponding to each row of Table B |
| Table 473 | 473-1~473-710 | 5-Chloropyrazin-2-yl | A-1 | 5-CH3 | represents a combination of substituents corresponding to each row of Table B |
| Table 474 | 474-1~474-710 | 6-Chloropyridazin-3-yl | A-1 | 5-CH3 | represents a combination of substituents corresponding to each row of Table B |
| Table 475 | 475-1~475-710 | 2-Chloro-5-oxazolyl | A-1 | 5-CH3 | represents a combination of substituents corresponding to each row of Table B |
| Table 476 | 476-1~476-710 | 6-trifluoromethyl-3-pyridyl | A-1 | 5-CH3 | represents a combination of substituents corresponding to each row of Table B |

TABLE 16

Table A

| Compound No. | | Ar | A | Y | R |
|---|---|---|---|---|---|
| Table 477 | 477-1~477-710 | 3-tetrahydrofuranyl | A-1 | 5-CH3 | represents a combination of substituents corresponding to each row of Table B |
| Table 478 | 478-1~478-710 | 6-Chloro-3-pyridyl | A-1 | 6-CH3 | represents a combination of substituents corresponding to each row of Table B |
| Table 479 | 479-1~479-710 | 2-Chloro-5-thiazolyl | A-1 | 6-CH3 | represents a combination of substituents corresponding to each row of Table B |
| Table 480 | 480-1~480-710 | 6-Fluoro-3-pyridyl | A-1 | 6-CH3 | represents a combination of substituents corresponding to each row of Table B |
| Table 481 | 481-1~481-710 | 6-Bromo-3-pyridyl | A-1 | 6-CH3 | represents a combination of substituents corresponding to each row of Table B |
| Table 482 | 482-1~482-710 | 6-Chloro-5-fluoro-3-pyridyl | A-1 | 6-CH3 | represents a combination of substituents corresponding to each row of Table B |
| Table 483 | 483-1~483-710 | 2-Chloro-5-pyrimidinyl | A-1 | 6-CH3 | represents a combination of substituents corresponding to each row of Table B |

TABLE 16-continued

Table A

| Compound No. | Ar | A | Y | R |
|---|---|---|---|---|
| Table 484 | 484-1~484-710 | 5-Chloropyrazin-2-yl | A-1 | 6-CH3 | represents a combination of substituents corresponding to each row of Table B |
| Table 485 | 485-1~485-710 | 6-Chloropyridazin-3-yl | A-1 | 6-CH3 | represents a combination of substituents corresponding to each row of Table B |
| Table 486 | 486-1~486-710 | 2-Chloro-5-oxazolyl | A-1 | 6-CH3 | represents a combination of substituents corresponding to each row of Table B |
| Table 487 | 487-1~487-710 | 6-trifluoromethyl-3-pyridyl | A-1 | 6-CH3 | represents a combination of substituents corresponding to each row of Table B |
| Table 488 | 488-1~488-710 | 3-tetrahydrofuranyl | A-1 | 6-CH3 | represents a combination of substituents corresponding to each row of Table B |
| Table 489 | 489-1~489-710 | 6-Chloro-3-pyridyl | A-1 | 3-NO2 | represents a combination of substituents corresponding to each row of Table B |
| Table 490 | 490-1~490-710 | 2-Chloro-5-thiazolyl | A-1 | 3-NO2 | represents a combination of substituents corresponding to each row of Table B |
| Table 491 | 491-1~491-710 | 6-Fluoro-3-pyridyl | A-1 | 3-NO2 | represents a combination of substituents corresponding to each row of Table B |
| Table 492 | 492-1~492-710 | 6-Bromo-3-pyridyl | A-1 | 3-NO2 | represents a combination of substituents corresponding to each row of Table B |
| Table 493 | 493-1~493-710 | 6-Chloro-5-Fluoro-3-pyridyl | A-1 | 3-NO2 | represents a combination of substituents corresponding to each row of Table B |
| Table 494 | 494-1~494-710 | 2-Chloro-5-pyrimidinyl | A-1 | 3-NO2 | represents a combination of substituents corresponding to each row of Table B |
| Table 495 | 495-1~495-710 | 5-Chloropyrazin-2-yl | A-1 | 3-NO2 | represents a combination of substituents corresponding to each row of Table B |
| Table 496 | 496-1~496-710 | 6-Chloropyridazin-3-yl | A-1 | 3-NO2 | represents a combination of substituents corresponding to each row of Table B |
| Table 497 | 497-1~497-710 | 2-Chloro-5-oxazolyl | A-1 | 3-NO2 | represents a combination of substituents corresponding to each row of Table B |
| Table 498 | 498-1~498-710 | 6-trifluoromethyl-3-pyridyl | A-1 | 3-NO2 | represents a combination of substituents corresponding to each row of Table B |
| Table 499 | 499-1~499-710 | 3-tetrahydrofuranyl | A-1 | 3-NO2 | represents a combination of substituents corresponding to each row of Table B |
| Table 500 | 500-1~500-710 | 6-Chloro-3-pyridyl | A-1 | 4-NO2 | represents a combination of substituents corresponding to each row of Table B |
| Table 501 | 501-1~501-710 | 2-Chloro-5-thiazolyl | A-1 | 4-NO2 | represents a combination of substituents corresponding to each row of Table B |
| Table 502 | 502-1~502-710 | 6-Fluoro-3-pyridyl | A-1 | 4-NO2 | represents a combination of substituents corresponding to each row of Table B |
| Table 503 | 503-1~503-710 | 6-Bromo-3-pyridyl | A-1 | 4-NO2 | represents a combination of substituents corresponding to each row of Table B |
| Table 504 | 504-1~504-710 | 6-Chloro-5-fluoro-3-pyridyl | A-1 | 4-NO2 | represents a combination of substituents corresponding to each row of Table B |
| Table 505 | 505-1~505-710 | 2-Chloro-5-pyrimidinyl | A-1 | 4-NO2 | represents a combination of substituents corresponding to each row of Table B |
| Table 506 | 506-1~506-710 | 5-Chloropyrazin-2-yl | A-1 | 4-NO2 | represents a combination of substituents corresponding to each row of Table B |
| Table 507 | 507-1~507-710 | 6-Chloropyridazin-3-yl | A-1 | 4-NO2 | represents a combination of substituents corresponding to each row of Table B |

TABLE 16-continued

Table A

| Compound No. | Ar | A | Y | R |
|---|---|---|---|---|
| Table 508 | 508-1~508-710 | 2-Chloro-5-oxazolyl | A-1 | 4-NO2 | represents a combination of substituents corresponding to each row of Table B |

TABLE 17

Table A

| Compound No. | Ar | A | Y | R |
|---|---|---|---|---|
| Table 509 | 509-1~509-710 | 6-trifluoromethyl-3-pyridyl | A-1 | 4-NO2 | represents a combination of substituents corresponding to each row of Table B |
| Table 510 | 510-1~510-710 | 3-tetrahydro-furanyl | A-1 | 4-NO2 | represents a combination of substituents corresponding to each row of Table B |
| Table 511 | 511-1~511-710 | 6-Chloro-3-pyridyl | A-1 | 5-NO2 | represents a combination of substituents corresponding to each row of Table B |
| Table 512 | 512-1~512-710 | 2-Chloro-5-thiazolyl | A-1 | 5-NO2 | represents a combination of substituents corresponding to each row of Table B |
| Table 513 | 513-1~513-710 | 6-Fluoro-3-pyridyl | A-1 | 5-NO2 | represents a combination of substituents corresponding to each row of Table B |
| Table 514 | 514-1~514-710 | 6-Bromo-3-pyridyl | A-1 | 5-NO2 | represents a combination of substituents corresponding to each row of Table B |
| Table 515 | 515-1~515-710 | 6-Chloro-5-fluoro-3-pyridyl | A-1 | 5-NO2 | represents a combination of substituents corresponding to each row of Table B |
| Table 516 | 516-1~516-710 | 2-Chloro-5-pyrimidinyl | A-1 | 5-NO2 | represents a combination of substituents corresponding to each row of Table B |
| Table 517 | 517-1~517-710 | 5-Chloro-pyrazin-2-yl | A-1 | 5-NO2 | represents a combination of substituents corresponding to each row of Table B |

TABLE 17-continued

Table A

| Compound No. | Ar | A | Y | R |
|---|---|---|---|---|
| Table 518 | 518-1~518-710 | 6-Chloro-pyridazin-3-yl | A-1 | 5-NO2 | represents a combination of substituents corresponding to each row of Table B |
| Table 519 | 519-1~519-710 | 2-Chloro-5-oxazolyl | A-1 | 5-NO2 | represents a combination of substituents corresponding to each row of Table B |
| Table 520 | 520-1~520-710 | 6-tri-fluoromethyl-3-pyridyl | A-1 | 5-NO2 | represents a combination of substituents corresponding to each row of Table B |
| Table 521 | 521-1~521-710 | 3-tetrahydro-furanyl | A-1 | 5-NO2 | represents a combination of substituents corresponding to each row of Table B |
| Table 522 | 522-1~522-710 | 6-Chloro-3-pyridyl | A-1 | 6-NO2 | represents a combination of substituents corresponding to each row of Table B |
| Table 523 | 523-1~523-710 | 2-Chloro-5-thiazolyl | A-1 | 6-NO2 | represents a combination of substituents corresponding to each row of Table B |
| Table 524 | 524-1~524-710 | 6-Fluoro-3-pyridyl | A-1 | 6-NO2 | represents a combination of substituents corresponding to each row of Table B |
| Table 525 | 525-1~525-710 | 6-Bromo-3-pyridyl | A-1 | 6-NO2 | represents a combination of substituents corresponding to each row of Table B |
| Table 526 | 526-1~526-710 | 6-Chloro-5-Fluoro-3-pyridyl | A-1 | 6-NO2 | represents a combination of substituents corresponding to each row of Table B |
| Table 527 | 527-1~527-710 | 2-Chloro-5-pyrimidinyl | A-1 | 6-NO2 | represents a combination of substituents corresponding to each row of Table B |
| Table 528 | 528-1~528-710 | 5-Chloro-pyrazin-2-yl | A-1 | 6-NO2 | represents a combination of substituents corresponding to each row of Table B |
| Table 529 | 529-1~529-710 | 6-Chloro-pyridazin-3-yl | A-1 | 6-NO2 | represents a combination of substituents corresponding to each row of Table B |
| Table 530 | 530-1~530-710 | 2-Chloro-5-oxazolyl | A-1 | 6-NO2 | represents a combination of substituents |

TABLE 17-continued

Table A

| Compound No. | Ar | A | Y | R |
|---|---|---|---|---|
| Table 531 | 531-1~531-710 | 6-trifluoromethyl-3-pyridyl | A-1 | 6-NO2 | represents a combination of substituents corresponding to each row of Table B |
| Table 532 | 532-1~532-710 | 3-tetrahydrofuranyl | A-1 | 6-NO2 | represents a combination of substituents corresponding to each row of Table B |
| Table 533 | 533-1~533-710 | 6-Chloro-3-pyridyl | A-1 | 3-OCH3 | represents a combination of substituents corresponding to each row of Table B |
| Table 534 | 534-1~534-710 | 2-Chloro-5-thiazolyl | A-1 | 3-OCH3 | represents a combination of substituents corresponding to each row of Table B |
| Table 535 | 535-1~535-710 | 6-Fluoro-3-pyridyl | A-1 | 3-OCH3 | represents a combination of substituents corresponding to each row of Table B |
| Table 536 | 536-1~536-710 | 6-Bromo-3-pyridyl | A-1 | 3-OCH3 | represents a combination of substituents corresponding to each row of Table B |
| Table 537 | 537-1~537-710 | 6-Chloro-5-fluoro-3-pyridyl | A-1 | 3-OCH3 | represents a combination of substituents corresponding to each row of Table B |
| Table 538 | 538-1~538-710 | 2-Chloro-5-pyrimidinyl | A-1 | 3-OCH3 | represents a combination of substituents corresponding to each row of Table B |
| Table 539 | 539-1~539-710 | 5-Chloro-pyrazin-2-yl | A-1 | 3-OCH3 | represents a combination of substituents corresponding to each row of Table B |
| Table 540 | 540-1~540-710 | 6-Chloro-pyridazin-3-yl | A-1 | 3-OCH3 | represents a combination of substituents corresponding to each row of Table B |

TABLE 18

Table A

| Compound No. | Ar | A | Y | R |
|---|---|---|---|---|
| Table 541 | 541-1~541-710 | 2-Chloro-5-oxazolyl | A-1 | 3-OCH3 | represents a combination of substituents corresponding to each row of Table B |
| Table 542 | 542-1~542-710 | 6-trifluoromethyl-3-pyridyl | A-1 | 3-OCH3 | represents a combination of substituents corresponding to each row of Table B |
| Table 543 | 543-1~543-710 | 3-tetrahydrofuranyl | A-1 | 3-OCH3 | represents a combination of substituents corresponding to each row of Table B |
| Table 544 | 544-1~544-710 | 6-Chloro-3-pyridyl | A-1 | 4-OCH3 | represents a combination of substituents corresponding to each row of Table B |
| Table 545 | 545-1~545-710 | 2-Chloro-5-thiazolyl | A-1 | 4-OCH3 | represents a combination of substituents corresponding to each row of Table B |
| Table 546 | 546-1~546-710 | 6-Fluoro-3-pyridyl | A-1 | 4-OCH3 | represents a combination of substituents corresponding to each row of Table B |
| Table 547 | 547-1~547-710 | 6-Bromo-3-pyridyl | A-1 | 4-OCH3 | represents a combination of substituents corresponding to each row of Table B |
| Table 548 | 548-1~548-710 | 6-Chloro-5-Fluoro-3-pyridyl | A-1 | 4-OCH3 | represents a combination of substituents corresponding to each row of Table B |
| Table 549 | 549-1~549-710 | 2-Chloro-5-pyrimidinyl | A-1 | 4-OCH3 | represents a combination of substituents corresponding to each row of Table B |
| Table 550 | 550-1~550-710 | 5-Chloro-pyrazin-2-yl | A-1 | 4-OCH3 | represents a combination of substituents corresponding to each row of Table B |
| Table 551 | 551-1~551-710 | 6-Chloro-pyridazin-3-yl | A-1 | 4-OCH3 | represents a combination of substituents corresponding to each row of Table B |
| Table 552 | 552-1~552-710 | 2-Chloro-5-oxazolyl | A-1 | 4-OCH3 | represents a combination of substituents corresponding to each row of Table B |

TABLE 18-continued

Table A

| Compound No. | Ar | A | Y | R |
|---|---|---|---|---|
| Table 553 | 553-1~553-710 | 6-trifluoromethyl-3-pyridyl | A-1 | 4-OCH3 | represents a combination of substituents corresponding to each row of Table B |
| Table 554 | 554-1~554-710 | 3-tetrahydrofuranyl | A-1 | 4-OCH3 | represents a combination of substituents corresponding to each row of Table B |
| Table 555 | 555-1~555-710 | 6-Chloro-3-pyridyl | A-1 | 5-OCH3 | represents a combination of substituents corresponding to each row of Table B |
| Table 556 | 556-1~556-710 | 2-Chloro-5-thiazolyl | A-1 | 5-OCH3 | represents a combination of substituents corresponding to each row of Table B |
| Table 557 | 557-1~557-710 | 6-Fluoro-3-pyridyl | A-1 | 5-OCH3 | represents a combination of substituents corresponding to each row of Table B |
| Table 558 | 558-1~558-710 | 6-Bromo-3-pyridyl | A-1 | 5-OCH3 | represents a combination of substituents corresponding to each row of Table B |
| Table 559 | 559-1~559-710 | 6-Chloro-5-fluoro-3-pyridyl | A-1 | 5-OCH3 | represents a combination of substituents corresponding to each row of Table B |
| Table 560 | 560-1~560-710 | 2-Chloro-5-pyrimidinyl | A-1 | 5-OCH3 | represents a combination of substituents corresponding to each row of Table B |
| Table 561 | 561-1~561-710 | 5-Chloro-pyrazin-2-yl | A-1 | 5-OCH3 | represents a combination of substituents corresponding to each row of Table B |
| Table 562 | 562-1~562-710 | 6-Chloro-pyridazin-3-yl | A-1 | 5-OCH3 | represents a combination of substituents corresponding to each row of Table B |
| Table 563 | 563-1~563-710 | 2-Chloro-5-oxazolyl | A-1 | 5-OCH3 | represents a combination of substituents corresponding to each row of Table B |
| Table 564 | 564-1~564-710 | 6-trifluoromethyl-3-pyridyl | A-1 | 5-OCH3 | represents a combination of substituents corresponding to each row of Table B |
| Table 565 | 565-1~565-710 | 3-tetrahydrofuranyl | A-1 | 5-OCH3 | represents a combination of substituents corresponding to each row of Table B |
| Table 566 | 566-1~566-710 | 6-Chloro-3-pyridyl | A-1 | 6-OCH3 | represents a combination of substituents corresponding to each row of Table B |
| Table 567 | 567-1~567-710 | 2-Chloro-5-thiazolyl | A-1 | 6-OCH3 | represents a combination of substituents corresponding to each row of Table B |
| Table 568 | 568-1~568-710 | 6-Fluoro-3-pyridyl | A-1 | 6-OCH3 | represents a combination of substituents corresponding to each row of Table B |
| Table 569 | 569-1~569-710 | 6-Bromo-3-pyridyl | A-1 | 6-OCH3 | represents a combination of substituents corresponding to each row of Table B |
| Table 570 | 570-1~570-710 | 6-Chloro-5-Fluoro-3-pyridyl | A-1 | 6-OCH3 | represents a combination of substituents corresponding to each row of Table B |
| Table 571 | 571-1~571-710 | 2-Chloro-5-pyrimidinyl | A-1 | 6-OCH3 | represents a combination of substituents corresponding to each row of Table B |
| Table 572 | 572-1~572-710 | 5-Chloro-pyrazin-2-yl | A-1 | 6-OCH3 | represents a combination of substituents corresponding to each row of Table B |

TABLE 19

Table A

| Compound No. | Ar | A | Y | R |
|---|---|---|---|---|
| Table 573 | 573-1~573-710 | 6-Chloro-pyridazin-3-yl | A-1 | 6-OCH3 | represents a combination of substituents corresponding to each row of Table B |
| Table 574 | 574-1~574-710 | 2-Chloro-5-oxazolyl | A-1 | 6-OCH3 | represents a combination of substituents corresponding to each row of Table B |

TABLE 19-continued

Table A

| Compound No. | Ar | A | Y | R |
|---|---|---|---|---|
| Table 575 | 575-1~575-710 | 6-tri-fluoromethyl-3-pyridyl | A-1 | 6-OCH3 | represents a combination of substituents corresponding to each row of Table B |
| Table 576 | 576-1~576-710 | 3-tetra-hydrofuranyl | A-1 | 6-OCH3 | represents a combination of substituents corresponding to each row of Table B |
| Table 577 | 577-1~577-710 | 2,6-dichloro-3-pyridyl | A-1 | H | represents a combination of substituents corresponding to each row of Table B |
| Table 578 | 578-1~578-710 | 3-pyridyl | A-1 | H | represents a combination of substituents corresponding to each row of Table B |
| Table 579 | 579-1~579-710 | 4-pyridyl | A-1 | H | represents a combination of substituents corresponding to each row of Table B |
| Table 580 | 580-1~580-710 | 6-chloro-3-pyridyl-N-oxide | A-1 | H | represents a combination of substituents corresponding to each row of Table B |

TABLE B

| | R |
|---|---|
| 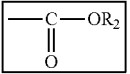 | R1 |
| 1 | H |
| 2 | CF3 |
| 3 | CHF2 |
| 4 | CF2Cl |
| 5 | CF2CF3 |
| 6 | CH2Cl |
| 7 | CHCl2 |
| 8 | CCl3 |
| 9 | CHClBr |
| 10 | 2,2-difluorocyclopropyl |
| 11 | 2,3,3-trifluoroacryl |
| 12 | CH2CHF2 |
| 13 | CH2CF3 |
| 14 | CH=CH2 |
| 15 | CH2C≡CH |
| 16 | CH2CH2C≡CH |

TABLE B-continued

| | R |
|---|---|
| 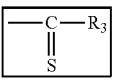 | R2 |
| 17 | CH2CF3 |
| 18 | CH(Me)CF3 |
| 19 | CH(CF3)2 |
| 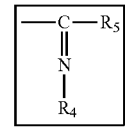 | R3 |
| 20 | CF3 |
| 21 | CHF2 |
| 22 | CF2Cl |
| 23 | CF2CF3 |
| 24 | CH2Cl |
| 25 | CHCl2 |
| 26 | CCl3 |
| 27 | CHClBr |
| 28 | CHBr2 |
| 29 | 2,3,3-trifluoroacryl |
| 30 | CH2CHF2 |
| 31 | CH2CF3 |
| 32 | CH=CH2 |
| 33 | CH2C≡CH |
| 34 | CH2CF3 |
| 35 | CH2CH2Ph |
| 36 | Me |
| 37 | Et |
| 38 | n-Pr |
| 39 | i-Pr |
| 40 | cyclopropyl |

TABLE B

| | R | |
|---|---|---|
| 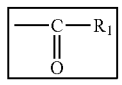 | | |
| | R4 | R5 |
| 41 | H | CF3 |
| 42 | Me | CF3 |
| 43 | Et | CF3 |
| 44 | n-Pr | CF3 |
| 45 | i-Pr | CF3 |
| 46 | t-Bu | CF3 |
| 47 | n-Bu | CF3 |
| 48 | n-Pentyl | CF3 |
| 49 | n-Hexyl | CF3 |
| 50 | cyclopropyl | CF3 |
| 51 | cyclobutyl | CF3 |
| 52 | cyclopentyl | CF3 |
| 53 | cyclohexyl | CF3 |
| 54 | CH=CH2 | CF3 |
| 55 | CH2CH=CH2 | CF3 |
| 56 | CH2C≡CH | CF3 |
| 57 | CH2CH2C≡CH | CF3 |
| 58 | CH2CHF2 | CF3 |
| 59 | CH2CCF3 | CF3 |
| 60 | CH2CH2Cl | CF3 |
| 61 | CH2CHCl2 | CF3 |
| 62 | 2-fluoro-2-chloroethyl | CF3 |
| 63 | CH2CCl3 | CF3 |
| 64 | CH2CN | CF3 |
| 65 | CH2CH2CN | CF3 |

TABLE B-continued

R

| | C—R5 |
| | ‖ |
| | N |
| | \| |
| | R4 |

| | R4 | R5 |
|---|---|---|
| 66 | CH2CH(CN)CH2CN | CF3 |
| 67 | CH2CH2OH | CF3 |
| 68 | CH2CH2CH2OH | CF3 |
| 69 | CH2CH(OH)CH2OH | CF3 |
| 70 | CH2CH2NO2 | CF3 |
| 71 | Phenyl | CF3 |
| 72 | CH2-Phenyl | CF3 |
| 73 | CH(Me)-Phenyl | CF3 |
| 74 | C(Me2)-Phenyl | CF3 |
| 75 | C(cyclopropyl)-Phenyl | CF3 |
| 76 | CH2CH2-Phenyl | CF3 |
| 77 | CH2-(2-Methylphenyl) | CF3 |
| 78 | CH2-(3-Methylphenyl) | CF3 |
| 79 | CH2-(4-Methylphenyl) | CF3 |
| 80 | CH2-(2-Methoxylphenyl) | CF3 |
| 81 | CH2-(3-Methoxylphenyl) | CF3 |
| 82 | CH2-(4-Methoxylphenyl) | CF3 |
| 83 | CH2-(2-fluorolphenyl) | CF3 |
| 84 | CH2-(3-fluorolphenyl) | CF3 |
| 85 | CH2-(4-fluorolphenyl) | CF3 |
| 86 | CH2-(2-Chlorophenyl) | CF3 |
| 87 | CH2-(3-Chlorophenyl) | CF3 |
| 88 | CH2-(4-Chlorophenyl) | CF3 |
| 89 | CH2-(2-Bromophenyl) | CF3 |
| 90 | CH2-(3-Bromophenyl) | CF3 |
| 91 | CH2-(4-Bromophenyl) | CF3 |
| 92 | CH2-(2-iodophenyl) | CF3 |
| 93 | CH2-(3-iodophenyl) | CF3 |

TABLE B

| | R4 | R5 |
|---|---|---|
| 94 | CH2-(4-iodophenyl) | CF3 |
| 95 | CH2-(1-naphthalenyl) | CF3 |
| 96 | CH2-(2-naphthalenyl) | CF3 |
| 97 | naphthalen-1-ylmethyl | CF3 |
| 98 | naphthalen-2-ylmethyl | CF3 |
| 99 | quinolin-2-ylmethyl | CF3 |
| 100 | quinolin-7-ylmethyl | CF3 |
| 101 | isoquinolin-7-ylmethyl | CF3 |

TABLE B-continued

| | R4 | R5 |
|---|---|---|
| 102 | isoquinolin-6-ylmethyl | CF3 |
| 103 | quinolin-6-ylmethyl | CF3 |
| 104 | quinolin-3-ylmethyl | CF3 |
| 105 | isoquinolin-3-ylmethyl | CF3 |
| 106 | isoquinolin-1-ylmethyl | CF3 |
| 107 | isoquinolin-4-ylmethyl | CF3 |
| 108 | quinolin-4-ylmethyl | CF3 |
| 109 | quinolin-5-ylmethyl | CF3 |
| 110 | isoquinolin-5-ylmethyl | CF3 |
| 111 | isoquinolin-8-ylmethyl | CF3 |
| 112 | quinolin-8-ylmethyl | CF3 |
| 113 | CH2O-Phenyl | CF3 |
| 114 | CH2CH2O-Phenyl | CF3 |
| 115 | 2-pyridyl | CF3 |
| 116 | 3-pyridyl | CF3 |
| 117 | 4-pyridyl | CF3 |
| 118 | CH2-(2-pyridyl) | CF3 |
| 119 | CH2-(3-pyridyl) | CF3 |
| 120 | CH2-(4-Chloro-3-pyridyl) | CF3 |
| 121 | CH2-(4-pyridyl) | CF3 |
| 122 | CH2-(2-thienyl) | CF3 |
| 123 | CH2-(3-thienyl) | CF3 |
| 124 | CH2-(2-furanyl) | CF3 |
| 125 | CH2-(3-furanyl) | CF3 |
| 126 | CH2-(2-tetrahydrofuranyl) | CF3 |
| 127 | CH2-(3-tetrahydrofuranyl) | CF3 |
| 128 | (1H-imidazol-2-yl)methyl | CF3 |
| 129 | (1H-imidazol-1-yl)methyl | CF3 |
| 130 | (1H-imidazol-4-yl)methyl | CF3 |
| 131 | CH2-(2-thiazolyl) | CF3 |
| 132 | CH2-(3-thiazolyl) | CF3 |
| 133 | CH2-(2-pyrrolyl) | CF3 |
| 134 | CH2-(3-pyrrolyl) | CF3 |
| 135 | CH2-(5-methylpyrazol-1-yl) | CF3 |
| 136 | CH2-(1-pyrazolyl) | CF3 |
| 137 | CH2-(2-pyrazolyl) | CF3 |
| 138 | CH2-(3-pyrazolyl) | CF3 |
| 139 | CH2-(4-pyrazolyl) | CF3 |
| 140 | CH2-(5-pyrazolyl) | CF3 |
| 141 | CH2-(2-oxazolyl) | CF3 |
| 142 | CH2-(3-oxazolyl) | CF3 |
| 143 | CH2-(3-isoxazolyl) | CF3 |
| 144 | CH2-(4-isoxazolyl) | CF3 |
| 145 | CH2-(5-isoxazolyl) | CF3 |
| 146 | CH2CH2OCH3 | CF3 |
| 147 | CH2CH2OCH2CH3 | CF3 |

TABLE B

| | R4 | R5 |
|---|---|---|
| 148 | CH2CH2CH2OCH3 | CF3 |
| 149 | CH2CH2CH2OCH2CH3 | CF3 |
| 150 | CH2CH2SCH3 | CF3 |
| 151 | CH2CH2SCH2CH3 | CF3 |
| 152 | CH2CH2CH2SCH3 | CF3 |
| 153 | CH2CH2CH2SCH2CH3 | CF3 |
| 154 | Me | CHF2 |

TABLE B-continued

R / C=N structure with R5 and R4

| | R4 | R5 |
|---|---|---|
| 155 | Et | CHF2 |
| 156 | n-Pr | CHF2 |
| 157 | i-Pr | CHF2 |
| 158 | t-Bu | CHF2 |
| 159 | n-Bu | CHF2 |
| 160 | n-Pentyl | CHF2 |
| 161 | n-Hexyl | CHF2 |
| 162 | cyclopropyl | CHF2 |
| 163 | cyclobutyl | CHF2 |
| 164 | cyclopentyl | CHF2 |
| 165 | cyclohexyl | CHF2 |
| 166 | CH=CH2 | CHF2 |
| 167 | CH2CH=CH2 | CHF2 |
| 168 | CH2C≡CH | CHF2 |
| 169 | CH2CH2C≡CH | CHF2 |
| 170 | CH2CHF2 | CHF2 |
| 171 | CH2CCF3 | CHF2 |
| 172 | CH2CH2Cl | CHF2 |
| 173 | CH2CHCl2 | CHF2 |
| 174 | 2-fluoro-2-chloroethyl | CHF2 |
| 175 | CH2CCl3 | CHF2 |
| 176 | CH2CH2CN | CHF2 |
| 177 | CH2CH2CH2CN | CHF2 |
| 178 | CH2CH(CN)CH2CN | CHF2 |
| 179 | CH2CH2OH | CHF2 |
| 180 | CH2CH2CH2OH | CHF2 |
| 181 | CH2CH(OH)CH2OH | CHF2 |
| 182 | CH2CH2NO2 | CHF2 |
| 183 | Phenyl | CHF2 |
| 184 | CH2-Phenyl | CHF2 |
| 185 | CH(Me)-Phenyl | CHF2 |
| 186 | C(Me2)-Phenyl | CHF2 |
| 187 | C(cyclopropyl)-Phenyl | CHF2 |
| 188 | CH2CH2-Phenyl | CHF2 |
| 189 | CH2-(2-Methylphenyl) | CHF2 |
| 190 | CH2-(3-Methylphenyl) | CHF2 |
| 191 | CH2-(4-Methylphenyl) | CHF2 |
| 192 | CH2-(2-Methoxylphenyl) | CHF2 |
| 193 | CH2-(3-Methoxylphenyl) | CHF2 |
| 194 | CH2-(4-Methoxylphenyl) | CHF2 |
| 195 | CH2-(2-fluorolphenyl) | CHF2 |
| 196 | CH2-(3-fluorolphenyl) | CHF2 |
| 197 | CH2-(4-fluorolphenyl) | CHF2 |
| 198 | CH2-(2-Chlorophenyl) | CHF2 |
| 199 | CH2-(3-Chlorophenyl) | CHF2 |
| 200 | CH2-(4-Chlorophenyl) | CHF2 |
| 201 | CH2-(2-Bromophenyl) | CHF2 |
| 202 | CH2-(3-Bromophenyl) | CHF2 |
| 203 | CH2-(4-Bromophenyl) | CHF2 |
| 204 | CH2-(2-iodophenyl) | CHF2 |
| 205 | CH2-(3-iodophenyl) | CHF2 |
| 206 | CH2-(4-iodophenyl) | CHF2 |
| 207 | CH2-(1-naphthalenyl) | CHF2 |
| 208 | CH2-(2-naphthalenyl) | CHF2 |
| 209 | naphthalen-1-ylmethyl | CHF2 |
| 210 | naphthalen-2-ylmethyl | CHF2 |
| 211 | quinolin-2-ylmethyl | CHF2 |
| 212 | quinolin-7-ylmethyl | CHF2 |
| 213 | isoquinolin-7-ylmethyl | CHF2 |
| 214 | isoquinolin-6-ylmethyl | CHF2 |
| 215 | quinolin-6-ylmethyl | CHF2 |
| 216 | quinolin-3-ylmethyl | CHF2 |
| 217 | isoquinolin-3-ylmethyl | CHF2 |
| 218 | isoquinolin-1-ylmethyl | CHF2 |
| 219 | isoquinolin-4-ylmethyl | CHF2 |
| 220 | quinolin-4-ylmethyl | CHF2 |
| 221 | quinolin-5-ylmethyl | CHF2 |
| 222 | isoquinolin-5-ylmethyl | CHF2 |
| 223 | isoquinolin-8-ylmethyl | CHF2 |
| 224 | quinolin-8-ylmethyl | CHF2 |
| 225 | CH2O-Phenyl | CHF2 |
| 226 | CH2CH2O-Phenyl | CHF2 |
| 227 | 2-pyridyl | CHF2 |
| 228 | 3-pyridyl | CHF2 |
| 229 | 4-pyridyl | CHF2 |
| 230 | CH2-(2-pyridyl) | CHF2 |
| 231 | CH2-(3-pyridyl) | CHF2 |
| 232 | CH2-(4-Chloro-3-pyridyl) | CHF2 |
| 233 | CH2-(4-pyridyl) | CHF2 |
| 234 | CH2-(2-thienyl) | CHF2 |
| 235 | CH2-(3-thienyl) | CHF2 |
| 236 | CH2-(2-furanyl) | CHF2 |
| 237 | CH2-(3-furanyl) | CHF2 |
| 238 | CH2-(2-tetrahydrofuranyl) | CHF2 |
| 239 | CH2-(3-tetrahydrofuranyl) | CHF2 |
| 240 | (1H-imidazol-2-yl)methyl | CHF2 |
| 241 | (1H-imidazol-1-yl)methyl | CHF2 |
| 242 | (1H-imidazol-4-yl)methyl | CHF2 |
| 243 | CH2-(2-thiazolyl) | CHF2 |
| 244 | CH2-(3-thiazolyl) | CHF2 |
| 245 | CH2-(2-pyrrolyl) | CHF2 |
| 246 | CH2-(3-pyrrolyl) | CHF2 |
| 247 | CH2-(5-methylpyrazol-1-yl) | CHF2 |
| 248 | CH2-(1-pyrazolyl) | CHF2 |
| 249 | CH2-(2-pyrazolyl) | CHF2 |
| 250 | CH2-(3-pyrazolyl) | CHF2 |
| 251 | CH2-(4-pyrazolyl) | CHF2 |
| 252 | CH2-(5-pyrazolyl) | CHF2 |
| 253 | CH2-(2-oxazolyl) | CHF2 |
| 254 | CH2-(3-oxazolyl | CHF2 |
| 255 | CH2-(3-isoxazolyl) | CHF2 |
| 256 | CH2-(4-isoxazolyl) | CHF2 |
| 257 | CH2-(5-isoxazolyl) | CHF2 |
| 258 | CH2CH2OCH3 | CHF2 |
| 259 | CH2CH2OCH2CH3 | CHF2 |
| 260 | CH2CH2CH2OCH3 | CHF2 |

TABLE B-continued

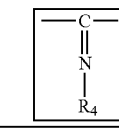

| | R4 | R5 |
|---|---|---|
| 261 | CH2CH2CH2OCH2CH3 | CHF2 |
| 262 | CH2CH2SCH3 | CHF2 |
| 263 | CH2CH2SCH2CH3 | CHF2 |
| 264 | CH2CH2CH2SCH3 | CHF2 |
| 265 | CH2CH2CH2SCH2CH3 | CHF2 |
| 266 | Me | CF2Cl |
| 267 | Et | CF2Cl |
| 268 | n-Pr | CF2Cl |
| 269 | i-Pr | CF2Cl |
| 270 | t-Bu | CF2Cl |
| 271 | n-Bu | CF2Cl |
| 272 | n-Pentyl | CF2Cl |
| 273 | n-Hexyl | CF2Cl |
| 274 | cyclopropyl | CF2Cl |
| 275 | cyclobutyl | CF2Cl |
| 276 | cyclopentyl | CF2Cl |
| 277 | cyclohexyl | CF2Cl |
| 278 | CH=CH2 | CF2Cl |
| 279 | CH2CH=CH2 | CF2Cl |
| 280 | CH2C≡CH | CF2Cl |
| 281 | CH2CH2C≡CH | CF2Cl |
| 282 | CH2CHF2 | CF2Cl |
| 283 | CH2CCF3 | CF2Cl |
| 284 | CH2CH2Cl | CF2Cl |
| 285 | CH2CHCl2 | CF2Cl |
| 286 | 2-fluoro-2-chloroethyl | CF2Cl |
| 287 | CH2CCl3 | CF2Cl |
| 288 | CH2CH2CN | CF2Cl |
| 289 | CH2CH2CH2CN | CF2Cl |
| 290 | CH2CH(CN)CH2CN | CF2Cl |
| 291 | CH2CH2OH | CF2Cl |
| 292 | CH2CH2CH2OH | CF2Cl |
| 293 | CH2CH(OH)CH2OH | CF2Cl |
| 294 | CH2CH2NO2 | CF2Cl |
| 295 | Phenyl | CF2Cl |
| 296 | CH2-Phenyl | CF2Cl |
| 297 | CH(Me)-Phenyl | CF2Cl |
| 298 | C(Me2)-Phenyl | CF2Cl |
| 299 | C(cyclopropyl)-Phenyl | CF2Cl |
| 300 | CH2CH2-Phenyl | CF2Cl |
| 301 | CH2-(2-Methylphenyl) | CF2Cl |
| 302 | CH2-(3-Methylphenyl) | CF2Cl |
| 303 | CH2-(4-Methylphenyl) | CF2Cl |
| 304 | CH2-(2-Methoxylphenyl) | CF2Cl |
| 305 | CH2-(3-Methoxylphenyl) | CF2Cl |
| 306 | CH2-(4-Methoxylphenyl) | CF2Cl |
| 307 | CH2-(2-fluorolphenyl) | CF2Cl |
| 308 | CH2-(3-fluorolphenyl) | CF2Cl |
| 309 | CH2-(4-fluorolphenyl) | CF2Cl |

TABLE B

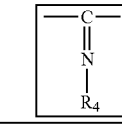

| | R4 | R5 |
|---|---|---|
| 310 | CH2-(2-Chlorophenyl) | CF2Cl |
| 311 | CH2-(3-Chlorophenyl) | CF2Cl |
| 312 | CH2-(4-Chlorophenyl) | CF2Cl |
| 313 | CH2-(2-Bromophenyl) | CF2Cl |

TABLE B-continued

| | R4 | R5 |
|---|---|---|
| 314 | CH2-(3-Bromophenyl) | CF2Cl |
| 315 | CH2-(4-Bromophenyl) | CF2Cl |
| 316 | CH2-(2-iodophenyl) | CF2Cl |
| 317 | CH2-(3-iodophenyl) | CF2Cl |
| 318 | CH2-(4-iodophenyl) | CF2Cl |
| 319 | CH2-(1-naphthalenyl) | CF2Cl |
| 320 | CH2-(2-naphthalenyl) | CF2Cl |
| 321 | naphthalen-1-ylmethyl | CF2Cl |
| 322 | naphthalen-2-ylmethyl | CF2Cl |
| 323 | quinolin-2-ylmethyl | CF2Cl |
| 324 | quinolin-7-ylmethyl | CF2Cl |
| 325 | isoquinolin-7-ylmethyl | CF2Cl |
| 326 | isoquinolin-6-ylmethyl | CF2Cl |
| 327 | quinolin-6-ylmethyl | CF2Cl |
| 328 | quinolin-3-ylmethyl | CF2Cl |
| 329 | isoquinolin-3-ylmethyl | CF2Cl |
| 330 | isoquinolin-1-ylmethyl | CF2Cl |
| 331 | isoquinolin-4-ylmethyl | CF2Cl |
| 332 | quinolin-4-ylmethyl | CF2Cl |
| 333 | quinolin-5-ylmethyl | CF2Cl |
| 334 | isoquinolin-5-ylmethyl | CF2Cl |
| 335 | isoquinolin-8-ylmethyl | CF2Cl |
| 336 | quinolin-8-ylmethyl | CF2Cl |
| 337 | CH2O-Phenyl | CF2Cl |
| 338 | CH2CH2O-Phenyl | CF2Cl |
| 339 | 2-pyridyl | CF2Cl |
| 340 | 3-pyridyl | CF2Cl |
| 341 | 4-pyridyl | CF2Cl |
| 342 | CH2-(2-pyridyl) | CF2Cl |
| 343 | CH2-(3-pyridyl) | CF2Cl |
| 344 | CH2-(4-Chloro-3-pyridyl) | CF2Cl |
| 345 | CH2-(4-pyridyl) | CF2Cl |
| 346 | CH2-(2-thienyl) | CF2Cl |
| 347 | CH2-(3-thienyl) | CF2Cl |
| 348 | CH2-(2-furanyl) | CF2Cl |
| 349 | CH2-(3-furanyl) | CF2Cl |
| 350 | CH2-(2-tetrahydrofuranyl) | CF2Cl |
| 351 | CH2-(3-tetrahydrofuranyl) | CF2Cl |
| 352 | (1H-imidazol-2-yl)methyl | CF2Cl |
| 353 | (1H-imidazol-1-yl)methyl | CF2Cl |
| 354 | (1H-imidazol-4-yl)methyl | CF2Cl |
| 355 | CH2-(2-thiazolyl) | CF2Cl |
| 356 | CH2-(3-thiazolyl) | CF2Cl |
| 357 | CH2-(2-pyrrolyl) | CF2Cl |
| 358 | CH2-(3-pyrrolyl) | CF2Cl |
| 359 | CH2-(1-pyrazolyl) | CF2Cl |
| 360 | CH2-(2-pyrazolyl) | CF2Cl |
| 361 | CH2-(3-pyrazolyl) | CF2Cl |
| 362 | CH2-(4-pyrazolyl) | CF2Cl |
| 363 | CH2-(5-pyrazolyl) | CF2Cl |

TABLE B

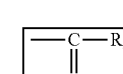

| | R4 | R5 |
|---|---|---|
| 364 | CH2-(5-pyrazolyl) | CF2Cl |
| 365 | CH2-(2-oxazolyl) | CF2Cl |
| 366 | CH2-(3-oxazolyl) | CF2Cl |

TABLE B-continued

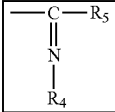

| | R4 | R5 |
|---|---|---|
| 367 | CH2-(3-isoxazolyl) | CF2Cl |
| 368 | CH2-(4-isoxazolyl) | CF2Cl |
| 369 | CH2-(5-isoxazolyl) | CF2Cl |
| 370 | CH2CH2OCH3 | CF2Cl |
| 371 | CH2CH2OCH2CH3 | CF2Cl |
| 372 | CH2CH2CH2OCH3 | CF2Cl |
| 373 | CH2CH2CH2OCH2CH3 | CF2Cl |
| 374 | CH2CH2SCH3 | CF2Cl |
| 375 | CH2CH2SCH2CH3 | CF2Cl |
| 376 | CH2CH2CH2SCH3 | CF2Cl |
| 377 | CH2CH2CH2SCH2CH3 | CF2Cl |
| 378 | Me | CF2CF3 |
| 379 | Et | CF2CF3 |
| 380 | n-Pr | CF2CF3 |
| 381 | i-Pr | CF2CF3 |
| 382 | t-Bu | CF2CF3 |
| 383 | n-Bu | CF2CF3 |
| 384 | n-Pentyl | CF2CF3 |
| 385 | n-Hexyl | CF2CF3 |
| 386 | cyclopropyl | CF2CF3 |
| 387 | cyclobutyl | CF2CF3 |
| 388 | cyclopentyl | CF2CF3 |
| 389 | cyclohexyl | CF2CF3 |
| 390 | CH=CH2 | CF2CF3 |
| 391 | CH2CH=CH2 | CF2CF3 |
| 392 | CH2C≡CH | CF2CF3 |
| 393 | CH2CH2C≡CH | CF2CF3 |
| 394 | CH2CHF2 | CF2CF3 |
| 395 | CH2CCF3 | CF2CF3 |
| 396 | CH2CH2Cl | CF2CF3 |
| 397 | CH2CHCl2 | CF2CF3 |
| 398 | 2-fluoro-2-chloroethyl | CF2CF3 |
| 399 | CH2CCl3 | CF2CF3 |
| 400 | CH2CH2CN | CF2CF3 |
| 401 | CH2CH2CH2CN | CF2CF3 |
| 402 | CH2CH(CN)CH2CN | CF2CF3 |
| 403 | CH2CH2OH | CF2CF3 |
| 404 | CH2CH2CH2OH | CF2CF3 |
| 405 | CH2CH(OH)CH2OH | CF2CF3 |
| 406 | CH2CH2NO2 | CF2CF3 |
| 407 | Phenyl | CF2CF3 |
| 408 | CH2-Phenyl | CF2CF3 |
| 409 | CH(Me)-Phenyl | CF2CF3 |
| 410 | C(Me2)-Phenyl | CF2CF3 |
| 411 | C(cyclopropyl)-Phenyl | CF2CF3 |
| 412 | CH2CH2-Phenyl | CF2CF3 |
| 413 | CH2-(2-Methylphenyl) | CF2CF3 |
| 414 | CH2-(3-Methylphenyl) | CF2CF3 |
| 415 | CH2-(4-Methylphenyl) | CF2CF3 |
| 416 | CH2-(2-Methoxylphenyl) | CF2CF3 |
| 417 | CH2-(3-Methoxylphenyl) | CF2CF3 |

TABLE B

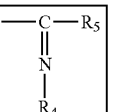

| | R4 | R5 |
|---|---|---|
| 418 | CH2-(4-Methoxylphenyl) | CF2CF3 |
| 419 | CH2-(2-fluorolphenyl) | CF2CF3 |

TABLE B-continued

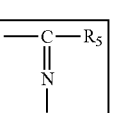

| | R4 | R5 |
|---|---|---|
| 420 | CH2-(3-fluorolphenyl) | CF2CF3 |
| 421 | CH2-(4-fluorolphenyl) | CF2CF3 |
| 422 | CH2-(2-Chlorophenyl) | CF2CF3 |
| 423 | CH2-(3-Chlorophenyl) | CF2CF3 |
| 424 | CH2-(4-Chlorophenyl) | CF2CF3 |
| 425 | CH2-(2-Bromophenyl) | CF2CF3 |
| 426 | CH2-(3-Bromophenyl) | CF2CF3 |
| 427 | CH2-(4-Bromophenyl) | CF2CF3 |
| 428 | CH2-(2-iodophenyl) | CF2CF3 |
| 429 | CH2-(3-iodophenyl) | CF2CF3 |
| 430 | CH2-(4-iodophenyl) | CF2CF3 |
| 431 | CH2-(1-naphthalenyl) | CF2CF3 |
| 432 | CH2-(2-naphthalenyl) | CF2CF3 |
| 433 | naphthalen-1-ylmethyl | CF2CF3 |
| 434 | naphthalen-2-ylmethyl | CF2CF3 |
| 435 | quinolin-2-ylmethyl | CF2CF3 |
| 436 | quinolin-7-ylmethyl | CF2CF3 |
| 437 | isoquinolin-7-ylmethyl | CF2CF3 |
| 438 | isoquinolin-6-ylmethyl | CF2CF3 |
| 439 | quinolin-6-ylmethyl | CF2CF3 |
| 440 | quinolin-3-ylmethyl | CF2CF3 |
| 441 | isoquinolin-3-ylmethyl | CF2CF3 |
| 442 | isoquinolin-1-ylmethyl | CF2CF3 |
| 443 | isoquinolin-4-ylmethyl | CF2CF3 |
| 444 | quinolin-4-ylmethyl | CF2CF3 |
| 445 | quinolin-5-ylmethyl | CF2CF3 |
| 446 | isoquinolin-5-ylmethyl | CF2CF3 |
| 447 | isoquinolin-8-ylmethyl | CF2CF3 |
| 448 | quinolin-8-ylmethyl | CF2CF3 |
| 449 | CH2O-Phenyl | CF2CF3 |
| 450 | CH2CH2O-Phenyl | CF2CF3 |
| 451 | 2-pyridyl | CF2CF3 |
| 452 | 3-pyridyl | CF2CF3 |
| 453 | 4-pyridyl | CF2CF3 |
| 454 | CH2-(2-pyridyl) | CF2CF3 |
| 455 | CH2-(3-pyridyl) | CF2CF3 |
| 456 | CH2-(4-Chloro-3-pyridyl) | CF2CF3 |
| 457 | CH2-(4-pyridyl) | CF2CF3 |
| 458 | CH2-(2-thienyl) | CF2CF3 |
| 459 | CH2-(3-thienyl) | CF2CF3 |
| 460 | CH2-(2-furanyl) | CF2CF3 |
| 461 | CH2-(3-furanyl) | CF2CF3 |
| 462 | CH2-(2-tetrahydrofuranyl) | CF2CF3 |
| 463 | CH2-(3-tetrahydrofuranyl) | CF2CF3 |
| 464 | (1H-imidazol-2-yl)methyl | CF2CF3 |
| 465 | (1H-imidazol-1-yImethyl | CF2CF3 |
| 466 | (1H-imidazol-4-yl)methyl | CF2CF3 |
| 467 | CH2-(2-thiazolyl) | CF2CF3 |
| 468 | CH2-(3-thiazolyl) | CF2CF3 |
| 469 | CH2-(2-pyrrolyl) | CF2CF3 |
| 470 | CH2-(3-pyrrolyl) | CF2CF3 |
| 471 | CH2-(5-methylpyrazolyl-1-yl) | CF2CF3 |

TABLE B

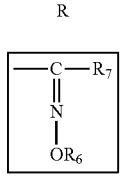

| | R4 | R5 |
|---|---|---|
| 472 | CH2-(1-pyrazolyl) | CF2CF3 |
| 473 | CH2-(2-pyrazolyl) | CF2CF3 |
| 474 | CH2-(3-pyrazolyl) | CF2CF3 |
| 475 | CH2-(4-pyrazolyl) | CF2CF3 |
| 476 | CH2-(5-pyrazolyl) | CF2CF3 |
| 477 | CH2-(2-oxazolyl) | CF2CF3 |
| 478 | CH2-(3-oxazolyl) | CF2CF3 |
| 479 | CH2-(3-isoxazolyl) | CF2CF3 |
| 480 | CH2-(4-isoxazolyl) | CF2CF3 |
| 481 | CH2-(5-isoxazolyl) | CF2CF3 |
| 482 | CH2CH2OCH3 | CF2CF3 |
| 483 | CH2CH2OCH2CH3 | CF2CF3 |
| 484 | CH2CH2CH2OCH3 | CF2CF3 |
| 485 | CH2CH2CH2OCH2CH3 | CF2CF3 |
| 486 | CH2CH2SCH3 | CF2CF3 |
| 487 | CH2CH2SCH2CH3 | CF2CF3 |
| 488 | CH2CH2CH2SCH3 | CF2CF3 |
| 489 | CH2CH2CH2SCH2CH3 | CF2CF3 |
| 490 | Me | CH2CF3 |
| 491 | Et | CH2Cl |
| 492 | n-Pr | CHCl2 |
| 493 | i-Pr | CCl3 |
| 494 | t-Bu | CHClBr |
| 495 | n-Bu | CHBr2 |
| 496 | n-Pentyl | CH=CH2 |
| 497 | n-Hexyl | CH2CH=CH2 |
| 498 | cyclopropyl | CH2C≡CH |

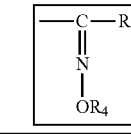

| | R6 | R7 |
|---|---|---|
| 499 | H | CF3 |
| 500 | Me | CF3 |
| 501 | Et | CF3 |
| 502 | n-Pr | CF3 |
| 503 | i-Pr | CF3 |
| 504 | t-Bu | CF3 |
| 505 | cyclopropyl | CF3 |
| 506 | CH=CH2 | CF3 |
| 507 | CH2CH=CH2 | CF3 |
| 508 | CH2C≡CH | CF3 |
| 509 | Ph | CF3 |
| 510 | CH2Ph | CF3 |
| 511 | COMe | CF3 |
| 512 | COEt | CF3 |
| 513 | CO-n-Pr | CF3 |
| 514 | CO-i-Pr | CF3 |
| 515 | CO-cyclopropyl | CF3 |
| 516 | COCH=CH2 | CF3 |
| 517 | COCH2CH=CH2 | CF3 |
| 518 | COCH2C≡CH | CF3 |
| 519 | COPh | CF3 |
| 520 | CO-(2-pyridyl) | CF3 |
| 521 | CO-(3-pyridyl) | CF3 |
| 522 | CO-(4-pyridyl) | CF3 |
| 523 | COOMe | CF3 |
| 524 | COOEt | CF3 |
| 525 | COO-i-Pr | CF3 |
| 526 | COO-t-Bu | CF3 |
| 527 | COOPh | CF3 |
| 528 | SO2Me | CF3 |
| 529 | SO2Et | CF3 |
| 530 | SO2Ph | CF3 |
| 531 | SO2-(4-methylphenyl) | CF3 |
| 532 | NHMe | CF3 |
| 533 | NHEt | CF3 |
| 534 | NH-n-Pr | CF3 |
| 535 | NHCH2CH2Cl | CF3 |
| 536 | NHCH2Ph | CF3 |
| 537 | N(Me)2 | CF3 |
| 538 | Me | CHF2 |
| 539 | Et | CHF2 |
| 540 | n-Pr | CHF2 |
| 541 | i-Pr | CHF2 |
| 542 | t-Bu | CHF2 |
| 543 | cyclopropyl | CHF2 |
| 544 | CH=CH2 | CHF2 |
| 545 | CH2CH=CH2 | CHF2 |
| 546 | CH2C≡CH | CHF2 |
| 547 | Ph | CHF2 |
| 548 | CH2Ph | CHF2 |
| 549 | COMe | CHF2 |
| 550 | COEt | CHF2 |
| 551 | CO-n-Pr | CHF2 |
| 552 | CO-i-Pr | CHF2 |
| 553 | CO-cyclopropyl | CHF2 |
| 554 | COCH=CH2 | CHF2 |
| 555 | COCH2CH=CH2 | CHF2 |
| 556 | COCH2C≡CH | CHF2 |
| 557 | COPh | CHF2 |
| 558 | CO-(2-pyridyl) | CHF2 |
| 559 | CO-(3-pyridyl) | CHF2 |
| 560 | CO-(4-pyridyl) | CHF2 |
| 561 | COOMe | CHF2 |
| 562 | COOEt | CHF2 |
| 563 | COO-i-Pr | CHF2 |
| 564 | COO-t-Bu | CHF2 |
| 565 | COOPh | CHF2 |
| 566 | SO2Me | CHF2 |
| 567 | SO2Et | CHF2 |
| 568 | SO2Ph | CHF2 |
| 569 | SO2-(4-methylphenyl) | CHF2 |
| 570 | Me | CF2Cl |
| 571 | Et | CF2Cl |
| 572 | n-Pr | CF2Cl |
| 573 | i-Pr | CF2Cl |
| 574 | t-Bu | CF2Cl |

TABLE B

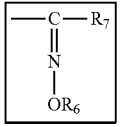

| | R6 | R7 |
|---|---|---|
| 575 | cyclopropyl | CF2Cl |
| 576 | CH=CH2 | CF2Cl |
| 577 | CH2CH=CH2 | CF2Cl |
| 578 | CH2C≡CH | CF2Cl |
| 579 | Ph | CF2Cl |
| 580 | CH2Ph | CF2Cl |
| 581 | COMe | CF2Cl |
| 582 | COEt | CF2Cl |
| 583 | CO-n-Pr | CF2Cl |
| 584 | CO-i-Pr | CF2Cl |
| 585 | CO-cyclopropyl | CF2Cl |
| 586 | COCH=CH2 | CF2Cl |
| 587 | COCH2CH=CH2 | CF2Cl |
| 588 | COCH2C≡CH | CF2Cl |
| 589 | COPh | CF2Cl |
| 590 | CO-(2-pyridyl) | CF2Cl |
| 591 | CO-(3-pyridyl) | CF2Cl |
| 592 | CO-(4-pyridyl) | CF2Cl |
| 593 | COOMe | CF2Cl |
| 594 | COOEt | CF2Cl |
| 595 | COO-i-Pr | CF2Cl |
| 596 | COO-t-Bu | CF2Cl |
| 597 | COOPh | CF2Cl |
| 598 | SO2Me | CF2Cl |
| 599 | SO2Et | CF2Cl |
| 600 | SO2Ph | CF2Cl |
| 601 | SO2-(4-methylphenyl) | CF2Cl |
| 602 | Me | CF2CF3 |
| 603 | Et | CF2CF3 |
| 604 | n-Pr | CF2CF3 |
| 605 | i-Pr | CF2CF3 |
| 606 | t-Bu | CF2CF3 |
| 607 | cyclopropyl | CF2CF3 |
| 608 | CH=CH2 | CF2CF3 |
| 609 | CH2CH=CH2 | CF2CF3 |
| 610 | CH2C≡CH | CF2CF3 |
| 611 | Ph | CF2CF3 |
| 612 | CH2Ph | CF2CF3 |
| 613 | COMe | CF2CF3 |
| 614 | COEt | CF2CF3 |
| 615 | CO-n-Pr | CF2CF3 |
| 616 | CO-i-Pr | CF2CF3 |
| 617 | CO-cyclopropyl | CF2CF3 |
| 618 | COCH=CH2 | CF2CF3 |
| 619 | COCH2CH=CH2 | CF2CF3 |
| 620 | COCH2C≡CH | CF2CF3 |
| 621 | COPh | CF2CF3 |
| 622 | CO-(2-pyridyl) | CF2CF3 |
| 623 | CO-(3-pyridyl) | CF2CF3 |
| 624 | CO-(4-pyridyl) | CF2CF3 |
| 625 | COOMe | CF2CF3 |
| 626 | COOEt | CF2CF3 |
| 627 | COO-i-Pr | CF2CF3 |

TABLE B

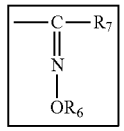

| | R6 | R7 |
|---|---|---|
| 628 | COO-t-Bu | CF2CF3 |
| 629 | COOPh | CF2CF3 |
| 630 | SO2Me | CF2CF3 |
| 631 | SO2Et | CF2CF3 |
| 632 | SO2Ph | CF2CF3 |
| 633 | SO2-(4-methylphenyl) | CF2CF3 |
| 634 | Me | CH2CF3 |
| 635 | Et | CH2Cl |
| 636 | n-Pr | CHCl2 |
| 637 | i-Pr | CCl3 |
| 638 | t-Bu | CHClBr |
| 639 | cyclopropyl | CHBr2 |
| 640 | CH=CH2 | CH=CH2 |
| 641 | CH2CH=CH2 | CH2CH=CH2 |
| 642 | CH2C≡CH | CH2C≡CH |

TABLE B

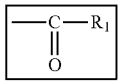

| | R1 |
|---|---|
| 643 | C6F5 |
| 644 | CH2OCH2C6H5 |

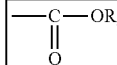

| | R2 |
|---|---|
| 645 | CH2C6H5 |
| 646 | isopropyl |
| 697 | CH2CH2CH=CH2 |

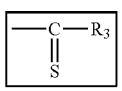

| | R3 |
|---|---|
| 648 | C6F5 |
| 649 | CH2OCH2C6H5 |

TABLE B

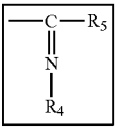

| | R4 | R5 |
|---|---|---|
| 650 | Ethyl | CH2CF3 |
| 651 | n-Propyl | CH2CF3 |
| 652 | iso-Propyl | CH2CF3 |
| 653 | t-Butyl | CH2CF3 |
| 654 | n-Butyl | CH2CF3 |
| 655 | cyclopropyl | CH2CF3 |
| 656 | cyclopentyl | CH2CF3 |
| 657 | cyclohexyl | CH2CF3 |
| 658 | n-hexa decyl | CF3 |
| 659 | n-tridecyl | CF3 |
| 660 | CH(CH3)CH2CH3 | CF3 |
| 661 | CH(CH3)CH2CH2CH3 | CF3 |
| 662 | CH(CH3)-isopropyl | CF3 |
| 663 | 1-phenylethyl | CF3 |
| 664 | 1,2,3,4-tetrahydronaphthalen-1-yl | CF3 |
| 665 | 1-(naphthalen-1-yl)ethyl | CF3 |
| 666 | 1-(naphthalen-1-yl)propyl | CF3 |
| 667 | 1-(furan-2-yl)ethyl | CF3 |
| 668 | 3.3-dimethylbutan-2-yl | CF3 |
| 669 | 1-(thiophen-2-yl)ethyl | CF3 |
| 670 | CH2CH2F | CF3 |
| 671 | n-Octyl | CF3 |
| 672 | n-Octyl | CHF2 |
| 673 | n-Octyl | CF2Cl |
| 674 | n-Octyl | CF2CF3 |
| 675 | n-Octyl | CF2CF3 |
| 676 | CH(C6H5)2 | CF3 |
| 677 | CH(C6H5)2 | CHF2 |
| 678 | CH(C6H5)2 | CF2Cl |
| 679 | CH(C6H5)2 | CF2CF3 |
| 680 | CH(C6H5)2 | CH2CF3 |
| 681 | CH(CH2CH3)2 | CF3 |
| 682 | CH(CH2CH3)2 | CHF2 |
| 683 | CH(CH2CH3)2 | CF2Cl |
| 684 | CH(CH2CH3)2 | CF2CF3 |
| 685 | CH(CH2CH3)2 | CH2CF3 |
| 686 | CH(CH2CH2CH3)2 | CF3 |
| 687 | CH(CH2CH2CH3)2 | CHF2 |
| 688 | CH(CH2CH2CH3)2 | CF2Cl |
| 689 | CH(CH2CH2CH3)2 | CF2CF3 |
| 690 | CH(CH2CH2CH3)2 | CF2CF3 |

TABLE B

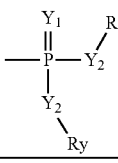

| | Y1 | Y2 | Ry |
|---|---|---|---|
| 691 | O | O | Methyl |
| 692 | O | O | Ethyl |
| 693 | O | O | Propyl |
| 694 | O | O | isopropyl |
| 695 | S | O | Methyl |
| 696 | S | O | Ethyl |
| 697 | S | O | Propyl |
| 698 | S | O | isopropyl |
| 699 | S | S | Methyl |
| 700 | S | S | Ethyl |

TABLE B-continued

| | | | |
|---|---|---|---|
| 701 | S | S | Propyl |
| 702 | S | S | isopropyl |

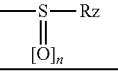

| | n | Rz |
|---|---|---|
| 703 | 1 | CF3 |
| 704 | 1 | CF2CF3 |
| 705 | 1 | CH2CF3 |
| 706 | 1 | Me |
| 707 | 2 | CF3 |
| 708 | 2 | CF2CF3 |
| 709 | 2 | CH2CF3 |
| 710 | 2 | Me |

Examples of preferred compounds of Formula (I) include compounds shown in the following Tables.

TABLE 36

| Compound No | Ar | A | Y | R |
|---|---|---|---|---|
| 266-2 | 6-Chloro-3-pyridyl | A-38 | H | COCF3 |
| 444-2 | 2-chloro-5-thiazolyl | A-38 | H | COCF3 |
| 190-2 | 6-Chloro-3-pyridyl | A-13 | H | COCF3 |
| 201-2 | 6-Chloro-3-pyridyl | A-14 | H | COCF3 |
| 223-2 | 6-Chloro-3-pyridyl | A-16 | H | COCF3 |
| 146-2 | 6-Chloro-3-pyridyl | A-1 | 3-OH | COCF3 |
| 224-2 | 2-chloro-5-thiazolyl | A-16 | H | COCF3 |
| 102-2 | 6-Chloro-3-pyridyl | A-1 | 3-CN | COCF3 |
| 212-2 | 6-Chloro-3-pyridyl | A-15 | H | COCF3 |
| 1-20 | 6-Chloro-3-pyridyl | A-1 | H | CSCF3 |
| 12-2 | 2-Chloro-4-pyridyl | A-1 | H | COCF3 |
| 213-2 | 2-chloro-5-thiazolyl | A-15 | H | COCF3 |
| 1-17 | 6-Chloro-3-pyridyl | A-1 | H | COOCH2CF3 |
| 1-18 | 6-Chloro-3-pyridyl | A-1 | H | COOCH(Me)CF3 |
| 1-19 | 6-Chloro-3-pyridyl | A-1 | H | COOCH(CF3)2 |
| 7-2 | 5-Chloro-pyrazin-2-yl | A-1 | H | COCF3 |
| 1-13 | 6-Chloro-3-pyridyl | A-1 | H | COCH2CF3 |
| 168-2 | 6-Chloro-3-pyridyl | A-1 | 5-OH | COCF3 |
| 1-21 | 6-Chloro-3-pyridyl | A-1 | H | CSCHF2 |
| 3-20 | 6-Fluoro-3-pyridyl | A-1 | H | CSCF3 |
| 4-20 | 6-Bromo-3-pyridyl | A-1 | H | CSCF3 |
| 3-3 | 6-Fluoro-3-pyridyl | A-1 | H | COCHF2 |
| 4-3 | 6-Bromo-3-pyridyl | A-1 | H | COCHF2 |
| 5-5 | 6-Chloro-5-fluoro-3-pyridyl | A-1 | H | COCF2CF3 |
| 6-5 | 2-Chloro-5-pyrimidinyl | A-1 | H | COCF2CF3 |
| 1-22 | 6-Chloro-3-pyridyl | A-1 | H | CSCF2Cl |

TABLE 36-continued

| Compound No | Ar | A | Y | R |
|---|---|---|---|---|
| 1-23 | 6-Chloro-3-pyridyl | A-1 | H | CSCF2CF3 |
| 5-20 | 6-Chloro-5-fluoro-3-pyridyl | A-1 | H | CSCF3 |
| 5-3 | 6-Chloro-5-fluoro-3-pyridyl | A-1 | H | COCHF2 |
| 6-3 | 2-Chloro-5-pyrimidinyl | A-1 | H | COCHF2 |
| 8-2 | 6-Chloro-pyridazin-3-yl | A-1 | H | COCF3 |
| 5-4 | 6-Chloro-5-fluoro-3-pyridyl | A-1 | H | COCF2Cl |
| 4-4 | 6-Bromo-3-pyridyl | A-1 | H | COCF2Cl |
| 6-4 | 2-Chloro-5-pyrimidinyl | A-1 | H | COCF2Cl |
| 4-5 | 6-Bromo-3-pyridyl | A-1 | H | COCF2CF3 |
| 2-20 | 2-chloro-5-thiazolyl | A-1 | H | CSCF3 |
| 10-20 | 6-tri-fluoromethyl-3-pyridyl | A-1 | H | CSCF3 |
| 3-4 | 6-Fluoro-3-pyridyl | A-1 | H | COCF2Cl |
| 3-5 | 6-Fluoro-3-pyridyl | A-1 | H | COCF2CF3 |
| 11-20 | 3-THF | A-1 | H | CSCF3 |
| 1-14 | 6-Chloro-3-pyridyl | A-1 | H | COCH=CH2 |
| 1-37 | 6-Chloro-3-pyridyl | A-1 | H | CSEt |
| 1-39 | 6-Chloro-3-pyridyl | A-1 | H | CS—i-Pr |
| 1-40 | 6-Chloro-3-pyridyl | A-1 | H | CS-cyclopropyl |
| 1-15 | 6-Chloro-3-pyridyl | A-1 | H | COCH2C≡CH |
| 1-35 | 6-Chloro-3-pyridyl | A-1 | H | CSCH2CH2Ph |
| 1-501 | 6-Chloro-3-pyridyl | A-1 | H | C(=NOEt)CF3 |
| 1-499 | 6-Chloro-3-pyridyl | A-1 | H | C(=NOH)CF3 |
| 1-510 | 6-Chloro-3-pyridyl | A-1 | H | C(=NOCH2Ph)CF3 |
| 1-511 | 6-Chloro-3-pyridyl | A-1 | H | C(=NOCOMe)CF3 |
| 1-519 | 6-Chloro-3-pyridyl | A-1 | H | C(=NOCOPh)CF3 |
| 1-523 | 6-Chloro-3-pyridyl | A-1 | H | C(=NOCOOMe)CF3 |

TABLE 37

| Compound No | Ar | A | Y | R |
|---|---|---|---|---|
| 1-528 | 6-Chloro-3-pyridyl | A-1 | H | C(=NOSO2Me)CF3 |
| 1-531 | 6-Chloro-3-pyridyl | A-1 | H | C(=NOSO2-(4-Methylphenyl))CF3 |
| 1-507 | 6-Chloro-3-pyridyl | A-1 | H | C(=NOCH2CH=CH2)CF3 |
| 1-516 | 6-Chloro-3-pyridyl | A-1 | H | C(=NOCOCH=CH2)CF3 |
| 1-518 | 6-Chloro-3-pyridyl | A-1 | H | C(=NOCOCH2C≡CH)CF3 |
| 1-527 | 6-Chloro-3-pyridyl | A-1 | H | C(=NOCOOPh)CF3 |
| 1-521 | 6-Chloro-3-pyridyl | A-1 | H | C(=NOCO-3-pyr)CF3 |
| 1-43 | 6-Chloro-3-pyridyl | A-1 | H | C(=NEt)CF3 |
| 1-536 | 6-Chloro-3-pyridyl | A-1 | H | C(=NOCONHCH2Ph)CF3 |
| 1-42 | 6-Chloro-3-pyridyl | A-1 | H | C(=NMe)CF3 |
| 1-500 | 6-Chloro-3-pyridyl | A-1 | H | C(=NOMe)CF3 |
| 1-504 | 6-Chloro-3-pyridyl | A-1 | H | C(=NOtBu)CF3 |
| 1-534 | 6-Chloro-3-pyridyl | A-1 | H | C(=NOCONHnPr)CF3 |
| 1-535 | 6-Chloro-3-pyridyl | A-1 | H | C(=NOCONHCH2CH2Cl)CF3 |
| 1-72 | 6-Chloro-3-pyridyl | A-1 | H | C(=NCH2Ph)CF3 |
| 1-150 | 6-Chloro-3-pyridyl | A-1 | H | C(=NCH2CH2SMe)CF3 |
| 1-67 | 6-Chloro-3-pyridyl | A-1 | H | C(=NCH2CH2OH) |
| 1-515 | 6-Chloro-3-pyridyl | A-1 | H | C(=NOCO-cyclopropyl)CF3 |
| 1-56 | 6-Chloro-3-pyridyl | A-1 | H | C(=NCH2C≡CH)CF3 |
| 1-512 | 6-Chloro-3-pyridyl | A-1 | H | C(=NOCOCH2CH3)CF3 |
| 1-514 | 6-Chloro-3-pyridyl | A-1 | H | C(=NOCOiPr)CF3 |
| 1-50 | 6-Chloro-3-pyridyl | A-1 | H | C(=N-cyclopropyl)CF3 |
| 1-114 | 6-Chloro-3-pyridyl | A-1 | H | C(=NCH2CH2OPh)CF3 |
| 1-44 | 6-Chloro-3-pyridyl | A-1 | H | C(=N—n-Pr)CF3 |
| 1-118 | 6-Chloro-3-pyridyl | A-1 | H | C(=NCH2-(2-pyridyl))CF3 |
| 1-119 | 6-Chloro-3-pyridyl | A-1 | H | C(=NCH2-(3-pyridyl))CF3 |
| 1-47 | 6-Chloro-3-pyridyl | A-1 | H | C(=N—n-Bu)CF3 |
| 1-55 | 6-Chloro-3-pyridyl | A-1 | H | C(=N—CH2CH=CH2)CF3 |
| 1-122 | 6-Chloro-3-pyridyl | A-1 | H | C(=NCH2-(2-thienyl))CF3 |
| 1-45 | 6-Chloro-3-pyridyl | A-1 | H | C(=N—i-Pr)CF3 |
| 1-124 | 6-Chloro-3-pyridyl | A-1 | H | C(=NCH2-(2-furanyl))CF3 |
| 1-126 | 6-Chloro-3-pyridyl | A-1 | H | C(=NCH2-(2-tetrahydrofuranyl))CF3 |
| 1-64 | 6-Chloro-3-pyridyl | A-1 | H | C(=NCH2CN)CF3 |
| 1-146 | 6-Chloro-3-pyridyl | A-1 | H | C(=NCH2CH2OCH3)CF3 |
| 1-52 | 6-Chloro-3-pyridyl | A-1 | H | C(=N-cyclopentyl)CF3 |
| 1-121 | 6-Chloro-3-pyridyl | A-1 | H | C(=NCH2-(4-pyridyl))CF3 |
| 1-53 | 6-Chloro-3-pyridyl | A-1 | H | C(=N-cyclohexyl)CF3 |
| 1-76 | 6-Chloro-3-pyridyl | A-1 | H | C(=NCH2CH2Ph)CF3 |
| 267-2 | 6-Chloro-3-pyridyl | A-39 | H | COCF3 |
| 253-2 | 6-Chloro-3-pyridyl | A-25 | H | COCF3 |
| 251-2 | 6-Chloro-3-pyridyl | A-23 | H | COCF3 |
| 13-2 | 3-Cyanophenyl | A-1 | H | COCF3 |
| 1-1 | 6-Chloro-3-pyridyl | A-1 | H | CHO |
| 1-41 | 6-Chloro-3-pyridyl | A-1 | H | C(=NH)CF3 |

TABLE 38

| Compound No. | Ar | A | Y | R |
|---|---|---|---|---|
| 1-647 | 6-Chloro-3-pyridyl | A-1 | H | COOCH2CH2CH=CH2 |
| 1-670 | 6-Chloro-3-pyridyl | A-1 | H | C(=NCH2CH2F)CF3 |
| 157-2 | 6-Chloro-3-pyridyl | A-1 | 4-OH | COCF3 |
| 1-10 | 6-Chloro-3-pyridyl | A-1 | H | CO(2,2-difluonocyclopropyl) |
| 580-2 | 6-chloro-3-pyridyl-N-oxid | A-1 | H | COCF3 |
| 1-671 | 6-Chloro-3-pyridyl | A-1 | H | C(=N(CH2)7CH3)CF3 |
| 1-658 | 6-Chloro-3-pyridyl | A-1 | H | C(=N(CH2)15CH3)CF3 |
| 1-659 | 6-Chloro-3-pyridyl | A-1 | H | C(=N(CH2)11CH3)CF3 |
| 1-660 | 6-Chloro-3-pyridyl | A-1 | H | C(=NCH(CH3)CH2CH3)CF3 |
| 1-681 | 6-Chloro-3-pyridyl | A-1 | H | C(=NCH(CH2CH3)2)CF3 |
| 1-686 | 6-Chloro-3-pyridyl | A-1 | H | C(=NCH(CH2CH2CH3)2)CF3 |
| 1-661 | 6-Chloro-3-pyridyl | A-1 | H | C(=NCH(CH3)CH2CH2CH3)CF3 |
| 1-662 | 6-Chloro-3-pyridyl | A-1 | H | C(=NCH(iso-propyl)CH3)CF3 |
| 1-663 | 6-Chloro-3-pyridyl | A-1 | H | C(=N(1-phenylethyl))CF3 |
| 1-664 | 6-Chloro-3-pyridyl | A-1 | H | C(=N(1,2,3,4-tetrahydronaphthalen-1-yl)CF3 |
| 1-665 | 6-Chloro-3-pyridyl | A-1 | H | C(=N(1-(naphthalen-1-yl)ethyl))CF3 |
| 1-666 | 6-Chloro-3-pyridyl | A-1 | H | C(=N(1-(naphthalen-1-yl)propyl))CF3 |
| 1-667 | 6-Chloro-3-pyridyl | A-1 | H | C(=N(1-(furan-2-yl)ethyl))CF3 |
| 1-676 | 6-Chloro-3-pyridyl | A-1 | H | C(=NCH(C6H5)2)CF3 |
| 1-668 | 6-Chloro-3-pyridyl | A-1 | H | C(=N(3,3-dimethylbutan-2-yl))CF3 |
| 47-2 | 6-Chloro-3-pyridyl | A-1 | 6-F | COCF3 |
| 91-2 | 6-Chloro-3-pyridyl | A-1 | 6-Cl | COCF3 |
| 478-2 | 6-Chloro-3-pyridyl | A-1 | 6-CH3 | COCF3 |
| 479-2 | 2-Chloro-5-thiazolyl | A-1 | 6-CH3 | COCF3 |
| 1-51 | 6-Chloro-3-pyridyl | A-1 | H | C(=N-cyclobutyl)CF3 |
| 566-2 | 6-Chloro-3-pyridyl | A-1 | 6-CH3O | COCF3 |
| 488-2 | 3-tetrahydrofuranyl | A-1 | 6-CH3 | COCF3 |
| 511-2 | 6-Chloro-3-pyridyl | A-1 | 5-NO2 | COCF3 |
| 1-669 | 6-Chloro-3-pyridyl | A-1 | H | C(=N(1-(thiophen-2-yl)ethyl))CF3 |
| 179-2 | 6-Chloro-3-pyridyl | A-1 | 6-OH | COCF3 (also represents a tautomer) |
| 555-2 | 6-Chloro-3-pyridyl | A-1 | 5-OCH3 | COCF3 |
| 577-2 | 2,6-dichrolo-3-pyridyl | A-1 | H | COCF3 |
| 544-2 | 6-Chloro-3-pyridyl | A-1 | 4-OCH3 | COCF3 |
| 168-2 | 6-Chloro-3-pyridyl | A-1 | 5-OH | COCF3 |
| 1-644 | 6-Chloro-3-pyridyl | A-1 | H | COCH2OCH2C6H5 |
| 578-644 | 3-pyridyl | A-1 | H | COCH2OCH2C6H5 |
| 1-703 | 6-Chloro-3-pyridyl | A-1 | H | SOCF3 |

TABLE 38-continued

| Compound No. | Ar | A | Y | R |
|---|---|---|---|---|
| 1-707 | 6-Chloro-3-pyridyl | A-1 | H | SO2CF3 |
| 1-706 | 6-Chloro-3-pyridyl | A-1 | H | SOCH3 |
| 1-692 | 6-Chloro-3-pyridyl | A-1 | H | P(=O)(OEt)2 |
| 1-700 | 6-Chloro-3-pyridyl | A-1 | H | P(=S)(SEt)2 |
| 1-701 | 6-Chloro-3-pyridyl | A-1 | H | P(=S)(S-n-propyl)2 |
| 1-702 | 6-Chloro-3-pyridyl | A-1 | H | P(=S)(S-isopropyl)2 |
| 1-646 | 6-Chloro-3-pyridyl | A-1 | H | COO-iso-Pr |
| 1-645 | 6-Chloro-3-pyridyl | A-1 | H | COOCH2C6H5 |
| 1-643 | 6-Chloro-3-pyridyl | A-1 | H | COC6F5 |
| 2-643 | 2-Chloro-5-thiazolyl | A-1 | H | COC6F5 |

TABLE 39

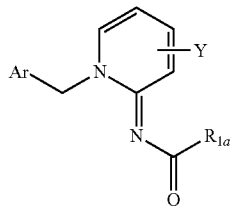

| Compound No. | Ar | R1a | Y |
|---|---|---|---|
| P212 | 6-chloro-3-pyridyl | CF3 | H |
| P213 | 2-chloro-5-thiazolyl | CF3 | H |
| P214 | 6-chloro-3-pyridyl | OCH3 | H |
| P215 | 6-chloro-3-pyridyl | CF3 | 5-Cl |
| P216 | 6-chloro-3-pyridyl | CF3 | 5-F |
| P217 | 6-chloro-3-pyridyl | CF3 | 4-Cl |
| P218 | 2-chloro-5-thiazolyl | CF3 | 5-Cl |
| P219 | 2-chloro-5-thiazolyl | CF3 | 5-F |
| P220 | 2-chloro-5-thiazolyl | CF3 | 4-Cl |
| P221 | 6-chloro-3-pyridyl | CF3 | 3-Me |
| P222 | 6-chloro-3-pyridyl | CF3 | 4-Me |
| P223 | 6-chloro-3-pyridyl | CF3 | 5-Me |
| P224 | phenyl | CF3 | H |
| P225 | 4-chloro-phenyl | CF3 | H |
| P226 | 3-pyridyl | CF3 | H |
| P227 | 6-chloro-5-fluoro-3-pyridyl | CF3 | H |
| P228 | 6-trifluoromethyl-3-pyridyl | CF3 | H |
| P229 | 6-fluoro-3-pyridyl | CF3 | H |
| P230 | 5,6-dichloro-3-pyridyl | CF3 | H |

TABLE 39-continued

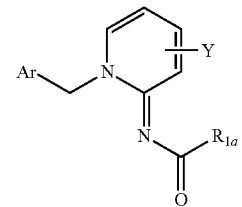

| Compound No. | Ar | R1a | Y |
|---|---|---|---|
| P231 | 6-bromo-3-pyridyl | CF3 | H |
| P232 | 6-chloro-3-pyridyl | CF3 | 4-F |
| P233 | 6-chloro-3-pyridyl | CF3 | 3-F |
| P234 | 6-chloro-3-pyridyl | CHCl2 | H |
| P235 | 6-chloro-3-pyridyl | CCl3 | H |
| P236 | 6-chloro-3-pyridyl | CH2Cl | H |
| P238 | 6-chloro-3-pyridyl | CHF2 | H |
| P239 | 6-chloro-3-pyridyl | CF2Cl | H |
| P240 | 6-chloro-3-pyridyl | CHClBr | H |
| P241 | 6-chloro-3-pyridyl | CHBr2 | H |
| P242 | 6-chloro-3-pyridyl | CF2CF3 | H |
| P243 | 2-chloro-5-pyrimidinyl | CF3 | H |
| P244 | 6-chloro-3-pyridyl | CH2Br | H |

Examples of more preferred compounds include N-[1-((6-chloropyridin-3-yl)methyl)pyridin-2(1H)-ylidene]-2,2,2-trifluoroacetamide (Compound P212) and N-[1-((6-chloropyridin-3-yl)methyl)pyridin-2(1H)-ylidene]-2,2,2-trifluoroethanethioamide (Compound 1-20), N-[1-((6-chloropyridin-3-yl)methyl)pyridin-2(1H)-ylidene]-2,2,2-trifluoro-N'-isopropylacetimidamide (Compound 1-45).

In addition, in the present invention, an acid addition salt of a novel iminopyridine derivative represented by Formula (I) (preferably, an agriculturally and zootechnically acceptable acid addition salt) may also be used, and examples thereof include an acid addition salt such as hydrochloride, nitrate, sulfate, phosphate, or acetate and the like.

The novel iminopyridine derivative represented by Formula (I) itself shows excellent pest control effects against pest insects, and is mixed and used with other pest control agents, thereby showing excellent pest control effects compared to when a single agent is used. Therefore, the present invention provides a pest control composition prepared by containing at least one of novel iminopyridine derivatives represented by Formula (I) and at least one of other pest control agents. Furthermore, the present invention provides an excellent pest control composition prepared by containing at least one of novel iminopyridine derivatives represented by Formula (I) and at least one of other insecticides and/or fungicides.

Examples of a pest control composition provided by the present invention include a pest control agent for agricultural and horticultural, a control agent for animal parasitic pests, an agent for controlling hygiene pests, an agent for controlling nuisance pests, an agent for controlling stored grain and stored product pests, an agent for controlling house pests and the like, preferred examples thereof include a pest control agent for agricultural and horticultural and a control agent for animal parasitic pests.

Examples of the insect species against which a pest control composition containing a novel iminopyridine derivative represented by Formula (I) or at least one of acid addition salts thereof, and at least one of other pest control agents shows pest control effects include lepidopteran pests (for example, *Spodoptera litura*, cabbage armyworm, *Mythimna separata*, cabbageworm, cabbage moth, *Spodoptera exigua*, rice stem borer, grass leaf roller, tortricid, codling moth, leafminer moth, tussock moth, *Agrotis* spp), *Helicoverpa* spp, *Heliothis* spp and the like), hemipteran pests (for example, aphids (Aphididae, Adelgidae, Phylloxeridae) such as *Myzus persicae*, *Aphis gossypii*, *Aphis fabae*, corn leaf aphid, pea aphid, *Aulacorthum solani*, *Aphis craccivora*, *Macrosiphum euphorbiae*, *Macrosiphum avenae*, *Methopolophium dirhodum*, *Rhopalosiphum padi*, greenbug, *Brevicoryne brassicae*, *Lipaphis erysimi*, *Aphis citricola*, Rosy apple aphid, apple blight, *Toxoptera aurantii* and *Toxoptera citricidus*, leafhoppers such as *Nephotettix cincticeps* and *Empoasca vitis*, planthoppers such as *Laodelphax striatellus*, *Nilaparvata lugens* and *Sogatella furcifera*, Pentatomorpha such as *Eysarcoris ventralis*, *Nezara viridula* and *Trigonotylus coelestialium*, whiteflies (Aleyrodidae) such as silverleaf whitefly, *Bemisia tabaci* and greenhouse whitefly, and scale insects (Diaspididae, Margarodidae, Ortheziidae, Aclerdiae, Dactylopiidae, Kerridae, Pseudocccidae, Coccidae, Eriococcidae, Asterolecaniidae, Beesonidae, Lecanodiaspididae, Cerococcidae and the like) such as *Pseudococcus comstocki*, *Planococcus citri*, *Pseudaulacaspis pentagona* and *Aonidiella aurantii*), coleopteran pests (for example, *Lissorhoptrus oryzophilus*, *Callosobruchus chinensis*, *Tenebrio molitor*, *Diabrotica virgifera virgifera*, *Diabrotica undecimpunctata howardi*, *Anomala cuprea*, *Anomala rufocuprea*, *Phyllotreta striolata*, *Aulacophora femoralis*, *Leptinotarsa decemlineata*, *Oulema oryzae*, Bostrichidae, Cerambycidae and the like), Acarina (for example, *Tetranychus urticae*, *Tetranychus kanzawai*, *Panonychus citri* and the like), hymenopteran pests (for example, Tenthredinidae), orthopteran pests (for example, Acridioidea), dipteran pests (for example, Agromyzidae), thysanopteran pests (for example, *Thrips palmi*, *Frankliniella occidentalis* and the like), phytoparasitic nematode (for example, *Meloidogyne*, *Pratylenchus*, *Aphelenchoides besseyi*, *Bursaphelenchus xylophilus* and the like), and the like, examples of zooparasites include Ixodidae (for example, *Amblyomma americanum*, *Amblyomma maculatum*, *Boophilus microplus*, *Dermacentor andersoni*, *Dermacentor occidentalis*, *Dermacentor variabilis*, *Haemaphysalis campanulata*, *Haemaphysalis flava*, *Haemaphysalis longicornis*, *Haemaphysalis megaspinosa Saito*, *Ixodes nipponensis*, *Ixodes ovatus*, *Ixodes pacifcus*, *Ixodes persulcatus*, *Ixodes ricinus*, *Ixodes scapularis*, *Ornithodoros moubata pacifcus* and *Rhipicephalus sanguineus*), Cheyletidae (for example, *Cheyletiella blakei* and *Cheyletiella yasguri*), Demodex (for example, *Demodex canis* and *Demodex cati*), Psoroptidae (for example, *Psoroptes communis*), Sarcoptidae (for example, *Chorioptes bovis* and *Otodectes cynotis*), Dermanyssidae (for example, *Ornithonyssus sylviarum*), *Dermanyssus gallinae*, Pterolichus (for example, *Megninia cubitalis* and *Pterolichus obtusus*), Trombiculidae (for example, *Helenicula miyagawai* and *Leptotrombidium akamushi*), Shiphonaptera (for example, *Ctenocephalides felis*, *Pulex irritans*, *Xenopsylla cheopis* and *Xenopsylla*), Mallophaga (for example, *Trichodectes canis* and *Menopon gallinae*), Anoplura (for example, *Haematopinus suis*, *Linognathus setosus*, *Pediculus humanus humanus*, *Pediculus humanus*, *Pthirus pubis* and *Cimex lectularius*), Diptera (for example, *Musca domestica*, *Hypoderma bovis*, *Stomoxys calcitrans* and *Gasterophilus*), Psychodidae (for example, *Phlebotomus*), *Glossina morsitans*, Tabanidae, *Ormosia tokionis* (for example, *Aedes albopictus* and *Aedes aegypti*), Culicidae (for example, *Culex pipiens pallens*), Anophelini, Ceratopogonidae and the like), Simuliidae, Ceratopogonidae, Reduviidae, *Monomorium pharaonis*, Nematoda (for example, *Strongyloides*, Ancylostomatoidea, Strongyloidea (for example, *Haemonchus contortus* and *Nippostrongylus braziliensis*), Trichostrongyloidea, Metastrongyloidea (for example, *Metastrongylus elongatus*, *Angiostrongylus cantonensis* and *Aelurostrongylus abstrutus*), Oxyuroidea, Haterakoidea (for example, *Ascaridia galli*), Ascaridoidea (for example, *Anisakis simplex*, *Ascaris suum*, *Parascaris equorum*, *Toxocara canis* and *Toxocara cati*), Spiruroidea (for example, Subuluroidea, *Gnathostoma spinigerum*, *Physaloptea praeputialis*, *Ascarops strongylina*, *Draschia megastoma* and *Ascaria hamulosa*, *Dracunculus medinensis*), Filarioidea (for example, *Dirofilaria immitis*, lymphatic filarial, *Onchocerca volvulus* and *Loa loa*), Dioctophymatoidea, Trichinella (for example, *Trichuris vulpis* and *Trichinella spiralis*), Trematoda (for example, *Schistosoma japonicum* and *Fasciola hepatica*), Acanthocephala, Taenia (for example, Pseudophyllidea (for example, *Spirometra erinaceieuropaei*) and Cyclophyllidea (for example, *Dipylidium caninum*)), Protozoa, and the like, and examples of hygiene pests include Periplaneta (for example, *Blattella germanica*), Acaridae (for example, *Tyrophagus putrescentiae*), and Isoptera (for example, *Coptotermes formosanus*). Among them, preferred examples of an insect species, to which the pest control agent of the present invention is applied, include lepidopteran pests, hemipteran pests, thysanopteran pests, dipteran pests, coleopteran pests, zooparasitic Shiphonaptera or Acari, *Dirofilaria immitis*, *Periplaneta* and Isoptera (for example, at least one insect species selected from the group consisting of cabbage moth, *Spodoptera litura*, *Aphis gossypii*, *Myzus persicae*, *Laodelphax striatellus*, *Nilaparvata lugens*, *Sogatella furcifera*, *Nephotettix cincticeps*, *Frankliniella occidentalis*, *Aulacophora femoralis*, *Oulema oryzae*, *Lissorhoptrus oryzophilus*, *Trigonotylus coelestialium*, *Musca domestica*, *Haemaphysalis longicornis*, *Dirofilaria immitis*, *Blattella germanica* and *Coptotermes formosanus*), and particularly preferred examples thereof include cabbage moth, *Aphis gossypii, Myzus persicae, Laodelphax striatellus, Nilaparvata lugens, Sogatella furcifera, Nephotettix cincticeps, Aulacophora femoralis, Oulema oryzae, Lissorhoptrus oryzophilus, Trigonotylus coelestialium, Musca domestica* and *Haemaphysalis longicornis*.

In the present specification, examples of other pest control agents which may be mixed with the novel iminopyridine derivative represented by Formula (I) include an insecticide, a fungicide, a miticide, a herbicide, a plant growth regulator and a control agent for animal parasites, and examples of a specific chemical include those described in The Pesticide Manual (13th edition and published by the British Crop Protection Council) and the SHIBUYA INDEX (15th edition, 2010 and published by SHIBUYA INDEX RESEARCH GROUP).

Examples of other pest control agents which may be mixed with the novel iminopyridine derivative represented by Formula (I) preferably include an insecticide, a fungicide, a herbicide and a control agent for animal parasitic pests, and also those prepared by mixing a fungicide with an insecticide.

Preferred examples of other pest control agents which may be mixed with the novel iminopyridine derivative represented by Formula (I) include an organic phosphoric ester compound, a carbamate-based compound, a nereistoxin derivative, an organochlorine compound, a pyrethroid-based compound, a benzoyl urea-based compound, a juvenile hormone-like compound, a molting hormone-like compound, a neonicotinoid-based compound, a sodium channel blocker for nerve cells, an insecticidalmacrocyclic lactone, a γ-aminobutyric acid (GABA) antagonist, a ryanodine receptor agonistic compound, insecticidal ureas, a BT agent, an entomopathogenic viral agent and the like, as an insecticide, and more preferred examples thereof include an organic phosphoric ester compound such as acephate, dichlorvos, EPN, fenitrothion, fenamifos, prothiofos, profenofos, pyraclofos, chlorpyrifos-methyl, diazinon, trichlorfon, tetrachlorvinphos, bromofenofos and cythioate, a carbamate-based compound such as methomyl, thiodicarb, aldicarb, oxamyl, propoxur, carbaryl, fenobucarb, ethiofencarb, fenothiocarb, pirimicarb, carbofuran and benfuracarb, a nereistoxin derivative such as cartap and thiocyclam, an organochlorine compound such as dicofol and tetradifon, a pyrethroid-based compound such as allethrin, d•d-T allethrin, dl•d-T80 allethrin, pyrethrins, phenothrin, flumethrin, cyfluthrin, d•d-T80 prarethrin, phthalthrin, transfluthrin, resmethrin, cyphenothrin, pyrethrum extract, synepirin222, synepirin500, permethrin, tefluthrin, cypermethrin, deltamethrin, cyhalothrin, fenvalerate, fluvalinate, ethofenprox and silafluofen, a benzoyl urea-based compound such as diflubenzuron, teflubenzuron, flufenoxuron, chlorfluazuron and lufenuron, a juvenile hormone-like compound such as methoprene and a molting hormone-like compound such as chromafenozide. In addition, examples of other compounds include buprofezin, hexythiazox, amitraz, chlordimeform, pyridaben, fenpyroximate, Pyrimidifen, tebufenpyrad, tolfenpyrad, acequinocyl, cyflumetofen, flubendizmide, ethiprole, fipronil, etoxazole, imidacloprid, clothianidin, thiamethoxam, acetamiprid, nitenpyram, thiacloprid, dinotefuran, pymetrozine, bifenazate, spirodiclofen, spiromesifen, spirotetramat, flonicamid, chlorfenapyr, pyriproxyfen, indoxacarb, pyridalyl, spinosad, spinetoram, avermectin, milbemycin, pyflubumide, cyenopyrafen, pyrifluquinazon, chlorantraniliprole, cyantraniliprole, lepimectin, metaflumizone, pyrafluprole, pyriprole, hydramethylnon, triazamate, sulfoxaflor, flupyradifurone, flometoquin, ivermectin, selamectin, moxidectin, doramectin, eprinomectin, milbemycin oxime, deet, metoxadiazon, cyromazine, triflumuron, star anise oil, triclabendazole, flubendazole, fenbendazole, antimony sodium gluconate, levamisole hydrochloride, bithionol, dichlorofen, phenothiazine, piperazine carbon bisulfide, piperazine phosphate, piperazine adipate, piperazine citrate, melarsomine dihydrochloride, metyridine, santonin, pyrantel pamoate, pyrantel, praziquantel, febantel, emodepside, emamectin benzoate, cycloxaprid, 1-((6-chloropyridin-3-yl)methyl)-4-oxo-3-phenyl-4H-pyrido[1,2-a]pyrimidin-1-ium-2-olate, an organic metal-based compound, a dinitro-based compound, an organic sulfur compound, a urea-based compound, a triazine-based compound, a hydrazine-based compound, and a compound represented by the following Formula (II) or agriculturally and zootechnically acceptable acid addition salts thereof. Examples of those acid addition salts include hydrochloride, nitrate, sulfate, phosphate, or acetate and the like.

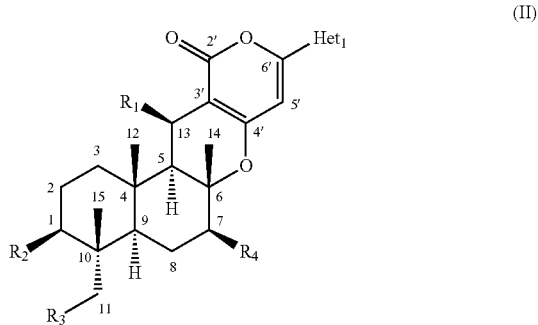

(II)

[in the formula (II), Het1 represents a 3-pyridyl group,
R1 represents a hydroxyl group,
R2 and R3 represent a cyclopropylcarbonyloxy group, and
R4 represents a hydroxyl group]

More preferred examples of other insecticides which may be mixed with the novel iminopyridine derivative represented by Formula (I) include acetamiprid, imidacloprid, nitenpyram, clothianidin, acetamiprid, dinotefuran, thiacloprid, thiamethoxam, pymetrozine, spinosad, spinetram, fipronil, chloranthraniliprole, cyantraniliprole), cartap, thiocyclam, benfuracarb, buprofezin, ethofenprox, silafluofen, ethiprole, flonicamid, sulfoxaflor, flupyradifurone, flometoquin, emamectin benzoate, cycloxaprid, 1-((6-chloropyridin-3-yl)methyl)-4-oxo-3-phenyl-4H-pyrido[1,2-a]pyrimidin-1-ium-2-olate, afidopyropen, and the compound represented by Formula (II), or agriculturally and zootechnically acceptable acid addition salts thereof, and particularly preferred examples thereof include permethrin, acetamiprid, imidacloprid, clothianidin, dinotefuran, thiacloprid, thiamethoxam, pymetrozine, spinosad, spinetram, fipronil, chloranthraniliprole, cyantraniliprole, amitraz, ethofenprox, silafluofen, ethiprole, flonicamid, sulfoxaflor, flupyradifurone, flometoquin, ivermectin, moxidectin, emamectin benzoate, cycloxaprid, 1-((6-chloropyridin-3-yl)methyl)-4-oxo-3-phenyl-4H-pyrido[1,2-a]pyrimidin-1-ium-2-olate, and afidopyropen, or agriculturally and zootechnically acceptable acid addition salts thereof.

The novel iminopyridine derivative represented by Formula (I) may be used together or in combination with a microbial pesticide such as a BT agent and an entomopathogenic viral agent.

Examples of the fungicide which may be mixed with the novel iminopyridine derivative represented by Formula (I) include, for example, a strobilurin-based compound such as azoxystrobin, orysastrobin, kresoxym-methyl and trifloxystrobin, an anilinopyrimidine-based compound such as mepanipyrim, pyrimethanil and cyprodinil, an azole-based compound such as triadimefon, bitertanol, triflumizole, etaconazole, propiconazole, penconazole, flusilazole, myclobutanil, cyproconazole, tebuconazole, hexaconazole, prochloraz and simeconazole, a quinoxaline-based compound such as quinomethionate, a dithiocarbamate-based compound such as maneb, zineb, mancozeb, polycarbamate and propineb, a phenyl carbamate-based compound such as diethofencarb, an organochlorine compound such as chlorothalonil and quintozene, a benzimidazole-based compound such as benomyl, thiophanate-methyl and carbendazole, a phenyl amide-based compound such as metalaxyl, oxadixyl, ofurase, benalaxyl, furalaxyl and cyprofuram, a sulfenic acid-based compound such as dichlofluanid, a copper-based compound such as copper hydroxide and copper oxyquinoline (oxine-copper), an isoxazole-based compound such as hydroxyisoxazole, an organic phosphorus-based compound such as fosetyl-aluminium and tolclofos-methyl, an N-halogenothioalkyl-based compound such as captan, captafol and folpet, a dicarboximide-based compound such as procymidone, iprodione and vinchlozolin, a benzanilide-based compound such as thifluzamide, furametpyr, flutolanil and mepronil, a morpholine-based compound such as fenpropimorph and dimethomorph, an organic tin-based compound such as fenthin hydroxide and fenthin acetate, a cyanopyrrole-based compound such as fludioxonil and fenpiclonil, 9-membered cyclic dilactone compounds such as acibenzolar-S-methyl, isotianil, tiadinil, carpropamid, diclocymet, fenoxanil, tricyclazole, pyroquilon, ferimzone, fthalide, fluazinam, cymoxanil, triforine, pyrifenox, probenazole, fenarimol, fenpropidin, pencycuron, cyazofamid, iprovalicarb, tebufloquin, benthiavalicarb-isopropyl, tolprocarb, validamycin, Kasugamycin, Streptomycin and UK-2As, a compound represented by the following Formula (III), which is described in JP-A No. 2009-078991, a compound represented by the following Formula (IV), which is described in Republication No. WO08/066148, and a compound represented by the following Formula (V), which is described in Republication No. WO09/028280, or agriculturally and zootechnically acceptable acid addition salts thereof.

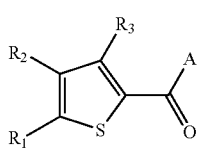
(III)

[in the formula (III), R1 and R2 represent a hydrogen atom or a haloalkyl group having 1 to 6 carbon atoms and the like (however, at least one of R1 and R2 represents a haloalkyl group having 1 to 6 carbon atoms), R3 represents a hydrogen atom and the like, A represents OR4, SR5, NR6R7 or NR8NR9R10, R4 represents an alkyl group having 8 to 12 carbon atoms and the like, R5 represents an alkyl group having 1 to 12 carbon atoms and the like, R6 and R7 represent a hydrogen atom or an alkyl group having 8 to 12 carbon atoms, and R8, R9 and R10 represent a hydrogen atom or an alkyl group having 1 to 12 carbon atoms and the like]

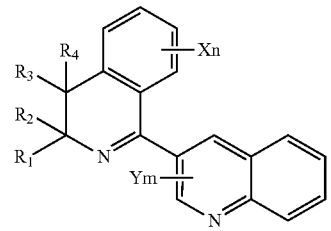
(IV)

[in the formula (IV), R1 and R2 represent a C1 to C6 alkyl group, an aryl group, a heteroaryl group, or a aralkyl group,
R3 and R4 represent a hydrogen atom, a C1 to C6 alkyl group, a halogen atom, or a C1 to C6 alkoxy group,
X represents a hydrogen atom, a halogen atom, a C1 to C6 alkyl group, a C2 to C6 alkenyl group, a C2 to C6 alkynyl group, an aryl group, a heteroaryl group, or a C1 to C6 alkoxy group,
Y represents a hydrogen atom a halogen atom, a C1 to C6 alkyl group, or a C1 to C 6 alkoxy group, and
n represents 0 to 4, and m represents 0 to 6]

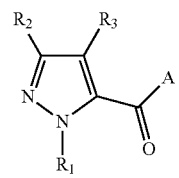
(V)

[in the formula (V), R1 represents an alkyl group and the like, R2 and R3 each independently represent a hydrogen atom, a haloalkyl group and the like (however, at least one of R2 and R3 is a haloalkyl group having 1 to 6 carbon atoms), A represents —OR4, —SR5, —NR6R7 or —NR8NR9R10, R4 represents an alkyl group having 3 to 12 carbon atoms, R5 represents an alkyl group having 1 to 12 carbon atoms, R6 represents a hydrogen atom, R7 represents an alkyl group having 5 to 12 carbon atoms, and R8, R9 and R10 each represent an alkyl group having 3 to 12 carbon atoms and the like, an alkyl group having 1 to 12 carbon atoms and the like, a hydrogen atom and the like, an alkyl group having 5 to 12 carbon atoms and the like, and an alkyl group having 1 to 12 carbon atoms, respectively.]

More preferred examples of other fungicides which may be mixed with the novel iminopyridine derivative represented by Formula (I) include azoxystrobin, orysastrobin, thifluzamide, furametpyr, fthalide, probenazole, acibenzolar-S-methyl, tiadinil, isotianil, carpropamid, diclocymet, fenoxanil, tricyclazole, pyroquilon, ferimzone, tebufloquin, simeconazole, validamycin, kasugamycin and pencycuron, and particularly preferred examples thereof include probenazole and tebufloquin.

Preferred examples of other pest control agents which may be mixed with the novel iminopyridine derivatives represented by Formula (I) also include herbicides such as lipid synthesis inhibitors, acetolactate synthesis inhibitors, photosystem inhibitors, protoporphyrinogen IX oxidation inhibitors, bleacher herbicides, amino acid synthesis inhibitors, dihydropteroate synthetase inhibitors, cell division inhibitors, very-long-chain fatty acid synthesis inhibitors, cellulose biosynthesis inhibitors, decoupling agents, auxin-like herbicides, auxin transport inhibitors, and the like. Specific examples here are alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-P-methyl, haloxyfop-P, haloxyfop-P-methyl ester, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, benfuresate, butylate, cycloate, dalapon, dimepiperate, ethyl dipropylthiocarbamat (EPTC), esprocarb, ethofumesate, flupropanate, molinate, orbencarb, pebulate, prosulfocarb, trichloroacetic acid (TCA), thiobencarb, tiocarbazil, triallate, vernolate, sulfonylureas (amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl, and tritosulfuron), imazamethabenz, imazamethabenz-methyl, imazamox, imazapic, imazapyr, imazaquin, imazethapyr, triazolopyrimidine herbicides (chloransulam, cloransulam-methyl, diclosulam, flumetsulam, florasulam, metosulam, penoxsulam, pyrimisulfan, and pyroxsulam), bispyribac, bispyribac-sodium, pyribenzoxim, pyriftalid, pyriminobac, pyriminobac-methyl, pyrithiobac, pyrithiobac-sodium, flucarbazone, flucarbazone-sodium, propoxycarbazon, propoxycarbazon-sodium, thiencarbazone, thiencarbazone-methyl, triazine herbicides (chlorotriazine, triazinones, triazindiones, methylthiotriazines, and pyridazinones (for example, ametryn, atrazine, chloridazone, cyanazine, desmetryn, dimethametryn, hexazinone, metribuzin, prometon, prometryn, propazine, simazin, simetryn, terbumeton, terbuthylazin, terbutryn, and trietazin)), arylureas (for example, chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron, and thiadiazuron), phenylcarbamate esters (for example, desmedipham, karbutilat, phenmedipham, and phenmedipham-ethyl), nitrile herbicides (for example, bromofenoxim, bromoxynil and its salts and esters, and ioxynil and its salts and esters), uracils (for example, bromacil, lenacil, and terbacil), bentazon, bentazon-sodium, pyridate, pyridafol, pentanochlor, propanil, inhibitors of the photosystem (such as diquat, diquat-dibromide, paraquat, paraquatdichloride, and paraquat dimethyl sulfate), acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, ozadiazon, oxyfluorfen, pentoxazone, profluazol, pyraclonil, pyraflufen, pyraflufen-ethyl, saflufenacil, sulfentrazone, thidiazimin, beflubutamid, diflufenican, fluridone, flurochloridone, flurtamone, norflurazon, pyrazolate, picolinafen, aclonifen, amitrole, clomazone, flumeturon, glyphosate and its salts, bialaphos, bialaphos-sodium, glufosinate, glufosinate-P, glufosinate-ammonium, asulam, dinitroanilines (for example, benfluralin, butralin, dinitramine, ethalfluralin, fluchloralin, oryzalin, pendimethalin, prodiamine, and trifluralin), phosphoramidate herbicides (for example, amiprophos, amiprophos-methyl, and butamifos), benzoic acid herbicides (for example, chlorthal and chlorthal-dimethyl), pyridines (for example, dithiopyr and thiazopyr), benzamides (for example, propyzamide and tebutam), chloroacetamides (for example, acetochlor, alachlor, butachlor, dimethachlor, dimethenamid, dimethenamid-P, metazachlor, metolachlor, metolachlor-S, pethoxamide, pretilachlor, propachlor, propisochlor, and thenylchlor), oxyacetanilides (for example, flufenacet and mefenacet), acetanilides (for example, diphenamide, naproanilide, and napropamide), tetrazolinones (for example, fentrazamide), anilofos, cafenstrole, fenoxasulfone, ipfencarbazone, piperophos, pyroxasulfone, chlorthiamid, dichlobenil, flupoxam, isoxaben, dinoseb, dinoterb, 4,6-dinitro-o-cresol (DNOC) and its salts, 2,4-D and its salts and esters, 2,4-B and its salts and esters, aminopyralid and its salts (for example, aminopyralid-tris(2-hydroxypropyl)ammonium) and esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr and its salts and esters, 2-methyl-4-chlorophenoxyacetic acid (MCPA) and its salts and esters, MCPA-thioethyl, 4-(2-methyl-4-chlorophenoxy)butyric acid (MCPB) and its salts and esters, mecoprop and its salts and esters, mecoprop-P and its salts and esters, picloram and its salts and esters, quinclorac, quinmerac, 2,3,6-trichlorobenzoic acid (TBA (2,3,6)) and its salts and esters, triclopyr and its salts and esters, aminocyclopyrachlor and its salts and esters, diflufenzopyr and its salts, naptalam and its salts, bromobutide, chlorflurenol, chlorflurenol-methyl, cinmethylin, cumyluron, dalapon, dazomet, difenzoquat, difenzoquat-methyl sulfate, dimethipin, disodium methanearsonate (DSMA), dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin, methyl azide, methyl bromide, methyl-dymron, methyl iodide, MSMA, oleic acid, oxaziclomefone, pelargonic acid, pyributicarb, quinoclamine, triaziflam, tridiphane, and 6-chloro-3-(2-cyclopropyl-6-methylphenoxy)-4-pyridazinol (CAS 499223-49-3) and its salts and esters.

Control agents for animal parasitic pests which may be mixed with the novel iminopyridine derivatives represented by Formula (I) can be exemplified by organophosphate ester compounds, carbamate-based compounds, nereistoxin derivatives, organochlorine compounds, pyrethroid-based compounds, benzoyl urea-based compounds, juvenile hormone-like compounds, molting hormone-like compounds, neonicotinoid-based compounds, sodium channel blockers for nerve cells, insecticidal macrocyclic lactones, γ-aminobutyric acid (GABA) antagonists, ryanodine receptor agonistic compounds, insecticidal ureas, and the like. More preferred specific examples include organophosphate esters such as dichlorvos, EPN, fenitrothion, fenamifos, prothiofos, profenofos, pyraclofos, chlorpyrifos-methyl, diazinon, trichlorfon, tetrachlorvinphos, bromofenofos, cythioate, and fenthion; carbamate-based compounds such as methomyl, thiodicarb, aldicarb, oxamyl, propoxur, carbaryl, fenobucarb, ethiofencarb, fenothiocarb, pirimicarb, carbofuran, and benfuracarb; nereistoxin derivatives such as cartap and thiocyclam; organochlorine compounds such as dicofol and tetradifon; pyrethroid-based compounds such as allethrin, d•d-T allethrin, dl·d-T80 allethrin, pyrethrins, phenothrin, flumethrin, cyfluthrin, d·d-T80 prarethrin, phthalthrin, transfluthrin, resmethrin, cyphenothrin, pyrethrum extract, synepirin 222, synepirin 500, permethrin, tefluthrin, cypermethrin, deltamethrin, cyhalothrin, fenvalerate, fluvalinate, ethofenprox, and silafluofen; benzoyl urea-based compounds such as diflubenzuron, teflubenzuron, flufenoxuron, chlorfluazuron, and lufenuron; juvenile hormone-like compounds such as methoprene; molting hormone-like compounds such as chromafenozide; and other compounds such as amitraz, chlordimeform, fipronil, etoxazole, imidacloprid, clothianidin, thiamethoxam, acetamiprid, nitenpyram, thiacloprid, dinotefuran, spirodiclofen, pyriproxyfen, indoxacarb, spinosad, spinetoram, avermectin, milbemycin, metaflumizone, pyrafluprole, pyriprole, hydramethylnon, triazamate, sulfoxaflor, flupyradifurone, ivermectin, selamectin, moxidectin, doramectin, eprinomectin, milbemycin oxim, diethylcarbamazine citrate, deet, metoxadiazon, cyromazine, triflumuron, star anise oil, triclabendazole, flubendazole, fenbendazole, antimony sodium gluconate, levamisole hydrochloride, bithionol, dichlorofen, phenothiazine, piperazine carbon bisulfide, piperazine phosphate, piperazine adipate, piperazine citrate, melarsomine dihydrochloride, metyridine, santonin, pyrantel pamoate, pyrantel, praziquantel, febantel, emodepside, derquantel, monopantel, emamectin benzoate, cycloxaprid, and a compound represented by the following Formula (VI) or agriculturally and zootechnically acceptable acid addition salts thereof. Examples of those acid addition salts include hydrochloride, nitrate, sulfate, phosphate, or acetate and the like.

More preferred examples are flumethrin, permethrin, fipronyl, pyriprol, imidacloprid, thiamethoxam, acetamiprid, dinotefuran, amitraz, metaflumizon, pyriproxyfen, fenitrothion, lufenuron, ethoxazol, spinosad, spinetoram, emodepside, emamectin benzoate, ivermectin, selamectin, moxidectin, doramectin, eprinomectin, derquantel, and monopantel.

Particularly preferred examples include amitraz and the like.

When the pest control composition is a pest control agent for agricultural and horticultural, particularly preferred examples for the present invention are pest control compositions in which the novel iminopyridine derivative represented by Formula (I) is at least one compound selected from N-[1-((6-chloropyridin-3-yl)methyl)pyridin-2(1H)-ylidene]-2,2,2-trifluoroacetamide (Compound P212), N-[1-((6-chloropyridin-3-yl)methyl)pyridin-2(1H)-ylidene]-2,2,2-trifluoroethanethioamide (compound 1-20), or N-[1-((6-chloropyridin-3-yl)methyl)pyridin-2(1H)-ylidene]-2,2,2-trifluoro-N'-isopropylacetimidamide (compound 1-45), and the other pest control agent includes at least one insecticide or fungicide selected from acetamiprid, imidacloprid, clothianidin, dinotefuran, thiacloprid, fipronil, thiamethoxam, pymetrozine, flonicamid, spinosad, cyantraniliprole, chloranthraniliprole, ethofenprox, silafluofen, ethiprole, sulfoxaflor, flupyradifurone, flometoquin, emamectin benzoate, cycloxaprid, 1-((6-chloropyridin-3-yl)methyl)-4-oxo-3-phenyl-4H-pyrido[1,2-a]pyrimidin-1-ium-2-olate, and afidopyropen, orysastrobin, thifluzamide, furametpyr, fthalide, probenazole, acibenzolar-S-methyl, tiadinil, isotianil, carpropamid, diclocymet, fenoxanil, tricyclazole, pyroquilon, ferimzone, tebufloquin, azoxystrobin, simeconazole, validamycin, thifluzamide, furametpyr, and pencycuron.

The pest control composition of the present invention may be prepared using the novel iminopyridine derivative represented by Formula (I), other insecticides, fungicides, herbicides, or control agents for animal parasites, and an agriculturally and zootechnically acceptable carrier (solid carrier, liquid carrier, gaseous carrier, surfactant, dispersant, and other preparation adjuvants).

(Specific Examples of Pesticide Preparations)

When the pest control composition of the present invention is a pest control agent for agricultural and horticultural, the composition is usually mixed with an agriculturally and horticulturally acceptable carrier (solid carrier, liquid carrier, gaseous carrier, surfactant, dispersant and other adjuvants for preparation to be provided in any formulation form of emulsifiable concentrates, liquid formulations, suspensions, wettable powders, flowables, dust, granules, tablets, oils, aerosols, fumigants and the like.

Examples of the solid carrier include talc, bentonite, clay, kaolin, diatomaceous earth, vermiculite, white carbon, calcium carbonate and the like.

Examples of the liquid carrier include alcohols such as methanol, n-hexanol and ethylene glycol, ketones such as acetone, methyl ethyl ketone and cyclohexanone, aliphatic hydrocarbons such as n-hexane, kerosene and lamp oil, aromatic hydrocarbons such as toluene, xylene and methyl naphthalene, ethers such as diethyl ether, dioxane and tetrahydrofuran, esters such as ethyl acetate, nitriles such as acetonitrile and isobutyl nitrile, acid amides such as dimethylformamide and dimethylacetamide, vegetable oils such as soybean oil and cottonseed oil, dimethyl sulfoxide, water and the like.

Further, examples of the gaseous carrier include LPG, air, nitrogen, carbonic acid gas, dimethyl ether and the like.

As the surfactant or dispersant for emulsification, dispersion, spreading and the like, it is possible to use, for example, alkylsulfate esters, alkyl (aryl) sulfonates, polyoxyalkylene alkyl (aryl) ethers, polyhydricalcohol esters, lignin sulfonates or the like.

In addition, as the adjuvant for improving the properties of the preparation, it is possible to use, for example, carboxymethylcellulose, gum arabic, polyethylene glycol, calcium stearate or the like.

The aforementioned solid carriers, liquid carriers, gaseous carriers, surfactants, dispersants and adjuvants may be used either alone or in combination, if necessary.

The content of active ingredients in the preparation is not particularly limited, but is usually in the range of 1 to 75% by weight for the emulsifiable concentrate, 0.3 to 25% by weight for the dust, 1 to 90% by weight for the wettable powder, and 0.5 to 10% by weight for the granular formulation.

The novel iminopyridine derivatives represented by Formula (I), a preparation including the same and a mixed formulation of other pest control agents with the same may be applied to pest insects, plants, plant propagation materials (for example, seeds, plant leaves and stems, roots, soil, water surface and materials for cultivation), rooms which require disturbing the invasion of pests and the like. The application thereof may be performed before and after the invasion of pests.

A pest control agent including at least one of the novel iminopyridine derivatives represented by Formula (I) may also be applied to genetically-modified crops.

In a preferred aspect thereof, examples of a pest control composition further including an agriculturally and horticulturally acceptable carrier include:

(1) a wettable powder composition containing 0.1 to 80% by weight of the novel iminopyridine derivative represented by Formula (I), 0.1 to 80% by weight of an insecticide as another pest control agent, 0.6 to 30% by weight of a wetting agent and a dispersant, and 20 to 95% by weight of an extender, (2) a water dispersible granule composition containing 0.1 to 80% by weight of the novel iminopyridine derivative represented by Formula (I), 0.1 to 80% by weight of an insecticide as another pest control agent, 0.6 to 30% by weight of a wetting agent, a dispersant and a binder, and 20 to 95% by weight of an extender, (3) a flowable composition containing 0.1 to 80% by weight of the novel iminopyridine derivative represented by Formula (I), 0.1 to 80% by weight of an insecticide as another pest control agent, 5 to 40% by weight of a dispersant, a thickener, an antifreeze, an antiseptic and an antifoaming agent, and 20 to 94% by weight of water, (4) an emulsifiable concentrate composition containing 0.1 to 80% by weight of the novel iminopyridine derivative represented by Formula (I), 0.1 to 80% by weight of an insecticide as another pest control agent, 1 to 30% by weight of an emulsifier and an emulsion stabilizer, and 20 to 97% by weight of an organic solvent, (5) a dust composition containing 0.1 to 80% by weight of the novel iminopyridine derivative represented by Formula (I), 0.1 to 80% by weight of an insecticide as another pest control agent, and 70 to 99.8% by weight of an extender, (6) a low drift dust composition containing 0.1 to 80% by weight of the novel iminopyridine derivative represented by Formula (I), 0.1 to 80% by weight of an insecticide as another pest control agent, and 70 to 99.8% by weight of an extender, (7) a microgranule fine composition containing 0.1 to 80% by weight of the novel iminopyridine derivative represented by Formula (I), 0.1 to 80% by weight of an insecticide as another pest control agent, 0.2 to 10% by weight of a solvent or binder, and 70 to 99.6% by weight of an extender, (8) a granule composition containing 0.1 to 80% by weight of the novel iminopyridine derivative represented by Formula (I), 0.1 to 80% by weight of an insecticide as another pest control agent, 0.5 to 30% by weight of a granulation auxiliary (surfactant) and a binder, and 20 to 98% by weight of an extender, and (9) a microcapsule composition containing 0.1 to 80% by weight of the novel iminopyridine derivative represented by Formula (I), 0.1 to 80% by weight of an insecticide as another pest control agent, 1 to 50% by weight of a covering agent, an emulsifier, a dispersant and an antiseptic, and 20 to 98% by weight of water. Preferably, examples thereof include compositions of (2), (3), (6) and (8).

(Specific Examples of Formulations for Animals)

When the pest control agent of the present invention is a control agent for animal parasitic pests, the agent is provided in the form of liquid formulations, emulsifiable concentrates, liquid drops, sprays, foam preparations, granules, fine granules, dust, capsules, pills, tablets, chewable formulations, injections, suppositories, creams, shampoos, rinses, resin agents, fumigants, poison baits and the like, and is particularly preferably provided in the form of liquid formulations and liquid drops. These forms can be prepared using the following pharmaceutically acceptable carriers.

The liquid formulation may also be blended with a typical adjuvant for preparation, such as an emulsifier, a dispersant, a spreading agent, a wetting agent, a suspending agent, a preservative and a propellant, and may also be blended with a typical film former. As the surfactant for emulsification, dispersion, spreading and the like, it is possible to use, for example, soaps, polyoxyalkylene alkyl (aryl) ethers, polyoxyethylene alkyl aryl ethers, polyoxyethylene fatty acid ester, higher alcohols, alkyl aryl sulfonates and the like. Examples of dispersants include casein, gelatin, polysaccharides, lignin derivatives, saccharides, synthetic water soluble polymers and the like. Examples of spreading-wetting agents include glycerin, polyethylene glycol and the like. Examples of suspending agents include casein, gelatin, hydroxypropylcellulose, gum arabic and the like, and examples of stabilizers include phenolic antioxidants (BHT, BHA and the like), amine antioxidants (diphenylamine and the like), organic sulfur antioxidants and the like. Examples of preservatives include methyl p-oxybenzoate, ethyl p-oxybenzoate, propyl p-oxybenzoate, butyl p-oxybenzoate and the like. The aforementioned carriers, surfactants, dispersants and adjuvants may be used either alone or in combination, if necessary. Furthermore, perfumes, synergists and the like may also be incorporated. The suitable content of the active ingredients in the pest control agent of the present invention is usually 1 to 75% by weight for the liquid formulation.

Examples of carriers used for the preparation of creams include non-volatile hydrocarbons (liquid paraffin and the like), lanolin hydrogenated fats and oils, higher fatty acids, fatty acid esters, animal and vegetable oils, silicone oils, water and the like. Further, emulsifiers, humectants, antioxidants, perfumes, borax and ultraviolet absorbers may also be used either alone or in combination, if necessary. Examples of emulsifiers include fatty acid sorbitan, polyoxyethylene alkyl ethers, and fatty acid polyoxyethylene and the like. The suitable content of the active ingredients in the pest control agent of the present invention is usually 0.5 to 75% by weight for the cream.

The capsules, pills or tablets may be used such that the active ingredients in the composition of the present invention are mixed with a carrier such as starch, lactose or talc, a disintegrator and/or a binder, such as magnesium stearate is added thereto, and, if necessary, the mixture is tableted.

Carriers for the preparation of injections need to be prepared as an aseptic solution, but the solution may contain other substances, for example, a salt or glucose enough to isotonicate the solution with blood. As available carriers, "injections need to be prepared as an aseptic solution. For injections, the solution may contain, for example, a salt or glucose enough to isotonicate the solution with blood. Examples of available carriers for the preparation of injections include esters such as fatty acid derivatives of glyceride, benzyl benzoate, isopropyl myristate and propylene glycol, and organic solvents such as N-methylpyrrolidone and glycerol formal. The content of the active ingredients in the pest control agent of the present invention is usually 0.01 to 10% by weight for the injection.

Examples of carriers for the preparation of resin agents include vinyl chloride polymers, polyurethane and the like. Plasticizers such as phthalic acid esters, adipic acid esters and stearic acid may be added to these bases, if necessary. After the active ingredients are kneaded into the base, the kneaded product may be molded by injection molding, extrusion molding, press molding and the like. In addition, the molded product may also be properly subjected to processes such as molding or cutting to form an ear tag for animals or insecticidal collar for animals.

Examples of carriers for toxic baits include bait substances and attraction substances (farina such as wheat flour and corn flour, starch such as corn starch and potato starch, saccharides such as granulated sugar, malt sugar and honey, food flavors such as glycerin, onion flavor and milk flavor, animal powders such as pupal powder and fish powder, various pheromones and the like). The suitable content of the active ingredients in the pest control agent of the present invention is usually 0.0001 to 90% by weight for the toxic bait.

The pest control composition according to the present invention may be used such that a preparation form prepared by independently including at least one of the novel iminopyridine derivative represented by Formula (I) as the active ingredient in the composition, or acid addition salts thereof and at least one of other pest control agents alone is formulated and these ingredients when used are mixed on the spot.

Therefore, according to another aspect of the present invention, there is provided a combined product prepared by including at least one of the novel iminopyridine derivative represented by Formula (I) as the active ingredient or acid addition salts thereof and at least one of other pest control agents.

According to another preferred aspect of the present invention, in the combined product, the novel iminopyridine derivative represented by Formula (I) or acid addition salts thereof is provided as a first composition prepared by including the same as active ingredients, and other pest control agents is provided as a second composition prepared by including the same as active ingredients. In this case, the first composition and the second composition may be any formulation form which uses appropriate carriers or adjuvants in combination thereof in the same manner as in the case of the aforementioned pest control composition. The combined product may be provided in the form of a pharmaceutical set.

According to still another aspect of the present invention, there is provided a method for protecting useful plants or animals from pests, including: simultaneously or independently (preferably, each ingredient simultaneously) applying at least one of the novel iminopyridine derivative represented by Formula (I), enantiomers thereof, mixtures thereof or acid addition salts thereof as an active ingredient and at least one of other pest control agents to a region to be treated.

In the method, "simultaneously" applying also includes mixing at least one of the novel iminopyridine derivative represented by Formula (I) or acid addition salts thereof and at least one of other pest control agents before being applied to a region to be treated, and applying the mixture thereto. "Independently" applying includes, without mixing these ingredients in advance, applying the novel iminopyridine derivative represented by Formula (I) or acid addition salts thereof earlier than the other ingredients, or applying the novel iminopyridine derivative represented by Formula (I) or acid addition salts thereof later than the other ingredients.

According to still another preferred aspect of the present invention, there is provided a method for protecting useful plants or animals from pests, including: applying (1) a first composition prepared by including at least one of the novel iminopyridine derivative represented by Formula (I) or acid addition salts thereof as an active ingredient, and (2) a second composition prepared by including at least one of other pest control agents as an active ingredient to a region to be treated.

According to yet another aspect of the present invention, there is provided a method for protecting useful plants from pests, including: applying the composition or combined product of the present invention as it is or diluted to pests, useful plants, seeds of useful plants, soil, cultivation carriers or animals as a target, and preferably to useful plants, soil or animals.

According to still yet another aspect of the present invention, there is provided a use of the composition or combined product of the present invention in order to protect useful plants or animals from pests.

Furthermore, preferred examples of the method for applying the composition or combined product of the present invention to pests, useful plants, seeds of useful plants, soil or cultivation carriers as a target include spray treatment, water surface treatment, soil treatment (mixing, irrigation and the like), nursery box treatment, surface treatment (application, dust coating and covering) or fumigation treatment (treatment in enclosed space, such as covering soil with a polyfilm after soil injection) and the like, and more preferred examples include water surface treatment, soil treatment, nursery box treatment or surface treatment.

The throughput in the case of application to plants by spray treatment is 0.1 g to 10 kg per 10 ares of cultivated land and preferably 1 g to 1 kg, as an amount of active ingredients of the composition of the present invention.

Further, examples of a method for treating seeds, roots, tubers, bulbs or rhizomes of plants include a dipping method, a dust coating method, a smearing method, a spraying method, a pelleting method, a coating method and a fumigating method for the seed. The dipping method is a method in which seeds are dipped in a liquid chemical solution, and the dust coating method is classified into a dry dust coating method in which a granular chemical is adhered onto dry seeds, and a wet dust coating method in which a powdery chemical is adhered onto seeds which have been slightly soaked in water. In addition, the smearing method is a method in which a suspended chemical is applied on the surface of seeds within a mixer and the spraying method is a method in which a suspended chemical is sprayed onto the surface of seeds. Furthermore, the pelleting method is a method in which a chemical is mixed with a filler and treated when seeds are pelleted together with the filler to form pellets having certain size and shape, the coating method is a method in which a chemical-containing film is coated onto seeds, and the fumigating method is a method in which seeds are sterilized with a chemical which has been gasified within a hermetically sealed container.

Examples of the preferred treatment method of the composition of the present invention include a dipping method, a dust coating method, a smearing method, a spraying method, a pelleting method and a coating method.

Further, the composition of the present invention may also be used to, in addition to seeds, germinated plants which are transplanted after germination or after budding from soil, and embryo plants. These plants may be protected by the treatment of the whole or a part thereof by dipping before transplantation.

The throughput in the case of application to seeds of plants is not particularly limited, but preferably 1 g to 10 kg and more preferably 100 g to 1 kg per 100 kg of seeds, as an amount of active ingredients of the composition of the present invention.

In addition, the method for application of the composition of the present invention to soil is not particularly limited, but preferred application methods are as follows.

Examples of the method include a method in which granules including the composition of the present invention are applied into soil or on soil. Particularly preferred soil application methods include spraying, stripe application, groove application, and planting hole application.

Furthermore, application by irrigating soil with a solution prepared by emulsifying or dissolving the composition of the present invention in water is also a preferred soil application method.

Besides these methods, examples of preferred soil application methods include application into a nutrient solution in nutrient solution culture systems such as solid medium culture, for example, hydroponic culture, sand culture, NFT (nutrient film technique), rock wool culture and the like for the production of vegetables and flowering plants, or application into a nursery box for paddy rice seedling (mixing with bed soil and the like). The compound of the present invention may be applied directly to artificial culture soil including vermiculite and a solid medium including an artificial mat for growing seedling.

The throughput of the composition of the present invention into water surface, a nursery box or soil is not particularly limited, but is 0.1 g to 10 kg of preferably active ingredients per 10 ares of cultivated land and preferably 1 g to 1 kg. Further, as the method for applying the composition or combined product of the present invention to an applied organism, it is possible to control pests by administering the pest control composition of the present invention into the applied organism either orally or by injection, wholly or partly administering the composition into the body surface of an applied animal, or mounting the pest control agent formulated into a resin preparation or sheet preparation on the applied organism. In addition, it is also possible to control pests by covering places in which the invasion, parasitism and movement of pests are expected with the pest control composition of the present invention.

The pest control composition of the present invention may be used as it is, but may be diluted with water, liquid carriers, commercially available shampoos, rinses, baits, breed cage bottoms and the like and applied in some cases. When the pest control composition of the present invention is diluted with a dilution liquid (water) such as an emulsifiable concentrate, a flowable and a wettable powder and used, the amount is not particularly limited, but, preferably, the composition is applied by diluting the composition in water and spraying the mixture such that the concentration of active ingredients is 10 to 10,000 ppm. Furthermore, when the pest control composition of the present invention is administered to a target organism, the administration amount thereof is not particularly limited, but when the composition is percutaneously applied, the amount of the composition is preferably in a range from 0.01 to 500 mg per 1 kg of the body weight of the target organism. When the composition is orally administered, the amount of the composition is in a range from 0.01 to 100 mg per 1 kg of the body weight of the target organism. When a resin preparation is mounted on the target organism, the amount of the composition contained in the resin preparation is preferably in a range from 0.01 to 50% by weight per weight of the resin preparation.

EXAMPLES

Hereinafter, the present invention will be specifically described with reference to Examples, but the present invention is not limited to the Examples.

Synthetic Example P1

N-[1-((6-chloropyridin-3-yl)methyl)pyridin-2(1H)-ylidene]-2,2,2-trifluoroacetamide (Compound P212)

(1) 25 g (270 mmol) of 2-aminopyridine was dissolved in 200 ml of anhydrous dichloromethane, 41 ml (30 g, 300 mmol) of triethylamine was added thereto, and the mixture was cooled to 0° C. 38 ml (57 g, 270 mmol) of anhydrous trifluoroacetic acid was added dropwise thereto over 15 minutes, and the resulting mixture was stirred at room temperature for 2 hours. After the reaction was completed, the reaction solution was injected into about 100 ml of iced water, and the mixture was stirred for 10 minutes. The mixture was transferred to a separatory funnel to perform liquid separation, and the organic layer was washed twice with 150 ml of water and twice with 150 ml of a 1% HCl aqueous solution, dried over anhydrous magnesium sulfate and concentrated under reduced pressure to obtain 36 g (yield 71%) of 2,2,2-trifluoro-N-(pyridin-2(1H)-ylidene)acetamide.

1H-NMR (CDCl3, δ, ppm): 7.20 (1H, ddd), 7.83 (1H, td), 8.20 (1H, d), 8.35 (1H, d), 10.07 (1H, brs)

13C-NMR (CDCl3, δ, ppm): 115.3, 115.5 (q), 121.6, 139.1, 147.9, 149.5, 155.3 (q)

MS: m/z=191 (M+H)

(2) 20 g (126 mmol) of 2-chloro-5-chloromethyl pyridine was dissolved in 200 ml of anhydrous acetonitrile, 24 g (126 mmol) of 2,2,2-trifluoro-N-(pyridin-2(1H)-ylidene)acetamide obtained by the above-described method and 21 g (151 mmol) of potassium carbonate were added thereto, and the resulting mixture was heated and refluxed for 6 hours, and then stirred at room temperature for 10 hours. After the reaction was completed, the reaction solution was filtered and the liquid was concentrated under reduced pressure. Diethyl ether was added thereto for crystallization, and the crystals thus obtained were collected and washed well with diethyl ether and water. The crystals thus obtained were dried under reduced pressure at 60° C. for 1 hour to obtain the subject material. Amount obtained 26 g (yield 66%).

1H-NMR (CDCl3, δ, ppm): 5.57 (2H, s), 6.92 (1H, td), 7.31 (1H, d), 7.80 (1H, td), 7.87 (1H, dd), 7.99 (1H, dd), 8.48 (2H, m)

13C-NMR (CDCl3, δ, ppm): 53.8, 115.5, 117.2 (q), 122.1, 124.7, 130.0, 139.2, 140.0, 142.5, 149.7, 151.8, 158.9, 163.5 (q)

MS: m/z=316 (M+H)

(3) Powder X-ray crystal analysis

In the powder X-ray diffraction, measurement was performed under the following conditions.

Device name: RINT-2200 (Rigaku Corporation)
X-ray: Cu-Kα (40 kV, 20 mA)
Scanning range: 4 to 400, sampling width: 0.02° and scanning rate: 1°/min The results are as follows.

Diffraction angle (2θ) 8.7°, 14.2°, 17.5°, 18.3°, 19.8°, 22.4°, 30.9° and 35.3°

(4) Differential Scanning Calorimetry (DSC)

In the differential scanning calorimetry, measurement was performed under the following conditions.

Device name: DSC-60
Sample cell: aluminum
Temperature range: 50° C. to 250° C. (heating rate: 10° C./min)

As a result, the melting point was observed at 155° C. to 158° C.

Another Method of Synthetic Example P1

3.00 g (18.6 mmol) of 2-chloro-5-chloromethyl pyridine was dissolved in 20 ml of anhydrous DMF, 1.75 g (18.6 mmol) of 2-aminopyridine was added thereto, and the resulting mixture was stirred at 80° C. for 8 hours and at room temperature for 5 hours. After the reaction was completed, DMF was distilled off under reduced pressure, acetonitrile was added thereto to precipitate a solid, and the solid was collected, washed well with acetonitrile and dried to obtain 2.07 g (yield 44%) of 1-[(6-chloropyridin-3-yl)methyl]pyridin-2(1H)-imine hydrochloride.

1H-NMR (DMSO-d6, δ, ppm): 5.65 (2H, s), 6.96 (1H, t), 7.23 (1H, m), 7.57 (1H, d), 7.80 (1H, m), 7.91 (1H, m), 8.28 (1H, m), 8.49 (1H, d), 9.13 (2H, brs)

50 mg (0.20 mmol) of the 1-[(6-chloropyridin-3-yl)methyl]pyridin-2(1H)-imine hydrochloride obtained by the above-described method was dissolved in 5 ml of anhydrous dichloromethane, 122 mg (1.00 mmol) of DMAP and 50 mg (0.24 mmol) of anhydrous trifluoroacetic acid were added thereto in sequence under ice cold conditions, and the resulting mixture was stirred at room temperature for 1 hour. After the reaction was completed, the reaction solution was diluted with dichloromethane, washed with 1% hydrochloric acid, and then dried over anhydrous magnesium sulfate. Dichloromethane was distilled off under reduced pressure to obtain the subject material. Amount obtained 42 mg (yield 67%). NMR was the same as that of the above-described method.

Synthetic Example P2

2,2-dibromo-N-[1-((6-chloropyridin-3-yl)methyl) pyridin-2(1H)-ylidene]-acetamide (Compound P241)

200 mg (0.78 mmol) of the 1-[(6-chloropyridin-3-yl)methyl]pyridin-2(1H)-imine hydrochloride obtained by the method described in another method of Synthetic Example P1, 238 mg (1.95 mmol) of DMAP and 224 mg (1.17 mmol) of EDC-HCl were dissolved in 10 ml of anhydrous dichloromethane, 101 µl (202 mg, 1.17 mmol) of dibromoacetic acid was added thereto, and the resulting mixture was stirred at room temperature overnight. After the reaction was completed, the reaction solution was diluted with dichloromethane, washed once with water and twice with a 1% HCl aqueous solution, and then dried over anhydrous magnesium sulfate and concentrated under reduced pressure to obtain the subject material. Amount obtained 50 mg (yield 15%)

1H-NMR (CDCl3, δ, ppm): 5.56 (2H, s), 5.99 (1H, s), 6.78 (1H, td), 7.33 (1H, d), 7.69 (1H, td), 7.76 (1H, dd), 7.93 (1H, dd), 8.39 (1H, d), 8.50 (1H, d)

13C-NMR (CDCl3, δ, ppm): 44.6, 53.1, 113.7, 121.9, 124.8, 130.1, 138.2, 139.7, 141.2, 149.5, 152.0, 159.4, 172.2

MS: m/z=418 (M+H)

Synthetic Example P3

N-[1-((6-chloro-5-fluoropyridin-3-yl)methyl)pyridin-2(1H)-ylidene]-2,2,2-trifluoroacetamide (Compound P227)

4.00 g (27.6 mmol) of 2-chloro-3-fluoro-5-methyl pyridine was dissolved in 80 ml of carbon tetrachloride, 7.37 g (41.4 mmol) of N-bromosuccinimide and 20 mg of benzoyl peroxide were added thereto, and the resulting mixture was heated and refluxed overnight. After the reaction was completed, the reaction solution was returned to room temperature, concentrated under reduced pressure and purified by silica gel column chromatography (hexane:ethyl acetate=19:1) to obtain 3.06 g (yield 51%) of 5-(bromomethyl)-2-chloro-3-fluoropyridine.

1H-NMR (CDCl3, δ, ppm): 4.45 (2H, s), 7.54 (1H, dd), 8.23 (1H, s)

50 mg (0.22 mmol) of the 5-(bromomethyl)-2-chloro-3-fluoropyridine obtained by the aforementioned method was dissolved in 5 ml of anhydrous acetonitrile, 42 mg (0.22 mmol) of 2,2,2-trifluoro-N-(pyridin-2(1H)-ylidene)acetoamide obtained by the method described in (1) of Reference Example 1 and 36 mg (0.26 mmol) of potassium carbonate were added thereto in sequence, and the resulting mixture was heated and refluxed for 7 hours. After the reaction was completed, the reaction solution was returned to room temperature to filter insoluble materials, and the filtrate was concentrated under reduced pressure. Diethyl ether was added thereto to precipitate a solid, and thus the solid was collected, washed with diethyl ether, and then dried under reduced pressure in a desiccator to obtain the subject material. Amount obtained 29 mg (yield 40%).

1H-NMR (CDCl3, δ, ppm): 5.54 (2H, s), 6.89 (1H, td), 7.76 (1H, dd), 7.80 (1H, td), 7.85 (1H, d), 8.29 (1H, d), 8.57 (1H, d)

MS: m/z=334 (M+H)

Synthetic Example P4

N-[1-((6-fluoropyridin-3-yl)methyl)pyridin-2(1H)-ylidene]-2,2,2-trifluoroacetamide (Compound P229)

500 mg (4.50 mmol) of 2-fluoro-5-methyl pyridine was dissolved in 50 ml of carbon tetrachloride, 1.20 g (6.76 mmol) of N-bromosuccinimide and 20 mg of benzoyl peroxide were added thereto, and the resulting mixture was heated and refluxed for 2.5 hours. After the reaction was completed, the reaction solution was returned to room temperature, and the solvent was distilled off under reduced pressure and purified by silica gel column chromatography (hexane:ethyl acetate=19:1) to obtain 300 mg (yield 35%) of 5-bromomethyl-2-fluoropyridine.

57 mg (0.30 mmol) of the 5-bromomethyl-2-fluoropyridine obtained by the aforementioned method was dissolved in 10 ml of anhydrous acetonitrile, 57 mg (0.30 mmol) of 2,2,2-trifluoro-N-(pyridin-2(1H)-ylidene)acetoamide synthesized by the method described in (1) of Synthetic Example P1 and 69 mg (0.50 mmol) of potassium carbonate were added thereto in sequence, and the resulting mixture was heated and refluxed for 6 hours. After the reaction was completed, the reaction solution was returned to room temperature to filter insoluble materials, and the filtrate was concentrated under reduced pressure. The filtrate was purified by silica gel column chromatography (hexane:ethyl acetate=1:1→3:1) to obtain the subject material. Amount obtained 21 mg (yield 23%).

1H-NMR (CDCl3, δ, ppm): 5.56 (2H, s), 6.89 (1H, td), 6.94 (1H, d), 7.79 (1H, td), 7.87 (1H, d), 8.03 (1H, m), 8.31 (1H, s), 8.54 (1H, d)

MS: m/z=300 (M+H)

Synthetic Example P5

N-[1-((6-bromopyridin-3-yl)methyl)pyridin-2(1H)-ylidene]-2,2,2-trifluoroacetamide (Compound P231)

500 mg (2.92 mmol) of 2-bromo-5-methylpyridine was dissolved in 15 ml of carbon tetrachloride, 623 mg (3.50 mmol) of N-bromosuccinimide and 10 mg of benzoyl peroxide were added thereto, and the resulting mixture was heated and refluxed for 19 hours. After the reaction was completed, the reaction solution was returned to room temperature, concentrated under reduced pressure and purified by silica gel column chromatography (hexane:ethyl acetate=19:1) to obtain 143 mg (yield 20%) of 2-bromo-5-bromomethylpyridine.

1H-NMR (CDCl3, δ, ppm): 4.42 (2H, s), 7.47 (1H, d), 7.59 (1H, dd), 8.38 (1H, d)

70 mg (0.28 mmol) of the 2-bromo-5-bromomethylpyridine obtained by the aforementioned method was dissolved in 10 ml of anhydrous acetonitrile, 54 mg (0.28 mmol) of 2,2,2-trifluoro-N-(pyridin-2(1H)-ylidene)acetoamide synthesized by the method described in (1) of Synthetic Example P1 and 46 mg (0.34 mmol) of potassium carbonate were added thereto in sequence, and the resulting mixture was heated and refluxed for 6 hours. After the reaction was completed, the reaction solution was returned to room temperature to filter insoluble materials, and the filtrate was concentrated under reduced pressure. Diethyl ether was added thereto to precipitate a solid, and thus the solid was collected, washed with diethyl ether, and then dried under reduced pressure in a desiccator to obtain the subject material. Amount obtained 81 mg (yield 82%).

1H-NMR (CDCl3, δ, ppm): 5.52 (2H, s), 6.88 (1H, t), 7.48 (1H, d), 7.78 (2H, m), 7.84 (1H, d), 8.44 (1H, d), 8.53 (1H, d)

MS: m/z=360 (M+H)

Synthetic Example P6

2-chloro-N-[1-((6-chloropyridin-3-yl)methyl)pyridin-2(1H)-ylidene]-acetamide (Compound P236)

70 mg (0.27 mmol) of the 1-[(6-chloropyridin-3-yl)methyl]pyridin-2(1H)-imine hydrochloride obtained by the method described in another method of Synthetic Example P1 was dissolved in 4 ml of anhydrous dichloromethane, 82 mg (0.67 mmol) of DMAP, 25 mg (0.27 mmol) of chloroacetic acid and 62 mg (0.32 mmol) of EDC-HCl were added thereto in sequence, and the resulting mixture was stirred at room temperature overnight. After the reaction was completed, dichloromethane was added thereto to dilute the mixture, and the mixture was washed with water and a 1% HCl aqueous solution, dried over anhydrous magnesium sulfate and concentrated under reduced pressure to obtain the subject material. Amount obtained 4 mg (yield 5%).

1H-NMR (CDCl3, δ, ppm): 4.17 (2H, s), 5.46 (2H, s), 6.64 (1H, td), 7.31 (1H, d), 7.60 (1H, td), 7.64 (1H, dd), 7.80 (1H, dd), 8.32 (1H, d), 8.45 (1H, d)

MS: m/z=296 (M+H)

Synthetic Example P7

N-[1-((6-chloropyridin-3-yl)methyl)pyridin-2(1H)-ylidene]-2,2-difluoroacetamide (Compound P238)

400 mg (4.26 mmol) of 2-aminopyridine was dissolved in 10 ml of anhydrous dichloromethane, 322 μl (490 mg, 5.11 mmol) of difluoroacetic acid, 982 mg (5.10 mmol) of EDC-HCl and 622 mg (5.11 mmol) of DMAP were added thereto, and the resulting mixture was stirred at room temperature for 61 hours. After the reaction was completed, the reaction solution was diluted with dichloromethane, washed once with water and twice with a 1% HCl aqueous solution, and then dried over anhydrous magnesium sulfate and concentrated under reduced pressure to obtain 102 mg (yield 14%) of 2,2-difluoro-N-(pyridin-2(1H)-ylidene)acetamide.

1H-NMR (CDCl3, δ, ppm): 6.03 (1H, t), 7.15 (1H, m), 7.78 (1H, td), 8.20 (1H, d), 8.34 (1H, dd), 8.72 (1H, brs)

100 mg (0.58 mmol) of the 2,2-difluoro-N-(pyridin-2(1H)-ylidene)acetamide obtained by the aforementioned method was dissolved in 10 ml of anhydrous acetonitrile, 94 mg (0.58 mmol) of 2-chloro-5-chloromethyl pyridine was dissolved in 5 ml of anhydrous acetonitrile and added thereto, and subsequently, 84 mg (0.63 mmol) of potassium carbonate was added thereto and the resulting mixture was heated and refluxed for 140 minutes. After the reaction was completed, the reaction solution was returned to room temperature to filter off insoluble materials, and the filtrate was concentrated under reduced pressure. Ether was added thereto to precipitate a solid, and thus the solid was collected and dried well to obtain the subject material. Amount obtained 63 mg (yield 37%).

1H-NMR (CDCl3, δ, ppm): 5.52 (2H, s), 5.90 (1H, t), 6.79 (1H, td), 7.33 (1H, d), 7.71 (1H, m), 7.77 (1H, dd), 7.85 (1H, dd), 8.45 (1H, d), 8.50 (1H, d)

13C-NMR (DMSO-d6, δ, ppm): 53.0, 111.0 (t), 115.2, 120.7, 124.7, 131.7, 140.6, 141.6, 143.2, 150.4, 150.9, 158.3, 169.4 (t)

MS: m/z=298 (M+H)

Synthetic Example P8

2-chloro-N-[1-((6-chloropyridin-3-yl)methyl)pyridin-2(1H)-ylidene]-2,2-difluoroacetamide (Compound P239)

200 mg (2.13 mmol) of 2-aminopyridine was dissolved in 5 ml of dichloromethane, 491 mg (2.55 mmol) of EDC-HCl, 311 mg (2.55 mmol) of DMAP and 187 μl (2.23 mmol, 290 mg) of chlorodifluoroacetic acid were added thereto in sequence, and the resulting mixture was stirred overnight. After the reaction was completed, the reaction solution was diluted with dichloromethane, washed with water and 1% hydrochloric acid, and then dried over anhydrous magnesium sulfate to obtain 105 mg (yield 24%) of 2-chloro-2,2-difluoro-N-(pyridin-2(1H)-ylidene)acetamide.

1H-NMR (CDCl3, δ, ppm): 7.19 (1H, dd), 7.82 (1H, m), 8.18 (1H, d), 8.36 (1H, d), 9.35 (1H, brs)

53 mg (0.33 mmol) of 2-chloro-5-chloromethyl pyridine dissolved in 6 ml of anhydrous acetonitrile was added to 68 mg (0.33 mmol) of the 2-chloro-2,2-difluoro-N-(pyridin-2 (1H)-ylidene)acetamide synthesized by the aforementioned method, and subsequently, 50 mg (0.36 mmol) of potassium carbonate was added thereto and the resulting mixture was heated and refluxed for 1 hours. After the reaction was completed, the reaction solution was returned to room temperature and then concentrated under reduced pressure. Diethyl ether was added thereto to precipitate a solid, and thus the solid was collected and dried to obtain the subject material. Amount obtained 49 mg (yield 45%).

1H-NMR (CDCl3, δ, ppm): 5.56 (2H, s), 6.92 (1H, t), 7.33 (1H, d), 7.82 (1H, m), 7.91 (1H, dd), 8.02 (1H, d), 8.45 (1H, d), 8.48 (1H, d)

13C-NMR (CDCl3, δ, ppm): 53.8, 115.2, 120.1 (t), 122.1, 124.8, 139.0, 140.0, 142.3, 150.0, 151.9, 159.1, 159.1, 165.8 (t)

MS: m/z=332 (M+H)

Synthetic Example P9

2,2,2-trichloro-N-[1-((6-chloropyridin-3-yl)methyl)pyridin-2(1H)-ylidene]-acetamide (Compound P235)

70 mg (0.27 mmol) of the 1-[(6-chloropyridin-3-yl)methyl]pyridin-2(1H)-imine hydrochloride obtained by the method described in another method of Synthetic Example P1 was dissolved in 4 ml of anhydrous dichloromethane, 94 μl (0.68 mmol, 68 mg) of triethylamine and 33 g (0.27 mmol, 49 mg) of trichloroacetyl chloride were added thereto in sequence, and the resulting mixture was stirred at room temperature for 1 hour. After the reaction was completed, water was added thereto to stop the reaction and liquid separation was performed with dichloromethane and water. The organic layer was washed once with water and twice with 1% hydrochloric acid, dried over anhydrous magnesium sulfate and concentrated under reduced pressure. Diethyl ether was added thereto to precipitate a solid, and thus the solid was collected and dried to obtain the subject material. Amount obtained 61 mg (yield 62%).

1H-NMR (CDCl3, δ, ppm): 5.59 (2H, s), 6.86 (1H, t), 7.32 (1H, d), 7.78 (1H, td), 7.91 (2H, m), 8.43 (1H, d), 8.50 (1H, d)
MS: m/z=364 (M+H)

Synthetic Example P10

N-[1-((6-chloropyridin-3-yl)methyl)pyridin-2(1H)-ylidene]-2,2,3,3,3-pentafluoropropanamide (Compound P242)

300 mg (3.19 mmol) of 2-aminopyridine was dissolved in 15 ml of anhydrous dichloromethane, 919 mg (4.78 mmol) of EDC-HCl, 583 mg (4.78 mmol) of DMAP and 397 μl (628 mg, 3.83 mmol) of pentafluoropropionic acid were added thereto in sequence, and the resulting mixture was stirred at room temperature overnight. After the reaction was completed, the reaction solution was diluted with dichloromethane, washed once with water and twice with 1% hydrochloric acid, and then dried over anhydrous magnesium sulfate and concentrated under reduced pressure to obtain 85 mg (yield 11%) of 2,2,3,3,3-pentafluoro-N-(pyridin-2(1H)-ylidene)propanamide.

52 mg (0.32 mmol) of 2-chloro-5-chloromethyl pyridine dissolved in 8 ml of anhydrous acetonitrile and 49 mg (0.35 mmol) of potassium carbonate were added to 77 mg (0.32 mmol) of the 2,2,3,3,3-pentafluoro-N-(pyridin-2(1H)-ylidene)propanamide obtained by the aforementioned method, and the resulting mixture was heated and refluxed for 11 hours. After the reaction was completed, the reaction solution was returned to room temperature to filter insoluble materials, and the filtrate was concentrated under reduced pressure. The filtrate was purified by silica gel column chromatography (hexane:ethyl acetate=1:3) to obtain the subject material. Amount obtained 12 mg (yield 10%).

1H-NMR (CDCl3, δ, ppm): 5.56 (2H, s), 6.90 (1H, td), 7.32 (1H, d), 7.79 (2H, m), 7.84 (1H, d), 8.43 (1H, d), 8.56 (1H, d)
MS: m/z=366 (M+H)

Synthetic Example P11

N-[1-((2-chloropyrimidin-5-yl)methyl)pyridin-2(1H)-ylidene]-2,2,2-trifluoroacetamide (Compound P243)

1.04 g (8.13 mmol) of 2-chloro-5-methyl pyrimidine was dissolved in 30 ml of carbon tetrachloride, 1.73 g (9.75 mmol) of N-bromosuccinimide and 20 mg of benzoyl peroxide were added thereto, and the resulting mixture was heated and refluxed for 6 hours. After the reaction was completed, the reaction solution was returned to room temperature, concentrated under reduced pressure and purified by silica gel column chromatography (hexane:ethyl acetate=3:1) to obtain 641 mg (yield 38%) of 5-bromomethyl-2-chloropyridine.

1H-NMR (CDCl3, δ, ppm): 4.42 (2H, s), 8.66 (2H, s)

104 mg (0.50 mmol) of the 5-bromomethyl-2-chloropyridine obtained by the aforementioned method was dissolved in 6 ml of anhydrous acetonitrile, 96 mg (0.50 mmol) of 2,2,2-trifluoro-N-(pyridin-2(1H)-ylidene)acetoamide obtained by the method described in (1) of Synthetic Example P1 and 76 mg (0.55 mmol) of potassium carbonate were added thereto, and the resulting mixture was heated and refluxed for 1 hour. After the reaction was completed, the reaction solution was returned to room temperature to filter off insoluble materials, and the filtrate was concentrated under reduced pressure. Diethyl ether was added thereto to precipitate a solid, and thus the solid was collected, washed with diethyl ether, and then dried under reduced pressure in a desiccator to obtain the subject material. Amount obtained 92 mg (yield 58%).

1H-NMR (CDCl3, δ, ppm): 5.54 (2H, s), 6.98 (1H, m), 7.87 (1H, m), 8.18 (1H, m), 8.48 (1H, m), 8.83 (2H, m)
13C-NMR (CDCl3, δ, ppm): 60.0, 115.6, 117.1 (q), 122.1, 127.5, 139.2, 142.9, 158.8, 160.3 (2C), 161.4, 163.8 (q)
MS: m/z=317 (M+H)

The compounds of P213 to P226, P228, P230, P232 to P234, P240 and P244 shown in the following Table were synthesized by the methods in accordance with Synthetic Examples P1 to P11.

TABLE 40

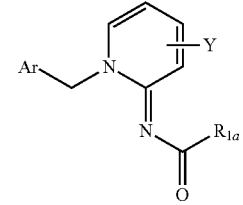

| Compound No. | Ar | R1a | Y | 1H-NMR (CDCl3, δ, ppm) or MS | IR (KBr, v, cm−1) |
|---|---|---|---|---|---|
| P212 | 6-chloro-3-pyridyl | CF3 | H | 5.57 (2H, s), 6.92 (1H, td), 7.31 (1H, d), 7.80 (1H, td), 7.87 (1H, dd), 7.99 (1H, dd), 8.48 (2H, m) | m/z = 316 (M + H) |
| P213 | 2-chloro-5-thiazolyl | CF3 | H | 5.61 (2H, s), 6.93 (1H, dd), 7.68 (1H, s), 7.83 (1H, td), 7.97 (1H, d), 8.53 (1H, d) | m/z = 322 (M + H) |
| P214 | 6-chloro-3-pyridyl | OCH3 | H | 3.74 (3H, s), 5.40 (2H, s), 6.45 (1H, td), 7.29 (1H, d), 7.46 (2H, m), 7.73 (1H, dd), 8.12 (1H, dd), 8.40 (1H, d) | m/z = 278 (M + H) |
| P215 | 6-chloro-3-pyridyl | CF3 | 5-Cl | 5.53 (2H, s), 7.34 (1H, d), 7.71 (1H, dd), 7.87 (1H, dd), 7.94 (1H, s), 8.49 (1H, d), 8.55 (1H, s) | m/z = 350 (M + H) |
| P216 | 6-chloro-3-pyridyl | CF3 | 5-F | 5.54 (2H, s), 7.34 (1H, d), 7.70 (1H, m), 7.80 (1H, m), 7.88 (1H, dd), 8.48 (1H, d), 8.64 (1H, m) | m/z = 334 (M + H) |
| P217 | 6-chloro-3-pyridyl | CF3 | 4-Cl | 5.49 (2H, s), 6.85 (1H, dd), 7.35 (1H, d), 7.76 (1H, dd), 7.85 (1H, dd), 8.44 (1H, d), 8.62 (1H, s) | m/z = 350 (M + H) |
| P218 | 2-chloro-5-thiazolyl | CF3 | 5-Cl | 5.56 (2H, s), 7.68 (1H, s), 7.74 (1H, dd), 7.84 (1H, d), 8.58 (1H, d) | m/z = 356 (M + H) |
| P219 | 2-chloro-5-thiazolyl | CF3 | 5-F | 5.60 (2H, s), 7.69 (1H, s), 7.72 (1H, td), 7.86 (1H, m), 8.67 (1H, m) | m/z = 340 (M + H) |
| P220 | 2-chloro-5-thiazolyl | CF3 | 4-Cl | 5.58 (2H, s), 6.90 (1H, d), 7.67 (1H, s), 7.90 (1H, d), 8.61 (1H, s) | m/z = 356 (M + H) |
| P221 | 6-chloro-3-pyridyl | CF3 | 3-Me | 2.31 (3H, s), 5.50 (2H, s), 6.98 (1H, m), 7.34 (1H, d), 7.73 (1H, dd), 7.77 (2H, m), 8.42 (1H, d) | m/z = 330 (M + H) |
| P222 | 6-chloro-3-pyridyl | CF3 | 4-Me | 2.40 (3H, s), 5.49 (2H, s), 6.70 (1H, dd), 7.32 (1H, d), | m/z = 330 (M + H) |

TABLE 40-continued

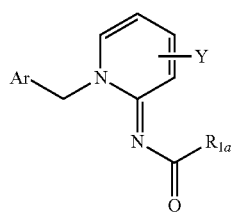

| Compound No. | Ar | R1a | Y | ¹H-NMR (CDCl3, δ, ppm) or MS | IR (KBr, v, cm⁻¹) |
|---|---|---|---|---|---|
| P223 | 6-chloro-3-pyridyl | CF3 | 5-Me | 2.29 (3H, s), 5.52 (2H, s), 7.32 (1H, d), 7.62 (1H, s), 7.65 (1H, dd), 7.88 (1H, dd), 8.46 (1H, d), 8.50 (1H, d) | m/z = 330 (M + H) |
| P224 | phenyl | CF3 | H | 5.58 (2H, s), 6.81 (1H, m), 7.37 (4H, m), 7.77 (2H, m), 8.50 (1H, d) | m/z = 281 (M + H) |
| P225 | 4-chloro-phenyl | CF3 | H | 5.52 (2H, s), 6.85 (1H, m), 7.30 (2H, d), 7.36 (2H, d), 7.75 (1H, td), 7.84 (1H, d), 8.47 (1H, d) | m/z = 315 (M + H) |
| P226 | 3-pyridyl | CF3 | H | 5.57 (2H, s), 6.86 (1H, m), 7.26-7.35 (2H, m), 7.78 (1H, td), 7.86 (1H, m), 8.63 (2H, m), 8.67 (1H, d) | m/z = 282 (M + H) |
| P227 | 6-chloro-5-fluoro-3-pyridyl | CF3 | H | 5.54 (2H, s), 6.89 (1H, td), 7.76 (1H, dd), 7.80 (1H, td), 7.85 (1H, d), 8.29 (1H, d), 8.57 (1H, d) | m/z = 334 (M + H) |
| P228 | 6-trifluoro-methyl-3-pyridyl | CF3 | H | 5.62 (2H, s), 6.90 (1H, t), 7.69 (1H, d), 7.81 (1H, t), 7.88 (1H, d), 8.06 (1H, d), 8.56 (1H, d), 8.78 (1H, s) | m/z = 350 (M + H) |
| P229 | 6-fluoro-3-pyridyl | CF3 | H | 5.56 (2H, s), 6.89 (1H, td), 6.94 (1H, d), 7.79 (1H, td), 7.87 (1H, d), 8.03 (1H, m), 8.31 (1H, s), 8.54 (1H, d) | m/z = 300 (M + H) |
| P230 | 5,6-dichloro-3-pyridyl | CF3 | H | 5.49 (2H, s), 6.89 (1H, t), 7.79-7.90 (2H, m), 8.04 (1H, d), 8.37 (1H, d), 8.56 (1H, m) | m/z = 350 (M + H) |

TABLE 41

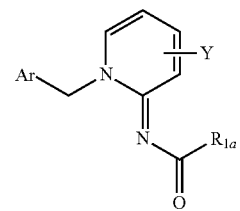

| Compound No. | Ar | R1a | Y | ¹H-NMR (CDCl3, δ, ppm) or MS | IR (KBr, v, cm⁻¹) |
|---|---|---|---|---|---|
| P231 | 6-bromo-3-pyridyl | CF3 | H | 5.52 (2H, s), 6.88 (1H, t), 7.48 (1H, d), 7.78 (2H, m), 7.84 (1H, d), 8.44 (1H, d), 8.53 (1H, d) | m/z = 360 (M + H) |
| P232 | 6-chloro-3-pyridyl | CF3 | 4-F | 5.52 (2H, s), 6.71 (1H, m), 7.35 (1H, d), 7.86 (1H, dd), 7.94 (1H, m), 8.33 (1H, dd), 8.44 (1H, d) | m/z = 334 (M + H) |
| P233 | 6-chloro-3-pyridyl | CF3 | 3-F | 5.53 (2H, s), 6.74 (1H, m), 7.33 (1H, d), 7.87 (1H, dd), 8.07 (1H, m), 8.29 (1H, dd), 8.45 (1H, d) | m/z = 334 (M + H) |
| P234 | 6-chloro-3-pyridyl | CHCl2 | H | 5.54 (2H, s), 6.02 (1H, s), 6.77 (1H, t), 7.32 (1H, m), 7.69 (1H, m), 7.77 (1H, d), 7.89 (1H, m), 8.42 (1H, m), 8.49 (1H, s) | m/z = 330 (M + H) |
| P235 | 6-chloro-3-pyridyl | CCl3 | H | 5.59 (2H, s), 6.86 (1H, t), 7.32 (1H, d), 7.78 (1H, td), 7.91 (2H, m), 8.43 (1H, d), 8.50 (1H, d) | m/z = 364 (M + H) |
| P236 | 6-chloro-3-pyridyl | CH2Cl | H | 4.17 (2H, s), 5.46 (2H, s), 6.64 (1H, td), 7.31 (1H, d), 7.60 (1H, td), 7.64 (1H, dd), 7.80 (1H, dd), 8.32 (1H, d), 8.45 (1H, d) | m/z = 296 (M + H) |
| P238 | 6-chloro-3-pyridyl | CHF2 | H | 5.52 (2H, s), 5.90 (1H, t), 6.79 (1H, td), 7.33 (1H, d), 7.71 (1H, m), 7.77 (1H, dd), 7.85 (1H, dd), 8.45 (1H, d), 8.50 (1H, d) | m/z = 298 (M + H) |
| P239 | 6-chloro-3-pyridyl | CF2Cl | H | 5.56 (2H, s), 6.92 (1H, t), 7.33 (1H, d), 7.82 (1H, m), 7.91 (1H, dd), 8.02 (1H, d), 8.45 (1H, d), 8.48 (1H, d) | m/z = 332 (M + H) |
| P240 | 6-chloro-3-pyridyl | CHClBr | H | 5.53 (1H, d), 5.58 (1H, d), 6.06 (1H, s), 6.76 (1H, td), 7.32 (1H, d), 7.69 (1H, m), 7.70 (1H, m), 7.90 (1H, dd), 8.40 (1H, d), 8.50 (1H, d) | m/z = 374 (M + H) |
| P241 | 6-chloro-3-pyridyl | CHBr2 | H | 5.56 (2H, s), 5.99 (1H, s), 6.78 (1H, td), 7.33 (1H, d), 7.69 (1H, td), 7.76 (1H, dd), 7.93 (1H, dd), 8.39 (1H, d), 8.50 (1H, d) | m/z = 418 (M + H) |
| P242 | 6-chloro-3-pyridyl | CF2CF3 | H | 5.56 (2H, s), 6.90 (1H, td), 7.32 (1H, d), 7.79 (2H, m), 7.84 (1H, d), 8.43 (1H, d), 8.56 (1H, d) | m/z = 366 (M + H) |

TABLE 41-continued

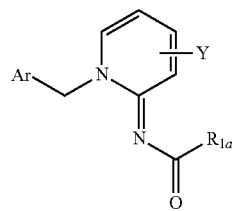

| Compound No. | Ar | R1a | Y | 1H-NMR (CDCl3, δ, ppm) | IR (KBr, v, cm$^{-1}$) or MS |
|---|---|---|---|---|---|
| P243 | 2-chloro-5-pyrimidinyl | CF3 | H | 5.54 (2H, s), 6.98 (1H, m), 7.87 (1H, m), 8.18 (1H, m), 8.48 (1H, m), 8.83 (2H, m) | m/z = 317 (M + H) |
| P244 | 6-chloro-3-pyridyl | CH2Br | H | 4.17 (2H, s), 5.46 (2H, s), 6.63 (1H, td), 7.31 (1H, d), 7.60 (1H, td), 7.65 (1H, dd), 7.80 (1H, dd), 8.32 (1H, d), 8.47 (1H, d) | |

Synthetic Example 1

2,2-difluoro-N-[1-((6-fluoropyridin-3-yl)methyl)pyridin-2(1H)-ylidene]acetamide (Compound 3-3)

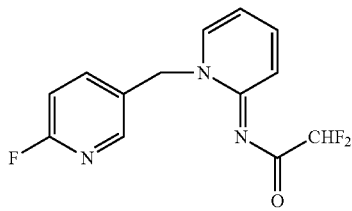 [SMILES: O=C(/N=c1\ccccn1Cc1ccc(F)nc1)C(F)F]

(1) 400 mg (4.26 mmol) of 2-aminopyridine was dissolved in 10 ml of anhydrous dichloromethane, 322 µl (490 mg, 5.11 mmol) of difluoroacetic acid, 982 mg (5.10 mmol) of EDC-HCl and 622 mg (5.11 mmol) of DMAP were added thereto, and the resulting mixture was stirred at room temperature for 61 hours. After the reaction was completed, the reaction solution was diluted with dichloromethane, washed once with water and twice with a 1% HCl aqueous solution, and then dried over anhydrous magnesium sulfate and concentrated under reduced pressure to obtain 102 mg (yield 14%) of 2,2-difluoro-N-(pyridin-2(1H)-ylidene)acetamide.

1H-NMR (CDCl3, δ, ppm): 6.03 (1H, t), 7.15 (1H, m), 7.78 (1H, td), 8.20 (1H, d), 8.34 (1H, dd), 8.72 (1H, brs)

(2) 128 mg (0.75 mmol) of 5-bromomethyl-2-fluoropyridine was dissolved in 3 ml of anhydrous DMF, 116 mg (0.68 mmol) of 2,2-difluoro-N-[pyridin-2(1H)-ylidene]acetamide was dissolved in 3 ml of anhydrous DMF and added thereto, and subsequently, 103 mg (0.75 mmol) of potassium carbonate was added thereto and the resulting mixture was stirred at 65° C. for 2 hours. After the reaction was completed, the reaction solution was returned to room temperature, and ethyl acetate and water were added thereto to perform liquid separation. The organic layer was washed with 1% hydrochloric acid, then dried over anhydrous magnesium sulfate and concentrated under reduced pressure. A small amount of hexane and diethyl ether were added thereto to precipitate crystals, and thus the crystals were collected and dried to obtain the subject material. Amount obtained 50 mg (yield 26%).

Synthetic Example 2

N-[1-((6-chloropyridin-3-yl)methyl)pyrimidin-2(1H)-ylidene]-2,2,2-trifluoroacetamide (Compound 190-2)

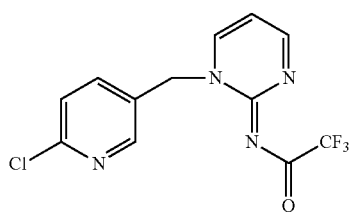 [SMILES: O=C(/N=c1\ncccn1Cc1ccc(Cl)nc1)C(F)(F)F]

(1) 300 mg (1.86 mmol) of 2-chloro-5-chloromethyl pyridine was dissolved in 6 ml of anhydrous DMF, 118 mg (1.24 mmol) of 2-aminopyrimidine was added thereto, and the resulting mixture was stirred at 80° C. for 8 hours. After the reaction was completed, the reaction solution was returned to room temperature to distill off DMF under reduced pressure. Diethyl ether was added thereto, and thus crystallization was occurred on the wall surface of an eggplant flask. Diethyl ether was removed by decantation and dried well to obtain 1-((6-chloropyridin-3-yl)methyl)pyrimidin-2(1H)-imine hydrochloride. Amount obtained 107 mg (yield 34%)

(2) 71 mg (0.27 mmol) of the 1-((6-chloropyridin-3-yl)methyl)pyrimidin-2(1H)-imine hydrochloride obtained by the aforementioned method was suspended in 5 ml of anhydrous dichloromethane, 114 µl (0.83 mmol, 83 mg) of triethylamine and 53 µl (0.38 mmol) of trifluoroacetic anhydride were added thereto in sequence, and the resulting mixture was stirred at room temperature for 2 hours. After the reaction was completed, dichloromethane and water were added to the reaction solution to perform liquid separation, and the organic layer was dried over anhydrous magnesium sulfate and then concentrated under reduced pressure. A small amount of diethyl ether was added thereto to precipitate crystals, and thus the crystals were collected, washed with a small amount of diethyl ether, and then dried to obtain the subject material. Amount obtained 24 mg (yield 28%).

Synthetic Example 3

2,2,2-trifluoroethyl-[1-((6-chloropyridin-3-yl)methyl)pyridin-(2H)-ylidene]carbamate (Compound 1-17)

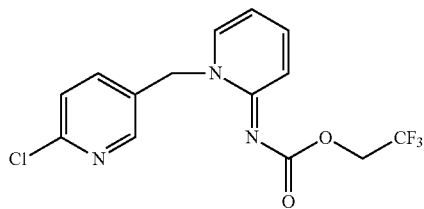 [SMILES: O=C(/N=c1\ccccn1Cc1ccc(Cl)nc1)OCC(F)(F)F]

(1) 3.00 g (18.6 mmol) of 2-chloro-5-chloromethyl pyridine was dissolved in 20 ml of anhydrous DMF, 1.75 g (18.6 mmol) of 2-aminopyridine was added thereto, and the resulting mixture was stirred at 80° C. for 8 hours and at room temperature for 5 hours. After the reaction was completed, DMF was distilled off under reduced pressure, acetonitrile was added thereto to precipitate a solid, and the solid was collected, washed well with acetonitrile and then dried to obtain 2.07 g (yield 44%) of 1-[(6-chloropyridin-3-yl)methyl]pyridin-2(1H)-imine hydrochloride.

1H-NMR (DMSO-d6, δ, ppm): 5.65 (2H, s), 6.96 (1H, t), 7.23 (1H, m), 7.57 (1H, d), 7.80 (1H, m), 7.91 (1H, m), 8.28 (1H, m), 8.49 (1H, d)

(2) 10 ml of anhydrous acetonitrile was added to 150 mg (0.66 mmol) of the 1-[(6-chloropyridin-3-yl)methyl]pyridin-2(1H)-imine hydrochloride obtained by the aforementioned method, 177 mg (0.66 mmol) of 4-nitrophenyl(2,2,2-trifluoroethyl)carbamate and 200 mg (1.46 mmol) of potassium carbonate were added, and the resulting mixture was stirred at 50° C. for 2 hours. After the reaction was completed, the reaction solution was returned to room temperature to filter off insoluble materials, and the filtrate was concentrated under reduced pressure. Dichloromethane and water were added thereto to perform liquid separation, and the organic layer was washed with 1% hydrochloric acid, then dried over anhydrous magnesium sulfate and concentrated under reduced pressure. A small amount of diethyl ether was added thereto to precipitate crystals, and thus the crystals were collected and dried well to obtain the subject material. Amount obtained 48 mg (yield 21%).

Synthetic Example 4

N-[1-((6-chloropyridin-3-yl)methyl)pyridin-2(1H)-ylidene]-2,2,2-trifluoroethanethioamide (Compound 1-20)

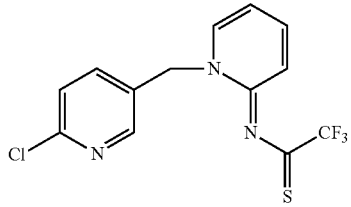 [SMILES: FC(F)(F)C(=S)/N=c1\ccccn1Cc1ccc(Cl)nc1]

(1) 25 g (270 mmol) of 2-aminopyridine was dissolved in 200 ml of anhydrous dichloromethane, 41 ml (30 g, 300 mmol) of triethylamine was added thereto, and the mixture was cooled to 0° C. 38 ml (57 g, 270 mmol) of anhydrous trifluoroacetic acid was added dropwise thereto over 15 minutes, and the resulting mixture was stirred at room temperature for 2 hours. After the reaction was completed, the reaction solution was injected into about 100 ml of iced water, and the mixture was stirred for 10 minutes. The mixture was transferred to a separatory funnel to perform liquid separation, and the organic layer was washed twice with 150 ml of water and twice with 150 ml of a 1% HCl aqueous solution, dried over anhydrous magnesium sulfate and concentrated under reduced pressure to obtain 36 g (yield 71%) of 2,2,2-trifluoro-N-(pyridin-2(1H)-ylidene)acetamide.

1H-NMR (CDCl3, δ, ppm): 7.20 (1H, m), 7.83 (1H, m), 8.20 (1H, d), 8.35 (1H, d), 10.07 (1H, brs)

13C-NMR (CDCl3, δ, ppm): 115.3, 115.5 (q), 121.6, 139.1, 147.9, 149.5, 155.3 (q)

(2) 20 g (126 mmol) of 2-chloro-5-chloromethyl pyridine was dissolved in 200 ml of anhydrous acetonitrile, 24 g (126 mmol) of 2,2,2-trifluoro-N-(pyridin-2(1H)-ylidene)acetamide obtained by the above-described method and 21 g (151 mmol) of potassium carbonate were added thereto, and the resulting mixture was heated and refluxed for 6 hours, and then stirred at room temperature for 10 hours. After the reaction was completed, the reaction solution was filtered and the filtrate was concentrated under reduced pressure. Diethyl ether was added thereto for crystallization, and the crystals thus obtained were collected and washed well with diethyl ether and water. The crystals thus obtained were dried under reduced pressure at 60° C. for 1 hour to obtain N-[1-((6-chloropyridin-3-yl)methyl)pyridin-2(1H)-ylidene]-2,2,2-trifluoroacetamide (P212). Amount obtained 26 g (yield 66%).

1H-NMR (CDCl3, δ, ppm): 5.57 (2H, s), 6.92 (1H, td), 7.31 (1H, d), 7.80 (1H, td), 7.87 (1H, dd), 7.99 (1H, dd), 8.48 (2H, m)

13C-NMR (CDCl3, δ, ppm): 53.8, 115.5, 117.2 (q), 122.1, 124.7, 130.0, 139.2, 140.0, 142.5, 149.7, 151.8, 158.9, 163.5 (q)

MS: m/z=316 (M+H)

(3) 180 ml of toluene was added to 16.3 g (36.7 mmol) of phosphorus pentasulfide, 6.72 g (63.4 mmol) of sodium carbonate was added thereto and the resulting mixture was stirred at room temperature for 5 minutes. 20.0 g (63.4 mmol) of the N-[1-((6-chloropyridin-3-yl)methyl)pyridin-2(1H)-ylidene]-2,2,2-trifluoroacetamide obtained by the above-described method was added thereto, and the resulting mixture was stirred at 50° C. for 19 hours. 150 ml of ethyl acetate was added to the reaction solution, the resulting mixture was stirred at 50° C. for 10 minutes, then insoluble materials were filtered off, and 250 ml of ethyl acetate was used to wash the mixture. The mixture was transferred to a separatory funnel, washed therein with 300 ml of a saturated sodium bicarbonate water and 200 ml of a saturated saline solution, and then concentrated under reduced pressure. 200 ml of water was added thereto to precipitate crystals. The mixture was stirred at room temperature for 1 hour, and then the crystals were collected, subjected to slurry washing twice with 150 ml of water and twice with 150 ml of hexane, and dried at 60° C. under reduced pressure for 2 hours to obtain the subject material. Amount obtained 19.5 g (yield 94%).

1H-NMR (CDCl3, δ, ppm): 5.48 (2H, s), 7.12 (1H, td), 7.34 (1H, d), 7.77 (1H, dd), 7.96 (1H, m), 8.05 (1H, dd), 8.45 (1H, d), 8.56 (1H, d)

MS: m/z=332 (M+H)

Synthetic Example 5

N-[1-((6-chloropyridin-3-yl)methyl)pyridin-2(1H)-ylidene]-2,2,2-trifluoro-N'-methylacetimidamide (Compound 1-42)

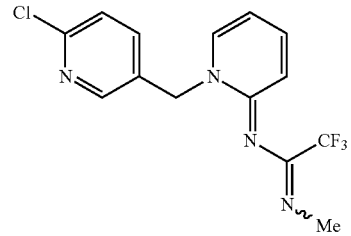

150 mg (0.45 mmol) of the N-[1-((6-chloropyridin-3-yl)methyl)pyridin-2(1H)-ylidene]-2,2,2-trifluoroethanethioamide (1-20) synthesized by the method in Synthetic Example 4 was dissolved in 5 ml of methanol, 105 μl (42 mg, 1.36 mmol) of methylamine (40% methanol solution) and 124 mg (0.45 mmol) of silver carbonate were added thereto, and the resulting mixture was stirred at 50° C. for 1 hour. After the reaction was completed, the reaction solution was returned to room temperature and subjected to suction filtration by using celite to remove insoluble materials. Ethyl acetate and water were added thereto to perform liquid separation, and the organic layer was dried over anhydrous magnesium sulfate, then concentrated under reduced pressure and purified with silica gel column chromatography (hexane:ethyl acetate=1:1) to obtain the subject material. Amount obtained 81 mg (yield 56%).

Synthetic Example 6

N'-(aryloxy)-N-[1-((6-chloropyridin-3-yl)methyl) pyridin-2(1H)-ylidene]-2,2,2-trifluoroacetimidamide (Compound 1-507)

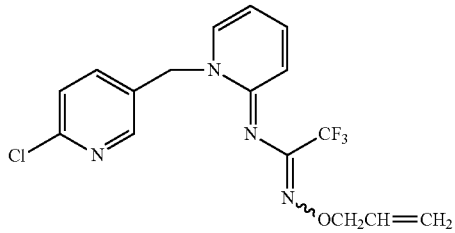

30 mg (0.09 mmol) of the N-[1-((6-chloropyridin-3-yl) methyl)pyridin-2(1H)-ylidene]-2,2,2-trifluoroethanethioamide (1-20) synthesized by the method in Synthetic Example 4 was dissolved in 5 ml of ethanol, 50 mg (0.45 mmol) of 0-ally hydroxylamine hydrochloride, 62 µl (0.45 mmol, 45 mg) of triethylamine and 25 mg (0.09 mmol) of silver carbonate were added thereto, and the resulting mixture was stirred at 50° C. for 5 hours and 20 minutes. After the reaction was completed, the reaction solution was returned to room temperature to filter off insoluble materials. The filtrate was concentrated under reduced pressure to perform liquid separation with ethyl acetate and 1% hydrochloric acid, then the ethyl acetate layer was washed with a saturated saline solution, and dried over anhydrous magnesium sulfate and then concentrated under reduced pressure. The ethyl acetate layer was purified by a TLC plate (one sheet of 0.5 mm plate, evolved with hexane:ethyl acetate=1:1) to obtain the subject material. Amount obtained 15 mg (yield 45%).

Synthetic Example 7

N-[1-((6-chloropyridin-3-yl)methyl)pyridin-2(1H)-ylidene]-2,2,2-trifluoro-N'-hydroxyacetimidamide (Compound 1-499)

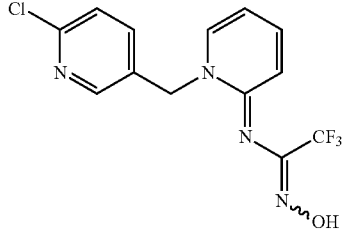 [SMILES: ON=C(/N=c1\ccccn1Cc1ccc(Cl)nc1)C(F)(F)F]

25 ml of ethanol was added to 1.00 g (3.00 mmol) of the N-[1-((6-chloropyridin-3-yl)methyl)pyridin-2(1H)-ylidene]-2,2,2-trifluoroethanethioamide (1-20) 1 synthesized by the method in Synthetic Example 4, 1.04 g (15.0 mmol) of hydroxylamine hydrochloride and 2.00 ml (1.50 g, 15.0 mmol) of triethylamine were added thereto in sequence, and the resulting mixture was stirred at 50° C. for 21.5 hours. After the reaction was completed, ethyl acetate and 1% hydrochloric acid were added to the reaction solution to perform liquid separation, and the organic layer was washed with water, dried over anhydrous magnesium sulfate and concentrated under reduced pressure. The organic layer was purified by silica gel column chromatography (hexane:ethyl acetate=1:1) to obtain the subject material. Amount obtained 625 mg (yield 63%).

Synthetic Example 8

N-(benzoyloxy)-N-[1-((6-chloropyridin-3-yl)methyl) pyridin-2(1H)-ylidene]-2,2,2-trifluoroacetimidamide (Compound 1-519)

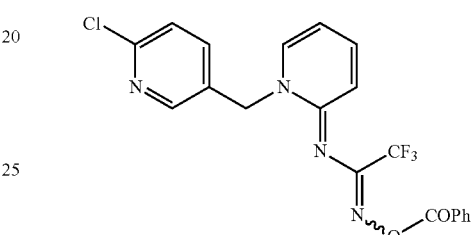

30 mg (0.09 mmol) of the N-[1-((6-chloropyridin-3-yl) methyl)pyridin-2(1H)-ylidene]-2,2,2-trifluoro-N'-hydroxyacetimidamide (1-499) synthesized by the method in Synthetic Example 7 was dissolved in 3 ml of anhydrous acetonitrile, 24 µl (17 mg, 0.17 mmol) of triethylamine and 20 µg (22 mg, 0.17 mmol) of benzoyl chloride were added thereto in sequence, and the resulting mixture was stirred at room temperature for 10 minutes. After the reaction was completed, ethyl acetate and 1% hydrochloric acid were added to the reaction solution to perform liquid separation, and the organic layer was washed with water, dried over anhydrous magnesium sulfate and concentrated under reduced pressure. The organic layer was purified by a TLC plate (one sheet of 0.5 mm plate, evolved with hexane:ethyl acetate=1:1) to obtain the subject material. Amount obtained 26 mg (yield 67%).

Synthetic Example 9

N-[1-((6-chloropyridin-3-yl)methyl)pyridin-2(1H)-ylidene]-2,2,2-trifluoro-N'-((propylcarbamoyl)oxy) acetimidamide (Compound 1-534)

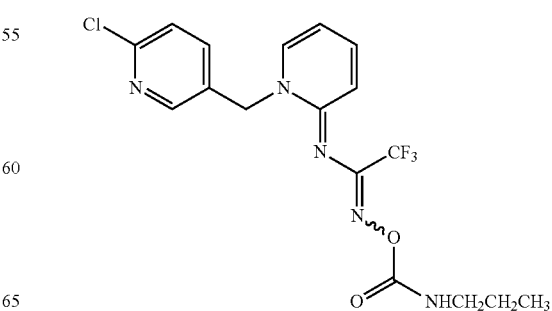

5 ml of anhydrous acetonitrile was added to 11 mg (0.13 mmol) of normal propyl isocyanate, 40 mg (0.12 mmol) of the N-[1-((6-chloropyridin-3-yl)methyl)pyridin-2(1H)-ylidene]-2,2,2-trifluoro-N'-hydroxyacetimidamide (1-499) synthesized by the method in Synthetic Example 7 and 4 mg (0.04 mmol) of potassium-t-butoxide were added thereto, and the resulting mixture was stirred at room temperature for 1 hour. After the reaction was completed, the reaction solution was concentrated under reduced pressure, and ethyl acetate and a saturated saline solution were added thereto to perform liquid separation. The ethyl acetate layer was dried over anhydrous magnesium sulfate, concentrated under reduced pressure and purified by a TLC plate (one sheet of 0.5 mm plate, evolved with hexane:ethyl acetate=1:3) to obtain the subject material. Amount obtained 16 mg (yield 32%).

Synthetic Example 10

Diisopropyl 1-((6-chloropyridin-3-yl)methyl)pyridyn-2(1H)-ylidenphospholamide trithioate (Compound 1-702)

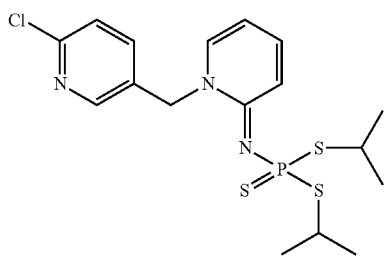 [SMILES: CC(C)SP(=S)(/N=c1\ccccn1Cc1ccc(Cl)nc1)SC(C)C]

4.0g (15.7 mmol) of 1-((6-chloropyridin-3-yl)methyl)pyridin-2(1H)-imine hydrochloride obtained by the above-described method was suspended in 24.6 ml of dichloromethane, and under ice-cooling 1.35 ml of phosphorous trichloride over 10 mins, following 3.16 g (31.2 mmol) of triethylamine dissolved in 37 ml of dichloromethane was added thereto. After the mixture was stirred for 2 hours at room temperature, 499 mg (15.6 mmol) of sulfur was added to the mixture, and the mixture was stirred over night at room temperature. Under ice-cooling 3.16 g (31.2 mmol) of triethylamine, following 2.38 g (31.2 mmol) of 2-propanethiol dissolved in 10 ml of dichloromethane were added to the mixture, additionary the mixture was stirred for a day. After the reaction was completed, the reaction solution was concentrated under reduced pressure, and was extracted by 100 ml of diethylether twice. The ether solution was concentrated under reduced pressure, and 2.49g of cruede compounds was obtained. 186 mg of crude compound was purified by a TLC plate (5 sheets of 0.5 mm plate, evolved with ethyl acetate to obtain the subject material (47 mg. yield 9%) and (1-((6-chloropyridin-3-yl)methyl)pyridin-2(1H)-ylidene)phosphoramidothioic dichloride (19 mg. yield 5%).

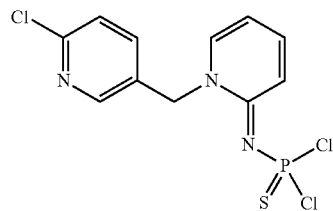 [SMILES: S=P(Cl)(Cl)/N=c1\ccccn1Cc1ccc(Cl)nc1]

(1-((6-chloropyridin-3-yl)methyl)pyridin-2(1H)-ylidene)phosphoramidothioic dichloride Synthetic Example 11

N-[1-((6-chloropyridin-3-yl)methyl)pyridin-2 (1H)-ylidene]-1,1,1-trifluoromethanesulfinamide (Compound 1-703)

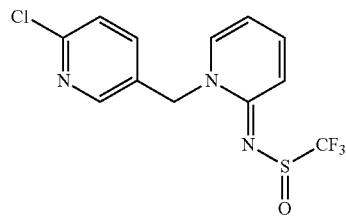 [SMILES: O=S(/N=c1\ccccn1Cc1ccc(Cl)nc1)C(F)(F)F]

330 mg (2 mmol) of sodium trifluoromethanesulfonate was added by 2 ml of ethylacetate and 154 mg (1 mmol) of phosphorus oxychloride and stirred for 5 min at room temperature. And 220 mg (0.86 mmol) of 1-((6-chloropyridin-3-yl)methyl)pyridin-2(1H)-imine hydrochloride obtained by the above-described method was added to the mixture, and stirred for 2 hours. After the reaction was completed, the reaction mixture was purified by silica-gel column chromatography (eluent ethylacetate:hexane=1:1) to obtain the subject material (115 mg. yield 39%)

The compounds shown in the following Table were prepared by the method in accordance with Synthetic Examples 1 to 11.

TABLE 42

| Compound No. | Raw material 1 | Raw material 2 | Base and the like | Solvent | Reaction temperature, Time | Method (Table) | Yield (%) |
|---|---|---|---|---|---|---|---|
| 266-2 | 69 mg (0.43 mmol) of 2-chloro-5-(chloromethyl)pyridine | 84 mg (0.43 mmol) of 2,2,2-trifluoro-N-(1,3,4-thiadiazol-2(3H)-ylidene))acetamide | 71 mg (0.52 mmol) of potassium carbonate | Acetonitrile | reflux, 20 h | A | 32 |
| 444-2 | 56 mg (0.41 mmol) of 2-chloro-5-(chloromethyl)thiazole | 66 mg (0.34 mmol) of 2,2,2-trifluoro-N-(1,3,4-thiadiazol-2(3H)-ylidene))acetamide | 56 mg (0.41 mmol) of potassium carbonate | Acetonitrile | reflux, 20 h | A | 21 |

TABLE 42-continued

| Compound No. | Raw material 1 | Raw material 2 | Base and the like | Solvent | Reaction temperature, Time | Method (Table) | Yield (%) |
| --- | --- | --- | --- | --- | --- | --- | --- |
| 190-2 | 71 mg (0.27 mmol) of 1-((6-chloropyridin-3-yl)methyl)pyrimidin-2(1H)-imine hydrochloride | 53 µl (0.38 mmol) of anhydrous trifluoroacetic acid | 53 µl (0.38 mmol) of triethylamine | Dichloromethane | Room temperature, 1 h | B | 28 |
| 201-2 | 120 mg (0.47 mmol) of 1-((6-chloropyridin-3-yl)methyl)pyrazin-2(1H)-imine hydrochloride | 99 µl (0.71 mmol) of anhydrous trifluoroacetic acid | 160 µl (1.17 mmol) of triethylamine | Dichloromethane | Room temperature, 30 min | B | 11 |
| 223-2 | 530 mg (2.07 mmol) of 2-chloro-2-((6-chloropyridin-3-yl)methyl)pyridazin-3(2H)-imine hydrochloride | 390 µl (2.79 mmol) of anhydrous trifluoroacetic acid | 537 µl (2.79 mmol) of triethylamine | Dichloromethane | Room temperature, 2 h | B | 14 |
| 146-2 | 113 mg (0.70 mmol) of 2-chloro-5-(chloromethyl)pyridine | 145 mg (0.70 mmol) of 2,2,2-trifluoro-N-(3-hydroxypyridin-2(1H)-ylidene))acetamide | 116 mg (0.84 mmol) of potassium carbonate | Acetonitrile | reflux, 13 h | A | 15 |
| 224-2 | 190 mg (0.73 mmol) of 2-((2-chlorothiazol-5-yl)methyl)pyridazin-3(2H)-imine hydrochloride | 168 µl (1.20 mmol) of anhydrous trifluoroacetic acid | 220 µl (1.60 mmol) of triethylamine | Dichloromethane | Room temperature, 5 min | B | 16 |
| 102-2 | 116 mg (0.72 mmol) of 2-chloro-5-(chloromethyl)pyridine | 155 mg (0.72 mmol) of N-(3-cyanopyridin-2(1H)-ylidene))2,2,2-trifluoroacetamide | 109 mg (0.79 mmol) of potassium carbonate | Acetonitrile | reflux, 8 h | A | 22 |
| 212-2 | 59 mg (0.37 mmol) of 2-chloro-5-(chloromethyl)pyridine | 70 mg (0.37 mmol) of 2,2,2-trifluoro-N-(pyrimidin-4(3H)-ylidene)acetamide | 55 mg (0.40 mmol) of potassium carbonate | Acetonitrile | reflux, 7 h | A | 32 |
| 1-20 | 20.0 g (63.4 mmol) of N-[1-((6-chloropyridin-3-yl)methyl)pyridin-2(1H)-ylidene]-2,2,2-trifluoroacetamide | 16.3 g (36.7 mmol) of phosphorus pentasulfide | 6.72 mg (63.4 mmol) of sodium carbonate | Toluene | 50° C., 19 h | D | 94 |
| 12-2 | 78 mg (0.38 mmol) of 2-chloro-4-(bromomethyl)pyridine | 73 mg (0.38 mmol) of 2,2,2-trifluoro-N-(pyridin-2(1H)-ylidene))acetamide | 58 mg (0.42 mmol) of potassium carbonate | Acetonitrile | reflux, 3.5 h | A | 44 |
| 213-2 | 79 mg (0.47 mmol) of 2-chloro-5-(chloromethyl)thiazole | 90 mg (0.47 mmol) of 2,2,2-trifluoro-N-(pyrimidin-4(3H)-ylidene))acetamide | 72 mg (0.52 mmol) of potassium carbonate | Acetonitrile | reflux, 12 h | A | 42 |
| 1-17 | 150 mg (0.66 mmol) of 1-[(6-chloropyridin-3-yl)methyl]pyridin-2(1H)-imine hydrochloride | 177 mg (0.66 mmol) of 4-nitrophenyl(2,2,2-trifluoroethyl)carbamate | 200 mg (1.46 mmol) of potassium carbonate | Acetonitrile | 50° C., 2 h | C | 21 |
| 1-18 | 150 mg (0.66 mmol) of 1-[(6-chloropyridin-3-yl)methyl]pyridin-2(1H)-imine hydrochloride | 184 mg (0.66 mmol) of 4-nitrophenyl(1,1,1-trifluoropropan-2-yl)carbamate | 200 mg (1.46 mmol) of potassium carbonate | Acetonitrile | 50° C., 2 h | C | 30 |
| 1-19 | 150 mg (0.66 mmol) of 1-[(6-chloropyridin-3-yl)methyl]pyridin-2(1H)-imine hydrochloride | 220 mg (0.66 mmol) of 1,1,1,3,3,3-hexafluoro-propan-2-yl(4-nitro-phenyl)carbamate | 200 mg (1.46 mmol) of potassium carbonate | Acetonitrile | 50° C., 3 h | C | 27 |
| 7-2 | 116 mg (0.72 mmol) of 2-chloro-5-(chloromethyl)pyrazine | 137 mg (0.72 mmol) of 2,2,2-trifluoro-N-(pyridin-2(1H)-ylidene))acetamide | 110 mg (0.80 mmol) of potassium carbonate | Acetonitrile | reflux, 5 h | A | 49 |
| 1-13 | 200 mg (0.78 mmol) of 1-[(6-chloropyridin-3-yl)methyl]pyridin 2(1H)-imine hydrochloride | 103 µl (1.17 mmol) of 2,2,2-trilfluoropropionic acid | EDC-HCl 225 mg (1.17 mmol), DMAP 238 mg (1.95 mmol) | Dichloromethane | Room temperature, 12 h | B | 21 |

TABLE 43

| Compound No. | Raw material 1 | Raw material 2 | Base and the like | Solvent | Reaction temperature, Time | Method (Table) | Yield (%) |
|---|---|---|---|---|---|---|---|
| 168-2 | 273 mg (1.70 mmol) of 2-chloro-5-(chloromethyl)pyridine | 350 mg (1.70 mmol) of 2,2,2-trifluoro-N-(5-hydroxypyridin-2(1H)-ylidene))acetamide | 248 mg (1.80 mmol) of potassium carbonate | DMF | 65° C., 2 h | A | 15 |
| 1-21 | 23 mg (0.077 mmol) of N-[1-((6-chloropyridin-3-yl)methyl)pyridin-2(1H)-ylidene]-2,2-difluoroacetamide | 41 mg (0.092 mmol) of phosphorus pentasulfide | 10 mg (0.092 mmol) of sodium carbonate | THF | Room temperature, 2 h | D | 49 |
| 3-20 | 30 mg (0.10 mmol) of N-[1-((6-fluoropyridin-3-yl)methyl)pyridin-2(1H)-ylidene]-2,2,2-trifluoroacetamide | 49 mg (0.11 mmol) of phosphorus pentasulfide | 12 mg (0.11 mmol) of sodium carbonate | THF | Room temperature, 3 h | D | 49 |
| 4-20 | 30 mg (0.083 mmol) of N-[1-((6-bromopyridin-3-yl)methyl)pyridin-2(1H)-ylidene]-2,2,2-trifluoroacetamide | 41 mg (0.09 mmol) of phosphorus pentasulide | 10 mg (0.09 mmol) of sodium carbonate | THF | Room temperature, 3 h | D | 61 |
| 3-3 | 116 mg (0.72 mmol) of 2-fluoro-5-(bromomethyl)pyridine | 116 mg (0.68 mmol) of 2,2-difluoro-N-(pyridin-2(1H)-ylidene))acetamide | 110 mg (0.80 mmol) of potassium carbonate | Acetonitrile | reflux, 6 h | A | 27 |
| 4-3 | 50 mg (0.20 mmol) of 2-bromo-5-(bromomethyl)pyridine | 35 mg (0.20 mmol) of 2,2-difluoro-N-(pyridin-2(1H)-ylidene))acetamide | 33 mg (0.24 mmol) of potassium carbonate | Acetonitrile | reflux, 6 h | A | 53 |
| 5-5 | 46 mg (0.21 mmol) of 5-(bromomethyl)-2-chloro-3-fluoropyridine | 50 mg (0.21 mmol) of 2,2,3,3,3-pentafluoro-N-(pyridin-2(1H)-ylidene))propanamide | 35 mg (0.25 mmol) of potassium carbonate | Acetonitrile | reflux, 2 h | A | 26 |
| 6-5 | 43 mg (0.21 mmol) of 5-(bromomethyl)-2-chloropyrimidine | 50 mg (0.21 mmol) of 2,2,3,3,3-pentafluoro-N-(pyridin-2(1H)-ylidene))propanamide | 35 mg (0.25 mmol) of potassium carbonate | Acetonitrile | reflux, 2 h | A | 21 |
| 1-22 | 37 mg (0.11 mmol) of 2-chloro-N-[1-((6-chloropyridin-3-yl)methyl)pyridin-2(1H)-ylidene]-2,2-difluoroacetamide | 49 mg (0.11 mmol) of phosphorus pentasulfide | 12 mg (0.11 mmol) of sodium carbonate | THF | Room temperature, 4 h | D | 31 |
| 1-23 | 31 mg (0.085 mmol) of N-[1-((6-chloropyridin-3-yl)methyl)pyridin-2(1H)-ylidene]-2,2,3,3,3-pentafluoropropanamide | 38 mg (0.085 mmol) of phosphorus pentasulfide | 9 mg (0.0854 mmol) of sodium carbonate | THF | Room temperature, 4 h | D | 59 |
| 5-20 | 36 mg (0.11 mmol) of N-[1-((6-chloro-5-fluoropyridin-3-yl)methyl)pyridin-2(1H)-ylidene]-2,2,2-trifluoroacetamide | 49 mg (0.11 mmol) of phosphorus pentasulfide | 12 mg (0.11 mmol) of sodium carbonate | THF | Room temperature, 4 h | D | 100 |
| 5-3 | 65 mg (0.29 mmol) of 5-(bromomethyl)-2-chloro-3-fluoropyridine | 50 mg (0.29 mmol) of 2,2-difluoro-N-(pyridin-2(1H)-ylidene))acetamide | 48 mg (0.35 mmol) of potassium carbonate | Acetonitrile | reflux, 3 h | A | 38 |
| 6-3 | 60 mg (0.29 mmol) of 5-(bromomethyl)-2-chloropyrimidine | 50 mg (0.29 mmol) of 2,2-difluoro-N-(pyridin-2(1H)-ylidene))acetamide | 48 mg (0.35 mmol) of potassium carbonate | Acetonitrile | reflux, 3 h | A | 37 |
| 8-2 | 73 mg (0.45 mmol) of 3-chloro-6-(chloromethyl)pyridazine | 97 mg (0.51 mmol) of 2,2,2-trifluoro-N-(pyridin-2(1H)-ylidene))acetamide | 83 mg (0.60 mmol) of potassium carbonate | DMF | 65° C., 3 h | A | 32 |

TABLE 43-continued

| Compound No. | Raw material 1 | Raw material 2 | Base and the like | Solvent | Reaction temperature, Time | Method (Table) | Yield (%) |
|---|---|---|---|---|---|---|---|
| 5-4 | 54 mg (0.24 mmol) of 5-(bromomethyl)-2-chloro-3-fluoropyridine | 50 mg (0.24 mmol) of 2-chloro-2,2-difluoro-N-(pyridin-2(1H)-ylidene))acetamide | 41 mg (0.30 mmol) of potassium carbonate | Acetonitrile | reflux, 6 h | A | 51 |
| 4-4 | 60 mg (0.24 mmol) of 2-bromo-5-bromomethylpyridine | 50 mg (0.24 mmol) of 2-chloro-2,2-difluoro-N-(pyridin-2(1H)-ylidene))acetamide | 41 mg (0.30 mmol) of potassium carbonate | Acetonitrile | reflux, 6 h | A | 48 |
| 6-4 | 49 mg (0.24 mmol) of 5-(bromomethyl)-2-chloropyrimidine | 50 mg (0.24 mmol) of 2-chloro-2,2-difluoro-N-(pyridin-2(1H)-ylidene))acetamide | 41 mg (0.30 mmol) of potassium carbonate | Acetonitrile | reflux, 6 h | A | 55 |
| 4-5 | 65 mg (0.26 mmol) of 2-bromo-5-bromomethylpyridine | 50 mg (0.26 mmol) of 2,2,3,3,3-pentafluoro-N-(pyridin-2(1H)-ylidene))propanamide | 41 mg (0.30 mmol) of potassium carbonate | Acetonitrile | reflux, 2 h | A | 8 |

TABLE 44

| Compound No. | Raw material 1 | Raw material 2 | Base and the like | Solvent | Reaction temperature, Time | Method (Table) | Yield (%) |
|---|---|---|---|---|---|---|---|
| 2-20 | 70 mg (0.22 mmol) of N-[1-((2-chlorothiazol-5-yl)methyl)pyridin-2(1H)-ylidene]-2,2,2-trifluoroacetamide | 107 mg (0.24 mmol) of phosphorus pentasulfide | 25 mg (0.24 mmol) of sodium carbonate | THF | Room temperature, 4 h | D | 11 |
| 10-20 | 130 mg (0.37 mmol) of 2,2,2-trifluoro-N-[1-((6-trifluoromethyl)pyridin-3-yl)methyl)pyridin-2(1H)-ylidene]-acetamide | 181 mg (0.41 mmol) of phosphorus pentasulfide | 43 mg (0.41 mmol) of sodium carbonate | THF | Room temperature, 4 h | D | 93 |
| 3-4 | 110 mg (0.58 mmol) of 2-fluoro-5-(bromomethyl)pyridine | 105 mg (0.51 mmol) of 2-chloro-2,2-difluoro-N-(pyridin-2(1H)-ylidene))acetamide | 103 mg (0.75 mmol) of potassium carbonate | DMF | 65° C., 2 h | A | 63 |
| 3-5 | 110 mg (0.58 mmol) of 2-fluoro-5-(bromomethyl)pyridine | 139 mg (0.58 mmol) of 2,2,3,3,3-pentafluoro-N-(pyridin-2(1H)-ylidene)propanamide | 88 mg (0.63 mmol) of potassium carbonate | DMF | 65° C., 2 h | A | 22 |
| 11-20 | 40 mg (0.15 mmol) of 2,2,2-trifluoro-N-[1-((tetrahydrofuran-3-yl)methyl)pyridin-2(1H)-ylidene]acetamide | 65 mg (0.11 mmol) of phosphorus pentasulfide | 16 mg (0.15 mmol) of sodium carbonate | THF | Room temperature, 4 h | D | 53 |
| 1-14 | 200 mg (0.78 mmol) of 1-[(6-chloropyridin-3-yl)methyl]pyridin-2(1H)-imine hydrochloride | 76 µl (0.94 mmol) of acrylic acid chloride | 32 µl (0.23 mmol) of triethylamine | Acetonitrile | reflux, 1 h | B | 28 |
| 1-37 | 78 mg (0.28 mmol) of N-[1-((6-chloropyridin-3-yl)methyl)pyridin-2(1H)-ylidene]-propionamide | 125 mg (0.28 mmol) of phosphorus pentasulfide | 30 mg (0.28 mmol) of sodium carbonate | THF | Room temperature, 2 h | D | 21 |
| 1-39 | 180 mg (0.96 mmol) of N-[1-((6-chloropyridin-3-yl)methyl)pyridin-2(1H)-ylidene]-isobutyramide | 341 mg (0.75 mmol) of phosphorus pentasulfide | 102 mg (0.96 mmol) of sodium carbonate | THF | Room temperature, 2 h | D | 29 |
| 1-40 | 54 mg (0.19 mmol) of N-[1-((6-chloropyridin-3-yl)methyl)pyridin-2(1H)-ylidene]-cyclopropane carboxamide | 54 mg (0.19 mmol) of phosphorus pentasulfide | 20 mg (0.19 mmol) of sodium carbonate | THF | Room temperature, 2 h | D | 12 |

TABLE 44-continued

| Compound No. | Raw material 1 | Raw material 2 | Base and the like | Solvent | Reaction temperature, Time | Method (Table) | Yield (%) |
|---|---|---|---|---|---|---|---|
| 1-15 | 200 mg (0.78 mmol) of 1-[(6-chloropyridin-3-yl)methyl]pyridin-2(1H)-imine hydrochloride | 83 mg (0.94 mmol) of propyol oxychloride | 320 μl (2.34 mmol) of triethylamine | Acetonitrile | reflux, 5 h | B | 19 |
| 1-35 | 26 mg (0.074 mmol) of N-[1-((6-chloropyridin-3-yl)methyl)pyridin-2(1H)-ylidene]-3-phyenylpropanamide | 26 mg (0.06 mmol) of phosphorus pentasulfide | 8 mg (0.074 mmol) of sodium carbonate | THF | Room temperature, 1.5 h | D | 23 |
| 1-501 | 100 mg (0.30 mmol) of N-[1-((6-chloropyridin-3-yl)methyl)pyridin-2(1H)-ylidene]-2,2,2-trifluoroethanethioamide | 145 mg (1.50 mmol) of O-ethyl hydroxylamine hydrochloride | 205 μl (1.50 mmol) of triethylamine | Ethanol | 50° C., 19.5 h | F | 14 |
| 1-499 | 1.00 g (3.00 mmol) of N-[1-((6-chloropyridin-3-yl)methyl)pyridin-2(1H)-ylidene]-2,2,2-trifluoroethanethioamide | 1.04 g (15.0 mmol) of hydroxylamine hydrochloride | 2.00 ml (15.0 mmol) of triethylamine | Ethanol | 50° C., 21 h | F | 63 |
| 1-510 | 1.00 g (3.00 mmol) of N-[1-((6-chloropyridin-3-yl)methyl)pyridin-2(1H)-ylidene]-2,2,2-trifluoroethanethioamide | 239 mg (1.50 mmol) of O-benzyl hydroxylamine hydrochloride | 205 μl (1.50 mmol) of triethylamine | Ethanol | 50° C., 19.5 h | F | 20 |
| 1-511 | 30 mg (0.09 mmol) of N-[1-((6-chloropyridin-3-yl)methyl)pyridin-2(1H)-ylidene]-2,2,2-trifluoro-N'-hydroxyacetimidamide | 20 μl (0.28 mmol) of acetyl chloride | 38 μl (0.28 mmol) of triethylamine | Acetonitrile | Room temperature, 15 min | G | 72 |

TABLE 45

| Compound No. | Raw material 1 | Raw material 2 | Base and the like | Solvent | Reaction temperature, Time | Method (Table) | Yield (%) |
|---|---|---|---|---|---|---|---|
| 1-519 | 30 mg (0.09 mmol) of N-1-((6-chloropyridin-3-yl)methyl)pyridin-2(1H)-ylidene]-2,2,2-trifluoro-N'-hydroxyacetimidamide | 20 μl (0.17 mmol) of benzoyl chloride | 24 μl (0.17 mmol) of triethylamine | Acetonitrile | Room temperature, 10 min | G | 67 |
| 1-523 | 30 mg (0.09 mmol) of N-[1-((6-chloropyridin-3-yl)methyl)pyridin-2(1H)-ylidene]-2,2,2-trifluoro-N'-hydroxyacetimidamide | 20 μl (0.26 mmol) of methyl chloroformate | 36 μl (0.26 mmol) of triethylamine | Acetonitrile | Room temperature, 20 min | G | 49 |
| 1-528 | 30 mg (0.09 mmol) of N-[1-((6-chloropyridin-3-yl)methyl)pyridin-2(1H)-ylidene]-2,2,2-trifluoro-N'-hydroxyacetimidamide | 20 μl (0.18 mmol) of methanesulfonyl chloride | 25 μl (0.18 mmol) of triethylamine | Acetonitrile | Room temperature, 20 min | G | 100 |
| 1-531 | 30 mg (0.09 mmol) of N-[1-((6-chloropyridin-3-yl)methyl)pyridin-2(1H)-ylidene]-2,2,2-trifluoro-N'-hydroxyacetimidamide | 28 mg (0.15 mmol) of 4-methylbenzene-sufonyl chloride | 21 μl (0.15 mmol) of triethylamine | Acetonitrile | Room temperature, 12 h | G | 100 |
| 1-507 | 30 mg (0.09 mmol) of N-[1-((6-chloropyridin-3-yl)methyl)pyridin-2(1H)-ylidene]-2,2,2-trifluoroethanethioamide | 50 mg (0.45 mmol) of O-allyl hydroxylamine hydrochloride | 62 μl (0.45 mmol) of triethylamine, 25 mg (0.09 mmol) of silver carbonate | Ethanol | 50° C., 5 h | F | 45 |
| 1-516 | 30 mg (0.09 mmol) of N-[1-((6-chloropyridin-3-yl)methyl)pyridin-2(1H)-ylidene]-2,2,2-trifluoro-N'-hydroxyacetimidamide | 20 μl (0.25 mmol) of acryloyl chloride | 34 μl (0.25 mmol) of triethylamine | Acetonitrile | Room temperature, 20 min | G | 64 |

TABLE 45-continued

| Compound No. | Raw material 1 | Raw material 2 | Base and the like | Solvent | Reaction temperature, Time | Method (Table) | Yield (%) |
|---|---|---|---|---|---|---|---|
| 1-518 | 30 mg (0.09 mmol) of N-[1-((6-chloropyridin-3-yl)methyl)pyridin-2(1H)-ylidene]-2,2,2-trifluoro-N'-hydroxyacetimidamide | 15 mg (0.18 mmol) of 3-butynoate | EDC-HCl 135 mg (0.18 mmol), DMAP 22 mg (0.18 mmol) | Dichloromethane | Room temperature, 21 h | G | 22 |
| 1-527 | 30 mg (0.09 mmol) of N-[1-((6-chloropyridin-3-yl)methyl)pyridin-2(1H)-ylidene]-2,2,2-trifluoro-N'-hydroxyacetimidamide | 20 µl (0.16 mmol) of phenyl chloroformate | 22 µl (0.16 mmol) of triethylamine | Acetonitrile | Room temperature, 1.5 h | G | 54 |
| 1-521 | 30 mg (0.09 mmol) of N-[1-((6-chloropyridin-3-yl)methyl)pyridin-2(1H)-ylidene]-2,2,2-trifluoro-N'-hydroxyacetimidamide | 20 mg (0.14 mmol) of nicotinic acid chloride hydrochloride | 40 µl (0.28 mmol) of triethylamine | Acetonitrile | Room temperature, 1.5 h | G | 46 |
| 1-43 | 100 mg (0.30 mmol) of N-[1-(6-chloropyridin-3-yl)methyl)pyridin-2(1H)-ylidene]-2,2,2-trifluoroethanethioamide | Ethylamine (30% methanol solution, 0.60 mmol) | 90 µl (0.60 mmol) of triethylamine, 91 mg (0.33 mmol) of silver carbonate | Ethanol | 50° C., 1.5 h | E | 57 |
| 1-536 | 50 mg (0.15 mmol) of N-[1-((6-chloropyridin-3-yl)methyl)pyridin-2(1H)-ylidene]-2,2,2-trifluoro-N'-hydroxyacetimidamide | 20 µl (0.17 mmol) of benzyl isocyanate | tBuOK 5 mg (0.04 mmol) | Acetonitrile | Room temperature, 1 h | H | 30 |

TABLE 46

| Compound No. | Raw material 1 | Raw material 2 | Base and the like | Solvent | Reaction temperature, Time | Method (Table) | Yield (%) |
|---|---|---|---|---|---|---|---|
| 1-42 | 150 mg (0.45 mmol) of N-[1-((6-chloropyridin-3-yl)methyl)pyridin-2(1H)-ylidene]-2,2,2-trifluoroethanethioamide | Methylamine (40% methanol solution, 1.36 mmol) | 124 mg (0.45 mmol) of silver carbonate | Methanol | 50°C, 1 h | E | 56 |
| 1-500 | 50 mg (0.15 mmol) of N-[1-((6-chloropyridin-3-yl)methyl)pyridin-2(1H)-ylidene]-2,2,2-trifluoroethanethioamide | 63 mg (0.75 mmol) of O-methyl hydroxylamine hydrochloride | 103 µl (0.75 mmol) of triethylamine, 41 mg (0.15 mmol) of silver carbonate | Ethanol | 50° C., 5 h | F | 50 |
| 1-504 | 50 mg (0.15 mmol) of N-[1-((6-chloropyridin-3-yl)methyl)pyridin-2(1H)-ylidene]-2,2,2-trifluoroethanethioamide | 95 mg (0.75 mmol) of O-t-butyl hydroxylamine hydrochloride | 165 µl (1.20 mmol) of triethylamine, 62 mg (0.23 mmol) of silver carbonate | Ethanol | 50° C., 5 h | F | 19 |
| 1-534 | 40 mg (0.12 mmol) of N-[1-((6-chloropyridin-3-yl)methyl)pyridin-2(1H)-ylidene]-2,2,2-trifluoro-N'-hydroxyacetimidamide | 11 mg (0.13 mmol) of n-propyl isocyanate | tBuOK 4 mg (0.04 mmol) | Acetonitrile | Room temperature, 1 h | H | 32 |
| 1-535 | 40 mg (0.12 mmol) of N-[1-((6-chloropyridin-3-yl)methyl)pyridin-2(1H)-ylidene]-2,2,2-trifluoro-N'-hydroxyacetimidamide | 14 mg (0.13 mmol) of chloroethyl isocyanate | tBuOK 4 mg (0.04 mmol) | Acetonitrile | Room temperature, 1 h | H | 54 |
| 1-72 | 150 mg (0.45 mmol) of N-[1-((6-chloropyridin-3-yl)methyl)pyridin-2(1H)-ylidene]-2,2,2-trifluoroethanethioamide | 74 µl (0.68 mmol) of benzylamine | 137 mg (0.50 mmol) of silver carbonate | Ethanol | 50° C., 3 h | E | 45 |

TABLE 46-continued

| Compound No. | Raw material 1 | Raw material 2 | Base and the like | Solvent | Reaction temperature, Time | Method (Table) | Yield (%) |
|---|---|---|---|---|---|---|---|
| 1-150 | 100 mg (0.30 mmol) of N-[1-((6-chloropyridin-3-yl)methyl)pyridin-2(1H)-ylidene]-2,2,2-trifluoroethanethioamide | 56 µl (0.60 mmol) of methylthioethylamine | 91 mg (0.33 mmol) of silver carbonate | Ethanol | 50° C., 5 h | E | 50 |
| 1-67 | 100 mg (0.30 mmol) of N-[1-((6-chloropyridin-3-yl)methyl)pyridin-2(1H)-ylidene]-2,2,2-trifluoroethanethioamide | 74 µl (1.20 mmol) of 2-aminoethanol | 91 mg (0.33 mmol) of silver carbonate | Ethanol | 50° C., 2 h | E | 49 |
| 1-515 | 30 mg (0.09 mmol) of N-[1-((6-chloropyridin-3-yl)methyl)pyridin-2(1H)-ylidene]-2,2,2-trifluoro-N'-hydroxyacetimidamide | 40 µl (0.44 mmol) of cyclopropanecarboxylic acid chloride | 30 µl (0.22 mmol) of triethylamine | Acetonitrile | 50° C. 2 h | G | 67 |
| 1-56 | 100 mg (0.30 mmol) of N-[1-((6-chloropyridin-3-yl)methyl)pyridin-2(1H)-ylidene]-2,2,2-trifluoroethanethioamide | 38 µl (0.60 mmol) of propargylamine | 91 mg (0.33 mmol) of silver carbonate | Ethanol | 50° C., 2 h → reflux, 2 h | E | 57 |
| 1-512 | 30 mg (0.09 mmol) of N-[1-((6-chloropyridin-3-yl)methyl)pyridin-2(1H)-ylidene]-2,2,2-trifluoro-N'-hydroxyacetimidamide | 20 µl (0.23 mmol) of propionyl chloride | 34 µl (0.25 mmol) of triethylamine | Acetonitrile | Room temperature, 30 min | G | 32 |
| 1-514 | 30 mg (0.09 mmol) of N-[1-((6-chloropyridin-3-yl)methyl)pyridin-2(1H)-ylidene]-2,2,2-trifluoro-N'-hydroxyacetimidamide | 20 µl (0.19 mmol) of isopropionyl chloride | 27 µl (0.20 mmol) of triethylamine | Acetonitrile | Room temperature, 2 h | G | 61 |
| 1-50 | 100 mg (0.30 mmol) of N-[1-((6-chloropyridin-3-yl)methyl)pyridin-2(1H)-ylidene]-2,2,2-trifluoroethanethioamide | 48 µl (1.20 mmol) of cyclopropylamine | 91 mg (0.33 mmol) of silver carbonate | Ethanol | 50° C., 1.5 h → reflux, 4.5 h | E | 44 |

TABLE 47

| Compound No. | Raw material 1 | Raw material 2 | Base and the like | Solvent | Reaction temperature, Time | Method (Table) | Yield (%) |
|---|---|---|---|---|---|---|---|
| 1-114 | 80 mg (0.30 mmol) of N-[1-((6-chloropyridin-3-yl)methyl)pyridin-2(1H)-ylidene]-2,2,2-trifluoroethanethioamide | 48 µl (0.36 mmol) of 2-phenyloxyethylamine | 73 mg (0.33 mmol) of silver carbonate | Ethanol | 50° C., 3.5 h | E | 52 |
| 1-44 | 80 mg (0.30 mmol) of N-[1-((6-chloropyridin-3-yl)methyl)pyridin-2(1H)-ylidene]-2,2,2-trifluoroethanethioamide | 60 µl (0.72 mmol) of n-propylamine | 73 mg (0.33 mmol) of silver carbonate | Ethanol | 50° C., 2 h | E | 55 |
| 1-118 | 100 mg (0.30 mmol) of N-[1-((6-chloropyridin-3-yl)methyl)pyridin-2(1H)-ylidene]-2,2,2-trifluoroethanethioamide | 62 µl (0.60 mmol) of 2-aminomethylpyridine | 91 mg (0.33 mmol) of silver carbonate | Ethanol | 50° C., 5 h | E | 70 |
| 1-119 | 100 mg (0.30 mmol) of N-[1-((6-chloropyridin-3-yl)methyl)pyridin-2(1H)-ylidene]-2,2,2-trifluoroethanethioamide | 62 µl (0.60 mmol) of 3-aminomethylpyridine | 91 mg (0.33 mmol) of silver carbonate | Ethanol | 50° C., 5 h | E | 58 |
| 1-47 | 100 mg (0.30 mmol) of N-[1-((6-chloropyridin-3-yl)methyl)pyridin-2(1H)-ylidene]-2,2,2-trifluoroethanethioamide | 44 mg (0.60 mmol) of n-butylamine | 91 mg (0.33 mmol) of silver carbonate | Ethanol | 50° C., 5 h | E | 49 |
| 1-55 | 100 mg (0.30 mmol) of N-[1-((6-chloropyridin-3-yl)methyl)pyridin-2(1H)-ylidene]-2,2,2-trifluoroethanethioamide | CH2=CHCH2NH2 34 mg (0.60 mmol) | 91 mg (0.33 mmol) of silver carbonate | Ethanol | 50° C., 2 h → reflux, 1 h | E | 53 |

TABLE 47-continued

| Compound No. | Raw material 1 | Raw material 2 | Base and the like | Solvent | Reaction temperature, Time | Method (Table) | Yield (%) |
|---|---|---|---|---|---|---|---|
| 1-122 | 100 mg (0.30 mmol) of N-[1-((6-chloropyridin-3-yl)methyl)pyridin-2(1H)-ylidene]-2,2,2-trifluoroethanethioamide | H2NCH2-(2-thienyl) 68 mg (0.60 mmol) | 91 mg (0.33 mmol) of silver carbonate | Ethanol | 50° C., 2 h → reflux, 1 h | E | 30 |
| 1-45 | 100 mg (0.30 mmol) of N-[1-((6-chloropyridin-3-yl)methyl)pyridin-2(1H)-ylidene]-2,2,2-trifluoroethanethioamide | 70 mg (1.20 mmol) of isopropylamine | 91 mg (0.33 mmol) of silver carbonate | Ethanol | 50° C., 2 h → reflux, 5 h | E | 35 |
| 1-124 | 100 mg (0.30 mmol) of N-[1-((6-chloropyridin-3-yl)methyl)pyridin-2(1H)-ylidene]-2,2,2-trifluoroethanethioamide | H2NCH2-(2-furanyl) 58 mg (0.60 mmol) | 91 mg (0.33 mmol) of silver carbonate | Ethanol | 50° C., 2.5 h | E | 56 |
| 1-126 | 100 mg (0.30 mmol) of N-[1-((6-chloropyridin-3-yl)methyl)pyridin-2(1H)-ylidene]-2,2,2-trifluoroethanethioamide | H2NCH2-(2-thienyldrofuranyl) 61 mg (0.60 mmol) | 91 mg (0.33 mmol) of silver carbonate | Ethanol | 50° C., 1 h | E | 43 |
| 1-64 | 100 mg (0.30 mmol) of N-[1-((6-chloropyridin-3-yl)methyl)pyridin-2(1H)-ylidene]-2,2,2-trifluoroethanethioamide | 110 mg (1.20 mmol) of aminoacetonitrile hydrochloride | 91 mg (0.33 mmol) of silver carbonate | Ethanol | 50° C., 1 h → reflux, 6 h | E | 22 |
| 1-146 | 100 mg (0.30 mmol) of N-[1-((6-chloropyridin-3-yl)methyl)pyridin-2(1H)-ylidene]-2,2,2-trifluoroethanethioamide | CH3OCH2CH2NH2 45 mg (0.60 mmol) | 91 mg (0.33 mmol) of silver carbonate | Ethanol | 50° C., 5 h | E | 30 |
| 1-52 | 100 mg (0.30 mmol) of N-[1-((6-chloropyridin-3-yl)methyl)pyridin-2(1H)-ylidene]-2,2,2-trifluoroethanethioamide | 51 mg (0.60 mmol) of cyclopentylamine | 91 mg (0.33 mmol) of silver carbonate | Ethanol | 50° C., 4 h | E | 30 |
| 1-121 | 100 mg (0.30 mmol) of N-[1-((6-chloropyridin-3-yl)methyl)pyridin-2(1H)-ylidene]-2,2,2-trifluoroethanethioamide | 65 mg (0.60 mmol) of 4-aminomethyl pyridine | 91 mg (0.33 mmol) of silver carbonate | Ethanol | 60° C., 4 h | E | 33 |

TABLE 48

| Compound No. | Raw material 1 | Raw material 2 | Base and the like | Solvent | Reaction temperature, Time | Method (Table) | Yield (%) |
|---|---|---|---|---|---|---|---|
| 1-53 | 100 mg (0.30 mmol) of N-[1-((6-chloropyridin-3-yl)methyl)pyridin-2(1H)-ylidene]-2,2,2-trifluoroethanethioamide | 59 mg (0.60 mmol) of cyclohexylamine | 91 mg (0.33 mmol) of silver carbonate | Ethanol | 60° C., 2 h | E | 28 |
| 1-76 | 100 mg (0.30 mmol) of N-[1-((6-chloropyridin-3-yl)methyl)pyridin-2(1H)-ylidene]-2,2,2-trifluoroethanethioamide | 73 mg (0.60 mmol) of phenethylamine | 91 mg (0.33 mmol) of silver carbonate | Ethanol | 60° C., 4 h | E | 60 |

TABLE 49

| Compound No. | 1H-NMR (CDCl3, δ, ppm) | MS or IR (KBr, v, cm⁻¹) |
|---|---|---|
| 266-2 | 5.62 (2H, s), 7.33 (1H, d), 7.83 (1H, d), 8.57 (2H, m) | m/z = 323 (M + H) |
| 444-2 | 5.73 (2H, s), 7.69 (1H, s), 8.56 (1H, s) | m/z = 329 (M + H) |
| 190-2 | 5.39 (2H, s), 6.87 (1H, dd), 7.36 (1H, d), 7.91 (1H, dd), 8.39 (1H, d), 8.49 (1H, s), 8.79 (1H, d) | m/z = 317 (M + H) |
| 201-2 | 5.45 (2H, s), 7.37 (1H, d), 7.65 (1H, d), 7.87 (1H, dd), 7.99 (1H, d), 8.49 (1H, d), 9.80 (1H, d) | m/z = 317 (M + H) |
| 223-2 | 5.69 (2H, s), 7.31 (1H, d), 7.55 (1H, dd), 7.92 (1H, dd), 8.28 (1H, dd), 8.59 (1H, d), 8.78 (1H, dd) | m/z = 317 (M + H) |
| 146-2 | 5.64 (2H, s), 7.14 (1H, dd), 7.33 (1H, d), 7.47 (1H, dd), 7.71 (1H, dd). 7.74 (1H, dd), 8.42 (1H, d), 11.64 (1H, br s) | m/z = 332 (M + H) |
| 224-2 | 5.78 (2H, s), 7.57, 7.63 (1H, dd × 2), 7.70 (1H, s), 8.26, 8.41 (1H, dd × 2), 8.82, 9.04 (1H, dd × 2) | m/z = 323 (M + H) |
| 102-2 | 5.56 (2H, s), 7.15 (1H, m), 7.38 (1H, d), 7.84 (1H, dd), 8.26 (1H, dd), 8.48 (1H, d), 8.60 (1H, d) | m/z = 341 (M + H) |
| 212-2 | 5.43 (2H, s), 7.35 (1H, d), 7.87 (1H, dd), 8.20 (1H, d), 8.29 (1H, d), 8.51 (1H, d), 8.77 (1H, s) | m/z = 317 (M + H) |
| 1-20 | 5.48 (2H, s), 7.12 (1H, td), 7.34 (1H, d), 7.77 (1H, dd), 7.96 (1H, m), 8.05 (1H, dd), 8.45 (1H, d), 8.56 (1H, d) | m/z = 332 (M + H) |
| 12-2 | 5.54 (2H, s), 6.96 (1H, m), 7.21 (1H, m), 7.87 (1H, m), 7.97 (1H, m), 8.34 (1H, d), 8.50 (1H, d) | m/z = 316 (M + H) |
| 213-2 | 5.51 (2H, s), 7.69 (1H, s), 8.25 (1H, d), 8.30 (1H, d), 8.57 (1H, s) | m/z = 323 (M + H) |
| 1-17 | 4.52 (2H, q), 5.44 (2H, s), 6.85 (1H, td), 7.31 (1H, d), 7.57 (2H, m), 7.79 (1H, dd), 8.14 (1H, d), 8.40 (1H, d) | m/z = 346 (M + H) |
| 1-18 | 1.44 (3H, d), 5.31 (1H, m), 5.42 (2H, q), 6.54 (1H, td), 7.30 (1H, d), 7.53 (2H, m). 7.79 (1H, dd), 8.10 (1H, d), 8.40 (1H, d) | m/z = 360 (M + H) |
| 1-19 | 5.47 (2H, s), 5.81 (1H, m), 6.69 (1H, m), 7.31 (1H, d), 7.65 (1H, m), 7.68 (1H, dd), 7.85 (1H, dd), 8.17 (1H, d), 8.40 (1H, d) | m/z = 414 (M + H) |
| 7-2 | 5.57 (2H, s), 6.91 (1H, m), 7.80 (1H, m), 8.10 (1H, m), 8.47 (1H, s), 8.49 (1H, d), 8.72 (1H, d) | |
| 1-13 | 3.22 (2H, q), 5.46 (2H, s), 6.65 (1H, td), 7.31 (1H, d), 7.62 (lH, m), 7.66 (1H, dd). 7.70 (1H, dd), 8.35 (1H, d), 8.41 (1H, d) | m/s = 330 |
| 168-2 | 5.11 (2H, s), 7.40 (2H, m), 7.75 (1H, dd), 8.09 (1H, d), 8.15 (1H, d), 8.46 (1H, d), 8.81 (1H, br s) | m/z = 332.0426 (M + H) |
| 1-21 | 5.49 (2H, s), 6.21 (1H, t), 7.05 (1H, td), 7.34 (1H, d), 7.82 (1H, dd), 7.90 (1H, m), 7.94 (1H, dd), 8.45 (1H, d), 8.49 (1H, d) | m/z = 314.0346 (M + H) |
| 3-20 | 5.51 (2H, s), 6.95 (1H, d), 7.15 (1H, td), 7.96 (2H, m), 8.09 (1H, d), 8.29 (1H, d), 8.52 (1H, d) | m/z = 316.0559 (M + H) |
| 4-20 | 5.47 (2H, s), 7.13 (1H, m), 7.50 (1H, m), 7.66 (1H, m), 7.97 (1H, m), 8.07 (1H, m), 8.43 (1H, s), 8.54 (1H, m) | m/z = 375.9 (M + H) |
| 3-3 | 5.54 (2H, s), 5.92 (1H, t), 6.79 (1H, td), 6.94 (1H, dd), 7.70 (1H, m), 7.78 (1H, dd), 8.03 (1H, td), 8.30 (1H, d), 8.50 (1H, d) | |
| 4-3 | 5.50 (2H, s), 5.90 (1H, t), 6.79 (1H, m), 7.48 (1H, d), 7.74 (3H, m), 8.43 (1H, d), 8.50 (1H, d) | m/z = 342 (M + H) |
| 5-5 | 5.56 (2H, s), 6.91 (1H, m), 7.69 (1H, dd), 7.82 (2H, m), 8.26 (1H, d), 8.60 (1H, d) | m/z = 384.0372 |
| 6-5 | 5.52 (2H, s), 6.93 (1H, m), 7.86 (2H, m). 8.61 (1H, d), 8.75 (2H, s) | m/z = 367.0687 (M + H) |
| 1-22 | 5.49 (2H, s), 7.09 (1H, td), 7.35 (1H, d), 7.78 (1H, dd), 7.95 (2H, m), 8.46 (1H, d), 8.55 (1H, d) | m/z = 347.9972 |
| 1-23 | 5.47 (2H, s), 7.10 (1H, td), 7.34 (1H, d), 7.68 (1H, dd), 7.95 (2H, m), 8.41 (1H, d), 8.55 (1H, dd) | m/z = 382.0246 |
| 5-20 | 5.49 (2H, s), 7.10 (1H, m), 7.65 (1H, dd), 7.96 (1H, m), 8.00 (1H, m), 8.27 (1H, d), 8.63 (1H, d) | m/z = 350.0188 |
| 5-3 | 5.53 (2H, s), 5.90 (1H, t), 6.80 (1H, td), 7.76 (2H, m), 8.29 (1H, d), 8.52 (1H, d) | m/z = 316.0507 (M + H) |

TABLE 50

| Compound No. | 1H-NMR (CDCl3, δ, ppm) | MS or IR (KBr, v, cm⁻¹) |
|---|---|---|
| 6-3 | 5.45 (2H, s), 5.89 (1H, t), 6.83 (1H, td), 7.75 (1H, m), 7.82 (1H, dd), 8.52 (1H, d), 8.81 (2H, s) | m/z = 299.0532 (M + H) |
| 8-2 | 5.73 (2H, s), 6.90 (1H, td), 7.54 (1H, td), 7.81 (1H, td), 7.97 (1H, d), 8.22 (1H, d), 8.53 (1H, d) | |
| 5-4 | 5.54 (2H, s), 6.86 (1H, td), 7.99 (3H, m). 8.30 (1H, d), 8.54 (1H, d) | m/z = 350.0082 (M + H) |
| 4-4 | 5.52 (2H, s), 6.86 (1H, td), 7.49 (1H, d), 7.77 (2H, m), 7.83 (1H, dd), 8.45 (1H, d), 8.52 (1H, d) | m/z = 375.96 (M + H) |
| 6-4 | 5.49 (2H, s), 6.90 (1H, td), 7.82 (1H, td), 7.87 (1H, dd), 8.54 (1H, d), 8.81 (2H, s) | m/z = 333.0121 (M + H) |
| 4-5 | 5.53 (2H, s), 6.89 (1H, td), 7.48 (1H, d), 7.70 (1H, dd), 7.82 (2H, m), 8.41 (1H, d), 8.58 (1H, d) | m/z = 410 (M + H) |
| 2-20 | 5.57 (2H, s), 7.12 (1H, m), 7.68 (1H, s), 7.97 (1H, m), 8.12 (1H, d), 8.67 (1H, d) | m/z = 338 (M + H) |
| 10-20 | 5.58 (2H, s), 7.12 (1H, m), 7.70 (1H, d), 7.97 (2H, m), 8.02 (1H, d), 8.62 (1H, d), 8.77 (1H, s) | m/z = 366 |
| 3-4 | 5.55 (2H, s), 6.86 (1H, td), 6.95 (1H, dd), 7.77 (1H, td), 7.85 (1H, dd), 8.06 (1H, d), 8.31 (1H, d), 8.53 (1H, d) | m/z = 316 (M + H) |
| 3-5 | 5.56 (2H, s), 6.89 (1H, m), 6.94 (1H, dd), 7.80 (2H, m), 7.97 (1H, td), 8.27 (1H, d), 8.58 (1H. d) | m/z = 350 (M + H) |
| 11-20 | 1.69 (1H, m), 2.07 (1H, m), 2.84 (1H, m), 3.59 (1H, dd), 3.71 (1H, dd), 3.77 (1H, m), 3.96 | m/z = 291 (M + H) |

TABLE 50-continued

| Compound No. | 1H-NMR (CDCl3, δ, ppm) | MS or IR (KBr, v. cm⁻¹) |
|---|---|---|
| | (1H, m), 4.13 (1H, dd), 4.42 (1H, dd), 7.11 (1H, m), 7.92 (1H, dd), 7.98 (1H, m), 8.40 (1H, d) | |
| 1-14 | 5.44 (2H, s), 5.61 (1H, dd), 6.28 (1H, dd), 6.36 (1H, dd), 6.52 (1H, m), 7.30 (1H, d), 7.52 (1H, m), 7.57 (1H, d), 7.73 (1H, dd), 8.28 (1H, d), 8.44 (1H, d) | m/z = 274 (M + H) |
| 1-37 | 1.28 (3H, t), 2.88 (2H, q), 5.41 (2H, s), 6.86 (1H, t), 7.35 (1H, d), 7.75 (3H, m), 8.10 (1H, d), 8.44 (1H, d) | m/z = 292 (M + H) |
| 1-39 | 1.26 (6H, d), 2.55 (1H, m), 5.51 (2H, s), 6.98 (1H, m), 7.36 (1H, d), 7.76 (1H, dd), 7.77 (2H, m), 8.08 (1H, d), 8.44 (1H, d) | m/z = 306 (M + H) |
| 1-40 | 0.92 (2H, m), 1.22 (2H, m), 2.40 (1H, m), 5.36 (2H, s), 6.77 (1H, td), 7.34 (1H, d), 7.66 (2H, m), 7.71 (1H, dd), 8.14 (1H, d), 8.41 (1H, d) | m/z = 304 (M + H) |
| 1-15 | 5.08 (2H, s), 5.40 (2H, s), 5.84 (1H, t), 6.50 (1H, m), 7.30 (1H, d), 7.50 (1H, m), 7.56 (1H, m), 7.80 (1H, dd), 8.25 (1H, d), 8.47 (1H, d) | m/z = 286 (M + H) |
| 1-35 | 3.18 (4H, m), 5.05 (2H, s), 6.83 (1H, td), 7.05 (1H, t), 7.25 (2H, m), 7.38 (3H, m), 7.59 (1H, dd), 7.67 (1H, d), 7.72 (1H, td), 7.99 (1H, d), 8.30 (1H, d) | m/z = 368 (M + H) |
| 1-501 | 1.20 (3H, t), 4.10 (2H, q), 5.22 (2H, s), 6.15 (1H, td), 6.27 (1H, d), 7.13 (1H, m), 7.27 (2H, m), 7.79 (1H, dd), 8.37 (1H, d) | m/z = 359 (M + H) |
| 1-499 | 5.26 (2H, s), 6.11 (1H, d), 6.31 (1H, m), 7.31 (1H, m), 7.50 (1H, d), 7.83 (1H, dd), 7.90 (1H, dd), 8.44 (1H, d), 11.0 (1H, s) | m/z = 331 (M + H) |
| 1-510 | 5.07 (2H, s), 5.19 (2H, s), 6.13 (1H, td), 6.22 (1H, d), 7.07 (1H, m), 7.18-7.40 (8H, m), 7.69 (1H, dd), 8.34 (1H, d) | m/z = 421 (M + H) |
| 1-511 | 1.99 (3H, s), 5.27 (2H, s), 6.37 (2H, m), 7.31 (2H, m), 7.44 (1H, dd), 7.76 (1H, dd), 8.37 (1H. d) | m/z = 373 (M + H) |
| 1-519 | 5.31 (2H, s), 6.36 (1H, t), 6.51 (1H, d), 7.17 (1H, d), 7.25 (4H, m), 7.50 (3H, m), 7.78 (1H, dd), 8.41 (1H, d) | m/z = 435 (M + H) |
| 1-523 | 3.84 (3H, s), 5.26 (2H, s), 6.35 (1H, m), 6.40 (1H, d), 7.30 (2H, m), 7.37 (1H, dd), 7.73 (1H, dd), 8.37 (1H, d) | m/z = 389 (M + H) |
| 1-528 | 3.14 (3H, s), 5.27 (2H, s), 6.44 (1H, td), 6.54 (1H, dd), 7.32 (1H, d), 7.41 (2H, m), 7.68 (1H, dd), 8.39 (1H, d) | m/z = 409 (M + H) |
| 1-531 | 2.45 (3H, s), 5.23 (2H, s), 6.37 (1H, d), 6.42 (1H, td), 7.29 (4H, m), 7.45 (1H, d), 7.70 (1H, dd), 7.80 (2H, d), 8.35 (1H, d) | m/z = 485 (M + H) |
| 1-507 | 4.54 (2H, m), 5.16 (2H, m), 5.22 (2H, s), 5.91 (1H, m), 6.17 (1H, td), 6.29 (1H, d), 7.15 (1H, m), 7.27 (2H, m), 7.79 (1H, dd), 8.37 (1H, d) | m/z = 371 (M + H) |

TABLE 51

| Compound No. | 1H-NMR (CDCl3, δ, ppm) | MS or IR (KBr, v, cm⁻¹) |
|---|---|---|
| 1-516 | 5.27 (2H, s), 5.76 (1H, dd), 5.91 (1H, dd), 6.22 (1H, dd), 6.36 (1H, m), 6.42 (1H, d), 7.29 (2H, m), 7.42 (1H, d), 7.76 (1H, dd), 8.37 (1H, d) | m/z = 385 (M + H) |
| 1-518 | 1.25 (1H, s), 1.98 (2H, s), 5.28 (2H, s), 6.38 (2H, m), 7.30 (2H, m), 7.41 (1H, d), 7.75 (1H, dd), 8.38 (1H, d) | m/z = 397 (M + H) |
| 1-527 | 5.28 (2H, s), 6.39 (1H, m), 6.50 (1H, d), 7.13 (1H, d), 7.22-7.41 (7H, m), 7.76 (1H, dd), 8.40 (1H, d) | m/z = 451 (M + H) |
| 1-521 | 5.30 (2H, s), 6.42 (1H, t), 6.52 (1H, d), 7.20 (1H, d), 7.32 (2H, m), 7.53 (1H, dd), 7.75 (1H, dd), 8.01 (1H, dd), 8.41 (1H, d), 8.54 (1H, d), 8.71 (1H, dd) | m/z = 436 (M + H) |
| 1-43 | 1.13(3H, t), 3.03 (2H, q), 5.15 (2H, s), 6.12 (1H, m), 6.19 (1H, d), 7.14(1H, m), 7.27 (1H, m), 7.33 (1H, d), 7.72 (1H, dd), 8.37 (1H, d) | m/z = 343 (M + H) |
| 1-536 | 4.48 (2H, d), 5.25 (2H, s), 6.36 (1H, td), 6.41 (1H, d), 6.79 (1H, m), 7.41 (7H, m), 7.73 (1H, dd), 8.40 (1H, d) | m/z = 464 (M + H) |
| 1-42 | 2.86 (3H, s), 5.16 (2H, s), 6.15 (2H, m), 7.16 (1H, m), 7.26 (1H, dd), 7.31 (1H, d), 7.73 (1H, dd), 8.38 (1H, d) | m/z = 329 (M + H) |
| 1-500 | 3.86 (3H, s), 5.22 (2H, s), 6.17 (1H, m), 6.26 (1H, d), 7.14 (1H, m), 7.23 (1H, dd), 7.30 (1H, d), 7.78 (1H, dd), 8.39 (1H, d) | m/z = 345 (M + H) |
| 1-504 | 1.23 ( 9H, s), 5.23 (2H, s), 6.10 (1H, m), 6.22 (1H, d), 7.09 (1H, m), 7.20 (1H, dd), 7.26 (1H, m), 7.79 (1H, dd), 8.35 (1H, d) | m/z = 387 (M + H) |
| 1-534 | 0.95 (3H, t), 1.61 (2H, m), 3.23 (2H, t), 5.24 (2H, s), 6.32 (1H, t), 6.39 (1H, d), 6.48 (1H, m), 7.33 (3H, m), 7.74 (1H, dd), 8.40 (1H, d) | m/z = 416 (M + H) |
| 1-535 | 3.65 (4H, m), 5.25 (2H, s), 6.36 (1H, t), 6.41 (1H, d), 6.82 (1H, m), 7.36 (3H, m), 7.74 (1H, dd), 8.41 (1H, d) | m/z = 436 (M + H) |
| 1-72 | 4.22 (2H, s), 5.13 (2H, s), 6.14 (1H, m), 6.21 (1H, d), 7.13 (1H, m), 7.26 (7H, m), 7.68 (1H, dd), 8.36 (1H, d) | m/z = 405 (M + H) |
| 1-150 | 2.08 (3H, s), 2.70 (2H, t), 3.22 (2H, t), 5.15 (2H, s), 6.16 (1H, t), 6.22 (1H, d), 7.17 (1H, m), 7.29 (1H, d), 7.33 (1H, d), 7.70 (1H, dd), 8.38 (1H, d) | m/z = 389 (M + H) |
| 1-67 | 3.13 (2H, m), 3.73 (2H, m), 5.15 (2H, s), 6.18 (2H, m), 7.17 (1H, m), 7.33 (2H, m), 7.71 (1H, dd), 8.37 (1H, d) | m/z = 359 (M + H) |
| 1-515 | 0.82 (2H, m), 0.93 (2H, m), 1.40 (1H, m), 5.27 (2H, s), 6.35 (1H, m), 6.42 (1H, d), 7.31 (2H, m), 7.41 (1H, d), 7.77 (1H, dd), 8.38 (1H, d) | m/z = 399 (M + H) |
| 1-56 | 2.13 (1H, t), 3.85 (2H, d), 5.18 (2H, s), 6.21 (1H, t), 6.25 (1H, d), 7.18 (1H, m), 7.29 (1H, d), 7.33 (1H, d), 7.70 (1H, dd), 8.38 (1H, d) | m/z = 353 (M + H) |
| 1-512 | 1.02 (3H, t), 2.23 (2H, q), 5.26 (2 H, s), 6.34 (1H, m), 6.39 (1H, m), 7.29 (2H, m), 7.40 (1H, d), 7.75 (1H, dd), 8.37 (1H, d) | m/z = 387 (M + H) |
| 1-514 | 0.97 (6H, d), 2.37 (1H, m), 5.26 (2H, s), 6.35 (1H, m), 6.40 (1H, d), 7.27 (2H, m), 7.42 (1H, dd), 7.77 (1H, dd), 8.38 (1H, d) | m/z = 399 (M + H) |

TABLE 51-continued

| Compound No. | 1H-NMR (CDCl3, δ, ppm) | MS or IR (KBr, v, cm$^{-1}$) |
|---|---|---|
| 1-50 | 0.74 (2H, m), 0.85 (2H, m), 2.51 (1H, m), 5.18 (2H, s), 6.12 (1H, m), 6.30 (1H, d), 7.15 (1H, m), 7.27 (1H, m), 7.31 (1H, d), 7.79 (1H, dd), 8.39 (1H, d) | m/z = 355 (M + H) |
| 1-114 | 3.44 (2H, td), 4.18 (2H, t), 5.14 (2H, s), 6.15 (1H, td), 6.26 (1H, d), 6.86 (2H, d), 6.92 (1H, m), 7.16 (1H, m), 7.28 (4H, m), 7.71 (1H, dd), 8.38 (1H, d) | m/z = 435 (M + H) |
| 1-44 | 0.83 (3H, t), 1.55 (2H, m), 2.91 (2H, m), 5.14 (2H, s), 6.12 (1H, td), 6.18 (1H, d), 7.13 (1H, m), 7.30 (2H, m), 7.71 (1H, dd), 8.36 (1H, d) | m/z = 357 (M + H) |
| 1-118 | 4.41 (2H, s), 5.15 (2H, s), 6.18 (1H, t), 6.24 (1H, d), 7.14 (2H, m), 7.26 (2H, m), 7.54 (1H, d), 7.68 (1H, dd), 7.71 (1H, dd), 8.38 (1H, d), 8.47 (1H, d) | m/z = 406 (M + H) |
| 1-119 | 4.22 (2H, s), 5.16 (2H, s), 6.20 (2H, m), 7.15-7.30 (3H, m), 7.34 (1H, dd), 7.61 (1H, d), 7.79 (1H, dd), 8.37 (1H, d), 8.42 (1H, d), 8.46 (1H, d) | m/z = 406 (M + H) |

TABLE 52

| Compound No. | 1H-NMR (CDCl3, δ, ppm) | MS or IR (KBr, v, cm$^{-1}$) |
|---|---|---|
| 1-47 | 0.85 (3H, t), 1.25 (2H, m), 1.53 (2H, m), 2.96 (2H, m), 5.14 (2H, s), 6.17 (1H, d), 6.10 (1H, m), 6.99 (1H, m), 7.27 (2H, m), 7.70 (1H, dd), 8.36 (1H, d) | m/z = 371 (M + H) |
| 1-55 | 3.65 (2H, m), 5.04 (2H, m), 5.15 (2H, s), 5.90 (1H, m), 6.13 (1H, m), 6.20 (1H, d), 7.13 (1H, m), 7.28 (2H, m), 7.71 (1H, dd), 8.36 (1H, d) | m/z = 355 (M + H) |
| 1-122 | 4.41 (2H, s), 5.17 (2H, s), 6.17 (2H, m), 6.82 (1H, m), 6.91 (1H, m), 7.16 (2H, m), 7.30 (2H, m), 7.70 (1H, dd), 8.38 (1H, d) | m/z = 411 (M + H) |
| 1-45 | 1.02 (6H, d), 3.34 (1H, m), 5.13 (2H, s), 6.10 (1H, d), 6.24 (1H, d), 7.11 (1H, m), 7.26 (1H, m), 7.31 (1H, d), 7.68 (1H, dd), 8.35 (1H, d) | m/z = 357 (M + H) |
| 1-124 | 4.20 (2H, s), 5.17 (2H, s), 6.13-6.29 (4H, m), 7.17 (1H, m), 7.30 (3H, m), 7.71 (1H, dd), 8.38 (1H, d) | m/z = 395 (M + H) |
| 1-126 | 1.49 (1H, m), 1.84 (2H, m), 1.99 (1H, m), 2.98 (1H, ddd), 3.14 (1H, ddd), 3.73 (2H, m), 4.09 (1H, m), 5.13 (2H, m), 6.13 (1H, m), 6.20 (1H, m), 7.14 (1H, m), 7.30 (2H, m), 7.70 (1H, dd), 8.37 (1H, d) | m/z = 399 (M + H) |
| 1-64 | 4.01 (2H, s), 5.24 (2H, s), 6.34 (2H, m), 7.34 (2H, m), 7.41 (1H, dd), 7.66 (1H, dd), 8.36 (1H, d) | m/z = 354 (M + H) |
| 1-146 | 3.21 (2H, m), 3.34 (2H, s), 3.57 (2H, t), 5.14 (2H, s), 6.15 (1H, m), 6.21 (1H, m), 7.15 (1H, m), 7.30 (2H, m), 7.72 (1H, dd), 8.37 (1H, d) | m/z = 373 (M + H) |
| 1-52 | 1.40-1.77 (8H, m), 3.48 (1H, m), 5.12 (2H, s), 6.09 (1H, m), 6.23 (1H, d), 7.12 (1H, m), 7.24 (1H, m), 7.31 (1H, d), 7.69 (1H, dd), 8.35 (1H, d) | m/z = 383 (M + H) |
| 1-121 | 4.18 (2H, s), 5.14 (2H, s), 6.20 (2H, m), 7.19 (3H, m), 7.26 (1H, m), 7.35 (1H, m), 7.75 (1H, dd), 8.36 (1H, d), 8.51 (2H, m) | m/z = 406 (M + H) |
| 1-53 | 0.98-1.72 (10H, m), 2.91 (1H, m), 5.11 (2H, s), 6.11 (1H, td), 6.24 (1H, d), 7.11 (1H, m), 7.29 (3H, m), 7.66 (1H, dd), 8.34 (1H, d) | m/z = 397 (M + H) |
| 1-76 | 2.90 (2H, t), 3.24 (2H, td), 5.07 (2H, s), 6.01 (1H, d), 6.09 (1H, td), 7.02-7.30 (8H, m), 7.61 (1H, dd), 8.34 (1H, d) | m/z = 419 (M + H) |
| 267-2 | 4.34 (1H, d), 4.62 (1H, d), 6.40 (1H, d), 7.20 (1H, d), 7.51 (2H, m), 7.59 (1H, dd), 7.63 (2H, m), 7.82 (1H, d), 8.23 (1H, d) | 1730, 1689, 1556, 1467, 1440, 1418 |
| 253-2 | 5.31 (2H, s), 7.28 (2H, m), 7.50 (1H, d), 7.72 (3H, m), 7.85 (1H, m), 8.25 (1H, d), 8.45 (1H, d) | 1644, 1557, 1508, 1483 |
| 251-2 | 5.20 (2H, s), 7.26 (2H, m), 7.63 (2H, m), 7.85 (2H, m), 8.02 (1H, d), 8.23 (2H, m) | 3065, 1696, 1463, 1403 |
| 13-2 | 5.76 (2H, s), 6.91 (1H, m), 7.46 (1H, m), 7.60 (1H, m), 7.70 (1H, d), 7.80 (2H, m), 8.12 (1H, d), 8.53 (1H, d) | 3060, 2226, 1641, 1556, 1509 |
| 1-1 | 5.49 (2H, s), 6.67 (1H, m), 7.30 (1H, m), 7.60 (1H, m), 7.72 (2H, m), 7.81 (1H, dd), 8.42 (1H, m), 9.06 (1H, s) | — |
| 1-41 | 5.64 (2H, s), 7.50 (2H, m), 7.70 (1H, d), 7.78 (1H, dd), 8.27 (1H, m), 8.37 (1H, d), 8.78 (1H, d) (methanol-d4) | m/z = 315.16 (M + H) |

TABLE 53

| Compound No. | 1H-NMR (CDCl3, δ, ppm) | MS or IR (KBr, v, cm$^{-1}$) |
|---|---|---|
| 2-2 | 2.47 (2H, m), 4.17 (2H, t), 5.07 (1H, d), 5.15 (1H, dd), 5.39 (2H, s), 5.85 (1H, m), 6.43 (1H, td), 7.30 (1H, d), 7.44 (2H, m), 7.75 (1H, dd), 8.08 (1H, d), 8.40 (1H, d) | m/z = 322 (M + H) |
| 1-647 | 2.47 (2H, m), 4.17 (2H, t), 5.07 (1H, d), 5.15 (1H, dd), 5.39 (2H, s), 5.85 (1H, m), 6.43 (1H, td), 7.30 (1H, d), 7.44 (2H, m), 7.75 (1H, dd), 8.08 (1H, d), 8.40 (1H, d) | m/z = 318.1013 (M + H) |
| 1-670 | 3.35 (2H, tdd), 5.17 (2H, s), 6.02 (1H, tt), 6.23 (2H, m), 7.22 (1H, m), 7.33 (2H, m), 7.69 (1H, dd), 8.37 (1H, d) | m/z = 379 (M + H) |
| 157-2 | 5.51 (2H, s), 6.63 (1H, dd), 7.42 (1H, d), 7.77 (1H, d), 7.84 (1H, dd), 8.26 (1H, d), 8.45 (1H, d) | m/z = 332 (M + H) |
| 1-10 | 1.61 (1H, m), 2.29 (2H, m), 4.73 (2H, s), 7.26 (1H, m), 7.31 (1H, m), 7.69 (1H, m), 7.79 (1H, m), 8.23 (1H, d), 8.40 (1H, d), 8.57 (1H, d) | m/z = 324 (M + H) |
| 580-2 | 5.47 (2H, s), 6.89 (1H, m), 7.47 (2H, m), 7.82 (2H, m), 8.41 (1H, s), 8.56 (1H, d) | m/z = 332 (M + H) |
| 1-671 | 0.87 (3H, t), 1.28 (10H, m), 1.55 (2H, m), 2.96 (2H, t), 5.14 (2H, s), 6.13 (1H, t), 6.18 (1H, d), 7.13 (1H, m), 7.30 (2H, m), 7.71 (1H, dd), 8.37 (1H, d) | m/z = 427 (M + H) |

TABLE 53-continued

| Compound No. | 1H-NMR (CDCl3, δ, ppm) | MS or IR (KBr, v, cm$^{-1}$) |
|---|---|---|
| 1-658 | 0.87 (3H, t), 1.25 (26H, m), 1.55 (2H, m), 2.96 (2H, t), 5.14 (2H, s), 6.11 (1H, t), 6.17 (1H, d), 7.13 (1H, m), 7.30 (2H, m), 7.70 (1H, dd), 8.36 (1H, d) | m/z = 539 (M + H) |
| 1-659 | 0.87 (3H, t), 1.26 (18H, m), 1.53 (2H, m), 2.95 (2H, t), 5.14 (2H, s), 6.12 (1H, t), 6.18 (1H, d), 7.13 (1H, m), 7.31 (2H, m), 7.71 (1H, dd), 8.36 (1H, d) | m/z = 483 (M + H) |
| 1-660 | 0.74 (3H, t), 0.97 (3H, d), 1.42 (2H, m), 3.08 (1H, m), 5.12 (2H, dd), 6.09 (1H, t), 6.23 (1H, d), 7.11 (1H, m), 7.24 (1H, m), 7.30 (1H, d), 7.67 (1H, dd), 8.35 (1H, d) | m/z = 371 (M + H) |
| 1-681 | 0.77, 0.90 (6H, t × 2), 1.40 (4H, m), 2.97 (1H, m), 5.11 (2H, s), 6.10 (1H, t), 6.25 (1H, d), 7.11 (1H, m), 7.24 (1H, d), 7.32 (1H, d), 7.66 (1H, dd), 8.34 (1H, d) | m/z = 385 (M + H) |
| 1-686 | 0.81, 0.91 (6H, t × 2), 1.02-1.45 (8H, m), 3.19 (1H, m), 5.12 (2H, s), 6.10 (1H, t), 6.25 (1H, d), 7.11 (1H, m), 7.22 (1H, d), 7.30 (1H, d), 7.64 (1H, dd), 8.33 (1H, d) | m/z = 413 (M + H) |
| 1-661 | 0.81 (3H, t), 0.97 (3H, d), 0.90-1.50 (4H, m), 3.19 (1H, m), 5.07 (1H, d), 5.15 (1H, d), 6.09 (1H, t), 6.24 (1H, d), 7.11 (1H, m), 7.27 (2H, m), 7.66 (1H, dd), 8.34 (1H, d) | m/z = 385 (M + H) |
| 1-662 | 0.75 (3H, d), 0.80 (3H, d), 0.94 (3H, d), 1.61 (1H, m), 2.86 (1H, m), 5.11 (2H, s), 6.09 (1H, t), 6.23 (1H, d), 7.11 (1H, t), 7.25 (1H, d), 7.30 (1H, d), 7.66 (1H, dd), 8.34 (1H, d) | m/z = 385 (M + H) |
| 1-663 | 1.35 (3H, d), 4.33 (1H, q), 5.05 (1H, d), 5.11 (1H, d), 6.00 (1H, d), 6.08 (1H, t), 6.96 (1H, m), 7.15-7.26 (7H, m), 7.63 (1H, dd), 8.33 (1H, d) | m/z = 419 (M + H) |
| 1-664 | 1.55-1.75 (3H, m), 1.95 (1H, m), 2.70-2.88 (2H, m), 4.36 (1H, t), 5.05 (1H, d), 5.20 (1H, d), 6.13 (1H, d), 6.38 (1H, d), 6.96 (1H, m), 7.02-7.20 (5H, m), 7.28 (1H, d), 7.62 (1H, dd), 8.3 (1H, d) | m/z = 445 (M + H) |
| 1-665 | 1.57 (3H, d), 4.78 (1H, d), 4.91 (1H, d), 5.18 (1H, q), 5.80 (1H, d), 5.93 (1H, t), 6.72 (1H, m), 7.05 (1H, d), 7.14 (1H, d), 7.38 (3H, m), 7.54 (1H, dd), 7.62 (1H, d), 7.66 (1H, d), 7.80 (1H, d), 7.84 (1H, d), 8.28 (1H, d) | m/z = 469 (M + H) |
| 1-666 | 0.74 (3H, t), 1.75 (2H, m), 4.03 (1H, t), 5.06 (2H, dd), 5.85 (1H, d), 6.05 (1H, m), 6.86 (1H, m), 7.10-7.28 (7H, m), 7.63 (1H, dd), 8.33 (1H, d) | m/z = 433 (M + H) |
| 1-667 | 1.34 (3H, d), 4.45 (1H, q), 5.11 (1H, d), 5.16 (1H, d), 6.07 (1H, m), 6.14 (1H, td), 6.26 (2H, m), 7.11 (1H, m), 7.28 (3H, m), 7.67 (1H, dd), 8.36 (1H, d) | m/z = 409 (M + H) |
| 1-676 | 5.06 (2H, s), 5.37 (1H, s), 5.38 (1H, d), 6.07 (1H, t), 6.85 (1H, t), 7.10-7.28 (12H, m), 7.61 (1H, d), 8.33 (1H, s) | m/z = 481 (M + H) |

TABLE 53-continued

| Compound No. | 1H-NMR (CDCl3, δ, ppm) | MS or IR (KBr, v, cm$^{-1}$) |
|---|---|---|
| 1-668 | 0.79 (9H, s), 0.85 (3H, d), 2.89 (1H, q), 5.11 (2H, s), 6.08 (1H, t), 6.23 (1H, d), 7.10 (1H, t), 7.23 (1H, d), 7.30 (1H, d), 7.65 (1H, d), 8.34 (1H, s) | m/z = 399 (M + H) |

TABLE 54

| Compound No. | 1H-NMR (CDCl3, δ, ppm) | MS or IR (KBr, v, cm$^{-1}$) |
|---|---|---|
| 47-2 | 5.68 (2H, d), 6.57 (1H, m), 7.34 (1H, d), 7.80 (1H, m), 7.97 (1H, dd), 8.39 (1H, d), 8.57 (1H, s) | m/z = 334 (M + H) |
| 91-2 | 5.92 (2H, s), 6.95 (1H, d), 7.30 (1H, d), 7.69 (1H, m), 7.86 (1H, dd), 8..49 (1H, dd), 8.53 (1H, d) | m/z = 350 (M + H) |
| 478-2 | 2.59 (3H, s), 5.77 (2H, s), 6.75 (1H, d), 7.31 (1H, d), 7.63 (1H, dd), 7.72 (1H, m), 8.33 (1H, d), 8.45 (1H, d) | m/z = 330 (M + H) |
| 479-2 | 2.73 (3H, s), 5.71 (2H, s), 6.73 (1H, d), 7.63 (1H, s), 7.69 (1H, t), 8.44 (1H, d) | m/z = 336 (M + H) |
| 1-51 | 1.60 (2H, m), 1.73 (1H, m), 2.03 (4H, m), 3.75 (1H, m), 5.12 (2H, s), 6.12 (1H, t), 6.16 (1H, d), 7.10 (1H, m), 7.25 (1H, d), 7.32 (1H, d), 7.71 (1H, dd), 8.37 (1H, d) | m/z = 369 (M + H) |
| 566-2 | 4.09 (3H, s), 5.71 (2H, s), 6.25 (1H, d), 7.29 (1H, d), 7.74 (1H, t), 7.97 (1H, dd), 8.17 (1H, d), 8.50 (1H, d) | m/z = 346 (M + H) |
| 488-2 | 1.77 (1H, m), 2.11 (1H, m), 2.62 (3H, s), 2.98 (1H, m), 3.53 (1H, dd), 3.67 (1H, dd), 3.78 (1H, m), 3.98 (1H, m), 4.22 (1H, m), 4.65 (1H, m), 6.73 (1H, d), 7.66 (1H, t), 8.32 (1H, d) | m/z = 289 (M + H) |
| 511-2 | 5.58 (2H, s), 7.38 (1H, d), 7.86 (1H, d), 8.40 (1H, dd), 8.47 (1H, d), 8.55 (1H, d), 8.93 (1H, d) | m/z = 361 (M + H) |
| 1-669 | 1.42 (3H, d), 4.65 (1H, q), 5.12 (2H, s), 6.13 (2H, m), 6.75 (1H, d), 6.88 (1H, dd), 7.07 (1H, m), 7.11 (1H, d), 7.26 (1H, m), 7.65 (1H, dd), 8.35 (1H, d) | m/z = 425 (M + H) |
| 179-2 | 5.30 (2H, s), 6.43 (1H, dd), 6.66 (1H, dd), 7.40 (1H, d), 7.60 (2H, m), 8.20 (1H, d) | m/z = 332 (M + H) |
| 555-2 | 3.87 (3H, s), 5.60 (2H, s), 7.51 (1H, d), 7.88 (1H, dd), 7.93 (1H, dd), 8.34 (1H, d), 8.49 (1H, d), 8.56 (1H, d) (DMSO-d6) | m/z = 346 (M + H) |
| 577-2 | 5.65 (2H, s), 6.87 (1H, td), 7.30 (1H, d), 7.81 (1H, m), 8.08 (1H, dd), 8.13 (1H, d), 8.54 (1H, d) | m/z = 349 (M + H) |
| 544-2 | 3.93 (3H, s), 5.45 (2H, s), 6.49 (1H, dd), 7.31 (1H, d), 7.66 (1H, d), 7.83 (1H, dd), 8.13 (1H, d), 8.42 (1H, d) | m/z = 346 (M + H) |
| 168-2 | 5.62 (2H, s), 7.43 (1H, d), 7.64 (1H, dd), 7.88 (1H, dd), 7.94 (1H, d), 8.26 (1H, d), 8.49 (1H, d) | m/z = 332 (M + H) |
| 1-644 | 4.18 (2H, s), 4.68 (2H, s), 5.36 (2H, s), 6.55 (1H, d), 7.16 (1H, d), 7.29 (1H, d), 7.35 (2H, m), 7.40 (2H, m), 1.52 (2H, m), 7.75 (1H, dd), 8.28 (1H, d), 8.40 (1H, d) | m/z = 368 (M + H) |

TABLE 54-continued

| Compound No. | 1H-NMR (CDCl3, δ, ppm) | MS or IR (KBr, v, cm⁻¹) |
|---|---|---|
| 578-644 | 4.19 (2H, s), 4.69 (2H, s), 5.42 (2H, s), 6.52 (1H, m), 7.20 (1H, m), 7.30 (1H, m), 7.32 (2H, m), 7.40 (2H, m), 7.55 (2H, m), 7.72 (1H, dd), 8.30 (1H, dd), 8.52 (1H, dd), 8.62 (1H, d) | m/z = 334 (M + H) |
| 1-703 | 5.20 (1H, d), 5.45 (1H, d), 6.55 (1H, m) 7.34 (1H, m), 7.50 (1H, m), 7.60 (1H, m), 7.79 (1H, dd), 8.39 (1H, d) | 1715, 1636, 1552, 1505, 1457, 1174, 1144 |
| 1-707 | 5.43 (2H, s), 6.93 (1H, m), 7.36 (1H, d), 7.77-7.85 (3H, m), 7.95 (1H, dd), 8.39 (1H, d) | (EI-HRMS) m/z = 351.0084 (M+) |
| 1-706 | 1.20 (6H, m), 2.67 (4H, m), 5.22 (2H, s), 6.52 (1H, m),. 7.31 (1H, m), 7.51 (1H, m), 7.60 (1H, dd), 7.73 (1H, m), 7.84 (1H, d), 8.41 (1H, d) | m/z = 298 (M + H) |
| 1-692 | 1.11 (3H, t), 1.20 (3H, t), 3.76 (2H, m), 3.92 (2H, m), 6.58 (1H, m), 7.26 (1H, d)., 7.53 (2H, m), 7.74 (1H, dd), 8.12 (1H, d), 8.40 (1H, d) (DMSO-d6) | m/z = 356 (M + H) |
| 1-700 | 1.20 (6H, m), 2.67 (4H, m), 5.22 (2H, s), 6.52 (1H, m),. 7.31 (1H, m), 7.51 (1H, m), 7.60 (1H, dd), 7.73 (1H, m), 7.84 (1H, d), 8.41 (1H, d) | m/z = 404 (M + H) |
| 1-701 | 0.95 (6H, m), 1.56 (4H, m), 2.62 (4H, m), 5.18 (2H, s), 6.52 (1H, m), 7.34 (1H, m), 7.49 (1H, m), 7.59 (1H, m), 7.77 (1H, dd), 7.84 (1H, d), 8.42 (1H, d) | m/z = 432 (M + H) |
| 1-702 | 1.13-1.46 (m, 12H), 3.20 (m, 2H), 5.27 (s, 2H), 6.51 (m, 1H), 7.31 (m, 1H), 7.52 (m, 1H), 7.63 (m, 1H), 7.78 (m, 2H), 8.43 (d, 1H) | m/z = 432 (M + H) |
| 1-646 | 1.31 (6H, d), 4.95 (1H, sep), 5.40 (2H, s), 6.40 (1H, m), 7.28 (1H, d), 7.40 (2H, m), 7.73 (1H, dd) 8.05 (1H, m), 8.40 (1H, d) | 1646, 1620, 1548, 1504, 1453, |
| 1-645 | 5.18 (2H, s), 5.37 (2H, s), 6.43 (1H, m), 7.25-7.36 (4H, m), 7.41-7.46 (4H, m), 7.72 (1H, dd), 8.12 (1H, m), 8.38 (1H, d) | 1655, 1518, 1455, 1399, 1235 |
| 1-643 | 5.52 (2H, s), 6.78 (1H, m), 7.31 (1H, d), 7.68-7.75 (3H, m), 8.39 (1H, m), 8.56 (1H, s) | 1633, 1601, 1541, 1502, 1482, 1453, 1384 |
| 2-643 | 5.51 (2H, s), 6.80 (1H, m), 7.60 (1H, s), 7.75 (2H, m), 8.57 (1H, m) | 1632, 1597, 1541, 1506, 1483, 1455, 1388 |

Further, the synthetic methods in the Table are described as follows.

A: the same method as in Synthetic Example 1

B: the same method as in Synthetic Example 2

C: the same method as in Synthetic Example 3

D: the same method as in Synthetic Example 4

E: the same method as in Synthetic Example 5

F: the same method as in Synthetic Example 6

G: the same method as in Synthetic Examples 7 and 8

H: the same method as in Synthetic Example 9

Preparation Example

Preparation Example 1 [Wettable Powder]

| Compound P212 | 10% by weight |
|---|---|
| Imidacloprid | 20% by weight |
| Clay | 50% by weight |
| White carbon | 2% by weight |
| Diatomaceous earth | 13% by weight |
| Calcium ligninsulfonate | 4% by weight |
| Sodium lauryl sulfate | 1% by weight |

The ingredients were homogeneously mixed and ground to obtain wettable powder.

Preparation Example 2 [Water Dispersible Granule]

| Compound P212 | 10% by weight |
|---|---|
| Imidacloprid | 20% by weight |
| Clay | 60% by weight |
| Dextrin | 5% by weight |
| Alkyl maleate copolymer | 4% by weight |
| Sodium lauryl sulfate | 1% by weight |

The ingredients were homogeneously ground and mixed, water was added thereto to knead the ingredients thoroughly and then the mixture was granulated and dried to obtain water dispersible granules.

Preparation Example 3 [Flowables]

| Compound 1-20 | 5% by weight |
|---|---|
| Imidacloprid | 20% by weight |
| POE polystyrylphenyl ether sulfate | 5% by weight |
| Propylene glycol | 6% by weight |
| Bentonite | 1% by weight |
| 1% xanthan-gum aqueous solution | 3% by weight |
| PRONALEX-300 (TOHO Chemical Industry Co., Ltd.) | 0.05% by weight |
| ADDAC827 (KI Chemical Industry Co., Ltd.) | 0.02% by weight |
| Water | added to 100% by weight |

All the ingredients except for the 1% xanthan-gum aqueous solution and a suitable amount of water were premixed together from the blending, and the mixture was then ground by a wet grinder. Thereafter, the 1% xanthan-gum aqueous solution and the remaining water were added thereto to obtain 100% by weight of flowables.

Preparation Example 4 [Emulsifiable Concentrate]

| Compound P212 | 2% by weight |
|---|---|
| Imidacloprid | 13% by weight |
| N,N-dimethylformamide | 20% by weight |
| Solvesso 150 (Exxon Mobil Corporation) | 55% by weight |
| Polyoxyethylene alkyl aryl ether | 10% by weight |

The ingredients were homogeneously mixed and dissolved to obtain an emulsifiable concentrate.

Preparation Example 5 [Dust]

| | |
|---|---|
| Compound P212 | 0.5% by weight |
| Imidacloprid | 1.5% by weight |
| Clay | 60% by weight |
| Talc | 37% by weight |
| Calcium stearate | 1% by weight |

The ingredients were homogeneously mixed to obtain dust.

Preparation Example 6 [DL Dust]

| | |
|---|---|
| Compound P212 | 1% by weight |
| Tebufloquin | 1% by weight |
| Ethofenprox | 1% by weight |
| DL clay | 94.5% by weight |
| White carbon | 2% by weight |
| Light liquid paraffin | 0.5% by weight |

The ingredients were homogeneously mixed to obtain dust.

Preparation Example 7 [Microgranule Fine]

| | |
|---|---|
| Compound P212 | 1% by weight |
| Imidacloprid | 1% by weight |
| Carrier | 94% by weight |
| White carbon | 2% by weight |
| Hisol SAS-296 | 2% by weight |

The ingredients were homogeneously mixed to obtain dust.

Preparation Example 8 [Granules]

| | |
|---|---|
| Compound 1-20 | 2% by weight |
| Chlorantraniliprole | 1% by weight |
| Bentonite | 39% by weight |
| Talc | 10% by weight |
| Clay | 46% by weight |
| Calcium ligninsulfonate | 2% by weight |

The ingredients were homogeneously ground and mixed, water was added thereto to knead the ingredients thoroughly, and then the mixture was granulated and dried to obtain granules.

Preparation Example 9 [Microcapsules]

| | |
|---|---|
| Compound 1-20 | 2% by weight |
| Imidacloprid | 3% by weight |
| Urethane resin | 25% by weight |
| Emulsifier/Dispersant | 5% by weight |
| Antiseptic | 0.2% by weight |
| Water | 64.8% by weight |

Microcapsules were obtained by forming a urethane resin coating on the surface of particles of the compound represented by Formula (I) and imidacloprid particles using the ingredients by interfacial polymerization.

Preparation Example 10 [Granules]

| | |
|---|---|
| Compound P212 | 2% by weight |
| Probenazole | 24% by weight |
| Sodium lauryl sulfate | 1% by weight |
| Bentonite | 2% by weight |
| Calcium stearate | 1% by weight |
| PVA | 2% by weight |
| Clay | 68% by weight |

The ingredients were homogeneously ground and mixed, water was added thereto to knead the ingredients thoroughly, and then the mixture was granulated and dried to obtain granules.

Preparation Example 11 [Granules]

| | |
|---|---|
| Compound P212 | 2% by weight |
| Chlorantraniliprole | 1% by weight |
| Probenazole | 24% by weight |
| Bentonite | 40% by weight |
| Talc | 10% by weight |
| Clay | 21% by weight |
| Calcium ligninsulfonate | 2% by weight |

The ingredients were homogeneously ground and mixed, water was added thereto to knead the ingredients thoroughly, and then the mixture was granulated and dried to obtain granules.

Preparation Example 12 [Liquid Drops]

| | |
|---|---|
| Compound 1-20 | 10% by weight |
| Fipronil | 1% by weight |
| Benzyl alcohol | 73.9% by weight |
| Propylene carbonate | 15% by weight |
| BHT | 0.1% by weight |

The ingredients were homogeneously stirred and dissolved to obtain liquid drops.

Preparation Example 13 [Liquid Drops]

| | |
|---|---|
| Compound P212 | 48% by weight |
| Fipronil | 2% by weight |
| Ethanol | 50% by weight |

The ingredients were homogeneously mixed to obtain liquid drops.

Preparation Example 14 [Emulsifiable Concentrate]

| | |
|---|---|
| Compound 1-20 | 5% by weight |
| Etoxazole | 5% by weight |
| Xylene | 35% by weight |
| Dimethyl sulfoxide | 35% by weight |

The ingredients were dissolved, and 14% by weight of polyoxyethylene styryl phenyl ether and 6% calcium dodecylbenzenesulfonate were added thereto, and the mixture was thoroughly stirred and mixed to obtain a 10% emulsifiable concentrate.

Preparation Example 15 [Liquid Drops]

| | |
|---|---|
| Compound P212 | 10% by weight |
| Etoxazole | 5% by weight |
| Glycol (glycol mono alkyl ether) | 85% by weight |
| BHT or BHA | appropriate amount |

An appropriate amount of sorbitan monooleate or sorbitan monolaurate, caprylic acid monoglyceride or isostearic acid monoglyceride, or propylene glycol monocaprylate was added to the ingredients, and alcohol or propylene carbonate, N-methyl-2-pyrrolidone or water was added thereto to obtain liquid drops as 100% by weight.

Reference Test Example

<Foliar Treatment Test of Single Agent>

Reference Test Example 1 Pest Control Test of *Plutella xylostella*

A leaf disk having a diameter of 5.0 cm was cut out from a cabbage in pot culture, and a drug solution of the compound of Formula (I) at a predetermined concentration, which had been prepared so as to be a 50% acetone water (0.05% Tween20 available), was sprayed to the leaf disk. After an air drying process, second instar larvae were released thereto. Thereafter, the larvae were left to stand in a thermostatic chamber (16 hours of light period-8 hours of dark period) at 25° C. Three days after the release, the larvae were observed for survival or death, and the mortality of larvae was calculated by the following equation. Test in duplicate.

Mortality (%)={number of dead larvae/(number of survived larvae+number of dead larvae)}×100

As a result, compounds P212 and 1-20 exhibited insecticidal activity having a mortality of 80% or higher by a foliar treatment at 100 ppm.

Reference Test Example 2 Pest Control Test of *Spodoptera litura*

A leaf disk having a diameter of 5.0 cm was cut out from a cabbage in pot culture, and a drug solution of the compound of Formula (I) at a predetermined concentration, which had been prepared so as to be a 50% acetone water (0.05% Tween20 available), was sprayed to the leaf disk. After an air drying process, third instar larvae were released thereto. Thereafter, the larvae were left to stand in a thermostatic chamber (16 hours of light period-8 hours of dark period) at 25° C. Three days after the release, the larvae were observed for survival or death, and the mortality of larvae was calculated by the following equation. Test in duplicate.

Mortality (%)={number of dead larvae/(number of survived larvae+number of dead larvae)}×100

As a result, compounds P212 and 1-20 exhibited insecticidal activity having a mortality of 80% or higher by a foliar treatment at 500 ppm.

Reference Test Example 3 Pest Control Test of *Aphis gossypii*

A leaf disk having a diameter of 2.0 cm was cut out from a cucumber in pot culture, and a drug solution of the compound of Formula (I) at a predetermined concentration, which had been prepared so as to be a 50% acetone water (0.05% Tween20 available), was sprayed to the leaf disk. After an air drying process, first instar larvae were released thereto. Thereafter, the larvae were left to stand in a thermostatic chamber (16 hours of light period-8 hours of dark period) at 25° C. Three days after the release, the larvae were observed for survival or death, and the mortality of larvae was calculated by the following equation. Test in duplicate.

Mortality (%)={number of dead larvae/(number of survived larvae+number of dead larvae)}×100

As a result, compounds P212 and 1-20 exhibited insecticidal activity having a mortality of 80% or higher by a foliar treatment at 100 ppm.

Reference Test Example 4 Pest Control Test of *Laodelphax striatella*

A drug solution of the compound of Formula (I) at a predetermined concentration, which had been prepared so as to be a 50% acetone water (0.05% Tween20 available), was foliar sprayed to a rice seedling in pot culture. After an air drying process, second instar larvae were released thereto. Thereafter, the larvae were left to stand in a thermostatic chamber (16 hours of light period-8 hours of dark period) at 25° C. Three days after the release, the larvae were observed for survival or death, and the mortality of larvae was calculated by the following equation. Test in duplicate.

Mortality (%)={number of dead larvae/(number of survived larvae+number of dead larvae)}×100

As a result, compounds P212 and 1-20 exhibited insecticidal activity having a mortality of 80% or higher by a foliar treatment at 100 ppm.

Reference Test Example 5 Pest Control Test of *Nilaparvata lugens*

A drug solution of the compound of Formula (I) at a predetermined concentration, which had been prepared so as to be a 50% acetone water (0.05% Tween20 available), was foliar sprayed to a rice seedling in pot culture. After an air drying process, second instar larvae were released thereto. Thereafter, the larvae were left to stand in a thermostatic chamber (16 hours of light period-8 hours of dark period) at 25° C. Six days after the release, the larvae were observed for survival or death, and the mortality of larvae was calculated by the following equation. Test in duplicate.

Mortality (%)={number of dead larvae/(number of survived larvae+number of dead larvae)}×100

As a result, compounds P212 and 1-20 exhibited insecticidal activity having a mortality of 80% or higher by a foliar treatment at 100 ppm.

Reference Test Example 6 Pest Control Test of *Sogatella furcifera*

A drug solution of the compound of Formula (I) at a predetermined concentration, which had been prepared so as to be a 50% acetone water (0.05% Tween20 available), was foliar sprayed to a rice seedling in pot culture. After an air drying process, second instar larvae were released thereto. Thereafter, the larvae were left to stand in a thermostatic chamber (16 hours of light period-8 hours of dark period) at 25° C. Four days after the release, the larvae were observed for survival or death, and the mortality of larvae was calculated by the following equation. Test in duplicate.

Mortality (%)={number of dead larvae/(number of survived larvae+number of dead larvae)}×100

As a result, compounds P212 and 1-20 exhibited insecticidal activity having a mortality of 80% or higher by a foliar treatment at 100 ppm.

Reference Test Example 7 Pest Control Test of *Nephotettix cincticeps*

A drug solution of the compound of Formula (I) at a predetermined concentration, which had been prepared so as to be a 50% acetone water (0.05% Tween20 available), was foliar sprayed to a rice seedling in pot culture. After an air drying process, second instar larvae were released thereto. Thereafter, the larvae were left to stand in a thermostatic chamber (16 hours of light period-8 hours of dark period) at 25° C. Four days after the release, the larvae were observed for survival or death, and the mortality of larvae was calculated by the following equation. Test in duplicate.

Mortality (%)={number of dead larvae/(number of survived larvae+number of dead larvae)}×100

As a result, compound P212 exhibited insecticidal activity having a mortality of 80% or higher by a foliar treatment at 100 ppm.

Reference Test Example 8 Pest Control Test of *Trialeurodes vaporariorum*

Adult greenhouse whiteflies were released to a cucumber in pot culture and allowed to lay eggs overnight. One day after the onset of egg laying, the adults were removed and the eggs were left to stand in a thermostatic chamber (16 hours of light period-8 hours of dark period) at 25° C. Three days after the completion of egg laying, a leaf disk having a diameter of 2.0 cm was cut out from the cucumber, it was confirmed that the eggs had been laid, and then a drug solution of the compound of Formula (I) at a predetermined concentration, which had been prepared so as to be a 50% acetone water (0.05% Tween20 available), was sprayed to the leaf disk. After the spraying, the leaf disk was left to stand in a thermostatic chamber (16 hours of light period-8 hours of dark period) at 25° C. Fourteen days after the spraying, larvae were observed for survival or death, and the mortality of larvae was calculated by the following equation. Test in duplicate.

Mortality of larvae (%)={(number of eggs laid −number of survived larvae)/number of eggs laid)}×100

As a result, compound P212 exhibited high insecticidal activity having a mortality of 80% or higher by a foliar treatment at 100 ppm.

Reference Test Example 9 Pest Control Test of *Frankliniella occidentalis*

A leaf disk having a diameter of 2.8 cm was cut out from a kidney bean in pot culture, and a drug solution of the compound of Formula (I) at a predetermined concentration, which had been prepared so as to be a 50% acetone water (0.05% Tween20 available), was sprayed to the leaf disk. After an air drying process, first instar larvae were released to the leaf disk. Thereafter, the larvae were left to stand in a thermostatic chamber (16 hours of light period-8 hours of dark period) at 25° C. Three days after the release, the larvae were observed for survival or death, and the mortality of larvae was calculated by the following equation. Test in duplicate.

Mortality of larvae (%)={number of dead larvae/ (number of survived larvae+number of dead larvae)}×100

As a result, compounds P212 and 1-20 exhibited high insecticidal activity having a mortality of 80% or higher by a foliage treatment at 500 ppm.

Reference Test Example 10 Pest Control Test of *Trigonotylus caelestialium*

Wheat seedling leaves and stems four days after the dissemination of seedlings were dipped for 30 seconds in a drug solution of the compound of Formula (I) at a predetermined concentration, which had been prepared so as to be a 50% acetone water (0.05% Tween20 available). After an air drying process, the wheat seedling leaves and stems were placed into a glass tube, and two second instar larvae of *Trigonotylus coelestialium* were released to the same glass tube. After the larvae were released, the tube was lidded to leave the larvae to stand in a thermostatic chamber at 25° C. In order to supply water to the wheat during the test, water was given to the wheat from the bottom of the glass tube. Three days after the treatment, the larvae were observed for survival or death, and the death rate of larvae was calculated by the following equation. Test in triplicate.

Mortality of larvae (%)={number of dead larvae/ (number of survived larvae+number of dead larvae)}×100

As a result, compounds P212 and 1-20 exhibited insecticidal activity having a mortality of 80% or higher by a dipping treatment of the drug solution at 50 ppm.

Reference Test Example 11 Pest Control Test of *Plautia crossota stali*

A drug solution of the compound of Formula (I) at a predetermined concentration, which had been prepared so as to be a 50% acetone water (0.05% Tween20 available), was sprayed to a young fruit of apple collected outdoors. After an air drying process, the young fruit was placed into a plastic cup, and two adults of *Plautia crossota* stall were released thereto. Six days after the release, the adults were observed for survival or death, the Mortality of adults was calculated by the following equation.

Mortality of adults (%)={number of dead adults/ (number of survived adults+number of dead adults)}×100

As a result, compound P212 exhibited insecticidal activity having a mortality of 60% or higher by a foliar treatment at 50 ppm.

Reference Test Example 12 Pest Control Test of *Oulema oryzae*

1 μL (/head) of a drug solution of the compound of Formula (I) prepared at a predetermined concentration with acetone was topically applied and treated to the back of adults collected outdoors by a micro syringe. After the drug treatment, the adults were transferred to rice seedlings and left to stand in a thermostatic chamber at 25° C. so as to obtain 5 heads per stem. Forty eight hours after the treatment, the adults were observed for survival or death, and the mortality of adults was calculated by the following equation. Test in duplicate.

Mortality of adults (%)={number of dead adults/ (number of survived adults+number of dead adults)}×100

As a result, compound P212 exhibited high insecticidal activity having a mortality of 80% or higher in a throughput of 0.5 μg/head.

Reference Test Example 13 Pest Control Test of *Musca domestica*

The backs of female adults raised indoors were treated with 1 μL (/head) of a drug solution of the compound of Formula (I) prepared at a predetermined concentration with acetone. After the drug treatment, the adults were transferred to a plastic cup and left to stand in a thermostatic chamber at 25° C. so as to obtain 5 heads per cup. Twenty four hours after the treatment, the agony situation of the adults was observed, and the rate of agonized adults was calculated by the following equation. Test in duplicate.

Mortality of adults (%)={number of dead adults/ (number of survived adults+dead adults)}×100

As a result, compounds P212 and 1-20 exhibited high insecticidal activity having a mortality of 80% or higher in a throughput of 2 μg/head.

<Soil Drench Test of Single Agent>

Reference Test Example 14 Pest Control Test of *Laodelphax striatella*

A rice seedling in pot culture was subjected to soil drench treatment with a drug solution of the compound of Formula (I) at a predetermined concentration, which had been prepared so as to be a 10% acetone water. Three days after the treatment, ten second instar larvae of *Laodelphax striatella* were each released thereto. Thereafter, the larvae were left to stand in a thermostatic chamber (16 hours of light period-8 hours of dark period) at 25° C. Three days after the release, the larvae were observed for survival or death, and the mortality of larvae was calculated by the following equation. Test in duplicate.

Mortality of larvae (%)={number of dead larvae/ (number of survived larvae+number of dead larvae)}×100

As a result, compounds P212 and 1-20 exhibited high insecticidal activity having a mortality of 80% or higher in a throughput of 0.05 mg/seedling.

Reference Test Example 15 Pest Control Test of *Sogatella furcifera*

A rice seedling in pot culture was subjected to soil drench treatment with a drug solution of the compound of Formula (I) at a predetermined concentration, which had been prepared so as to be a 10% acetone water. Three days after the treatment, ten second instar larvae of *Sogatella furcifera* were each released thereto. Thereafter, the larvae were left to stand in a thermostatic chamber (16 hours of light period-8 hours of dark period) at 25° C. Three days after the release, the larvae were observed for survival or death, and the mortality of larvae was calculated by the following equation. Test in duplicate.

Mortality of larvae (%)={number of dead larvae/ (number of survived larvae+number of dead larvae)}×100

As a result, compounds P212 and 1-20 exhibited high insecticidal activity having a mortality of 80% or higher in a throughput of 0.05 mg/seedling.

Reference Test Example 16 Pest Control Test of *Nilaparvata lugens*

A rice seedling in pot culture was subjected to soil drench treatment with a drug solution of the compound of Formula (I), which had been prepared so as to be a 10% acetone water. Three days after the treatment, ten second instar larvae of *Nilaparvata lugens* were each released thereto. Thereafter, the larvae were left to stand in a thermostatic chamber (16 hours of light period-8 hours of dark period) at 25° C. Three days after the release, the larvae were observed for survival or death, and the mortality of larvae was calculated by the following equation. Test in duplicate.

Mortality of larvae (%)={number of dead larvae/ (number of survived larvae+number of dead larvae)}×100

As a result, compounds P212 and 1-20 exhibited high insecticidal activity having a death rate of 80% or higher in a throughput of 0.05 mg/seedling.

Reference Test Example 17 Pest Control Test of *Lissorhoptrus oryzophilus*

A rice seedling in pot culture was subjected to soil drench treatment with a drug solution of the compound of Formula (I), which had been prepared so as to be a 10% acetone water. Two days after the treatment, five adults of *Lissorhoptrus oryzophilus* were each released thereto. Thereafter, the larvae were left to stand in a thermostatic chamber (16 hours of light period-8 hours of dark period) at 25° C. Three days after the release, the larvae were observed for survival or death, and the mortality of larvae was calculated by the following equation. Test in duplicate.

Mortality of larvae (%)={number of dead larvae/ (number of survived larvae+number of dead larvae)}×100

As a result, compound P212 exhibited high insecticidal activity having a mortality of 80% or higher in a throughput of 0.1 mg/seedling.

Reference Test Example 18 Pest Control Test of *Laodelphax striatella*

Wheat seedling roots forty eight hours after the dissemination of seeds were treated with a drug solution of the compound of the present invention at a predetermined concentration, which had been prepared so as to be a 10% acetone water. The drug was absorbed from the roots for 72 hours, and then ten second instar larvae of *Laodelphax striatella* were each released thereto. Thereafter, the larvae were left to stand in a thermostatic chamber (16 hours of light period-8 hours of dark period) at 25° C. Four days after the release, the larvae were observed for survival or death, and the mortality of larvae was calculated by the following equation. The test was performed in duplicate.

Mortality of larvae (%)={number of dead larvae/(number of survived larvae+number of dead larvae)}×100

As a result, compounds P212 and 1-204 exhibited insecticidal activity having a mortality of 80% or higher in a throughput of 20 kg/seedling.

The results of Reference Test Examples 1, 3 and 18 are shown in the following Table.

TABLE 55

| Reference Example Compound No. | Ar | Y | R | Plutella xylostella (Reference Test Example 1) | Aphisgossypii (Reference Test Example 3) | Laodelphax striatella (Reference Test Example 18) |
|---|---|---|---|---|---|---|
| P-212 | 6-chloro-3-pyridyl | H | COCF3 | 100 | 100 | 100 |
| P-213 | 2-chloro-5-thiazolyl | H | COCF3 | 100 | 100 | 100 |
| P-215 | 6-chloro-3-pyridyl | 5-Cl | COCF3 | 100 | 80 | 75 |
| P-216 | 6-chloro-3-pyridyl | 5-F | COCF3 | 100 | 95 | 100 |
| P-218 | 2-chloro-5-thiazolyl | 5-Cl | COCF3 | 100 | 60 | |
| P-219 | 2-chloro-5-thiazolyl | 5-F | COCF3 | 80 | 85 | |
| P-222 | 6-chloro-3-pyridyl | 4-Me | COCF3 | | 100 | 100 |
| P-223 | 6-chloro-3-pyridyl | 5-Me | COCF3 | | 75 | 75 |
| P-225 | 4-chloro-phenyl | H | COCF3 | | 90 | |
| P-226 | 3-pyridyl | H | COCF3 | 60 | 100 | |
| P-227 | 6-chloro-5-fluoro-3-pyridyl | H | COCF3 | 100 | 100 | 100 |
| P-228 | 6-trifluoromethyl-3-pyridyl | H | COCF3 | 30 | 95 | 100 |
| P-229 | 6-fluoro-3-pyridyl | H | COCF3 | 100 | 100 | 100 |
| P-230 | 5,6-dichloro-3-pyridyl | H | COCF3 | 100 | 100 | |
| P-231 | 6-bromo-3-pyridyl | H | COCF3 | 100 | 100 | 100 |
| P-232 | 6-chloro-3-pyridyl | 4-F | COCF3 | | 80 | |
| P-233 | 6-chloro-3-pyridyl | 3-F | COCF3 | | 100 | 75 |
| P-234 | 6-chloro-3-pyridyl | H | COCHCl2 | 100 | 100 | 100 |
| P-235 | 6-chloro-3-pyridyl | H | COCCl3 | 100 | 95 | 75 |
| P-236 | 6-chloro-3-pyridyl | H | COCH2Cl | | 100 | |
| P-238 | 6-chloro-3-pyridyl | H | COCHF2 | 100 | 100 | 100 |
| P-239 | 6-chloro-3-pyridyl | H | COCF2Cl | 100 | 100 | 100 |
| P-240 | 6-chloro-3-pyridyl | H | COCHClBr | | 100 | 100 |
| P-241 | 6-chloro-3-pyridyl | H | COCHBr2 | | 100 | 100 |
| P-242 | 6-chloro-3-pyridyl | H | COCF2CF3 | 100 | 100 | 100 |
| P-243 | 2-chloro-5-pyrimidinyl | H | COCF3 | 100 | 100 | 100 |
| P-244 | 6-chloro-3-pyridyl | H | COCH2Br | | 100 | 100 |
| 1-20 | 6-chloro-3-pyridyl | H | CSCF3 | 100 | 100 | 100 |

TABLE 55-continued

| Reference Example Compound No. | Ar | Y | R | Plutella xylostella (Reference Test Example 1) | Aphisgossypii (Reference Test Example 3) | Laodelphax striatella (Reference Test Example 18) |
|---|---|---|---|---|---|---|
| 1-21 | 6-chloro-3-pyridyl | H | CSCHF2 | 80 | 100 | 100 |
| 1-22 | 6-chloro-3-pyridyl | H | CSCF2Cl | 100 | | 100 |
| 1-23 | 6-chloro-3-pyridyl | H | CSCF2CF3 | 100 | | 100 |
| 1-42 | 6-chloro-3-pyridyl | H | C(=NOMe)CF3 | 100 | 100 | 100 |
| 1-150 | 6-chloro-3-pyridyl | H | C(=NCH2CH2SMe)CF3 | 100 | 100 | 80 |
| 3-3 | 6-fluoro-3-pyridyl | H | COCHF2 | 50 | 100 | 80 |
| 3-4 | 6-fluoro-3-pyridyl | H | COCF2Cl | 100 | 100 | 100 |
| 3-5 | 6-fluoro-3-pyridyl | H | COCF2CF3 | 100 | 55 | 80 |
| 3-20 | 6-fluoro-3-pyridyl | H | CSCF3 | 55 | 100 | 80 |
| 4-3 | 6-Bromo-3-pyridyl | H | COCHF2 | 100 | | 100 |
| 4-4 | 6-Bromo-3-pyridyl | H | COCF2Cl | 100 | | 100 |
| 4-5 | 6-Bromo-3-pyridyl | H | COCF2CF3 | 100 | 100 | 100 |
| 4-20 | 6-Bromo-3-pyridyl | H | CSCF3 | 100 | 100 | 100 |
| 5-3 | 6Chloro-5fluoro-3pyridyl | H | COCHF2 | 100 | | 100 |
| 5-4 | 6Chloro-5fluoro-3pyridyl | H | COCF2Cl | 100 | | 100 |
| 5-20 | 6Chloro-5fluoro-3pyridyl | H | CSCF3 | 100 | | 100 |
| 6-3 | 2-Cl-5-pyrimidinyl | H | COCHF2 | 80 | | 100 |
| 6-4 | 2-Cl-5-pyrimidinyl | H | COCF3Cl | 90 | 100 | 100 |
| 102-2 | 6-chloro-3-pyridyl | 3-CN | COCF3 | 10 | 100 | 100 |

<Effects Against Insecticide Resistant Pests>

Reference Test Example 19 Pest Control Test of *Nilaparvata lugens*

A rice seedling in pot culture was subjected to soil drench with a solution of the compound of Formula (I), which had been prepared so as to be a 10% acetone water. Three days after the treatment, ten second instar larvae of *Nilaparvata lugens*, which had been collected outdoors and proliferated indoors, were each released to the rice seedling. Thereafter, the larvae were left to stand in a thermostatic chamber (16 hours of light period-8 hours of dark period) at 25° C. Six days after the release, the larvae were observed for survival or death, and the mortality of larvae was calculated by the following equation. Test in duplicate.

Mortality of larvae (%)={number of dead larvae/(number of survived larvae+number of dead larvae)}×100

Furthermore, for comparison, the test against a species of *Nilaparvata lugens* which is highly susceptible to imidacloprid was performed by the same method as described above, and the results thereof are shown in Table 45. As described in Table 45, Compound P212 and Compound 1-20 exhibited high insecticidal effects against susceptible species and drug resistant species of *Nilaparvata lugens*, and the death rates of larvae at 0.005 mg/seedling were (susceptible species) 100% and 100%, (resistant population I) 95% and 77% and (resistant population II) 100% and 85%, respectively. Meanwhile, the death rates of imidacloprid at 0.05 mg/seedling were (susceptible species) 100%, (resistant population I) 38% and (resistant population II) 69%, and the insecticidal effect thereof was also low even at a high dose. From the above results, it became obvious that Compound P212 and Compound 1-20 have high insecticidal effects even against *Nilaparvata lugens* resistance against imidacloprid.

Further, for the origin of test pests, bugs collected outdoors from the Kumamoto prefecture (I) in 2007 and from the Fukuoka prefecture (II) in 2005 as resistant population of *Nilaparvata lugens*, and bugs collected from the Kagoshima prefecture and then successively reared indoors for a long time as the imidacloprid susceptible population of *Nilaparvata lugens* were used.

TABLE 56

Insecticidal effects against *Nilaparvata lugens* (death rate %)

| | | Effects against *Nilaparvata lugens* | | |
|---|---|---|---|---|
| | Throughput (mg/seedling) | Susceptible population six days after the treatment | Resistant population I six days after the treatment | Resistant population II six days after the treatment |
| P212 | 0.05 | 100 | 100 | 100 |
| | 0.005 | 100 | 95 | 100 |
| 1-20 | 0.01 | 95 | 100 | 100 |
| | 0.005 | 100 | 77 | 85 |
| Imidacloprid | 0.05 | 100 | 38 | 69 |
| | 0.01 | 100 | | 39 |

<Mixed Agent Test Example>

Test Example 1 Soil Irrigation Treatment Test of *Laodelphax striatella*

A rice seedling in pot culture was subjected to soil drench treatment with a drug solution of the compound of Formula (I) at a predetermined concentration, or a drug solution of a mixture of a compound of Formula (I) and an insecticide as indicated below at a predetermined concentration, which had been prepared so as to be a 10% acetone water. After the rice seedling was left to stand for 3 days, second instar larvae were released thereto. Thereafter, the larvae were left to stand in a thermostatic chamber (16 hours of light period-8 hours of dark period) at 25° C. Three days after the release, the larvae were observed for survival or death, and the mortality of larvae was calculated by the following equation. The test was performed in duplicate.

Mortality of larvae (%)={number of dead larvae/(number of survived larvae+number of dead larvae)}×100

In addition, when there was no synergistic effect, a theoretical value was calculated by the Colby's equation shown as follows, and the results are shown in the Table.

Colby's equation: theoretical value (%)=100−($A$×$B$)/100

(A: 100−(mortality of larvae or adults when treated only with Compound P212 or Compound 1-20)

B: 100−(mortality of larvae or adults when treated only with each of imidacloprid, fipronil, chlorantraniliprole, spinosad, clothianidin, dinotefuran, sulfoxaflor, pymetrozine, thiamethoxam, flupyradifurone and cycloxaprid))

Method for Judging Synergistic Effects

When the mortality against *Laodelphax striatella* in the case of a mixture with another agent exceeded the theoretical value by the Colby's equation, a synergistic effect was judged to be present.

It was demonstrated that mixed agents of the insecticides of imidacloprid, fipronil, chlorantraniliprole, spinosad, clothianidin, dinotefuran, sulfoxaflor, pymetrozine, thiamethoxam, flupyradifurone and cycoxaprid, which were provided and tested as Compound P212, all show a mortality of larvae or adults, exceed the theoretical value and have synergistic effects.

In addition, it was demonstrated that mixed agents of the insecticides of imidacloprid and fipronil, which were provided and tested as Compound 1-20, all show a mortality of larvae or adults, exceed the theoretical value and have synergistic effects.

Furthermore, it was demonstrated that mixed agents of the fungicides of probenazole, isotianil, tiadinil and orysastrobin, which were provided and tested as Compound P212, all exhibit insecticidal effect equal to or higher than the insecticidal effect when treated with Compound P212 alone and may be mixed and treated with a fungicide. Likewise, it was demonstrated that mixed agents of the fungicide of probenazole, which was provided and tested as Compound 1-20, exhibit insecticidal effect equal to or higher than the insecticidal effect when treated with Compound 1-20 alone and may be mixed and treated with a fungicide.

<Example of Mixed Agent with Insecticide>

TABLE 57

Mortality (%) of single agent and mixed agent against *Laodelphax striatella*

| | Rate | Compound P212 | |
|---|---|---|---|
| Insecticide name | mg/Seedling | 0 | 0.005 |
| — | — | 0 | 39 |
| Imidacloprid | 0.005 | 0 | 70 |
| Fipronil | 0.005 | 26 | 65 |
| Chlorantraniliprole | 0.05 | 9 | 60 |
| Spinosad | 0.5 | 0 | 62 |

TABLE 58

Theoretical value (%) by Colby's equation

| | Rate | Compound P212 | |
|---|---|---|---|
| Insecticide name | mg/Seedling | 0 | 0.005 |
| — | — | 0 | 39 |
| Imidacloprid | 0.005 | 0 | 39 |
| Fipronil | 0.005 | 26 | 55 |
| Chlorantraniliprole | 0.05 | 9 | 44 |
| Spinosad | 0.5 | 0 | 39 |

TABLE 59

Mortality (%) of single agent and mixed agent against *Laodelphax striatella*

| | Rate | Compound P212 | |
|---|---|---|---|
| Insecticide name | mg/Seedling | 0 | 0.005 |
| — | — | 0 | 18 |
| Clothianidin | 0.005 | 23 | 56 |
| Dinotefuran | 0.005 | 0 | 30 |
| Sulfoxaflor | 0.005 | 1 | 63 |
| Pymetrozine | 0.05 | 15 | 89 |

TABLE 60

Theoretical value (%) by Colby's equation

| | Rate | Compound P212 | |
|---|---|---|---|
| Insecticide name | mg/Seedling | 0 | 0.005 |
| — | — | 0 | 18 |
| Clothianidin | 0.005 | 23 | 37 |
| Dinotefuran | 0.005 | 0 | 18 |
| Sulfoxaflor | 0.005 | 1 | 19 |
| Pymetrozine | 0.05 | 15 | 30 |

TABLE 61

Mortality (%) of single agent and mixed agent against *Laodelphax striatella*

| | Rate | Compound P212 | |
|---|---|---|---|
| Insecticide name | mg/Seedling | 0 | 0.005 |
| — | — | 0 | 14 |
| Thiamethoxam | 0.01 | 23 | 45 |

TABLE 62

Theoretical value (%) by Colby's equation

| | Rate | Compound P212 | |
|---|---|---|---|
| Insecticide name | mg/Seedling | 0 | 0.005 |
| — | — | 0 | 14 |
| Thiamethoxam | 0.01 | 23 | 34 |

TABLE 63

Mortality (%) of single agent and mixed agent against *Laodelphax striatella*

| | Rate | Compound P212 | |
|---|---|---|---|
| Insecticide name | mg/Seedling | 0 | 0.005 |
| — | — | 0 | 45 |
| Flupyradifurone | 0.01 | 5 | 85 |

TABLE 64

Theoretical value (%) by Colby's equation

| | Rate | Compound P212 | |
|---|---|---|---|
| Insecticide name | mg/Seedling | 0 | 0.005 |
| — | — | 0 | 45 |
| Flupyradifurone | 0.01 | 5 | 48 |

TABLE 65

Mortality (%) of single agent and mixed agent against *Laodelphax striatella*

| | Rate | Compound 1-20 | |
|---|---|---|---|
| Insecticide name | mg/Seedling | 0 | 0.005 |
| — | — | 0 | 12 |
| Imidacloprid | 0.005 | 0 | 74 |
| Fipronil | 0.001 | 0 | 80 |

TABLE 66

Theoretical value (%) by Colby's equation

| | Rate | Compound 1-20 | |
|---|---|---|---|
| Insecticide name | mg/Seedling | 0 | 0.005 |
| — | — | 0 | 12 |
| Imidacloprid | 0.005 | 0 | 12 |
| Fipronil | 0.001 | 0 | 12 |

TABLE 67

Mortality (%) of single agent and mixed agent against *Laodelphax striatella*

| | Rate | Compound P212 | |
|---|---|---|---|
| Insecticide name | mg/Seedling | 0 | 0.005 |
| — | — | 0 | 0 |
| Cycloxaprid | 0.005 | 0 | 7 |

TABLE 68

Theoretical value (%) by Colby's equation

| | Rate | Compound P212 | |
|---|---|---|---|
| Insecticide name | mg/Seedling | 0 | 0.005 |
| — | — | 0 | 0 |
| Cycloxaprid | 0.005 | 0 | 0 |

TABLE 69

Mortality (%) of single agent and mixed agent against *Laodelphax striatella*

| | Rate | Compound P212 | | Compound 1-20 | |
|---|---|---|---|---|---|
| Fungicide name | mg/Seedling | 0 | 0.005 | 0 | 0.005 |
| — | — | 0 | 39 | 0 | 8 |
| Probenazole | 0.5 | 9 | 59 | 9 | 65 |

TABLE 70

Theoretical value (%) by Colby's equation

| | Rate | Compound P212 | | Compound 1-20 | |
|---|---|---|---|---|---|
| Fungicide name | mg/Seedling | 0 | 0.005 | 0 | 0.005 |
| — | — | 0 | 39 | 0 | 8 |
| Probenazole | 0.5 | 9 | 44 | 9 | 16 |

TABLE 71

Mortality (%) of single agent and mixed agent against *Laodelphax striatella*

| | Rate | Compound P212 | |
|---|---|---|---|
| Fungicide name | mg/Seedling | 0 | 0.005 |
| — | — | 0 | 19 |
| Isotianil | 0.5 | 5 | 30 |
| Tiadinil | 0.5 | 8 | 30 |
| Orysastrobin | 0.5 | 4 | 70 |

TABLE 72

Theoretical value (%) by Colby's equation

| Fungicide name | Rate mg/Seedling | Compound P212 0 | Compound P212 0.005 |
|---|---|---|---|
| — | — | 0 | 19 |
| Isotianil | 0.5 | 5 | 23 |
| Tiadinil | 0.5 | 8 | 25 |
| Orysastrobin | 0.5 | 4 | 22 |

Test Example 2 Foliar Treatment Test Against *Laodelphax striatella*

A drug solution of the compound of Formula (I) at a predetermined concentration, or a drug solution of a mixture of a compound of Formula (I) and an insecticide as indicated below at a predetermined concentration, which had been prepared so as to be a 50% acetone water (0.05% Tween20 available), was foliar sprayed to a rice seedling in pot culture. After an air drying process, second instar larvae were released thereto. Thereafter, the larvae were left to stand in a thermostatic chamber (16 hours of light period-8 hours of dark period) at 25° C. Three days after the release, the larvae were observed for survival or death, and the mortality of larvae was calculated by the following equation. The test was performed in duplicate.

Mortality of larvae (%)={number of dead larvae/(number of survived larvae+number of dead larvae)}×100

Further, when there was no synergistic effect, a theoretical value was calculated by the Colby's equation shown as follows, and the results are shown in the Table.

Theoretical value (%)=100−($A$×$B$)/100        Colby's equation:

(A: 100−(mortality of larvae or adults when treated only with Compound P212 or Compound 1-20)

B: 100−(mortality of larvae or adults when treated only with etofenprox or silafluofen))

Method for Judging Synergistic Effects

When the mortality against *Laodelphax striatella* in the case of a mixture with another agent exceeded the theoretical value by the Colby's equation, a synergistic effect was judged to be present.

It was demonstrated that mixed agents of the insecticides of etofenprox and silafluofen, which were provided and tested as Compound P212 or Compound 1-20, all show a mortality of larvae or adults approximately equal to the theoretical value, and may be mixed with the insecticide even in a foliar treatment-like usage.

TABLE 73

Mortality (%) of single agent and mixed agent against *Laodelphax s striatella*

| Insecticide name | Rate (ppm) | — 0 | Compound P212 0.625 | Compound 1-20 0.625 |
|---|---|---|---|---|
| — | | 0 | 95 | 90 |
| Etofenprox | 10 | 30 | 90 | 95 |
| Silafluofen | 5 | 55 | 100 | 100 |

TABLE 74

Theoretical value (%) by Colby's equation

| Insecticide name | Rate (ppm) | — 0 | Compound P212 0.625 | Compound 1-20 0.625 |
|---|---|---|---|---|
| — | | 0 | 95 | 90 |
| Etofenprox | 10 | 30 | 97 | 93 |
| Silafluofen | 5 | 55 | 98 | 95 |

Test Example 3 Pest Control Test of *Aphis gossypii*

A leaf disk having a diameter of 2.0 cm was cut out from a cucumber in pot culture, and a drug solution of the compound of Formula (I) at a predetermined concentration, or a drug solution of a mixture of a compound of Formula (I) and an insecticide as indicated below at a predetermined concentration, which had been prepared so as to be a 50% acetone water (0.05% Tween20 available), was sprayed thereto. After an air drying process, first instar larvae were released thereto. Thereafter, the larvae were left to stand in a thermostatic chamber (16 hours of light period-8 hours of dark period) at 25° C. Three days after the release, the larvae were observed for survival or death, and the mortality of larvae was calculated by the following equation. The test was performed in duplicate.

Mortality of larvae (%)={number of dead larvae/(number of survived larvae+number of dead larvae)}×100

In addition, when there was no synergistic effect, a theoretical value was calculated by the Colby's equation shown as follows, and the results are shown in the Table.

Theoretical value (%)=100−($A$×$B$)/100        Colby's equation:

(A: 100−(mortality of larvae or adults when treated only with Compound P212 or Compound 1-20)

B: 100−(mortality of larvae or adults when treated only with afidopyropen)

Method for Judging Synergistic Effects

When the mortality against *Aphis gossypii* in the case of a mixture with another agent exceeded the theoretical value by the Colby's equation, a synergistic effect was judged to be present.

It was demonstrated that mixed agents of compounds of Formula (II), which were provided and tested as Compound P212 or Compound 1-20, all show a mortality of larvae or adults, exceed the theoretical value and have synergistic effects.

TABLE 75

Mortality (%) of single agent and mixed agent against *Aphis gossypii*

| Insecticide name | Rate ppm | Compound P212 0 | Compound P212 0.313 | Compound 1-20 0 | Compound 1-20 0.625 |
|---|---|---|---|---|---|
| — | — | 0 | 45 | 0 | 19 |
| Afidopyropen | 0.002 | 25 | 70 | 25 | 40 |

TABLE 76

| Insecticide name | Rate ppm | Theoretical value (%) by Colby's equation | | | |
|---|---|---|---|---|---|
| | | Compound P212 | | Compound 1-20 | |
| | | 0 | 0.313 | 0 | 0.625 |
| — | — | 0 | 45 | 0 | 19 |
| Afidopyropen | 0.002 | 25 | 59 | 25 | 39 |

Test Example 4 Pest Control Test of *Plutella xylostella*

A leaf disk having a diameter of 5.0 cm was cut out from a cabbage in pot culture, and a drug solution of the compound of Formula (I) at a predetermined concentration, or a drug solution of a mixture of a compound of Formula (I) and an insecticide as indicated below at a predetermined concentration, which had been prepared so as to be a 50% acetone water (0.05% Tween20 available), was sprayed thereto. After an air drying process, second instar larvae were released thereto. Thereafter, the larvae were left to stand in a thermostatic chamber (16 hours of light period-8 hours of dark period) at 25° C. Three days after the release, the larvae were observed for survival or death, and the mortality of larvae was calculated by the following equation. The test was performed in duplicate.

Mortality of larvae (%)={number of dead larvae/
(number of survived larvae+number of dead larvae)}×100

Furthermore, when there was no synergistic effect, a theoretical value was calculated by the Colby's equation shown as follows, and the results are shown in the Table.

Theoretical value (%)=100−(A×B)/100    Colby's equation:

(A: 100−(mortality of larvae or adults when treated with only Compound P212)

B: 100−(mortality of larvae or adults when treated with only flometoquin, spinosad, fipronil, chlorantraniliprole, 1-((6-chloropyridin-3-yl)methyl)-4-oxo-3-phenyl-4H-pyrido[1,2-a]pyrimidin-1-ium-2-olate, or afidopyropen))

Method for Judging Synergistic Effects

When the mortality against *Plutella xylostella* in the case of a mixture with another agent exceeded the theoretical value by the Colby's equation, a synergistic effect was judged to be present.

It was demonstrated that a mixed agent of the insecticide of flometoquin, which was provided and tested, with Compound P212, shows a death rate of larvae or adults, exceeds the theoretical value and has synergistic effects.

TABLE 77

Mortality (%) of single agent and mixed agent against *Plutella xylostella*

| Insecticide name | Rate ppm | Compound P212 | |
|---|---|---|---|
| | | 0 | 1.25 |
| — | — | 0 | 0 |
| Flometoquin | 0.313 | 0 | 30 |

TABLE 78

Theoretical value (%) by Colby's equation

| Insecticide name | Rate ppm | Compound P212 | |
|---|---|---|---|
| | | 0 | 1.25 |
| — | — | 0 | 0 |
| Flometoquin | 0.313 | 0 | 0 |

TABLE 79

Mortality (%) of single agent and mixed agent against *Plutella xylostella*

| Insecticide name | | | Compound P212 Rate ppm | |
|---|---|---|---|---|
| | | | 0 | 1.0 |
| — | | | 0 | 40 |
| Afidopyropen | Rate | 10 | 20 | 70 |
| Spinosad | ppm | 0.01 | 11 | 70 |

TABLE 80

Theoretical value (%) by Colby's equation

| Insecticide name | | | Compound P212 Rate ppm | |
|---|---|---|---|---|
| | | | 0 | 1.0 |
| — | | | 0 | 40 |
| Afidopyropen | Rate | 10 | 20 | 52 |
| Spinosad | ppm | 0.01 | 11 | 45 |

TABLE 81

Mortality (%) of single agent and mixed agent against *Plutella xylostella*

| Insecticide name | | | Compound P212 Rate ppm | |
|---|---|---|---|---|
| | | | 0 | 1.0 |
| — | | | 0 | 30 |
| Afidopyropen | Rate ppm | 5 | 0 | 80 |

TABLE 82

Theoretical value (%) by Colby's equation

| Insecticide name | | | Compound P212 Rate ppm | |
|---|---|---|---|---|
| | | | 0 | 1.0 |
| — | | | 0 | 30 |
| Afidopyropen | Rate ppm | 5 | 0 | 30 |

TABLE 83

Mortality (%) of single agent and mixed agent against *Plutella xylostella*

|  |  |  | Compound P212 Rate ppm | |
|---|---|---|---|---|
| Insecticide name |  |  | 0 | 2.0 |
| — |  |  | 0 | 60 |
| Fipronil | Rate | 0.04 | 50 | 100 |
| Chlorantraniliprole | ppm | 0.002 | 60 | 100 |

TABLE 84

Theoretical value (%) by Colby's equation

|  |  |  | Compound P212 Rate ppm | |
|---|---|---|---|---|
| Insecticide name |  |  | 0 | 2.0 |
| — |  |  | 0 | 60 |
| Fipronil | Rate | 0.04 | 50 | 80 |
| Chlorantraniliprole | ppm | 0.002 | 60 | 84 |

TABLE 85

Mortality (%) of single agent and mixed agent against *Plutella xylostella*

|  |  |  | Compound P212 Rate ppm | |
|---|---|---|---|---|
| Insecticide name |  |  | 0 | 2.0 |
| — |  |  | 0 | 50 |
| 1-((6-chloropyridin-3-yl)methyl)-4-oxo-3-phenyl-4H-pyrido[1,2-a]pyrimidin-1-ium-2-olate | Rate ppm | 1 | 30 | 70 |
| Afidopyropen |  | 5 | 0 | 100 |

TABLE 86

Theoretical value (%) by Colby's equation

|  |  |  | Compound P212 Rate ppm | |
|---|---|---|---|---|
| Insecticide name |  |  | 0 | 2.0 |
| — |  |  | 0 | 50 |
| 1-((6-chloropyridin-3-yl)methyl)-4-oxo-3-phenyl-4H-pyrido[1,2-a]pyrimidin-1-ium-2-olate | Rate ppm | 1 | 30 | 65 |
| Afidopyropen |  | 5 | 0 | 50 |

Test Example 5 Pest Control Test of *Spodoptera litura*

A leaf disk having a diameter of 5.0 cm was cut out from a cabbage in pot culture, and a drug solution of the compound of Formula (I) at a predetermined concentration, or a drug solution of a mixture of a compound of Formula (I) and an insecticide as indicated below at a predetermined concentration, which had been prepared so as to be a 50% acetone water (0.05% Tween20 available), was sprayed thereto. After an air drying process, third instar larvae were released thereto. Thereafter, the larvae were left to stand in a thermostatic chamber (16 hours of light period-8 hours of dark period) at 25° C. Three days after the release, the larvae were observed for survival or death, and the larvae mortality was calculated by the following equation. The test was performed in duplicate.

Mortality of larvae (%)={number of dead larvae/(number of survived larvae+number of dead larvae)}×100

Furthermore, a theoretical value for the case of no synergistic effect was calculated using Colby's equation given below, and the results are shown in the tables.

Theoretical value (%)=100−($A \times B$)/100    Colby's equation:

(A: 100−(mortality of larvae or adults when treated only with Compound P212)

B: 100−(mortality of larvae or adults when treated with only the insecticide chlorantraniliprole, emamectin benzoate, flometoquin, or afidopyropen))

Method for Judging Synergistic Effects

When the mortality against *Spodoptera litura* in the case of a mixture with another agent exceeded the theoretical value given by Colby's equation, a synergistic effect was judged to be present.

It was demonstrated that a mixed agent of the insecticide chlorantraniliprole, emamectin benzoate, flometoquin, or afidopyropen tested with Compound P212 shows a mortality for larvae or adults in excess of the theoretical value and has synergistic effects.

TABLE 87

Mortality (%) of single agent and mixed agent against *Spodoptera litura* (1)

|  |  |  | Compound P212 Rate ppm | |
|---|---|---|---|---|
| Insecticide name |  |  | 0 | 20 |
| — |  |  | 0 | 40 |
| Afidopyropen | Rate ppm | 10 | 0 | 80 |

TABLE 88

Theoretical value (%) by Colby's equation

|  |  |  | Compound P212 Rate ppm | |
|---|---|---|---|---|
| Insecticide name |  |  | 0 | 20 |
| — |  |  | 0 | 40 |
| Afidopyropen | Rate ppm | 10 | 0 | 40 |

TABLE 89

Mortality (%) of single agent and mixed agent against *Spodoptera litura* (2)

| Insecticide name | | | Compound P212 Rate ppm 0 | Compound P212 Rate ppm 20 |
|---|---|---|---|---|
| — | | | 0 | 10 |
| Chlorantraniliprole | Rate | 0.02 | 20 | 30 |
| Emamectin benzoate | ppm | 0.02 | 0 | 20 |

TABLE 90

Theoretical value (%) by Colby's equation

| Insecticide name | | | Compound P212 Rate ppm 0 | Compound P212 Rate ppm 20 |
|---|---|---|---|---|
| — | | | 0 | 10 |
| Chlorantraniliprole | Rate | 0.02 | 20 | 28 |
| Emamectin benzoate | ppm | 0.02 | 0 | 10 |

TABLE 91

Mortality (%) of single agent and mixed agent against *Spodoptera litura* (3)

| Insecticide name | | | Compound P212 Rate ppm 0 | Compound P212 Rate ppm 50 |
|---|---|---|---|---|
| — | | | 0 | 10 |
| Flometoquin | Rate | 5 | 10 | 20 |
| Afidopyropen | ppm | 5 | 0 | 50 |

TABLE 92

Theoretical value (%) by Colby's equation

| Insecticide name | | | Compound P212 Rate ppm 0 | Compound P212 Rate ppm 50 |
|---|---|---|---|---|
| — | | | 0 | 10 |
| Flometoquin | Rate | 5 | 10 | 19 |
| Afidopyropen | ppm | 5 | 0 | 10 |

Test Example 6 Pest Control Test of *Frankliniella occidentalis*

A leaf disk having a diameter of 2.8 cm was cut out from the common bean in pot culture, and a drug solution of the compound of Formula (I) at a predetermined concentration, or a drug solution of a mixture of a compound of Formula (I) and an insecticide as indicated below at a predetermined concentration, which had been prepared so as to be a 50% acetone water (0.05% Tween20 available), was sprayed thereto. After an air drying process, first instar larvae were released thereto. Thereafter, the larvae were left to stand in a thermostatic chamber (16 hours of light period-8 hours of dark period) at 25° C. Three days after the release, the larvae were observed for survival or death, and the larvae mortality was calculated by the following equation. The test was performed in duplicate.

Mortality of larvae (%)={number of dead larvae/(number of survived larvae+number of dead larvae)}×100

Furthermore, a theoretical value for the case of no synergistic effect was calculated using Colby's equation given below, and the results are shown in the table.

Theoretical value (%)=100−($A \times B$)/100       Colby's equation:

(A: 100−(mortality of larvae or adults when treated only with Compound P212)

B: 100−(mortality of larvae or adults when treated with only the insecticide imidacloprid, dinotefuran, or acetamiprid))

Method for Judging Synergistic Effects

When the mortality against *Frankliniella occidentalis* in the case of a mixture with another agent exceeded the theoretical value given by Colby's equation, a synergistic effect was judged to be present.

It was demonstrated that a mixed agent of the insecticide imidacloprid or dinotefuran tested with Compound P212 shows a mortality for larvae or adults in excess of the theoretical value and has synergistic effects.

TABLE 93

Mortality (%) of single agent and mixed agent against *Frankliniella occidentalis* (1)

| Insecticide name | | | Compound P212 Rate ppm 0 | Compound P212 Rate ppm 10 |
|---|---|---|---|---|
| — | | | 0 | 69 |
| Imidacloprid | Rate ppm | 20 | 69 | 94 |

TABLE 94

Theoretical value (%) by Colby's equation

| Insecticide name | | | Compound P212 Rate ppm 0 | Compound P212 Rate ppm 10 |
|---|---|---|---|---|
| — | | | 0 | 69 |
| Imidacloprid | Rate ppm | 20 | 69 | 90 |

TABLE 95

Mortality (%) of single agent and mixed agent against *Frankliniella occidentalis* (2)

| Insecticide name | | | Compound P212 Rate ppm 0 | Compound P212 Rate ppm 20 |
|---|---|---|---|---|
| — | | | 0 | 70 |
| Dinotefuran | Rate ppm | 5 | 35 | 85 |

TABLE 96

Theoretical value (%) by Colby's equation

|  |  |  | Compound P212 Rate ppm | |
|---|---|---|---|---|
| Insecticide name |  |  | 0 | 20 |
|  | — |  | 0 | 70 |
| Dinotefuran | Rate ppm | 5 | 35 | 81 |

Test Example 7 Soil Irrigation Treatment Test on *Chilo suppressalis*

Rice seedlings in pot culture were submitted to a soil irrigation treatment with a drug solution of the compound of Formula (I) at a predetermined concentration, or a drug solution of a mixture of a compound of Formula (I) and an insecticide as indicated below at a predetermined concentration, which had been prepared so as to be a 10% acetone water. After standing for 3 days, second instar larvae were released thereto. This was followed by standing in a thermostatic chamber (16 hours of light period-8 hours of dark period) at 25° C. Six days after the release, the larvae were observed for survival or death, and the larvae mortality was calculated by the following equation. The test was performed in duplicate.

Mortality of larvae (%)={number of dead larvae/(number of survived larvae+number of dead larvae)}×100

Furthermore, a theoretical value for the case of no synergistic effect was calculated using Colby's equation given below, and the results are shown in the table.

Theoretical value (%)=100−(A×B)/100     Colby's equation:

(A: 100−(mortality of larvae or adults when treated only with Compound P212)
B: 100−(mortality of larvae or adults when treated with only the insecticide fipronil, cyantraniliprole or spinosad))
Method for Judging Synergistic Effects When the insecticidal effect (table) against *Chilo suppressalis* in the case of a mixture with another agent exceeded the theoretical value given by Colby's equation, a synergistic effect was judged to be present.

It was demonstrated that a mixed agent of the insecticide fipronil, cyantraniliprole or spinosad tested with Compound P212 shows a mortality for larvae or adults in excess of the theoretical value in both cases and has synergistic effects.

TABLE 97

Mortality (%) of single agent and mixed agent against *Chilo suppressalis* (1)

|  |  |  | Compound P212 Rate mg/seedling | |
|---|---|---|---|---|
| Insecticide name |  |  | 0 | 0.01 |
|  | — |  | 0 | 33 |
| Cyantraniliprole | Rate mg/seedling | 0.005 | 83 | 100 |

TABLE 98

Theoretical value (%) by Colby's equation

|  |  |  | Compound P212 Rate mg/seedling | |
|---|---|---|---|---|
| Insecticide name |  |  | 0 | 0.01 |
|  | — |  | 0 | 33 |
| Cyantraniliprole | Rate mg/seedling | 0.005 | 83 | 89 |

TABLE 99

Mortality (%) of single agent and mixed agent against *Chilo suppressalis* (2)

|  |  |  | Compound P212 Rate mg/seedling | |
|---|---|---|---|---|
| Insecticide name |  |  | 0 | 0.002 |
|  | — |  | 0 | 40 |
| Fipronil | Rate | 0.0005 | 40 | 80 |
| Chlorantraniliprole | mg/seedling | 0.0005 | 60 | 80 |
| Spinosad |  | 0.002 | 80 | 100 |

TABLE 100

Theoretical value (%) by Colby's equation

|  |  |  | Compound P212 Rate mg/seedling | |
|---|---|---|---|---|
| Insecticide name |  |  | 0 | 0.002 |
|  | — |  | 0 | 40 |
| Fipronil | Rate | 0.0005 | 40 | 64 |
| Chlorantraniliprole | mg/seedling | 0.0005 | 60 | 76 |
| Spinosad |  | 0.002 | 80 | 88 |

Test Example 8 Soil Irrigation Treatment Test on *Naranga aenescens*

Rice seedlings in pot culture were subjected to a soil irrigation treatment with a drug solution of the compound of Formula (I) at a predetermined concentration, or a drug solution of a mixture of a compound of Formula (I) and an insecticide as indicated below at a predetermined concentration, which had been prepared so as to be a 10% acetone water. After standing for 3 days, first instar larvae were released thereto. This was followed by standing in a thermostatic chamber (16 hours of light period-8 hours of dark period) at 25° C. Five days after the release, the larvae were observed for survival or death, and the larvae mortality was calculated by the following equation. The test was performed in duplicate.

Mortality of larvae (%)={number of dead larvae/(number of survived larvae+number of dead larvae)}×100

Furthermore, a theoretical value for the case of no synergistic effect was calculated using Colby's equation given below, and the results are shown in the table.

Theoretical value (%)=100−(A×B)/100     Colby's equation:

(A: 100−(mortality of larvae or adults when treated only with Compound P212)

B: 100−(mortality of larvae or adults when treated with only the insecticide spinosad or fipronil))

Method for Judging Synergistic Effects

When the mortality against *Naranga aenescens* in the case of a mixture with another agent exceeded the theoretical value given by Colby's equation, a synergistic effect was judged to be present.

It was demonstrated that a mixed agent of the insecticide spinosad or fipronil tested with Compound P212 shows a mortality for larvae or adults in excess of the theoretical value in all cases and has synergistic effects.

TABLE 101

Mortality (%) of single agent and mixed agent against *Naranga aenescens*

| Insecticide name | | | Compound P212 Rate mg/seedling | |
|---|---|---|---|---|
| | | | 0 | 0.01 |
| — | | | 0 | 60 |
| Spinosad | Rate | 0.005 | 40 | 100 |
| Fipronil | mg/seedling | 0.01 | 20 | 80 |

TABLE 102

Theoretical value (%) by Colby's equation

| Insecticide name | | | Compound P212 Rate mg/seedling | |
|---|---|---|---|---|
| | | | 0 | 0.01 |
| — | | | 0 | 60 |
| Spinosad | Rate | 0.005 | 40 | 76 |
| Fipronil | mg/seedling | 0.01 | 20 | 68 |

Test Example 9 Test on *Callosobruchus chinensis*

A compound of Formula (I) and the insecticide indicated below, prepared in predetermined concentrations using acetone, were separately topically applied to the back of the same adult *Callosobruchus chinensis*. The *Callosobruchus chinensis* was then introduced into a plastic cup and held in a thermostatic chamber (16 hours of light period-8 hours of dark period) at 25° C. One day after the release, the insects were observed for survival or death, and the insect mortality was calculated by the following equation. The test was performed in duplicate.

Insect mortality (%)={number of dead insects/(number of survived insects+number of dead insects)}×100

Furthermore, a theoretical value for the case of no synergistic effect was calculated using Colby's equation given below, and the results are shown in the table.

Theoretical value (%)=100−($A \times B$)/100    Colby's equation:

(A: 100−(insect mortality for treatment with only Compound P212)

B: 100−(insect mortality for treatment with only the insecticide fipronil or imidacloprid))

Method for Judging Synergistic Effects

When the mortality against *Callosobruchus chinensis* in the case of a mixture with another agent exceeded the theoretical value given by Colby's equation, a synergistic effect was judged to be present.

It was demonstrated that co-treatment with the insecticide fipronil or imidacloprid tested with Compound P212 shows an insect mortality in excess of the theoretical value in both cases and has synergistic effects.

TABLE 103

Mortality (%) of single agent and mixed agent against *Callosobruchus chinensis*

| Insecticide name | | | Compound P212 Rate ng/head | |
|---|---|---|---|---|
| | | | 0 | 0.2 |
| — | | | 0 | 20 |
| Fipronil | Rate | 0.2 | 0 | 36 |
| Imidacloprid | ng/head | 0.2 | 40 | 60 |

TABLE 104

Theoretical value (%) by Colby's equation

| Insecticide name | | | Compound P212 Rate ng/head | |
|---|---|---|---|---|
| | | | 0 | 0.2 |
| — | | | 0 | 20 |
| Fipronil | Rate | 0.2 | 0 | 20 |
| Imidacloprid | ng/head | 0.2 | 40 | 52 |

Test Example 10 Pest Control Test of Rice Blast

A rice seedling in pot culture was subjected to soil irrigation treatment with a drug solution of the compound of Formula (I) at a predetermined concentration, or a drug solution of a mixture of a compound of Formula (I) and an insecticide as indicated below at a predetermined concentration, which had been prepared with a 10% acetone water. Three days after the treatment, a spore suspension ($2 \times 10^5$ ea/mL, 0.05% Tween available) of rice blast bacteria was sprayed and inoculated thereto, and the rice seedling was placed in a moist chamber for 24 hours to promote infection. Thereafter, the larvae were left to stand in a thermostatic chamber (16 hours of light period-8 hours of dark period) at 25° C. Seven days after the inoculation, the number of lesions was measured, and the preventive value was calculated by the following equation. The test was performed in triplicate.

Preventive value={(number of lesions in a zone without treatment−number of lesions in a zone with treatment)/(number of lesions without treatment)}×100

As a result, it was demonstrated that in a throughput of probenazole at 0.125 mg/seedling, any one mixed agent of Compound P212 and Compound 1-20 exhibits insecticidal effect equal to the insecticidal effect when treated with probenazole alone and may be mixed and treated with a fungicide.

TABLE 105

| Insecticide name | | | Compound P212 Rate mg/seedling | | Compound 1-20 | |
|---|---|---|---|---|---|---|
| | | | 0 | 2.5 | 0 | 2.5 |
| — | | | 0 | 3.3 | 0 | 52.5 |
| Probenazole | Rate mg/seedling | 0.125 | 96.7 | 93.4 | 96.7 | 91.8 |

Test Example 11 Test of Rice Blast Control (Foliar Treatment)

Rice seedlings were treated by foliar application with a drug solution of the compound of Formula (I), or a drug solution of a mixture of a compound of Formula (I) and the fungicide indicated below, prepared in a predetermined concentration with 10% acetone water. After the treatment, a rice blast spore suspension ($1.5 \times 10^5$ ea/mL, 0.05% Tween available) was sprayed and inoculated thereto followed by holding in a thermostatic chamber (16 hours of light period-8 hours of dark period) at 25° C. Fourteen days after the inoculation, the number of lesions was measured, and the preventive value was calculated by the following equation. The test was performed in triplicate.

Preventive value={(number of lesions in a zone without treatment−number of lesions in a zone with treatment)/(number of lesions in a zone without treatment)}×100

As a result, it was demonstrated that at a treatment concentration of 0.5 ppm using tiadinil, isotianil, orysastrobin, tricyclazole, diclocymet, tebufloquin, azoxystrobin or kasugamycin, the mixed agent with Compound P212 also exhibits a fungicidal effect equal to that for treatment with tiadinil, isotianil, orysastrobin, tricyclazole, diclocymet, tebufloquin, azoxystrobin or kasugamycin alone and a mixed treatment with a fungicide is therefore possible.

TABLE 106

(Rice blast test 1)

| Fungicide name | | | Compound P212 Rate ppm | |
|---|---|---|---|---|
| | | | 0 | 50 |
| — | | | 0 | 4 |
| Tiadinil | Rate | 0.5 | 0 | 18 |
| Isotianil | ppm | 0.5 | 66 | 72 |

TABLE 107

(Rice blast test 2)

| Fungicide name | | | Compound P212 Rate ppm | |
|---|---|---|---|---|
| | | | 0 | 50 |
| — | | | 0 | 16 |
| Orysastrobin | Rate | 0.5 | 20 | 91 |
| Tricyclazole | ppm | 0.5 | 72 | 92 |

TABLE 107-continued (Rice blast test 2)

| Fungicide name | | Compound P212 Rate ppm | |
|---|---|---|---|
| | | 0 | 50 |
| Diclocymet | 0.5 | 8 | 52 |
| Tebufloquin | 0.5 | 48 | 72 |

TABLE 108

(Rice blast test 3)

| Fungicide name | | | Compound P212 Rate ppm | |
|---|---|---|---|---|
| | | | 0 | 50 |
| — | | | 0 | 0 |
| Azoxystrobin | Rate | 0.5 | 37 | 35 |
| Kasugamycin | ppm | 0.5 | 0 | 37 |

Test Example 12 Test of Control of Rice Sheath Blight (*Rhizoctonia solani*)

Six weeks after planting, rice seedlings were subjected to foliar spray treatment with a drug solution of the compound of Formula (I), or a drug solution of a mixture of a compound of Formula (I) and a fungicide as indicated below, prepared in a predetermined concentration with 10% acetone water. After an air drying process, a plug of growing *Rhizoctonia solani* (1.0 cm² agar square each) was allowed to stand at the base of the rice. This was followed by holding in a thermostatic chamber (30° C. 15 day-25° C. night, 16 hours of light period-8 hours of dark period). Six days after the inoculation, the lesion height was measured, and the preventive value was calculated by the following equation. The test was performed in duplicate.

Preventive value={(lesion height in a zone without treatment−lesion height in a zone with treatment)/(lesion height in a zone without treatment)}×100

As a result, it was demonstrated that, at a treatment concentration of 5 ppm using thifluzamide, furametpyr, pencycuron, azoxystrobin, simeconazole, validamycin, or orysastrobin, the mixed agent with 50 ppm Compound P212 presented the same fungicidal effect as for treatment with thifluzamide, furametpyr, pencycuron, azoxystrobin, simeconazole, validamycin, or orysastrobin alone, and mixed treatment with a fungicide is therefore possible.

TABLE 109

(Sheath blight test 1)

| Fungicide name | | | Compound P212 Rate ppm | |
|---|---|---|---|---|
| | | | 0 | 50 |
| — | | | 0 | 14 |
| Thifluzamide | Rate | 5 | 92 | 97 |
| Furametpyr | ppm | 5 | 77 | 94 |
| Pencycuron | | 5 | 69 | 77 |

TABLE 110

(Sheath blight test 2)

| Fungicide name | | | Compound P212 Rate ppm | |
|---|---|---|---|---|
| | | | 0 | 50 |
| — | | | 0 | 9 |
| Azoxystrobin | Rate | 5 | 95 | 100 |
| Simeconazole | ppm | 5 | 5 | 24 |
| Validamycin | | 5 | 32 | 74 |
| Orysastrobin | | 5 | 72 | 59 |

Test Example 13 Test with *Laodelphax striatellus* by Treatment During the Vegetative Phase Rice was planted in nursery boxes and emergence was carried out for three days a 30° C. followed by transfer of the nursery boxes to a glass greenhouse at 25° C. During the vegetative phase five days after planting, the nursery boxes were treated with a prescribed amount of a mixed granule of 0.24 mg/mg probenazole (24%) and 0.02 mg/mg Compound P212 (2%). The rice seedlings were transplanted to 1/5000a Wagner pots 22 days after planting and were grown in a greenhouse at 25° C. Second instar larvae of 15 *Laodelphax striatellus* were released at 13, 26, and 38 days post-transplantation to the Wagner pots; this was followed by holding in a glass greenhouse at 25° C. Five days after the release, the larvae were observed for survival or death, and the larvae mortality was calculated by the following equation. The test was performed in duplicate.

Mortality of larvae (%)={number of dead larvae/(number of survived larvae+number of dead larvae)}×100

According to the results, it was shown that the mixed granule of probenazole and Compound P212 presented a high insecticidal effect of 100% mortality and exhibited control at a practical level.

Test Example 14 Test with *Laodelphax striatellus* by Soil Irrigation Treatment Rice seedlings in pot cultivation were subjected to a soil irrigation treatment with a drug solution of a compound of Formula (I) or a drug solution of a mixture of a compound of Formula (I) and a paddy herbicide as indicated below, prepared in predetermined concentrations so as to be a 10% acetone water. After standing for three 20 days, second instar larvae were released thereto. Thereafter, the larvae were left to stand in a thermostatic chamber (16 hours of light period-8 hours of dark period) at 25° C. five days after the release, the larvae were observed for survival or death, and the larvae mortality was calculated by the following equation. The test was performed in duplicate.

Mortality of larvae (%)={number of dead larvae/(number of survived larvae+number of dead larvae)}×100

The mixed agent of Imazosulfuron, cafenstrole, cyhalofop-butyl, daimuron and pyrazolate tested with the Compound P212 was shown in all instances to exhibit an insecticidal effect at least equal to that for treatment with Compound P212 by itself, and a mixed treatment with a herbicide is thus possible.

TABLE 111

| Herbicide name | | | Compound P212 Rate mg/seedling | | |
|---|---|---|---|---|---|
| | | | 0 | 0.005 | 0.01 |
| — | | | 0 | 0 | 100 |
| Imazosulfuron | Rate | 0.05 | 0 | 0 | 100 |
| Cafenstrole | mg/seedling | 0.05 | 0 | 0 | 100 |
| Cyhalofop-butyl | | 0.05 | 0 | 0 | 100 |
| Daimuron | | 0.05 | 0 | 0 | 100 |
| Pyrazolate | | 0.05 | 0 | 0 | 100 |

Test Example 15 Test of the Control of *Haemaphysalis longicornis*

A capsule with a diameter of 2 cm and a height of 2 cm was attached to the dorsal surface of a mouse. A compound of Formula (I), ivermectin, moxidectin, permethrin, amitraz, fipronil, spinetram and the mixture of the compound of Formula (I) and each insecticide were dissolved in ethanol at the concentrations given in Table O, and each of these was dripped onto the surface of a mouse body within a capsule. After thorough drying, eight *Haemaphysalis longicornis* nymphs were released and the top of the capsule was sealed with a lid. The mouse was kept in a cage at 25° C. using a 12-hour light period and a 12-hour dark period. Five days after the release, the capsule was removed and the number of surviving and dead nymphs and the number of engorged individuals were counted and the insect mortality and agonal rate was calculated by the following equation.

Insect mortality and agonal rate (%)={number of dead and agonal insects/(number of survived insects+number of dead and agonal insects)}×100

The results showed that, at a rate of 0.009 μg of ivermectin or moxidectin, the mixed agent of either with Compound P212 also gave a tick control effect that was the same as treatment with ivermectin, moxidectin, permethrin, amitraz, fipronil and spinetram alone and mixed treatment with ivermectin, moxidectin, permethrin, amitraz, fipronil and spinetram is thus possible.

TABLE 112

Mortality (%) of single agent and mixed agent against *Haemaphysalis longicornis*(1)

| Insecticide name | | | Compound P212 Rate μg | |
|---|---|---|---|---|
| | | | 0 | 1.18 |
| — | | | 0 | 53 |
| Ivermectin | Rate | 0.009 | 3 | 53 |
| Moxidectin | μg | 0.009 | 6 | 44 |

TABLE 113

Mortality (%) of single agent and mixed agent against *Haemaphysalis longicornis*(2)

| Insecticide name | | | Compound P212 Rate μg | |
|---|---|---|---|---|
| | | | 0 | 1.18 |
| — | | | 0 | 60 |
| Amitraz | Rate | 0.38 | 41 | 90 |
| Permethrin | μg | 9.5 | 71 | 86 |

TABLE 114

Theoretical value (%) by Colby's equation

| Insecticide name | | | Compound P212 Rate μg | |
|---|---|---|---|---|
| | | | 0 | 1.18 |
| — | | | 0 | 60 |
| Amitraz | Rate | 0.38 | 41 | 77 |
| Permethrin | μg | 9.5 | 71 | 88 |

TABLE 115

Mortality (%) of single agent and mixed agent against *Haemaphysalis longicornis*(3)

| Insecticide name | | | Compound P212 Rate μg | |
|---|---|---|---|---|
| | | | 0 | 1.18 |
| — | | | 0 | 38 |
| fipronil | Rate | 0.38 | 78 | 93 |
| spinetoram | μg | 0.38 | 6 | 22 |

TABLE 116

Theoretical value (%) by Colby's equation

| Insecticide name | | | Compound P212 Rate μg | |
|---|---|---|---|---|
| | | | 0 | 1.18 |
| — | | | 0 | 38 |
| fipronil | Rate | 0.38 | 78 | 86 |
| spinetoram | μg | 0.38 | 6 | 41 |

TABLE 117

Mortality (%) of single agent and mixed agent against *Haemaphysalis longicornis*(4)

| Insecticide name | | | Compound P212 Rate μg | |
|---|---|---|---|---|
| | | | 0 | 1.18 |
| — | | | 0 | 18 |
| pyriproxyfen | Rate | 0.0475 | 2 | 44 |
| spinosad | μg | 1.9 | 2.5 | 43 |

TABLE 118

Theoretical value (%) by Colby's equation

| Insecticide name | | | Compound P212 Rate μg | |
|---|---|---|---|---|
| | | | 0 | 1.18 |
| — | | | 0 | 18 |
| pyriproxyfen | Rate | 0.0475 | 2 | 20 |
| spinosad | μg | 1.9 | 2.5 | 20 |

TABLE 119

Mortality (%) of single agent and mixed agent against *Haemaphysalis longicornis*(5)

| Insecticide name | | | Compound P212 Rate μg | |
|---|---|---|---|---|
| | | | 0 | 1.18 |
| — | | | 0 | 23 |
| imidacloprid | Rate | 1.9 | 7.7 | 60 |
| dinotefuran | μg | 1.9 | 0 | |

TABLE 120

Theoretical value (%) by Colby's equation

| Insecticide name | | | Compound P212 Rate μg | |
|---|---|---|---|---|
| | | | 0 | 1.18 |
| — | | | 0 | 23 |
| imidacloprid | Rate | 1.9 | 7.7 | 32 |
| dinotefuran | μg | 1.9 | 0 | 25 |

What is claimed is:

1. A pest control composition comprising:
   at least one iminopyridine derivative selected from the group consisting of N-[1-((6-chloropyridin-3-yl)methyl)pyridin-2(1H)-ylidene]-2,2,2-trifluoroacetamide, N-[1-((6-chloropyridin-3-yl)methyl)pyridin-2(1H)-ylidene]-2,2,2-trifluoroethanethioamide, N-[1-((6-chloropyridin-3-yl)methyl)pyridin-2(1H)-ylidene]-2,2,2-trifluoro-N'-isopropylacetimidamide and acid addition salts thereof; and
   at least one insecticide selected from the group consisting of thiamethoxam, pymetrozine, spinosad, fipronil, cyantraniliprole, silafluofen, sulfoxaflor, flupyradifurone, emamectin benzoate, cycloxaprid, 1-((6-chloropyridin-3-yl)methyl)-4-oxo-3-phenyl-4H-pyrido[1,2-a]pyrimidin-1-ium-2-olate, and agriculturally and/or zootechnically acceptable acid addition salts thereof.

2. A pest control composition comprising:
   at least one iminopyridine derivative selected from the group consisting of N[1-((6-chloropyridin-3-yl)methyl)pyridin-2(1H)-ylidene]-2,2,2-trifluoroacetamide, N-[1-((6-chloropyridin-3-yl)methyl)pyridin-2(1H)-ylidene]-2,2,2-trifluoroethanethioamide, N-[1-((6-chloropyridin-3-yl)methyl)pyridin-2(1H)-ylidene]-2,2,2-trifluoro-N'-isopropylacetimidamide and acid addition salts thereof; and
   at least one fungicide selected from the group consisting of orysastrobin, thifluzamide, furametpyr, probenazole, tiadinil, isotianil, diclocymet, tricyclazole, tebufloquin, simeconazole, pencycuron, and agriculturally and/or zootechnically acceptable acid addition salts thereof.

3. A combined product comprising:
   at least one iminopyridine derivative selected from the group consisting of N-[1((6-chloropyridin-3-yl)methyl)pyridin-2(1H)-ylidene]-2,2,2-trifluoroacetamide, N-[1-((6-chloropyridin-3-yl)methyl)pyridin-2(1H)-ylidene]-2,2,2-trifluoroethanethioamide, N-[1-((6-chloropyridin-3-yl)methyl)pyridin-2(1H)-ylidene]-2,2,2-trifluoro-N'-isopropylacetimidamide and acid addition salts thereof; and
   at least one insecticide selected from the group consisting of thiamethoxam, pymetrozine, spinosad, fipronil, cyantraniliprole, silafluofen, sulfoxaflor, flupyradifurone, emamectin benzoate, cycloxaprid, 1-((6-chloropyridin-3-yl)methyl)-4-oxo-3-phenyl-4H-pyrido[1,2-a]pyrimidin-1-ium-2-olate, and agriculturally and/or zootechnically acceptable acid addition salts thereof.

4. A pest control composition comprising:

at least one iminopyridine derivative selected from the group consisting of N[1-((6-chloropyridin-3-yl)methyl)pyridin-2(1H)-ylidene]-2,2,2-trifluoroacetamide, N-[1-((6-chloropyridin-3-yl)methyl)pyridin-2(1H)-ylidene]-2,2,2-trifluoroethanethioamide, N-[1-((6-chloropyridin-3-yl)methyl)pyridin-2(1H)-ylidene]-2,2,2-trifluoro-N'-isopropylacetimidamide and acid addition salts thereof; and at least one other pest control agent, wherein the other pest control agent is a control agent for animal parasitic pests and is selected from the group consisting of fipronil, amitraz, pyriproxyfen, spinosad, and agriculturally and/or zootechnically acceptable acid addition salts thereof.

5. A combined product comprising:

at least one iminopyridine derivative selected from the group consisting of N-[1((6-chloropyridin-3-yl)methyl)pyridin-2(1H)-ylidene]-2,2,2-trifluoroacetamide, N-[1-((6-chloropyridin-3-yl)methyl)pyridin-2(1H)-ylidene]-2,2,2-trifluoroethanethioamide, N-[1-((6-chloropyridin-3-yl)methyl)pyridin-2(1H)-ylidene]-2,2,2-trifluoro-N'-isopropylacetimidamide and acid addition salts thereof; and at least one fungicide selected from the group consisting of orysastrobin, thifluzamide, furametpyr, tiadinil, isotianil, diclocymet, tricyclazole, tebufloquin, simeconazole, pencycuron, and agriculturally and/or zootechnically acceptable acid addition salts thereof.

6. A combined product comprising:

at least one iminopyridine derivative selected from the group consisting of N-[1(6-chloropyridin-3-yl)methyl)pyridin-2(1H)-ylidene]-2,2,2-trifluoroacetamide, N-[1-((6-chloropyridin-3-yl)methyl)pyridin-2(1H)-ylidene]-2,2,2-trifluoroethanethioamide, N-[1-((6-chloropyridin-3-yl)methyl)pyridin-2(1H)-ylidene]-2,2,2-trifluoro-N'-isopropylacetimidamide and acid addition salts thereof; and at least one other pest control agent, wherein the other pest control agent is a control agent for animal parasitic pests and is selected from the group consisting of fipronil, amitraz, pyriproxyfen, spinosad, and agriculturally and/or zootechnically acceptable acid addition salts thereof.

7. A method for protecting useful plants or animals from pests comprising simultaneously or independently applying the pest control composition of claim 1, 2 or 4 to a region to be treated.

8. A method for protecting useful plants or animals from pests by treating pests, useful plants, seeds of useful plants, soil, cultivation carriers or animals as a target, with an effective amount of the pest control composition of claim 1, 2 or 4.

9. A method for protecting useful plants or animals from pests by applying the combined product of claim 3, 5 or 6 to pests, useful plants, seeds of useful plants, soil, cultivation carriers or animals as a target.

* * * * *